United States Patent
Hatakeyama et al.

(10) Patent No.: US 11,709,427 B2
(45) Date of Patent: Jul. 25, 2023

(54) POSITIVE RESIST COMPOSITION AND PATTERN FORMING PROCESS

(71) Applicant: Shin-Etsu Chemical Co., Ltd., Tokyo (JP)

(72) Inventors: Jun Hatakeyama, Joetsu (JP); Masahiro Fukushima, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 177 days.

(21) Appl. No.: 17/137,672

(22) Filed: Dec. 30, 2020

(65) Prior Publication Data

US 2021/0247694 A1    Aug. 12, 2021

(30) Foreign Application Priority Data

Feb. 4, 2020   (JP) .................. 2020-017215

(51) Int. Cl.
| | | |
|---|---|---|
| G03F 7/039 | (2006.01) | |
| C07D 213/30 | (2006.01) | |
| C08F 220/18 | (2006.01) | |
| C08F 220/38 | (2006.01) | |
| C08F 220/22 | (2006.01) | |
| C08F 212/14 | (2006.01) | |

(52) U.S. Cl.
CPC ........... *G03F 7/039* (2013.01); *C07D 213/30* (2013.01); *C08F 212/24* (2020.02); *C08F 220/1806* (2020.02); *C08F 220/1807* (2020.02); *C08F 220/1809* (2020.02); *C08F 220/22* (2013.01); *C08F 220/382* (2020.02)

(58) Field of Classification Search
CPC ....... C08F 212/26; C08F 220/34; G03F 7/004
See application file for complete search history.

(56) References Cited

U.S. PATENT DOCUMENTS

| | | | | |
|---|---|---|---|---|
| 7,932,016 B2* | 4/2011 | Winkle | ............... | H01L 24/11 430/324 |
| 8,426,108 B2* | 4/2013 | Masunaga | ............. | G03F 7/0397 430/905 |
| 8,470,511 B2* | 6/2013 | Masunaga | ............. | G03F 7/0382 430/905 |
| 9,360,760 B2* | 6/2016 | Hatakeyama | ......... | G03F 7/0046 |
| 9,594,303 B2* | 3/2017 | Osaki | ............... | C08F 220/26 |
| 9,696,625 B2* | 7/2017 | Hirano | ............... | G03F 7/0046 |
| 10,012,902 B2* | 7/2018 | Hatakeyama | ............. | G03F 7/11 |
| 2007/0231708 A1 | 10/2007 | Matsumaru et al. | | |
| 2008/0292577 A1* | 11/2008 | Mougin | ............... | C08F 220/26 8/405 |
| 2009/0197197 A1 | 8/2009 | Shimizu et al. | | |
| 2014/0242521 A1 | 8/2014 | Ongayi et al. | | |
| 2016/0103393 A1* | 4/2016 | Park | ............... | G03F 7/0392 430/281.1 |
| 2020/0192221 A1* | 6/2020 | Hatakeyama | ............. | G03F 7/039 |

FOREIGN PATENT DOCUMENTS

| | | | | | |
|---|---|---|---|---|---|
| JP | 2001114832 A | * | 4/2001 | ............. | C08F 12/34 |
| JP | 2006-45311 A | | 2/2006 | | |
| JP | 2006-178317 A | | 7/2006 | | |
| JP | 2008-133312 A | | 6/2008 | | |
| JP | 2009-181062 A | | 8/2009 | | |
| JP | 2011-39266 A | | 2/2011 | | |
| JP | 2015-025879 A | | 2/2015 | | |
| KR | 10-2014-0106433 A | | 9/2014 | | |
| WO | WO-2010024412 A1 | * | 3/2010 | ............. | B82Y 30/00 |
| WO | WO-2010116063 A1 | * | 10/2010 | ........... | A61K 8/8158 |
| WO | WO-2016098809 A1 | * | 6/2016 | ............. | C08F 220/34 |

OTHER PUBLICATIONS

Nakano et al, Synthesis and Chiral Recognition Ability of a Cross-Linked Polymer Gel Prepared by a Molecular Imprint Method Using Chiral Helical Polymers as Templates, Macromolecules, 34, 2405-2407 (2001). (Year: 2001).*
Cui et al, Helical Polymers as Templates, Macromolecular Chemistry and Physics 203, 2432-2437 (2002). (Year: 2002).*
Machine translation of WO 2016/098809 (no date).*
Elladiou, M., "Degradable Polymers Containing Labile Pyridinylalkyl Ester Groups in the Monomer Unit, Cross-linker, Initiator or Inimer", University of Cyprus, Faculty of Pure and Applied Sciences, 2017, cited in TW Office Action dated Dec. 3, 2021. (222 pages).
Office Action dated Dec. 3, 2021, issued in counterpart TW Application No. 110103613. (7 pages).
Kishikawa et al., "Assessment of trade-off between resist resolution and sensitivity for optimization of hyper-NA immersion lithography", SPIE, 2007, vol. 6520, pp. 65203L-1-65203L-9, cited in the specification (9 pages).
Office Action dated Jan. 10, 2023, issued in counterpart KR application No. 10-2021-0015784, with English translation. (14 pages).

* cited by examiner

*Primary Examiner* — Amanda C. Walke
(74) *Attorney, Agent, or Firm* — WHDA, LLP

(57) ABSTRACT

A positive resist composition comprising a base polymer comprising recurring units having a carboxyl group whose hydrogen is substituted by a pyridine ring-containing tertiary hydrocarbyl group.

12 Claims, No Drawings

POSITIVE RESIST COMPOSITION AND PATTERN FORMING PROCESS

CROSS-REFERENCE TO RELATED APPLICATION

This non-provisional application claims priority under 35 U.S.C. § 119(a) on Patent Application No. 2020-017215 filed in Japan on Feb. 4, 2020, the entire contents of which are hereby incorporated by reference.

TECHNICAL FIELD

This invention relates to a positive resist composition and a pattern forming process.

BACKGROUND ART

As integration density and operating speed of LSIs become higher, the effort to make the pattern rule finer is in rapid progress. In particular, the enlargement of the flash memory market and the increase in storage capacity drive forward the miniaturization technology. As the advanced miniaturization technology, manufacturing of microelectronic devices at the 10-nm node by the ArF immersion lithography has been implemented in a mass scale. As the candidates for 7 nm node devices and 5-nm node devices in the next generation, extreme ultraviolet (EUV) lithography with a wavelength of 13.5 m, double exposure (double patterning lithography) of ArF lithography, and the like have been studied.

In order to improve the accuracy of the line width, an electron beam (EB) exposure apparatus have been used as an exposure apparatus for mask production in place of an exposure apparatus in which laser light is used. The increase in the EB accelerating voltage with an electron gun allows further miniaturization. Therefore, the mainstream voltage is 10 kV to 30 kV, and recently, 50 kV. Furthermore, 100 kV of voltage is under consideration.

The increase in the accelerating voltage has caused a problem of reduction in the sensitivity of the resist film. The increase in the accelerating voltage reduces the influence of forward scattering in the resist film. Therefore, the contrast of the EB lithography energy is enhanced to improve the resolution and the dimensional controllability, but the sensitivity of the resist film is reduced because electrons freely pass through the resist film. In EB lithography, the exposure is performed with a single direct stroke of the EB. Therefore, the reduction in the sensitivity of the resist film leads to reduction in productivity, and the fact is not preferable. In order to meet demand for high sensitivity, chemically amplified resist compositions have been studied.

As the miniaturization is progressed, there has been a problem of image blurring due to acid diffusion. It has been proposed that in order to ensure the resolution with a fine pattern having a dimensional size of 45 nm or more, not only the previously proposed improvement of dissolution contrast but also the control of acid diffusion is important (Non-Patent Document 1). However, in chemically amplified resist compositions, the sensitivity and the contrast are increased by acid diffusion, therefore, if the acid diffusion is minimized by lowering the post-exposure bake (PEB) temperature or shortening the PEB time, the sensitivity and the contrast are significantly reduced.

The tradeoff relation is shown between the sensitivity, the resolution, and edge roughness in a triangle. The improvement of resolution needs the suppression of acid diffusion, but if the acid diffusion distance is reduced, the sensitivity is reduced.

It is effective to add an acid generator that generates a bulky acid to suppress acid diffusion. Therefore, it has been proposed to produce a polymer comprising recurring units derived from an onium salt having a polymerizable unsaturated bond. At this time, the polymer also functions as an acid generator (polymer-bound acid generator). Patent Document 1 discloses a sulfonium salt and an iodonium salt that have a polymerizable unsaturated bond that generates a specific sulfonic acid. Patent Document 2 discloses a sulfonium salt having a sulfonic acid directly attached to the main chain.

For suppressing acid diffusion, Patent Documents 3 and 4 discloses a resist composition comprising a polymer comprising recurring units having an amino group. Polymeric amines are characterized by a high acid diffusion suppressing effect. Patent Document 5 discloses a resist composition in which a polymer comprising recurring units that function as an acid generator and comprising recurring units having an amino group is used as a base polymer. This is a single component resist composition having the function as an acid generator and the function as a quencher in one polymer, and the influence of acid diffusion can be minimized. However, in this case, if the acid diffusion distance is too small, a problem is caused that the dissolution contrast and the sensitivity are reduced.

CITATION LIST

Patent Document 1: JP-A 2006-045311
Patent Document 2: JP-A 2006-178317
Patent Document 3: JP-A 2008-133312
Patent Document 4: JP-A 2009-181062
Patent Document 5: JP-A 2011-039266
Non-Patent Document 1: SPIE Vol. 6520 65203L-1 (2007)

SUMMARY OF THE INVENTION

An object of the present invention is to provide a positive resist composition which exhibits a higher sensitivity and resolution than conventional positive resist compositions, is reduced in edge roughness (LER, LWR) and size variation, and forms a pattern of good profile after exposure and development, and a pattern forming process using the resist composition. Making extensive investigations in search for a positive resist composition capable of meeting the current requirements including high resolution, reduced edge roughness and small size variation, the inventor has found the following.

To meet the requirements, the acid diffusion distance should be minimized. There arises the problem that the resolution of a two-dimensional pattern such as hole pattern is reduced by a lowering of sensitivity and a drop of dissolution contrast. Unexpectedly, better results are obtained when a polymer comprising recurring units having a carboxy group whose hydrogen is substituted by a pyridine ring-containing tertiary hydrocarbyl group is used as a base polymer. This improves the dissolution contrast and at the same time, the acid diffusion distance is minimized. Better results are thus obtainable using the polymer as a base polymer in a chemically amplified positive resist composition.

Further, for improving the dissolution contrast, recurring units having a carboxyl or phenolic hydroxyl group whose hydrogen is substituted by an acid labile group are incorporated into the base polymer. There is obtained a positive resist composition having a high sensitivity, a significantly increased contrast of alkali dissolution rate before and after exposure, a high acid diffusion suppressing effect, a high resolution, a good pattern profile after exposure, reduced edge roughness, and small size variation. The composition is thus suitable as a micropatterning material for the manufacture of VLSIs and photomasks.

Therefore, the invention provides a positive resist composition and a pattern forming process described below.

1. A positive resist composition comprising a base polymer comprising recurring units having a carboxyl group whose hydrogen is substituted by a pyridine ring-containing tertiary hydrocarbyl group.

2. The positive resist composition of the item 1, wherein the recurring units have the formula (a):

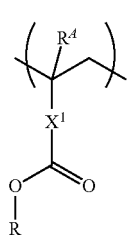

(a)

wherein $R^A$ is hydrogen or a methyl group, $X^1$ is a single bond, a phenylene group, a naphthylene group, or a $C_1$-$C_{12}$ linking group containing at least one selected from an ester bond, an ether bond, and a lactone ring, R is a group having the formula (a1):

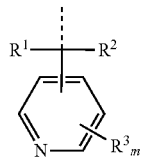

(a1)

wherein $R^1$ and $R^2$ are each independently a $C_1$-$C_6$ aliphatic hydrocarbyl group which may contain a heteroatom. $R^1$ and $R^2$ may bond together to form a ring with a carbon atom to which $R^1$ and $R^2$ are attached, $R^3$ is hydrogen or a $C_1$-$C_6$ alkyl group, m is an integer of 1 to 4, and a broken line designates a valence bond.

3. The positive resist composition of the item 1 or 2, further comprising recurring units of at least one type selected from recurring units having a carboxyl group whose hydrogen is substituted by an acid labile group other than a pyridine ring-containing tertiary hydrocarbyl group, or recurring units having a phenolic hydroxyl group whose hydrogen is substituted by an acid labile group.

4. The positive resist composition of the item 3, wherein the recurring units having a carboxyl group whose hydrogen is substituted by an acid labile group other than a pyridine ring-containing tertiary hydrocarbyl group, and the recurring units having a phenolic hydroxyl group whose hydrogen is substituted by an acid labile group are recurring units having the formula (b1) and recurring units having the formula (b2), respectively:

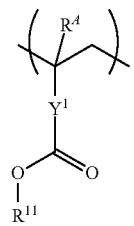

(b1)

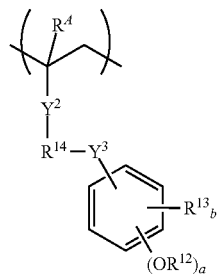

(b2)

wherein $R^A$ is each independently hydrogen or a methyl group, $Y^1$ is a single bond, a phenylene group, a naphthylene group, or a $C_1$-$C_{12}$ linking group containing at least one selected from an ester bond, an ether bond, and a lactone ring, $Y^2$ is a single bond, an ester bond, or an amide bond, $Y^3$ is a single bond, an ether bond, or an ester bond, $R^{11}$ is an acid labile group other than a pyridine ring-containing tertiary hydrocarbyl group, $R^{12}$ is an acid labile group, $R^{13}$ is fluorine, a trifluoromethyl group, a cyano group, or a $C_1$-$C_6$ saturated hydrocarbyl group, $R^{14}$ is a single bond or a $C_1$-$C_6$ alkanediyl group in which some carbon may be replaced by an ether bond or an ester bond, a is 1 or 2, b is an integer of 0 to 4, and $1 \leq a+b \leq 5$.

5. The positive resist composition of any one of the items 1 to 4, wherein the base polymer further comprises recurring units having an adhesive group selected from the group consisting of a hydroxyl group, a carboxyl group, a lactone ring, a carbonate group, a thiocarbonate group, a carbonyl group, a cyclic acetal group, an ether bond, an ester bond, a sulfonic acid ester bond, a cyano group, an amide bond, —O—C(=O)—S—, and —O—C(=)—NH—.

6. The positive resist composition of any one of the items 1 to 5, wherein the base polymer further comprises recurring units having any one of the formulae (d1) to (d3):

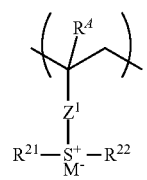

(d1)

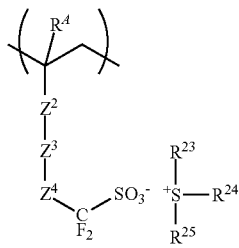 (d2)

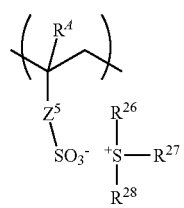 (d3)

wherein $R^4$ is each independently hydrogen or a methyl group, $Z^1$ is a single bond, a $C_1$-$C_6$ aliphatic hydrocarbylene group, a phenylene group, a naphthylene group, a $C_7$-$C_{18}$ group obtained from combination thereof —O—$Z^{11}$—, —C(=O)—O—$Z^{11}$—, or —C(=O)—NH—$Z^{11}$—. $Z^{11}$ is a $C_1$-$C_6$ aliphatic hydrocarbylene group, a phenylene group, a naphthylene group, or a $C_7$-$C_{18}$ combination thereof, which may contain a carbonyl group, an ester bond, an ether bond, or a hydroxyl group, $Z^2$ is a single bond or an ester bond, $Z^3$ is a single bond, —$Z^{31}$—C(=O)—O—, —$Z^{31}$—O—, or —$Z^{31}$—O—C(=O)—, $Z^{31}$ is a $C_1$-$C_{12}$ hydrocarbylene group, a phenylene group, or a C-Cis group obtained from combination thereof, which may contain a carbonyl group, an ester bond, an ether bond, bromine, or iodine, $Z^4$ is a methylene group, a 2,2,2-trifluoro-1,1-ethanediyl group, or a carbonyl group, $Z^5$ is a single bond, a methylene group, an ethylene group, a phenylene group, a fluorinated phenylene group, a trifluoromethyl-substituted phenylene group, —O—$Z^1$—, —C(=O)—O—$Z^{51}$—, or —C(=O)—NH—$Z^{51}$—, $Z^{51}$ is a $C_1$-$C_{16}$ aliphatic hydrocarbylene group, a phenylene group, a fluorinated phenylene group, or a trifluoromethyl-substituted phenylene group, which may contain a carbonyl group, an ester bond, an ether bond, a halogen, or a hydroxyl group, $R^{21}$ to $R^{28}$ are each independently fluorine, chlorine, bromine, iodine, or a $C_1$-$C_{20}$ hydrocarbyl group which may contain a heteroatom, $R^{23}$ and $R^{24}$, or $R^{26}$ and $R^{27}$ may bond together to form a ring with a sulfur atom to which $R^{23}$ and $R^{24}$, or $R^{26}$ and $R^{27}$ are attached, and $M^-$ is a non-nucleophilic counter ion.

7. The positive resist composition of any one of the items 1 to 6, further comprising an acid generator.

8. The positive resist composition of any one of the items 1 to 7, further comprising an organic solvent.

9. The positive resist composition of any one of the items 1 to 8, further comprising a quencher.

10. The positive resist composition of any one of the items 1 to 9, further comprising a surfactant.

11. A pattern forming process comprising the steps of applying the positive resist composition of any one of the items 1 to 10 onto a substrate to form a resist film thereon, exposing the resist film to high-energy radiation, and developing the exposed resist film in a developer.

12. The pattern forming process of the item 11, wherein the high-energy radiation is i-line, KrF excimer laser, ArF excimer laser, electron beam, or extreme ultraviolet of wavelength 3 to 15 nm.

13. A polymerizable monomer having the formula (Ma):

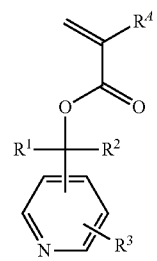 (Ma)

wherein $R^4$, $R^1$, $R^2$, and $R^3$ are as defined above.

Advantageous Effects of the Invention

The positive resist composition can enhance the decomposition efficiency of an acid generator, has a remarkable acid diffusion-suppressing effect, a high sensitivity, and a high resolution, and forms a pattern of good profile with improved edge roughness and size variation after exposure and development. By virtue of these properties, the resist composition is fully useful in commercial application and best suited as a micropatterning material for photomasks by EB lithography or for VLSIs by EB or EUV lithography. The positive resist composition may be used not only in the lithography for forming semiconductor circuits, but also in the formation of mask circuit patterns, micromachines, and thin-film magnetic head circuits.

DESCRIPTION OF THE PREFERRED EMBODIMENTS

As used herein, the singular forms "a," "an" and "the" include plural referents unless the context clearly dictates otherwise. The notation ($C_n$-$C_m$) means a group containing from n to m carbon atoms per group.

Positive Resist Composition

One embodiment of the invention is a positive resist composition comprising a base polymer comprising recurring units having a carboxyl group whose hydrogen is substituted by a pyridine ring-containing tertiary hydrocarbyl group (hereinafter, also referred to as recurring units (a)). Because a pyridine ring-containing tertiary hydrocarbon group has a high acid diffusion suppressing effect, the use of the base polymer comprising the recurring units (a) allows a resist film having a high dissolution contrast to be obtained. Herein the tertiary hydrocarbyl group refers to a group obtained from a hydrocarbon by eliminating the hydrogen atom on the tertiary carbon atom.

Preferably, the recurring units (a) have the formula (a).

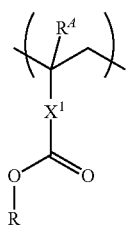

(a)

In the formula (a), $R^A$ is hydrogen or a methyl group. $X^1$ is a single bond, a phenylene group, a naphthylene group, or a $C_1$-$C_{12}$ linking group containing at least one selected from an ester bond, an ether bond, and a lactone ring.

In the formula (a), R is a pyridine ring-containing tertiary hydrocarbyl group having the formula (a1).

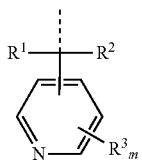

(a1)

Herein $R^1$ and $R^2$ are each independently a $C_1$-$C_6$ aliphatic hydrocarbyl group which may contain a heteroatom. $R^1$ and $R^2$ may bond together to form a ring with a carbon atom to which $R^1$ and $R^2$ are attached. $R^3$ is hydrogen or a $C_1$-$C_6$ alkyl group. m is an integer of 1 to 4. The broken line designates a valence bond.

The $C_1$-$C_6$ aliphatic hydrocarbyl group represented by $R^1$ and $R^2$ may be saturated or unsaturated, and may be straight, branched, or cyclic. Specific examples of the $C_1$-$C_6$ aliphatic hydrocarbyl group represented by $R^1$ and $R^2$ include alkyl groups such as methyl, ethyl, propyl, isopropyl, n-butyl, isobutyl, sec-butyl, tert-butyl, n-pentyl, neopentyl, and n-hexyl; cycloalkyl groups such as cyclopropyl, cyclobutyl, cyclopentyl, and cyclohexyl; alkenyl groups such as vinyl, 1-propenyl, 2-propenyl, butenyl, and hexenyl; cycloalkenyl groups such as cyclohexenyl; alkynyl groups such as ethynyl and butynyl; and groups obtained from combination thereof. Preferably, $R^1$ and $R^2$ are each methyl, ethyl, isopropyl, tert-butyl, cyclopentyl, cyclohexyl, vinyl, or ethynyl.

Examples of the $C_1$-$C_6$ alkyl group represented by $R^3$ include methyl, ethyl, propyl, isopropyl, n-butyl, isobutyl, sec-butyl, tert-butyl, n-pentyl, and tert-pentyl.

Examples of the group having the formula (a1) are shown below, but not limited thereto. Herein the broken line designates a valence bond.

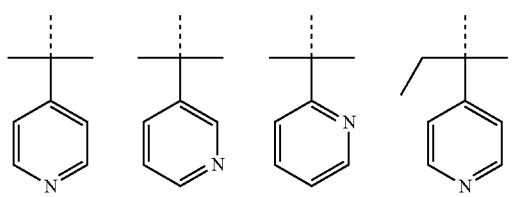

-continued

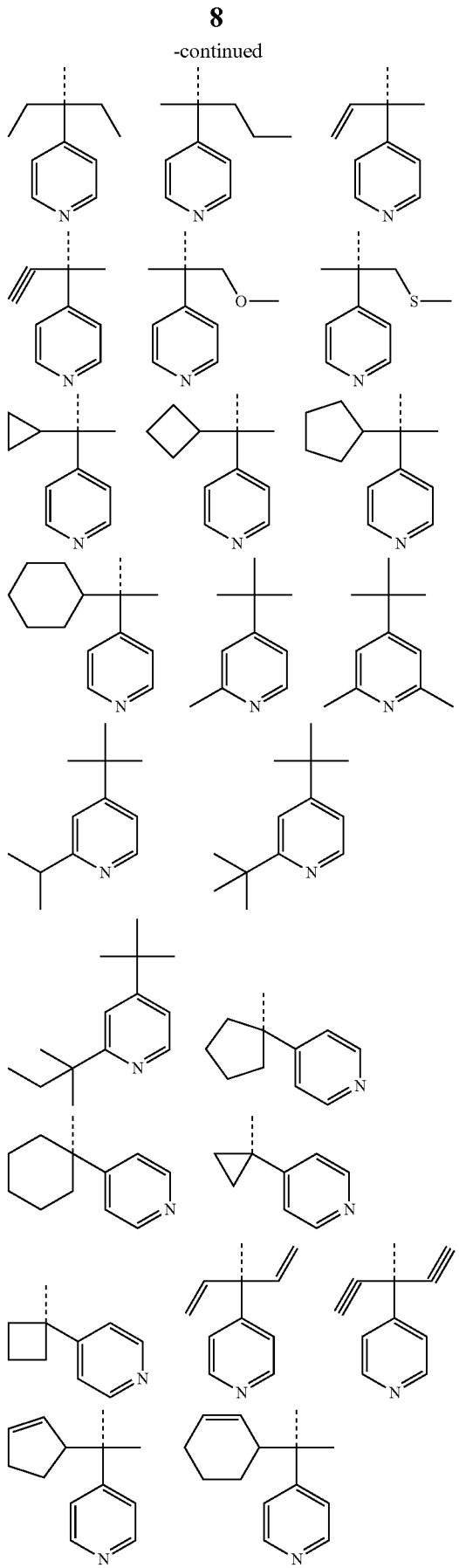

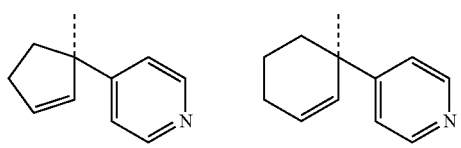
Examples of the monomer from which the recurring units (a) are derived are shown below, but not limited thereto. Herein $R^A$ and R are as defined above.
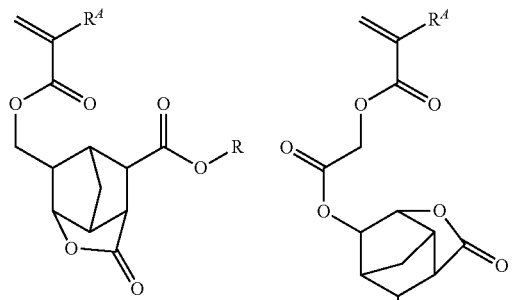
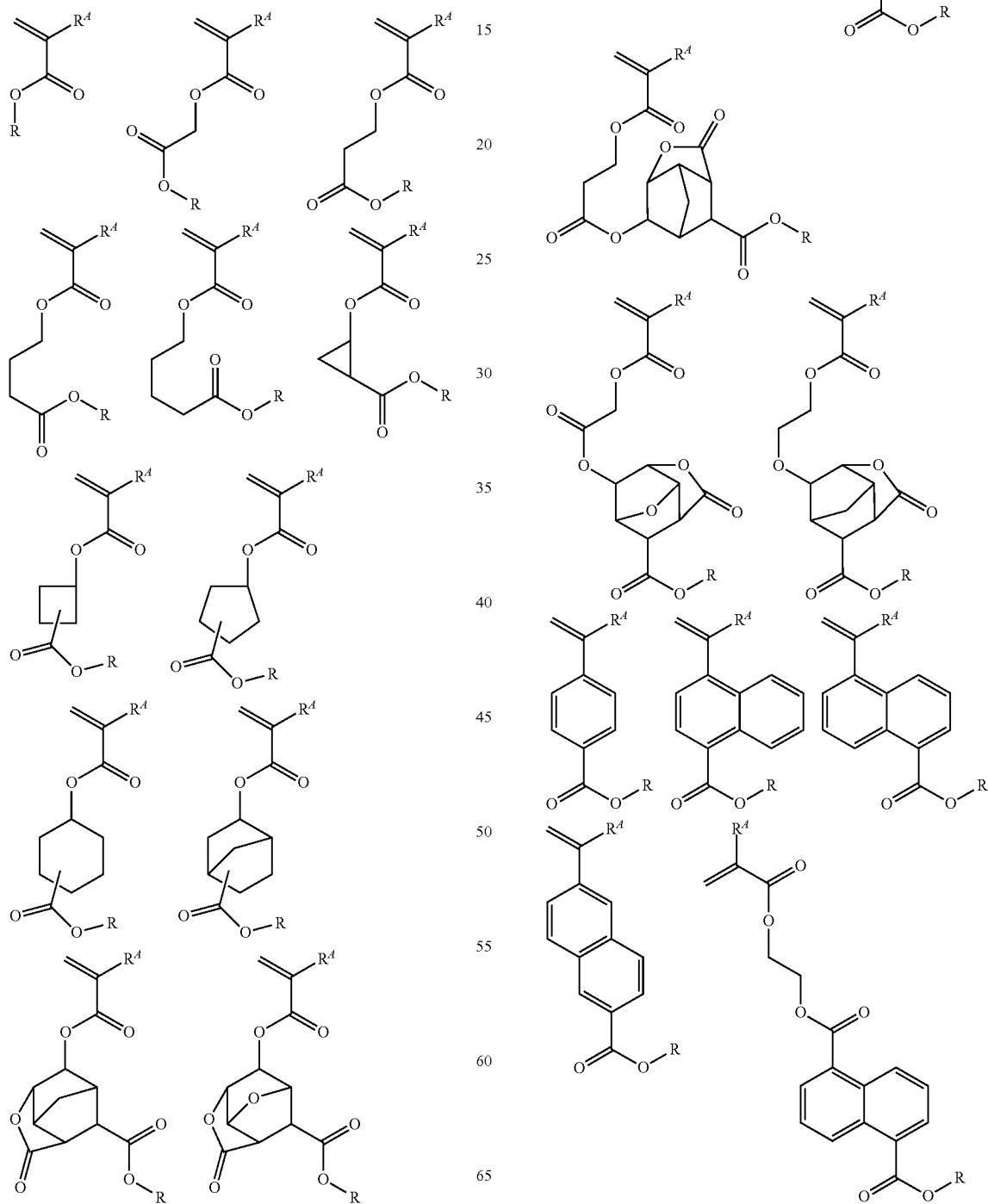

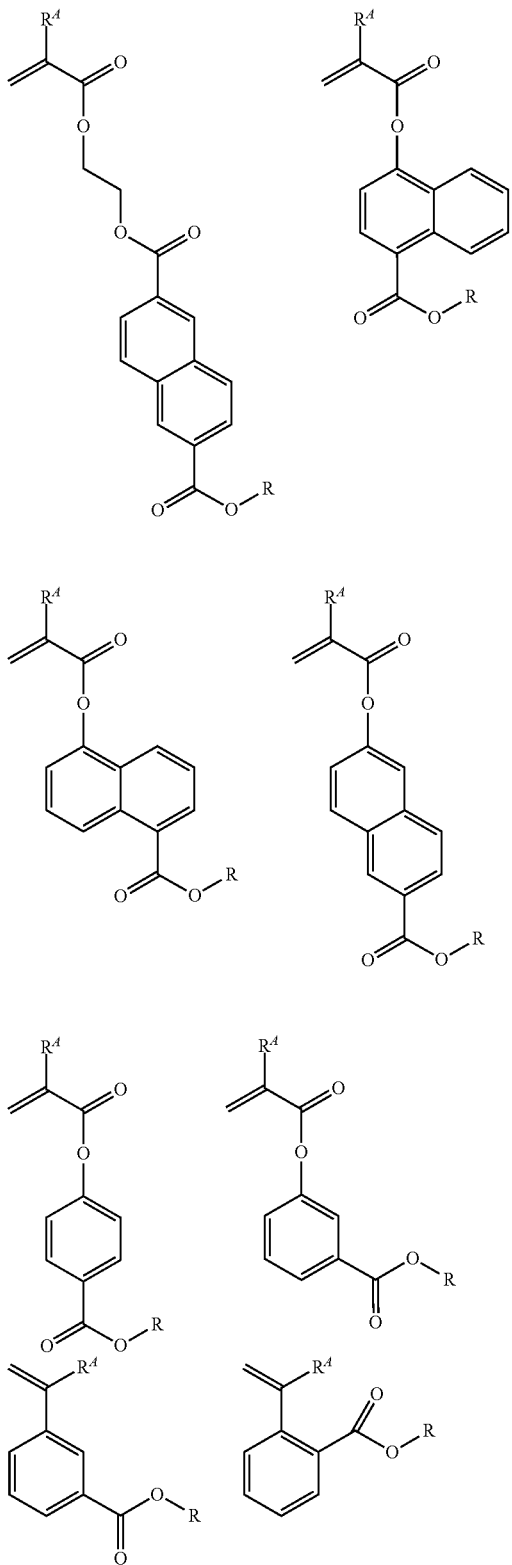

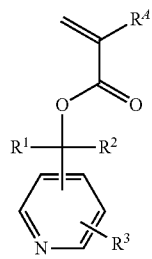
(Ma)

Herein $R^A$, $R^1$, $R^2$ and $R^3$ are as defined above.

Because the recurring units (a) have nitrogen, the recurring units (a) function as a quencher. That is, the base polymer is a quencher-bound polymer. The quencher-bound polymer is characterized by an extremely high acid diffusion suppressing effect and an excellent resolution. Further, because the recurring units (a) have a tertiary ester structure, the recurring units (a) are also an acid labile group unit. Although an ordinary acid labile group unit is a mechanism for polarity conversion by an acid, the recurring units (a) have a function of suppressing acid diffusion as well as of polarity conversion. As a result, while the acid diffusion is suppressed the dissolution contrast can be increased.

In order to further increase the dissolution contrast, the base polymer may comprise recurring units having a carboxyl group whose hydrogen is substituted by an acid labile group other than a pyridine ring-containing tertiary hydrocarbyl group (hereinafter, also referred to as recurring units (b1)), and/or recurring units having a phenolic hydroxyl group whose hydrogen is substituted by an acid labile group (hereinafter, also referred to as recurring units (b2)).

The preferred recurring units (b1) and (b2) are recurring units having the formulae (b1) and (b2), respectively.

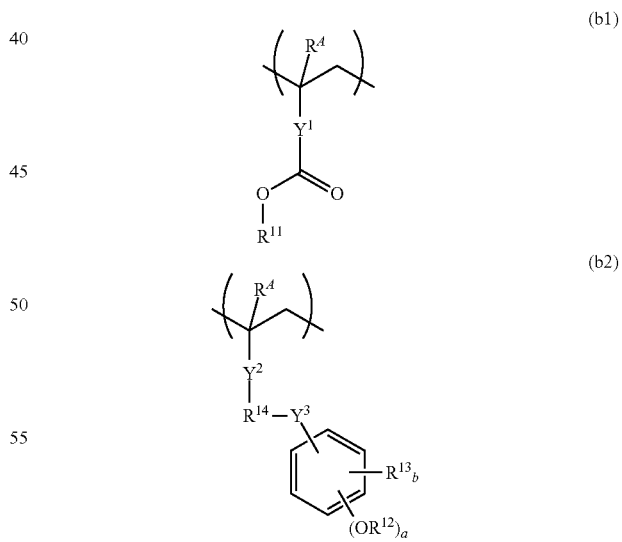

The monomer from which the recurring units (a) are derived is preferably a polymerizable monomer having the formula (Ma).

In the formulae (b1) and (b2), $R^A$ is each independently hydrogen or a methyl group. $Y^1$ is a single bond, a phenylene group, a naphthylene group, or a $C_1$-$C_{12}$ linking group containing at least one selected from an ester bond, an ether bond, and a lactone ring. $Y^2$ is a single bond, an ester bond, or an amide bond. $Y^3$ is a single bond, an ether bond, or an ester bond. $R^{11}$ is an acid labile group other than a pyridine ring-containing tertiary hydrocarbyl group. R$^{12}$ is an acid labile group. R$^{13}$ is fluorine, a trifluoromethyl group, a cyano group, or a C$_1$-C$_6$ saturated hydrocarbyl group. R$^{14}$ is a single bond or a C$_1$-C$_6$ alkanediyl group in which some carbon may be replaced by an ether bond or an ester bond, a is 1 or 2. b is an integer of 0 to 4. And 1≤a+b≤5.

Examples of the monomer from which the recurring units (b1) are derived are shown below, but not limited thereto. R$^A$ and R$^1$ are as defined above.

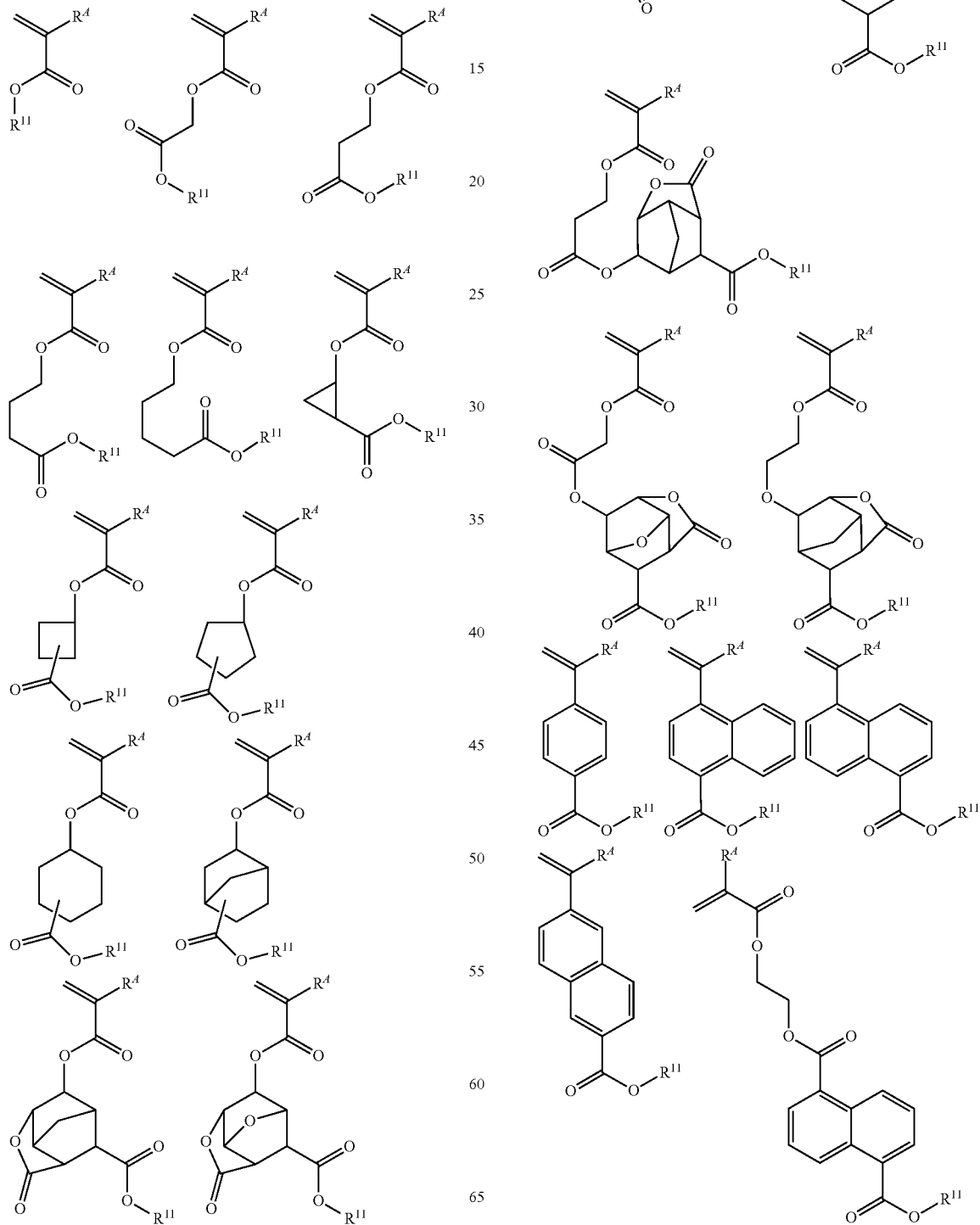
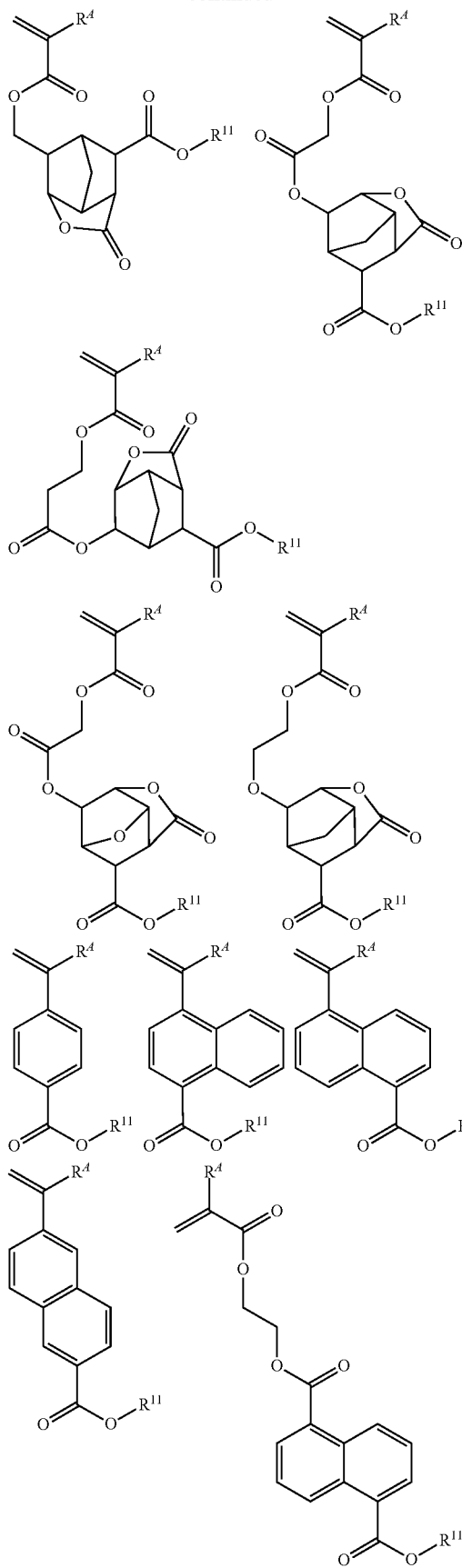

-continued

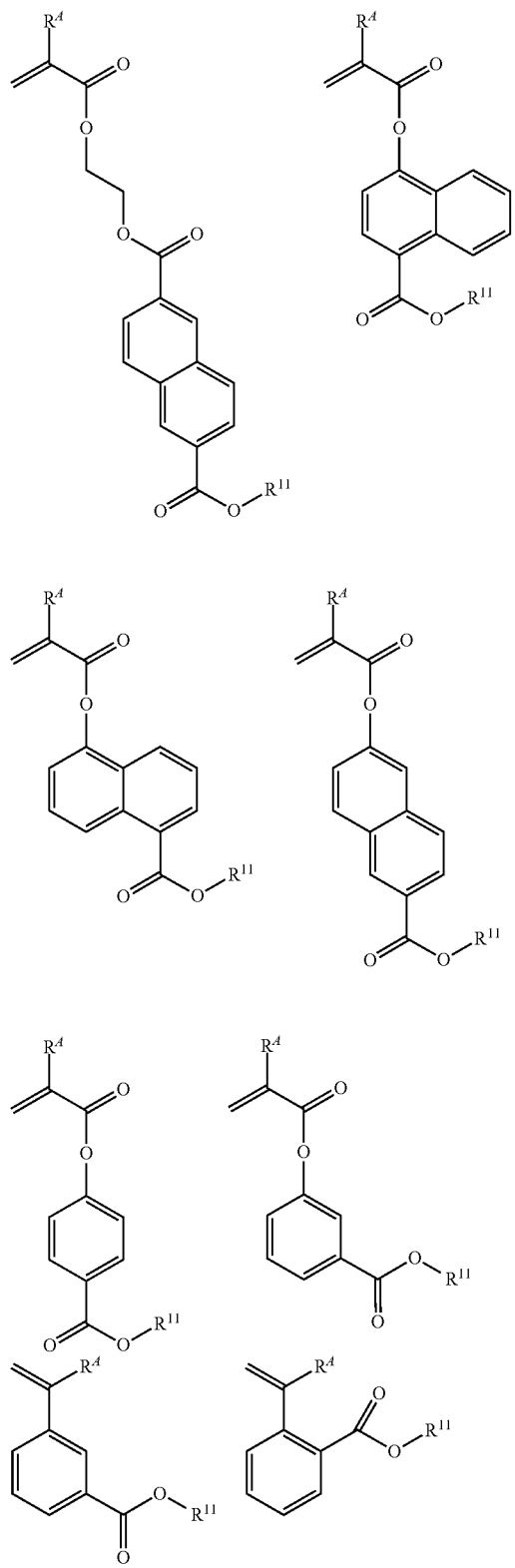
Examples of the monomer from which the recurring units (b2) are derived are shown below, but not limited thereto. $R^A$ and $R^{12}$ are as defined above.
The acid labile groups represented by $R^{11}$ and $R^{12}$ may be selected from a variety of such groups, for example, groups having the formulae (AL-1) to (AL-3).

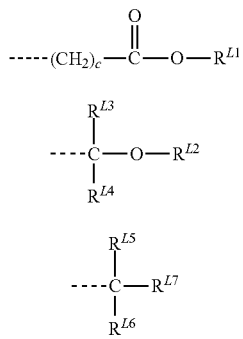
(AL-1)

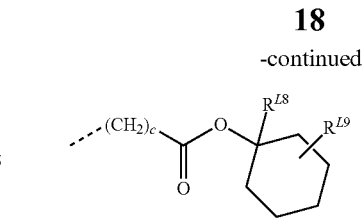
(AL-2)

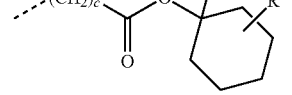
(AL-3)

Herein the broken line designates a valence bond.

In the formula (AL-1), e is an integer of 0 to 6. $R^{L1}$ is a $C_4$-$C_{20}$, preferably $C_4$-$C_{15}$ tertiary hydrocarbyl group, a trihydrocarbylsilyl group in which each hydrocarbyl group is a $C_1$-$C_6$ saturated hydrocarbyl group, a $C_4$-$C_{20}$ saturated hydrocarbyl group containing a carbonyl group, an ether bond, or an ester bond, or a group having the formula (AL-3).

The tertiary hydrocarbyl group represented by $R^{L1}$ may be saturated or unsaturated, and branched or cyclic. Examples of the tertiary hydrocarbyl group represented by $R^{L1}$ include tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Examples of the trialkylsilyl group include trimethylsily, triethylsilyl, and dimethyl-tert-butylsilyl. Examples of the saturated hydrocarbyl group containing a carbonyl group, an ether bond, or an ester bond may be straight, branched, or cyclic, preferably cyclic, and examples thereof include 3-oxocyclohexyl, 4-methyl-2-oxooxan-4-yl, 5-methyl-2-oxooxolan-5-yl, 2-tetrahydropyranyl, and 2-tetrahydrofuranyl.

Examples of the acid labile group having the formula (AL-1) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbouylmethyl, 2-tetrahydropyranyloxycarbonylmethyl, and 2-tetrahydrofuranyloxycarbonylmethyl.

Other examples of the acid labile group having the formula (AL-1) include groups having the formulae (AL-1)-1 to (AL-1)-10.

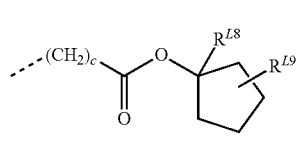
(AL-1)-1

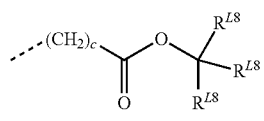
(AL-1)-2

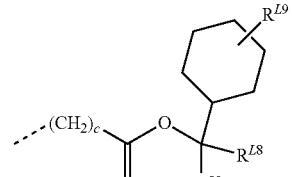
(AL-1)-3

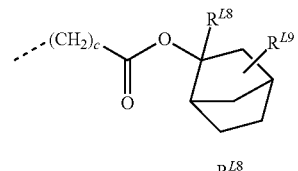
(AL-1)-4

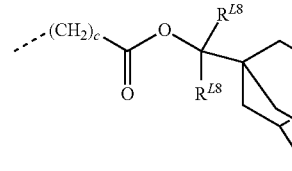
(AL-1)-5

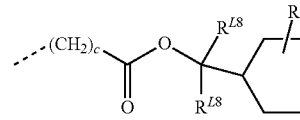
(AL-1)-6

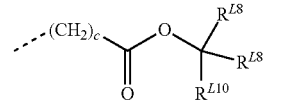
(AL-1)-7

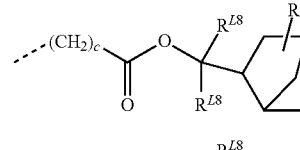
(AL-1)-8

(AL-1)-9

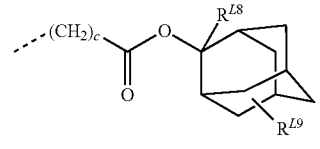
(AL-1)-10

Herein the broken line designates a valence bond.

In the formulae (AL-1)-1 to (AL-1)-10, cis as defined above. $R^{L8}$ is each independently a $C_1$-$C_{10}$ saturated hydrocarbyl group or a $C_6$-$C_{20}$ aryl group. $R^{L9}$ is hydrogen or a $C_1$-$C_{10}$ saturated hydrocarbyl group. $R^{L0}$ is a $C_2$-$C_{10}$ saturated hydrocarbyl group or a $C_6$-$C_{20}$ aryl group. The saturated hydrocarbyl group may be straight, branched, or cyclic.

In the formula (AL-2), $R^{L2}$ and $R^{L3}$ are each independently hydrogen or a $C_1$-$C_{18}$, preferably $C_1$-$C_{10}$ saturated hydrocarbyl group. The saturated hydrocarbyl group may be straight, branched, or cyclic and examples thereof include methyl, ethyl, propyl, isopropyl, n-butyl, sec-butyl, tert-butyl, cyclopentyl, cyclohexyl, 2-ethylhexyl, and n-octyl.

In the formula (AL-2), $R^{L4}$ is a $C_1$-$C_{18}$ preferably $C_1$-$C_{10}$ hydrocarbyl group which may contain a heteroatom. The hydrocarbyl group may be saturated or unsaturated, and may be straight, branched, or cyclic. Typical are $C_1$-$C_{18}$ saturated hydrocarbyl groups, in which some hydrogen may be substituted by hydroxyl, alkoxy, oxo, amino, or alkylamino. Examples of the substituted saturated hydrocarbyl group are shown below.

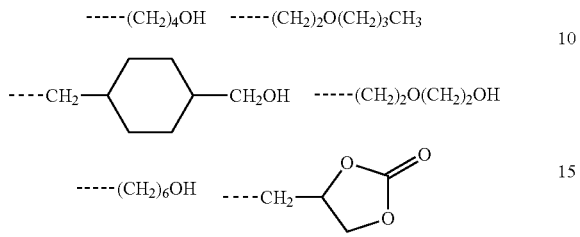

Herein the broken line designates a valence bond.

A pair of $R^{L2}$ and $R^{L3}$, $R^{L2}$ and $R^{L4}$, or $R^{L3}$ and $R^{L4}$ may bond together to form a ring with the carbon atom or carbon and oxygen atoms to which they are attached $R^{L2}$ and $R^{L3}$, $R^{L2}$ and $R^{L4}$, or $R^{L3}$ and $R^{L4}$ are each independently a $C_1$-$C_{18}$, preferably $C_1$-$C_{10}$ alkanediyl group when they form a ring. The ring thus formed is preferably of 3 to 10, more preferably 4 to 10 carbon atoms.

Of the acid labile groups having the formula (AL-2), suitable straight or branched groups include those having the formulae (AL-2)-1 to (AL-2)-69, but are not limited thereto. Herein the broken line designates a valence bond.

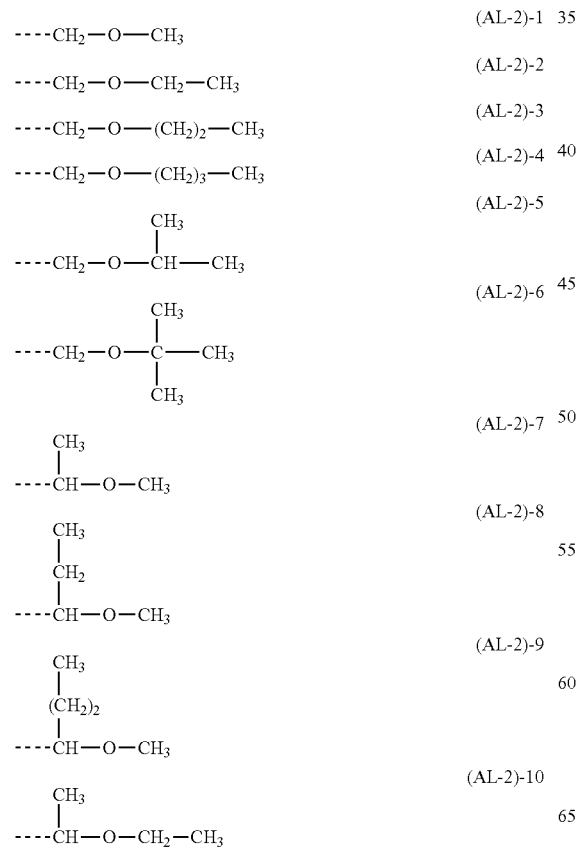

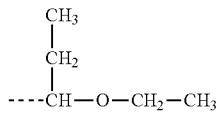
(AL-2)-11

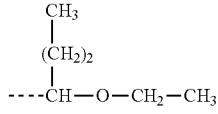
(AL-2)-12

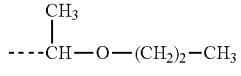
(AL-2)-13

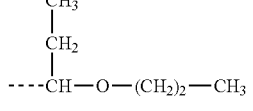
(AL-2)-14

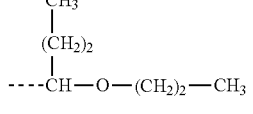
(AL-2)-15

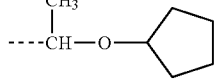
(AL-2)-16

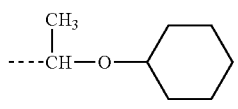
(AL-2)-17

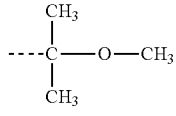
(AL-2)-18

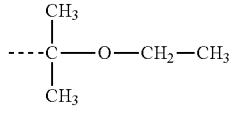
(AL-2)-19

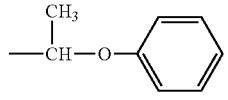
(AL-2)-20

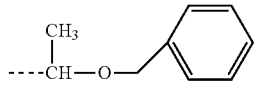
(AL-2)-21

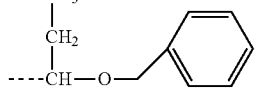
(AL-2)-22

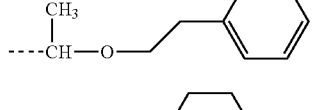
(AL-2)-23

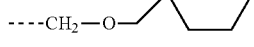
(AL-2)-24

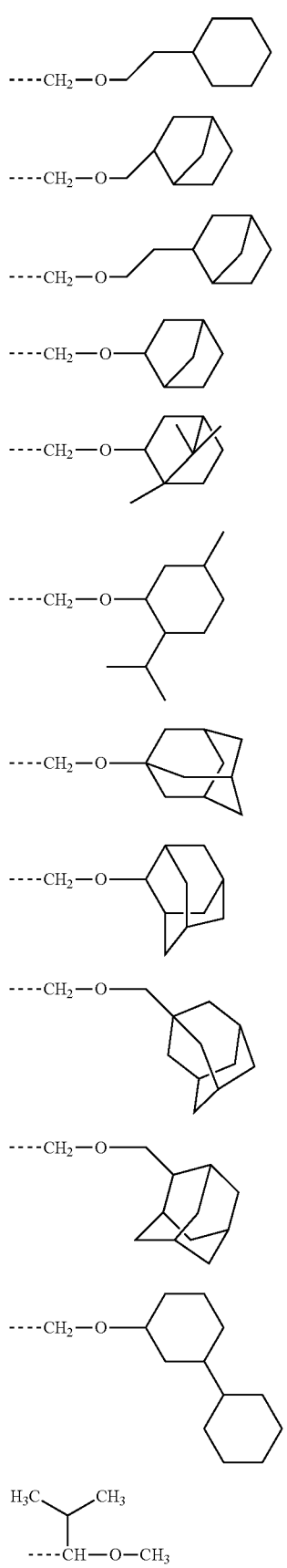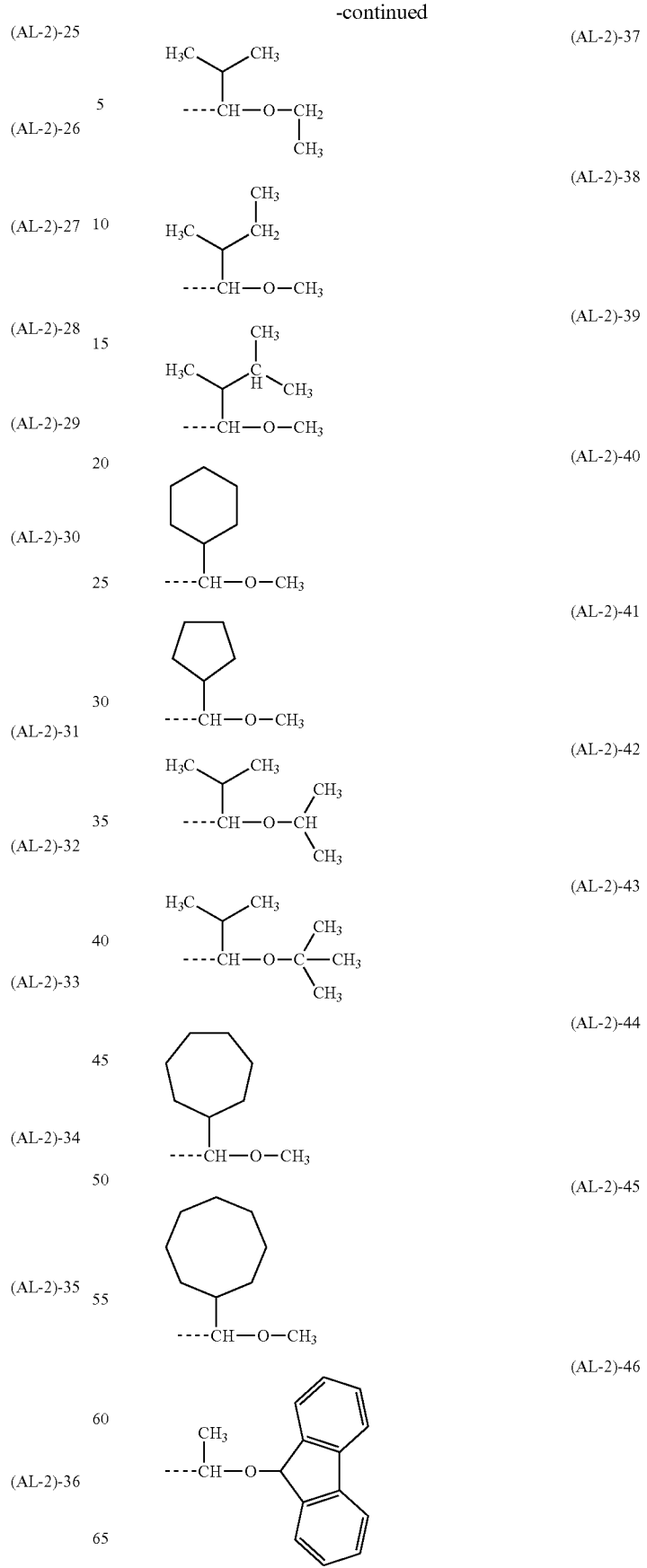

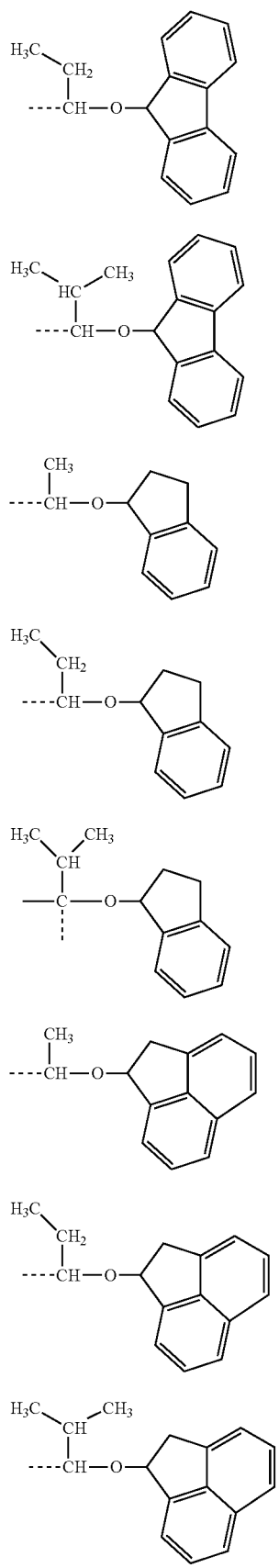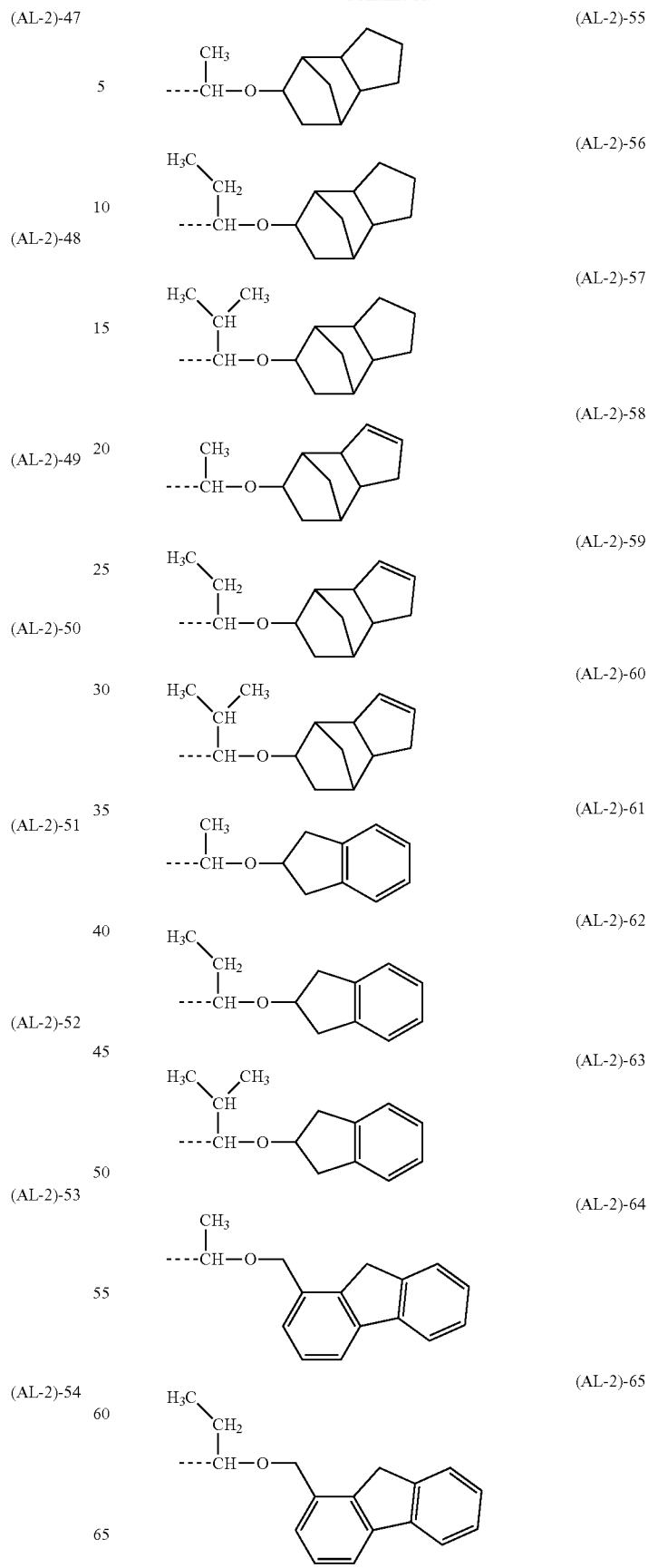

(AL-2)-66
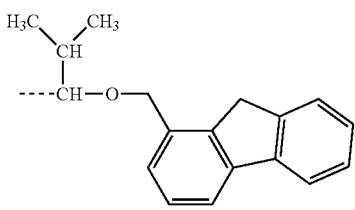

(AL-2)-67
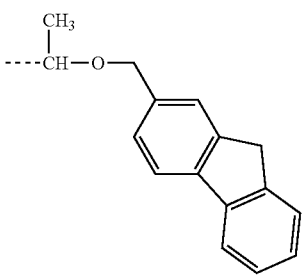

(AL-2)-68
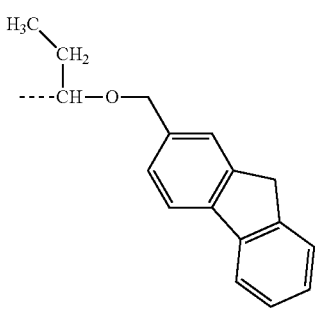

(AL-2)-69
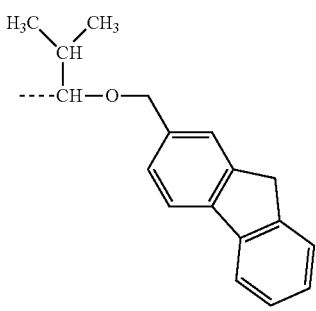

Of the acid labile groups having the formula (AL-2), suitable cyclic groups include tetrahydrofuran-2-yl, 2-methyltetrahydrofuran-2-yl, tetrahydropyran-2-yl, and 2-methyltetrahydropyran-2-yl.

Also included are acid labile groups having the following formulae (AL-2a) and (AL-2b). The base polymer may be crosslinked within the molecule or between molecules with these acid labile groups.

(AL-2a)
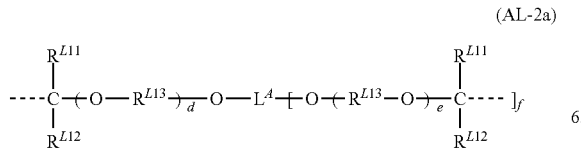

(AL-2b)
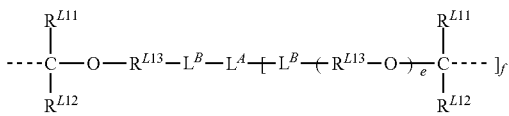

Herein the broken line designates a valence bond.

In the formula (AL-2a) or (AL-2b), $R^{L11}$ and $R^{L12}$ are each independently hydrogen or a $C_1$-$C_8$ saturated hydrocarbyl group. The saturated hydrocarbyl group may be straight, branched, or cyclic. Also, $R^{L11}$ and $R^{L12}$ may bond together to form a ring with the carbon atom to which they are attached, and in this case, $R^{L11}$ and $R^{L12}$ are each independently a $C_1$-$C_8$ alkanediyl group. $R^{L13}$ is each independently a $C_1$-$C_{10}$ saturated hydrocarbylene group. The saturated hydrocarbylene group may be straight, branched, or cyclic. d and e are each independently an integer of 0 to 10, preferably 0 to 5, and f is an integer of 1 to 7, preferably 1 to 3.

In the formula (AL-2a) or (AL-2b), $L^A$ is a (f+1)-valent $C_1$-$C_{50}$ aliphatic saturated hydrocarbon group, a (f+1)-valent $C_3$-$C_{50}$ alicyclic saturated hydrocarbon group, a (f+1)-valent $C_6$-$C_{50}$ aromatic hydrocarbon group, or a (f+1)-valent $C_3$-$C_{50}$ heterocyclic group. In these groups, some carbon may be replaced by a heteroatom-containing group, or some carbon-bonded hydrogen may be substituted by a hydroxyl, carboxyl, or acyl group, or fluorine. $L^A$ is preferably a $C_1$-$C_{20}$ saturated hydrocarbylene group, saturated hydrocarbon group (e.g., trivalent or tetravalent saturated hydrocarbon group), or $C_6$-$C_{30}$ arylene group. The saturated hydrocarbon group may be straight, branched, or cyclic. $L^B$ is —C(=O)—O—, —NH—C(=O)—O—, or —NH—C(=O)—NH—.

Examples of the crosslinking acetal groups having the formulae (AL-2a) and (AL-2b) include groups having the formulae (AL-2)-70 to (AL-2)-77.

(AL-2)-70
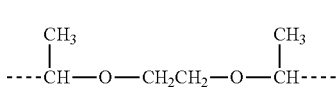

(AL-2)-71
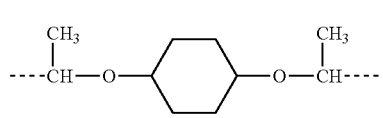

(AL-2)-72
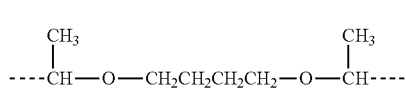

(AL-2)-73

(AL-2)-74
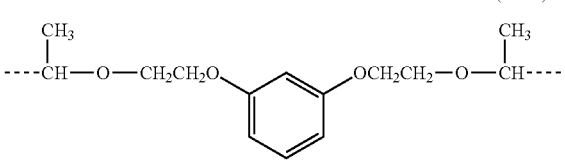

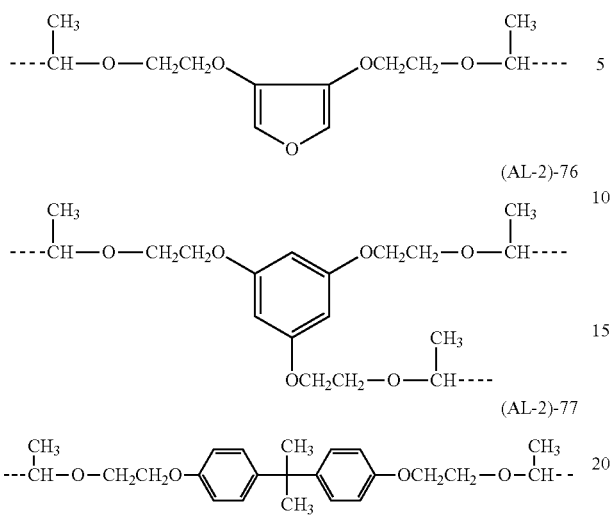

Herein the broken line designates a valence bond.

In the formula (AL-3), $R^{L5}$, $R^{L6}$, and $R^{L7}$ are each independently a $C_1$-$C_{20}$ hydrocarbyl group which may contain a heteroatom such as oxygen, sulfur, nitrogen, or fluorine. The hydrocarbyl group may be saturated or unsaturated, and may be straight, branched, or cyclic. Examples thereof include $C_1$-$C_{20}$ alkyl groups, $C_3$-$C_{20}$ cyclic saturated hydrocarbyl groups, $C_2$-$C_{20}$ alkenyl groups, $C_3$-$C_{20}$ cyclic unsaturated hydrocarbyl groups, and $C_6$-$C_{10}$ aryl groups. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Examples of the group having the formula (AL-3) include tert-butyl, 1,1-diethylpropyl, 1-ethylnorbornyl, 1-methylcyclopentyl, 1-isopropylcyclopentyl, 1-ethylcyclopentyl, 1-methylcyclohexyl, 2-(2-methyl)adamantyl, 2-(2-ethyl)adamantyl, and tert-pentyl.

Examples of the group having the formula (AL-3) also include groups having the formulae (AL-3)-1 to (AL-3)-19.

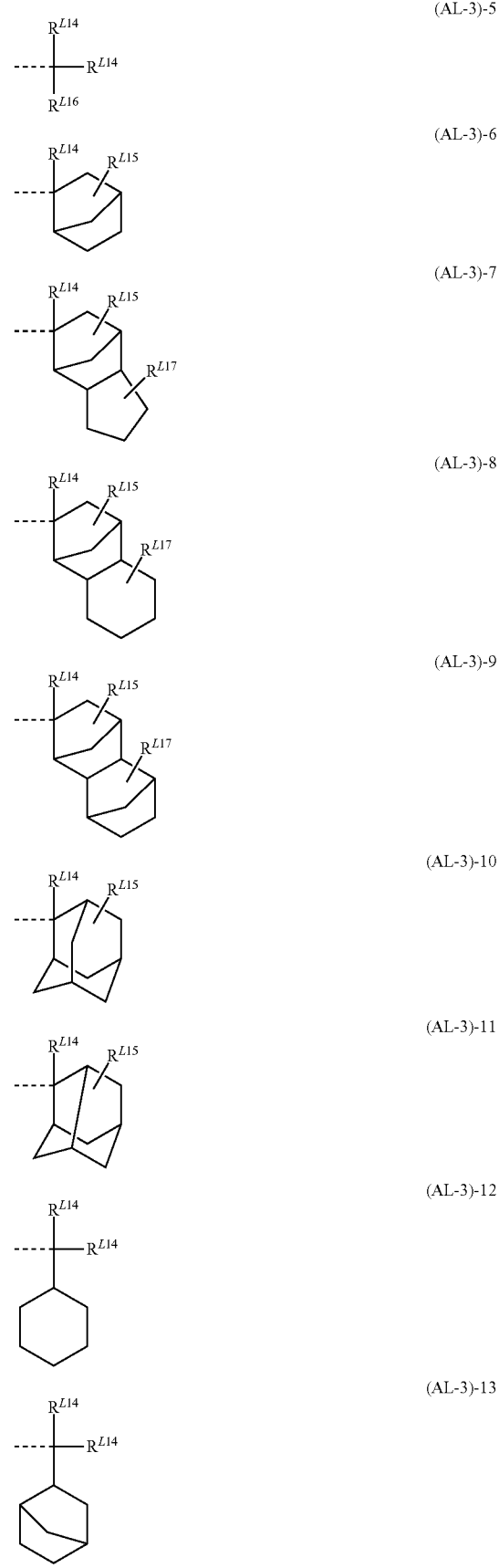

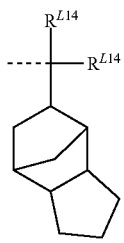
(AL-3)-14

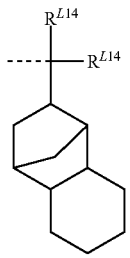
(AL-3)-15

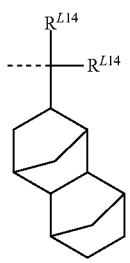
(AL-3)-16

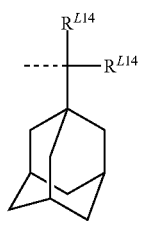
(AL-3)-17

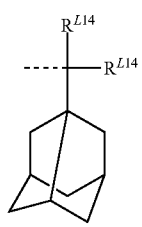
(AL-3)-18

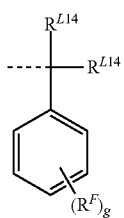
(AL-3)-19

Herein the broken line designates a valence bond.

In the formulae (AL-3)-1 to (AL-3)-19, $R^{L1}$ is each independently a $C_1$-$C_8$ saturated hydrocarbyl group or a $C_6$-$C_{20}$ aryl group. $R^{L15}$ and $R^{L17}$ are each independently hydrogen or a $C_1$-$C_{20}$ saturated hydrocarbyl group. $R^{L16}$ is a $C_6$-$C_{20}$ aryl group. The saturated hydrocarbyl group may be straight, branched, or cyclic. Typical of the aryl group is phenyl. $R^F$ is fluorine or a trifluoromethyl group, g is an integer of 1 to 5.

Other examples of the acid labile group include groups having the formulae (AL-3)-20 and (AL-3)-21. The base polymer may be crosslinked within the molecule or between molecules with these acid labile groups.

(AL-3)-20

(AL-3)-21

Herein the broken line designates a valence bond.

In the formulae (AL-3)-20 and (AL-3)-21, $R^{L14}$ is as defined above. $R^{L18}$ is a $C_1$-$C_{20}$ (h+1)-valent saturated hydrocarbylene group or $C_6$-$C_{20}$ (h+1)-valent arylene group, which may contain a heteroatom such as oxygen, sulfur, or nitrogen. The saturated hydrocarbylene group may be straight, branched, or cyclic, h is an integer of 1 to 3.

Examples of the monomer from which recurring units containing an acid labile group having the formula (AL-3) are derived include (meth)acrylates having an exo-form structure having the formula (AL-3)-22.

(AL-3)-22

In the formula (AL-3)-22, $R^A$ is as defined above. $R^{Lc1}$ is a $C_1$-$C_8$ saturated hydrocarbyl group or a $C_6$-$C_{20}$ aryl group which may be substituted. The saturated hydrocarbyl group may be straight, branched, or cyclic. $R^{Lc2}$ to $R^{Lc11}$ are each independently hydrogen or a $C_1$-$C_{15}$ hydrocarbyl group which may contain a heteroatom. Oxygen is a typical heteroatom. Suitable hydrocarbyl groups include $C_1$-$C_{15}$ alkyl groups and $C_6$-$C_{15}$ aryl groups. A pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$, taken together, may form a ring with the carbon atom to which they are attached, and each ring-forming participant is a $C_1$-$C_{15}$ hydrocarbylene group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

Examples of the monomer from which recurring units having the formula (AL-3)-22 are derived are described in JP-A 2000-327633. Illustrative non-limiting examples of suitable monomers are given below. Herein $R^A$ is as defined above.

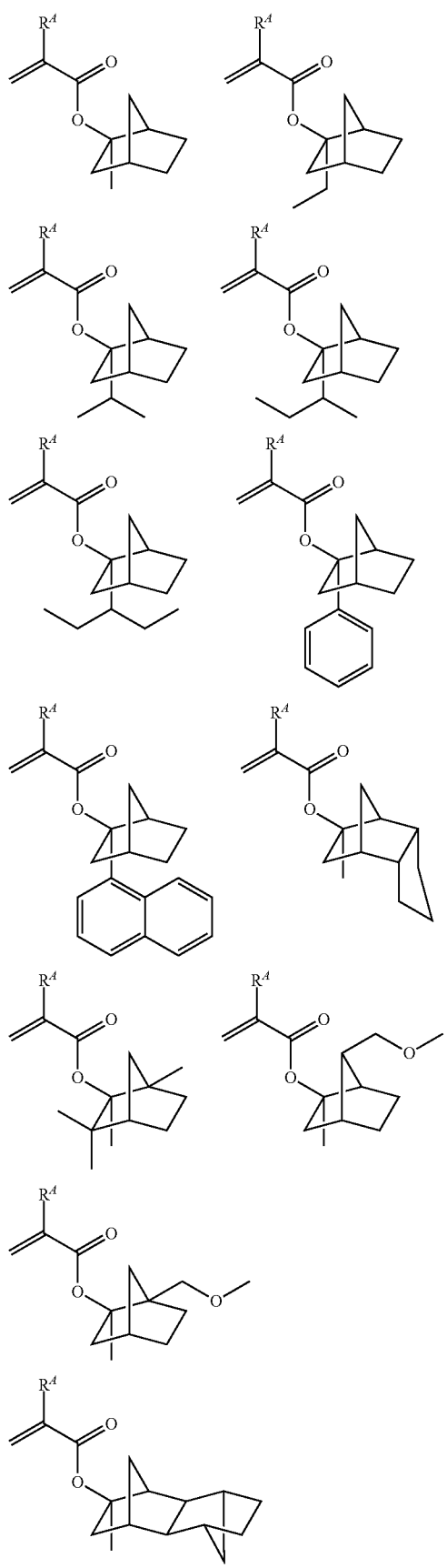
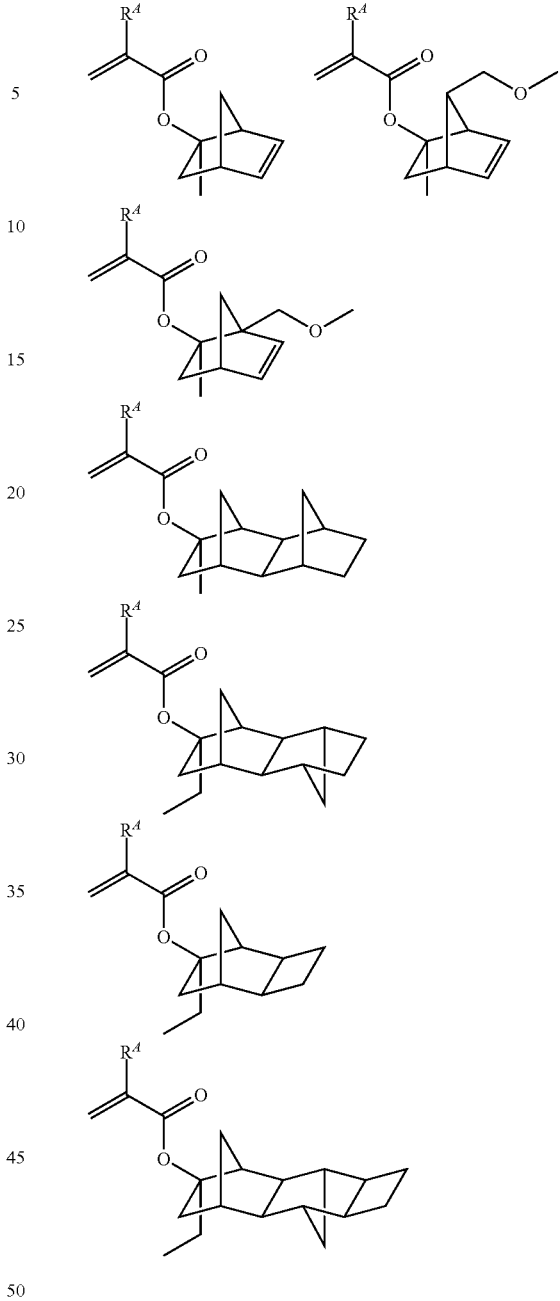
Examples of the monomer from which the recurring units having an acid labile group having the formula (AL-3) are derived include (meth)acrylates having a furandiyl, tetrahydrofurandiyl, or oxanorbornanediyl group having the formula (AL-3)-23.
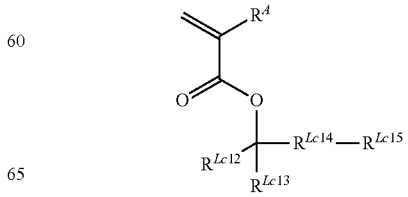
(AL-3)-23

In the formula (AL-3)-23, $R^A$ is as defined above. $R^{Lc12}$ and $R^{Lc13}$ are each independently a $C_1$-$C_{10}$ hydrocarbyl group. $R^{Lc12}$ and $R^{Lc13}$, taken together, may form an aliphatic ring with the carbon atom to which they are attached. $R^{Lc14}$ is furandiyl, tetrahydrofurandiyl, or oxanorbornanediyl. $R^{Lc15}$ is hydrogen or a $C_1$-$C_{10}$ hydrocarbyl group which may contain a heteroatom. The hydrocarbyl group may be straight, branched, or cyclic, and is typically a $C_1$-$C_{10}$ saturated hydrocarbyl group.

Examples of the monomer from which the recurring units having the formula (AL-3)-23 are derived are shown below, but not limited thereto. Herein $R^A$ is as defined above, Ac is an acetyl group, and Me is a methyl group.

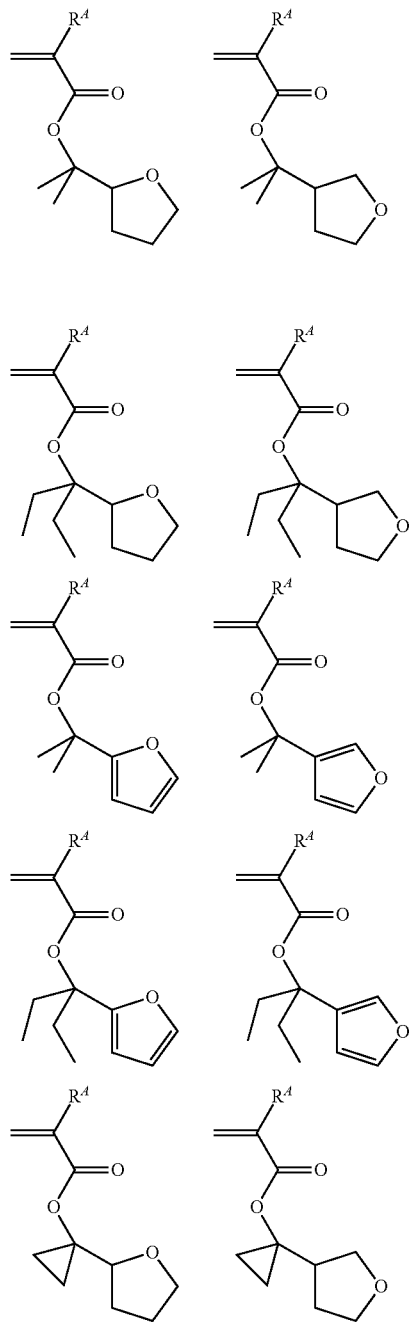

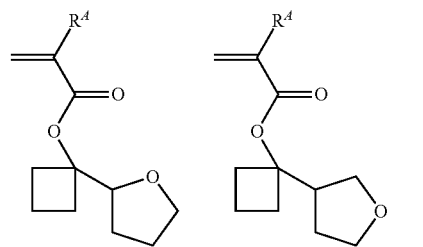

-continued

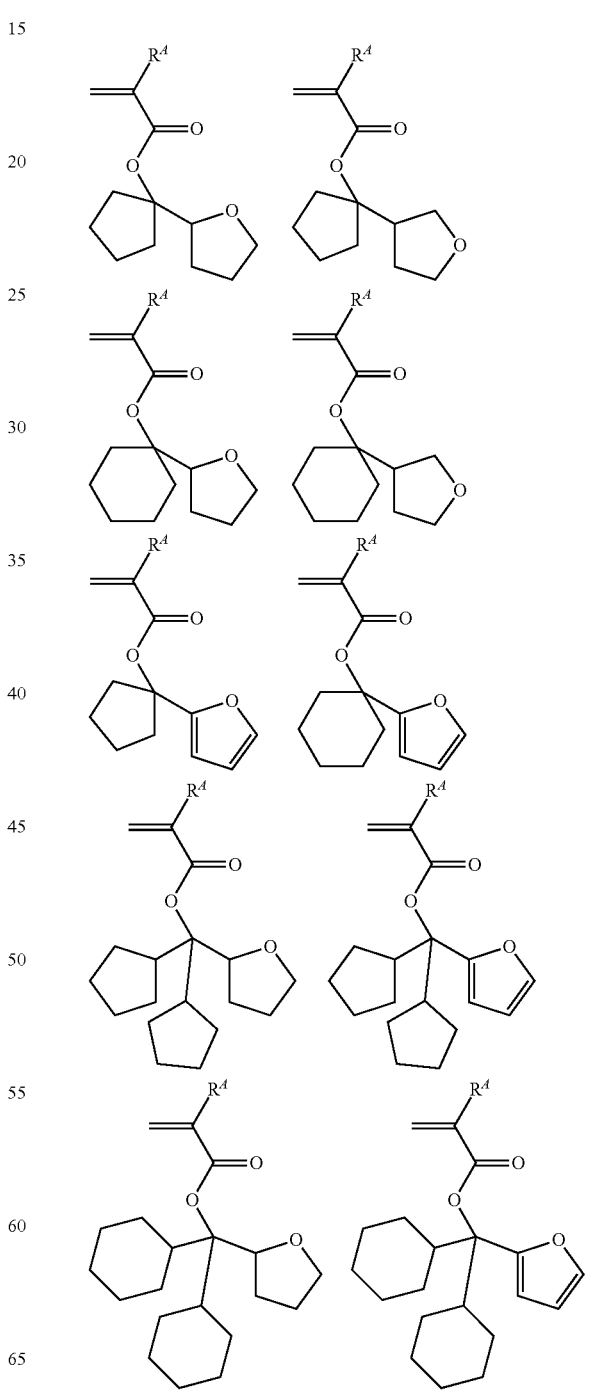

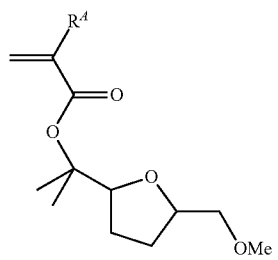
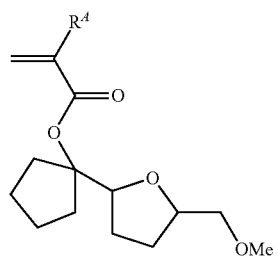
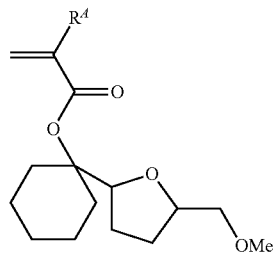
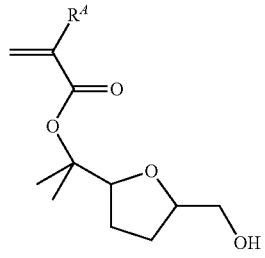
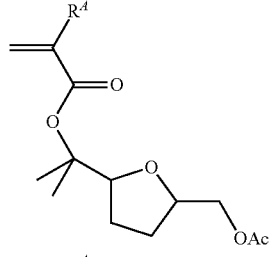
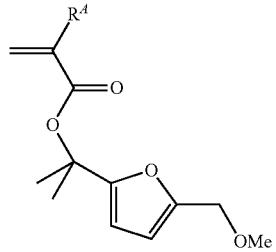
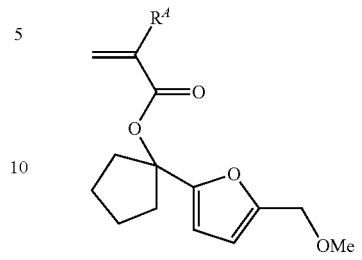
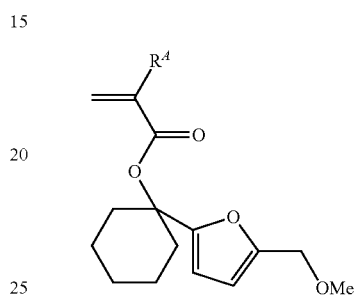
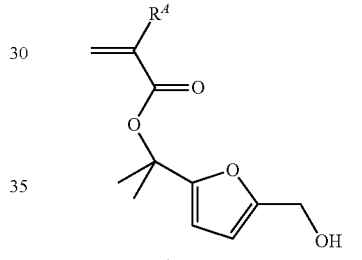
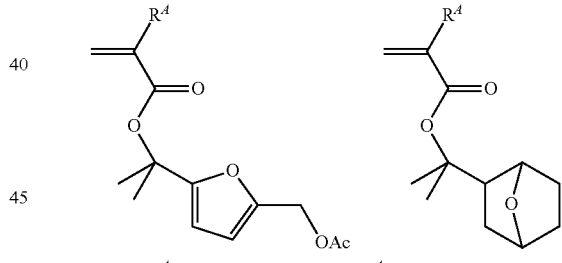
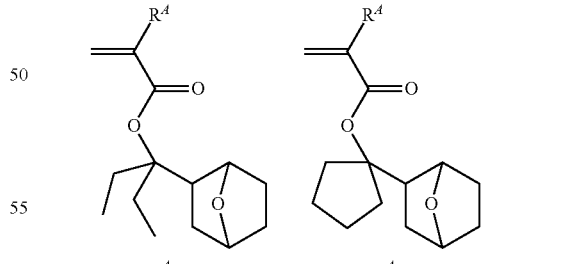
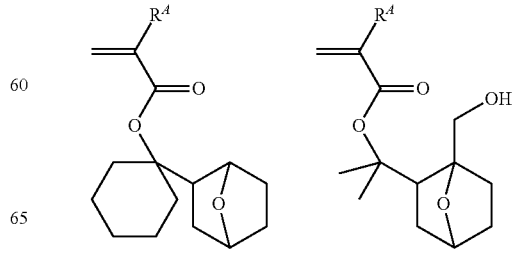

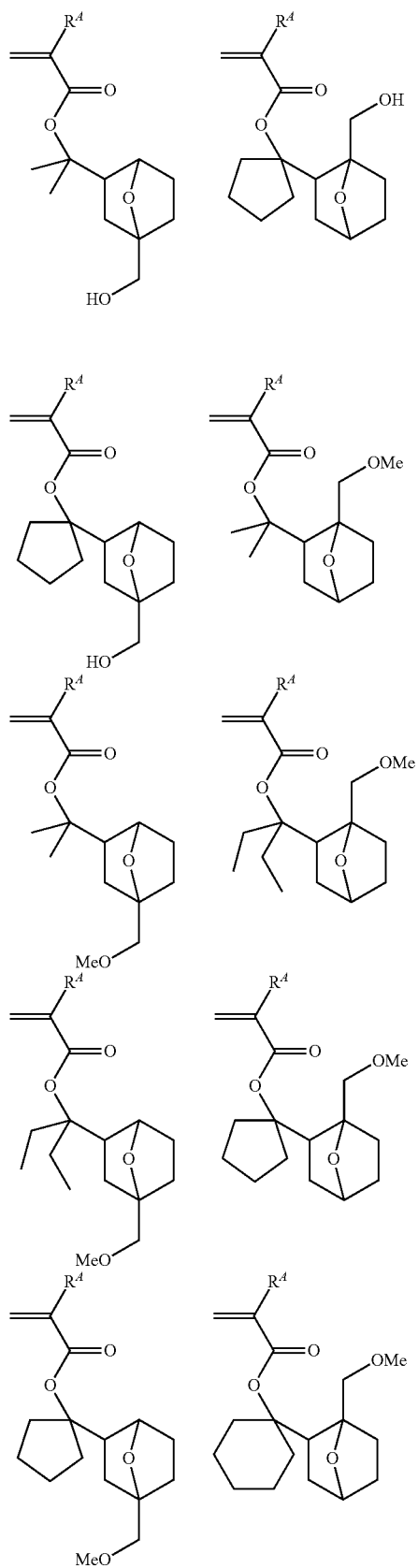
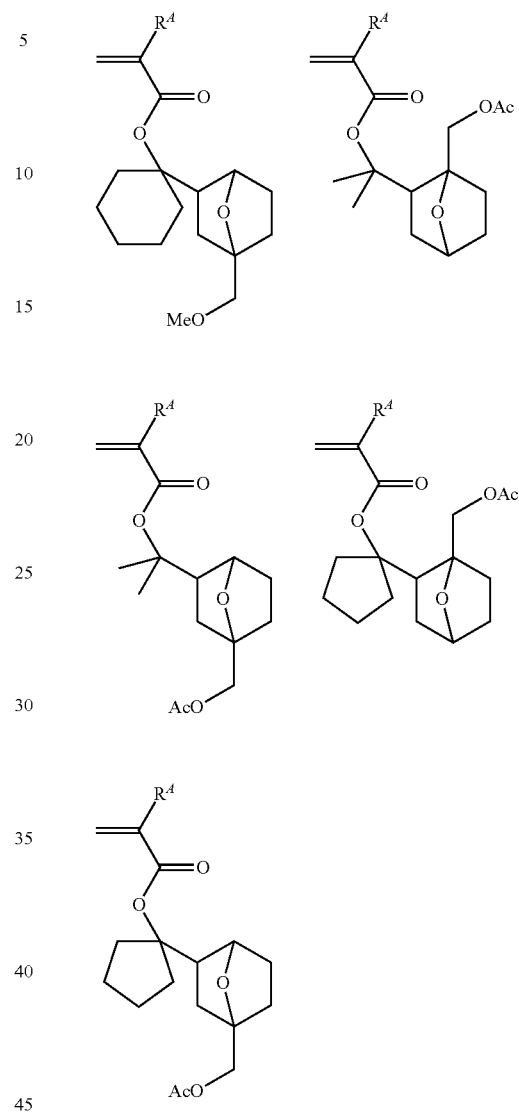

The base polymer may further include recurring units (c) having an adhesive group which is selected from hydroxyl, carboxyl, a lactone ring, carbonate, thiocarbonate, cabonyl, cyclic acetal, an ether bond, an ester bond, a sulfonic acid ester bond, cyano, an amide bond, —O—C(═O)—S—, and —O—C(═O)—NH—.

Examples of the monomer from winch the recurring units (c) are derived are shown below, but not limited thereto. Herein $R^A$ is as defined above.

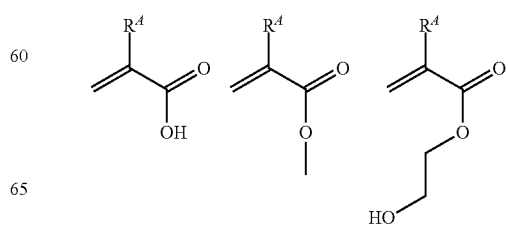

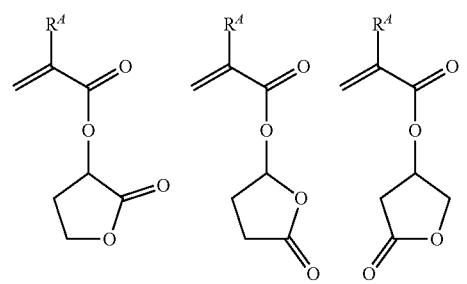
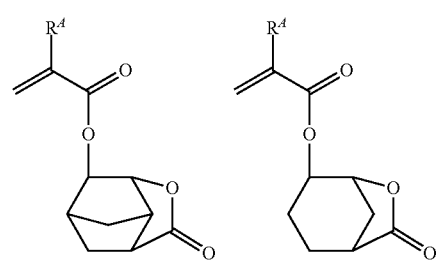
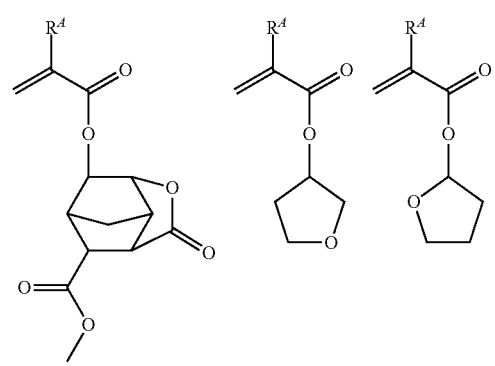
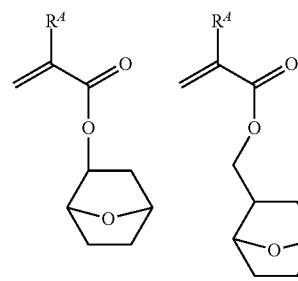
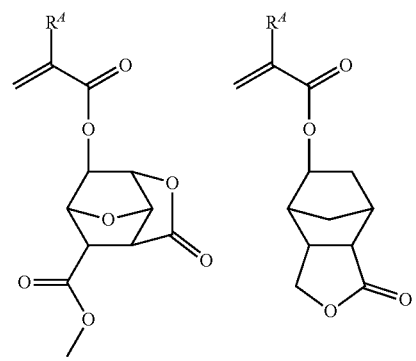
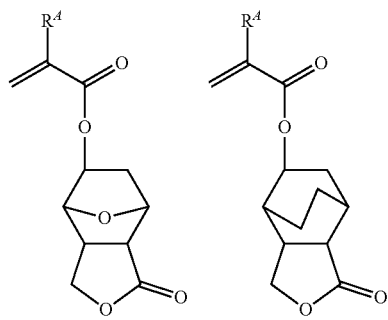
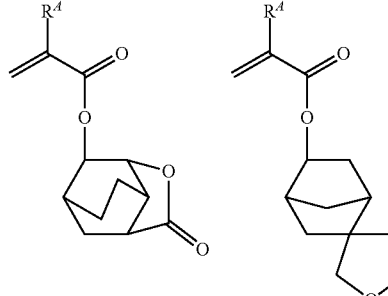
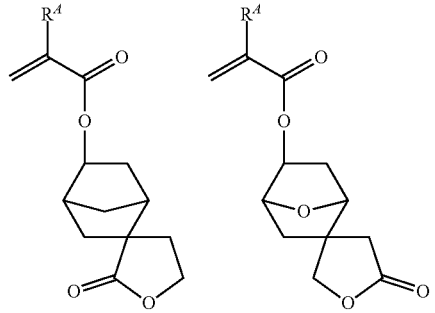
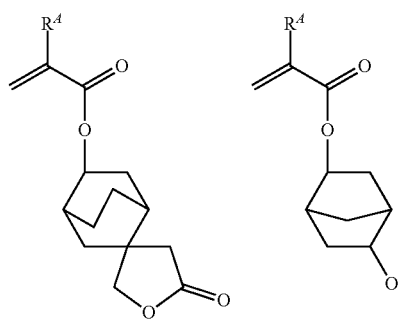
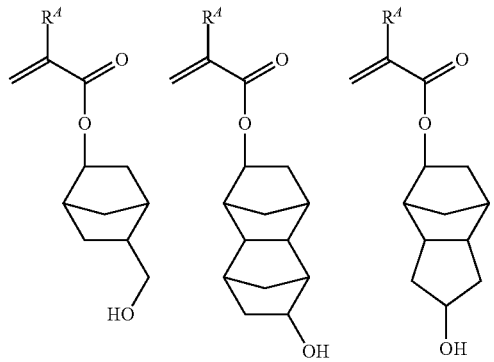

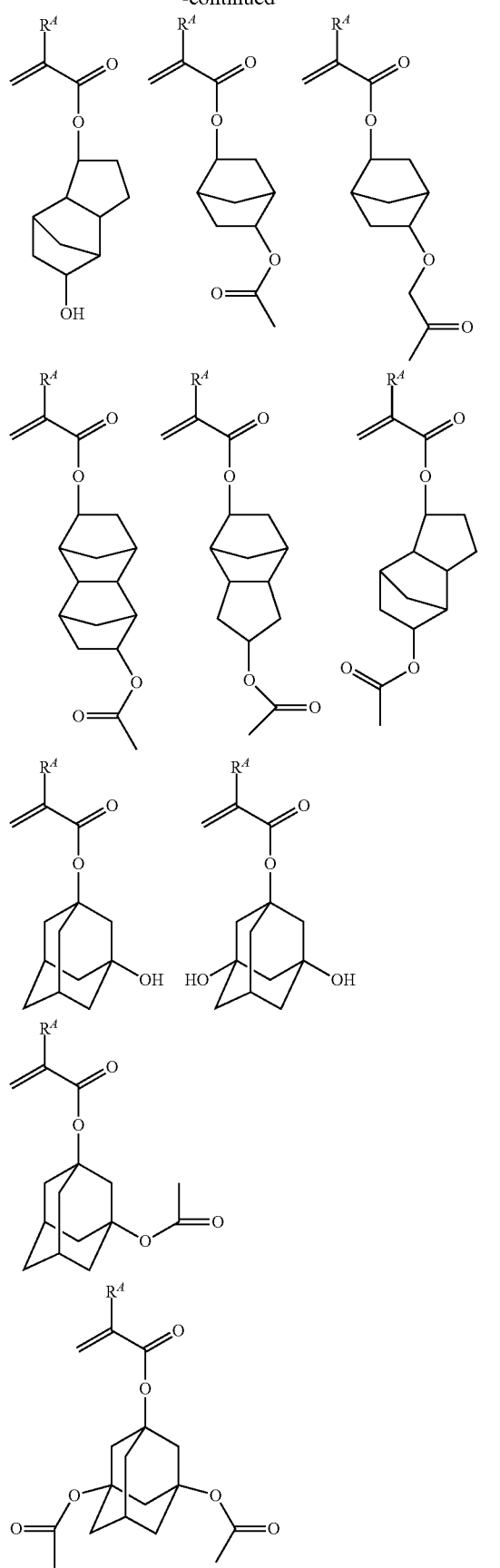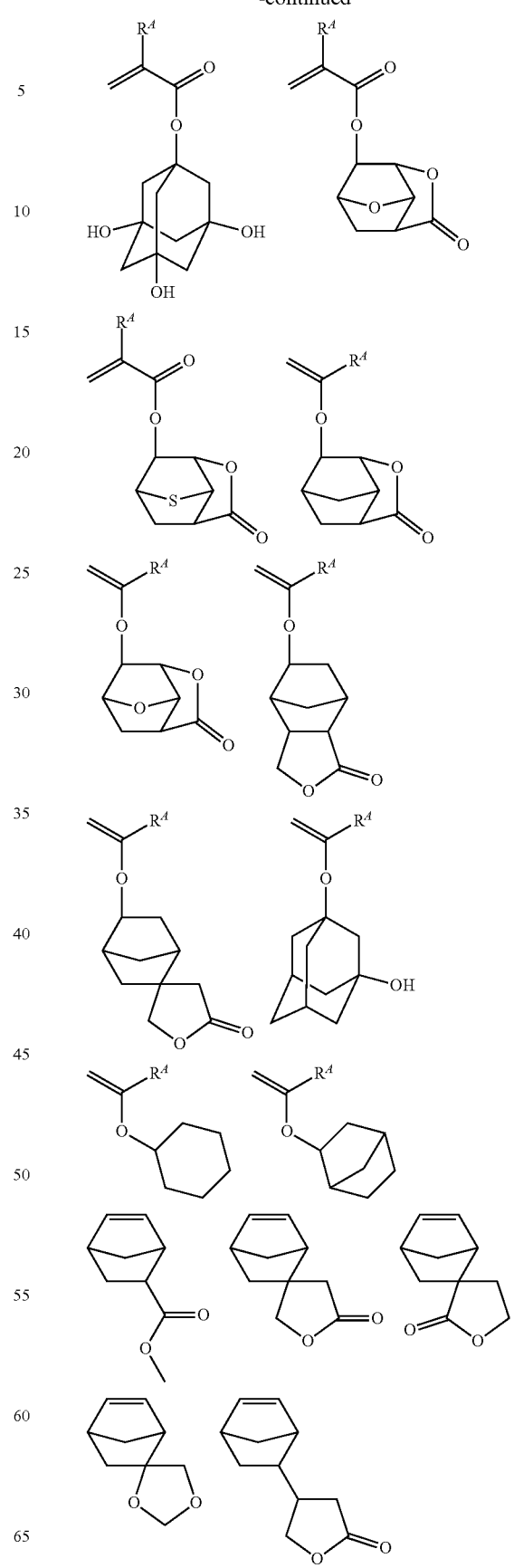

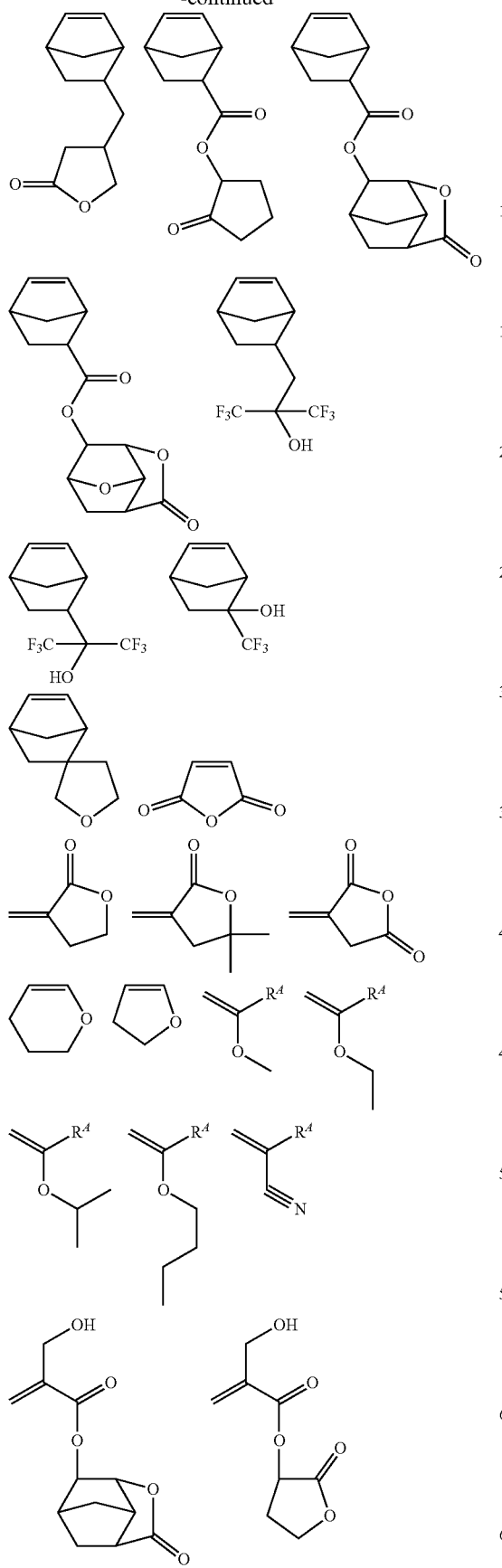
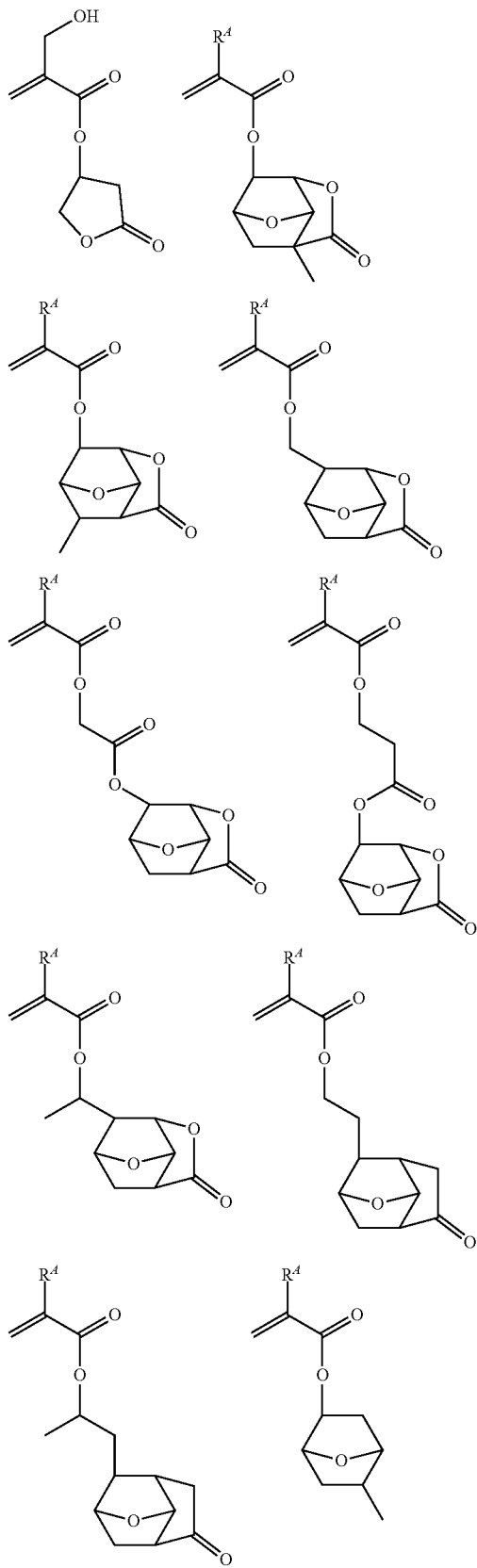

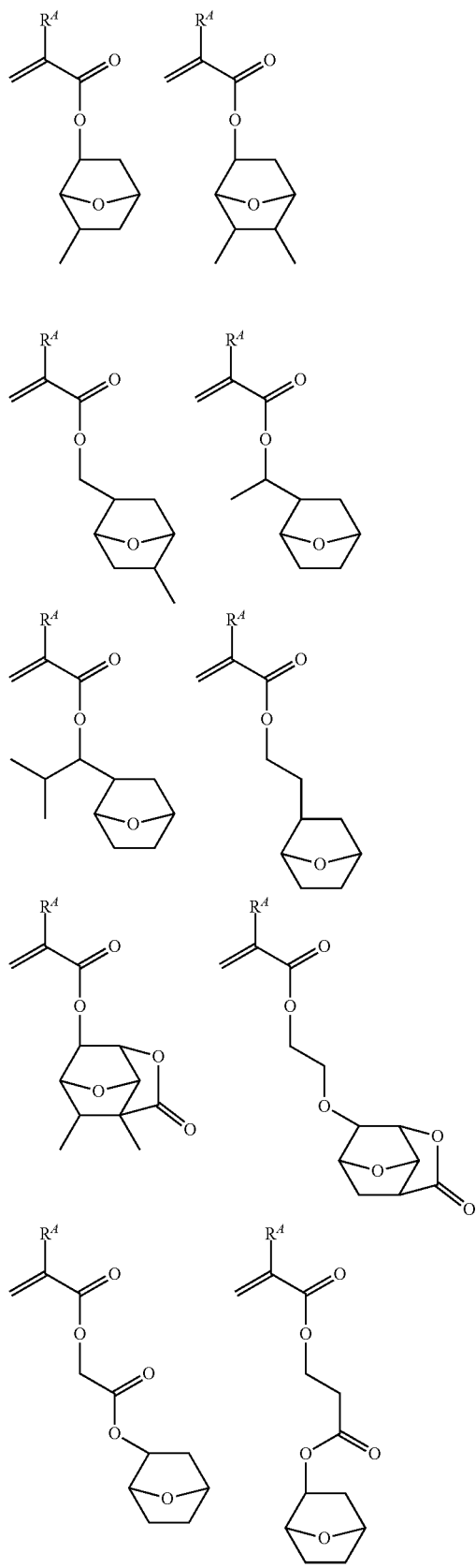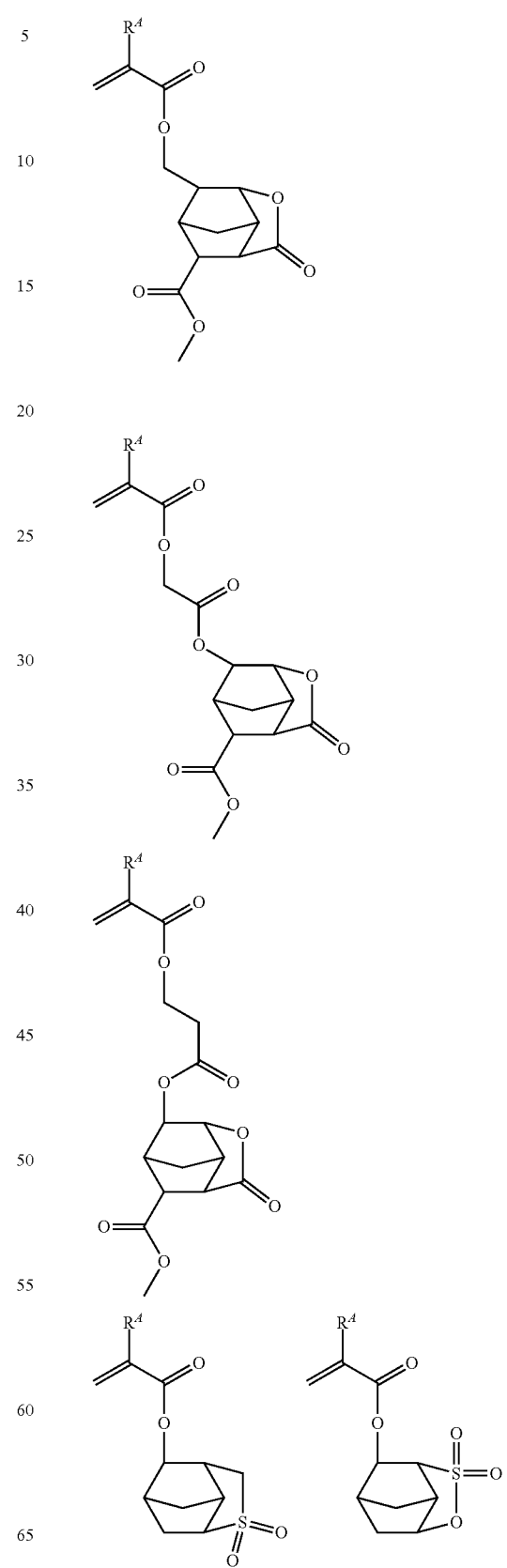

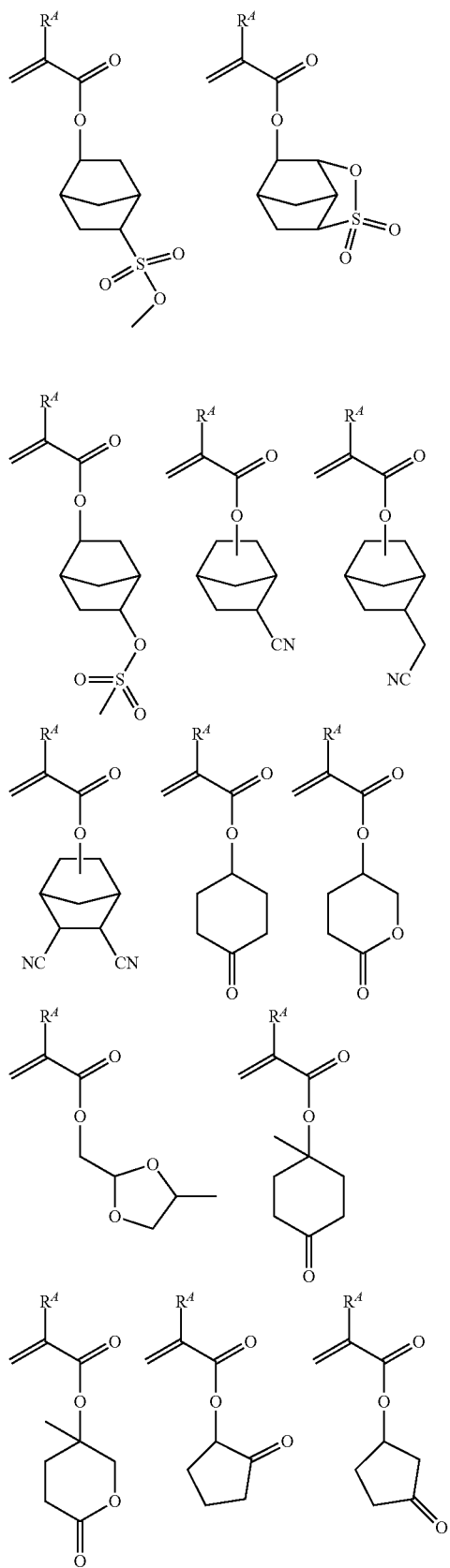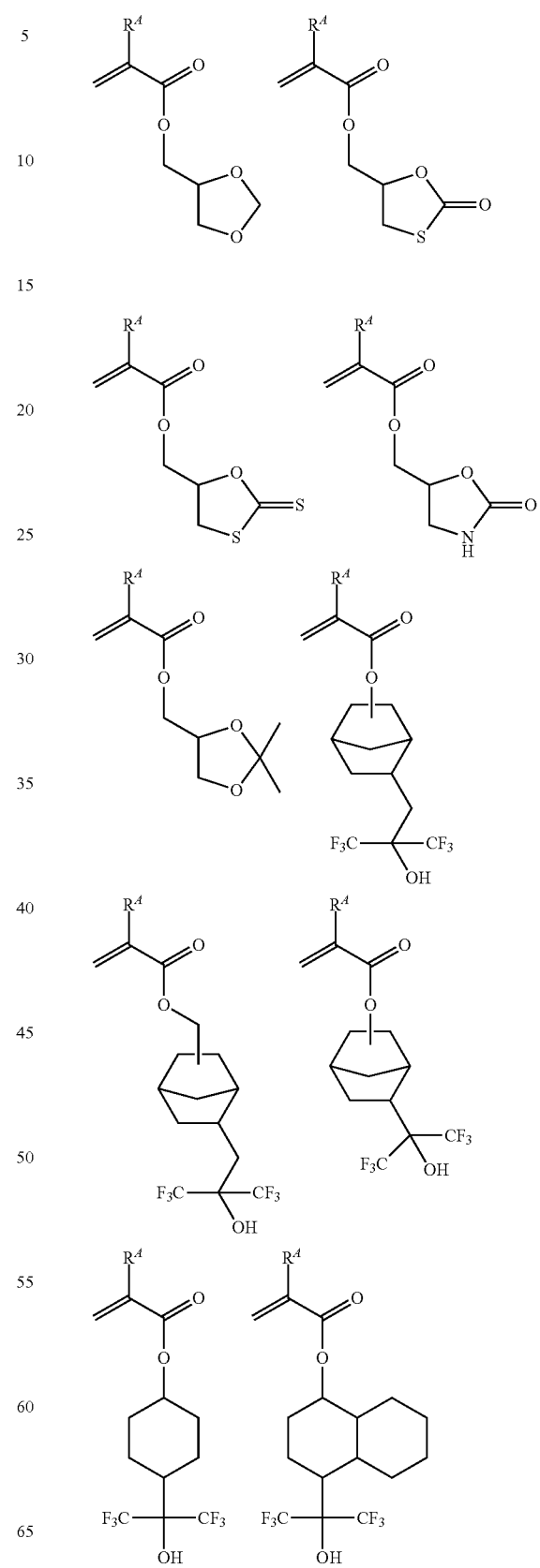

-continued
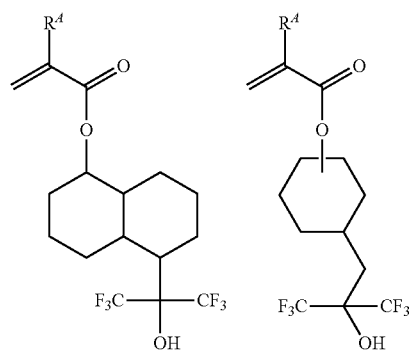
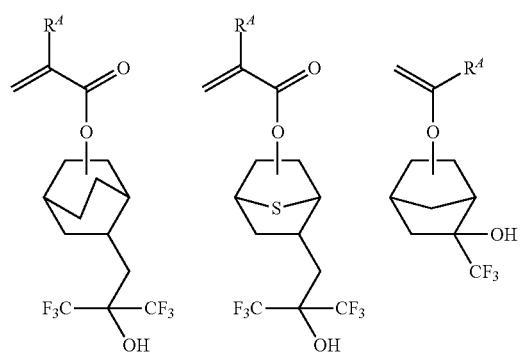
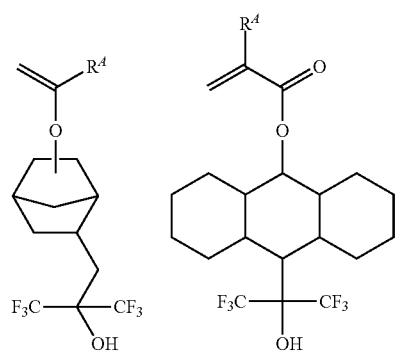
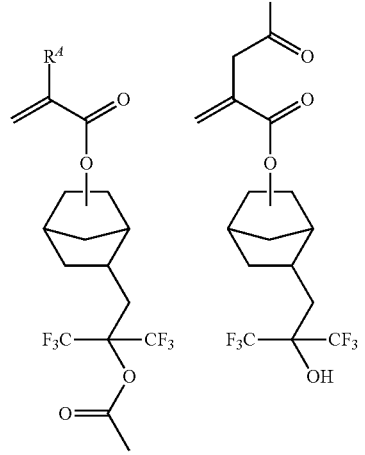
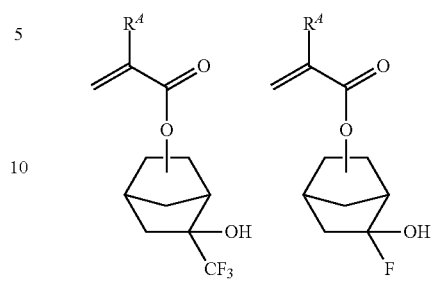
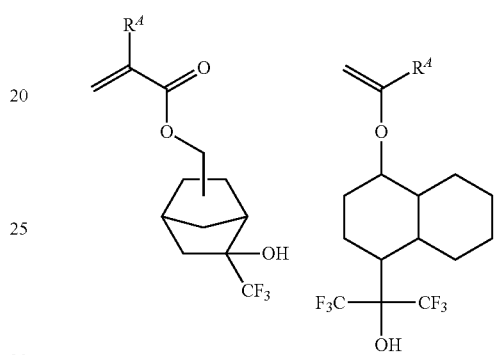
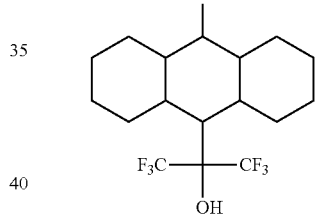
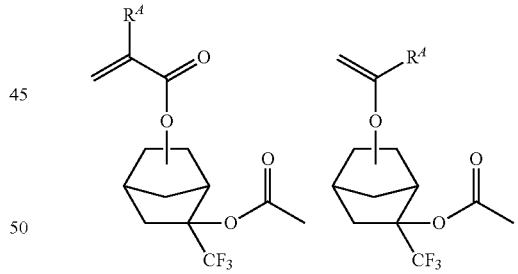
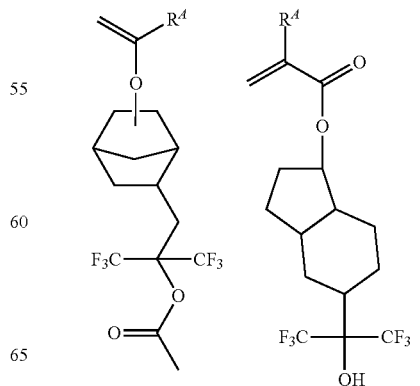

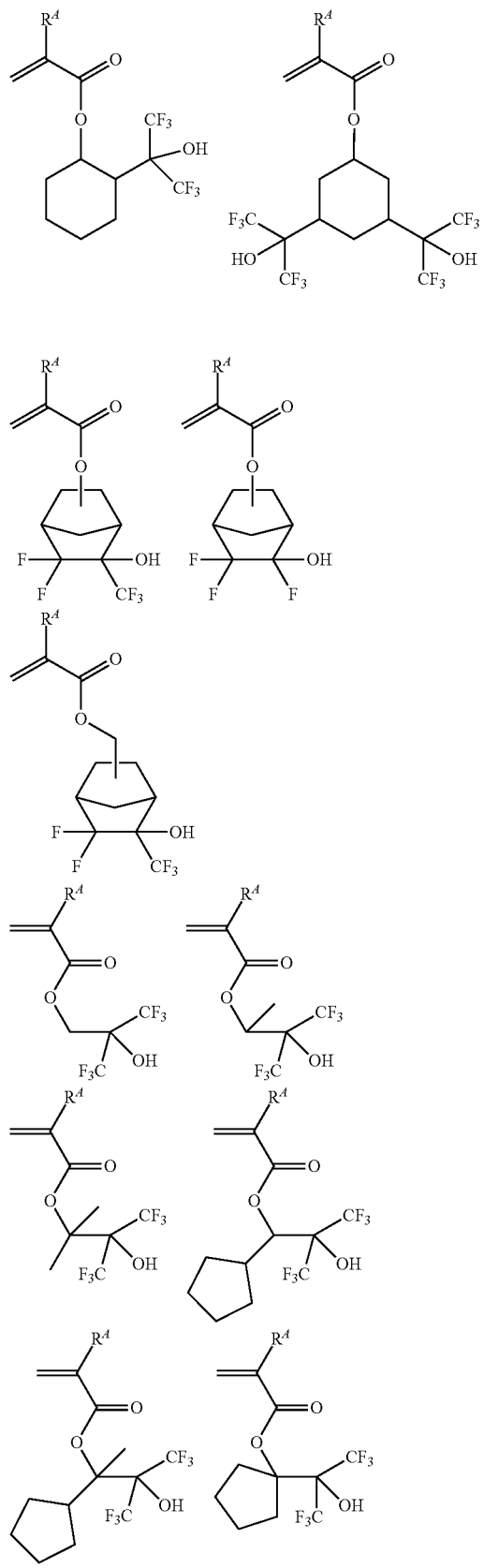
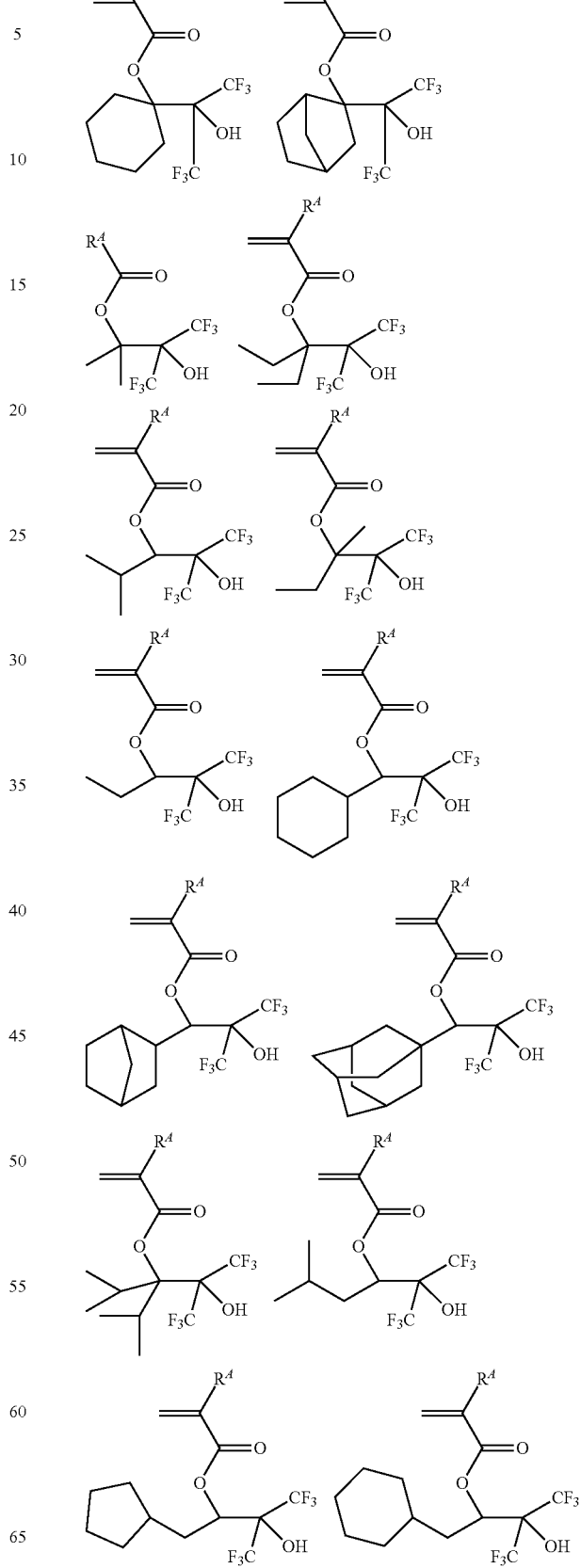

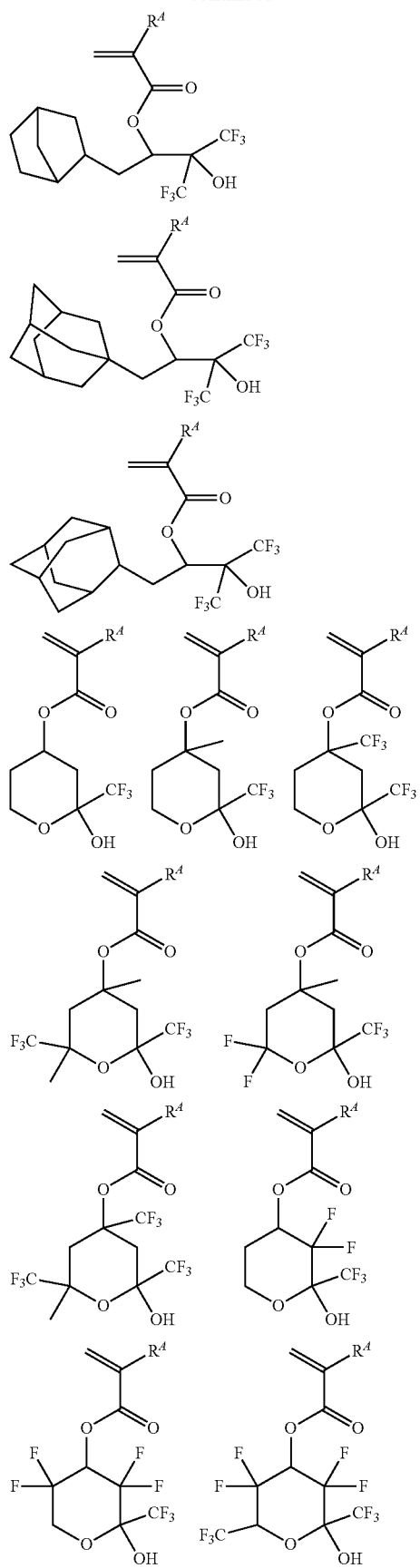
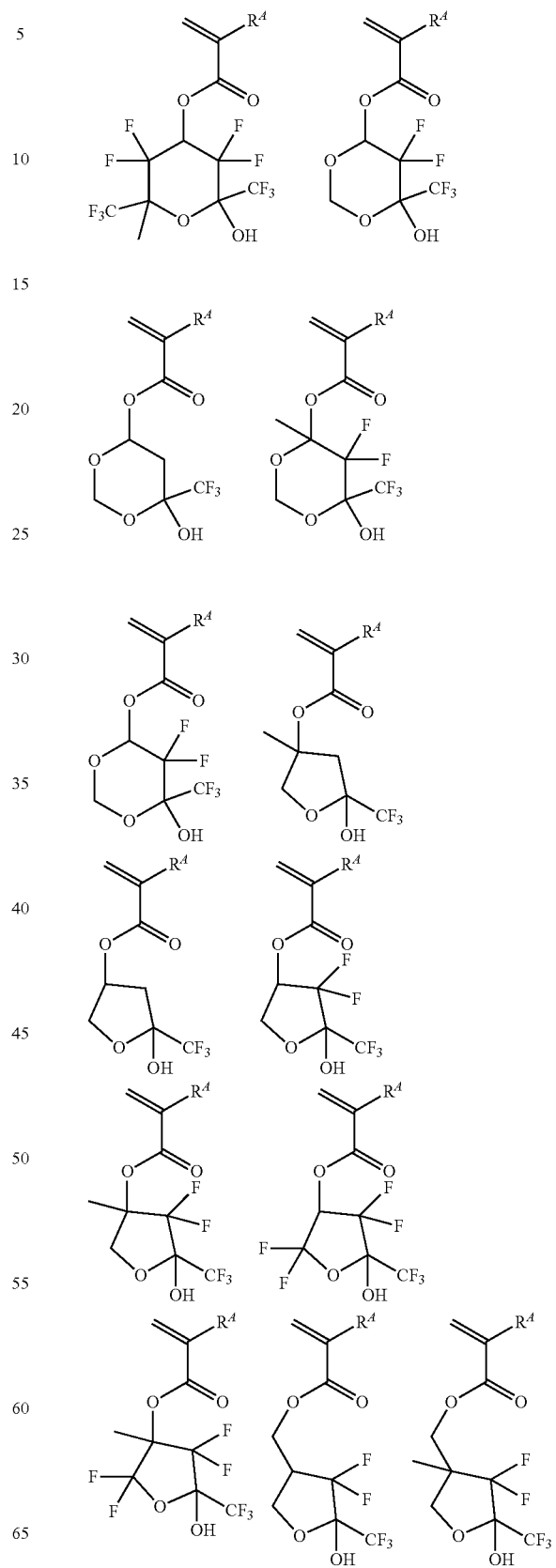

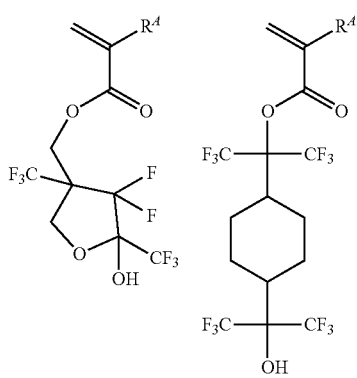
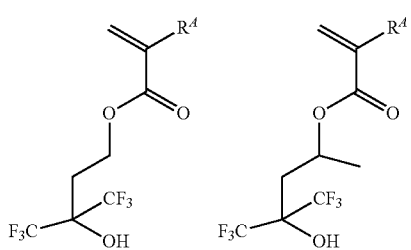
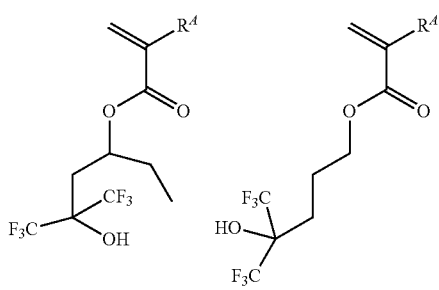
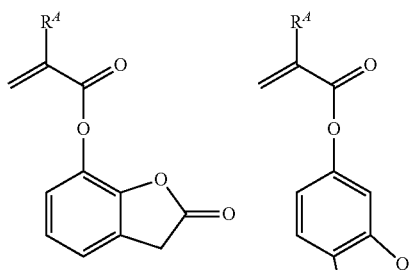
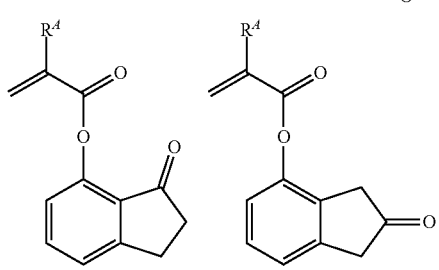
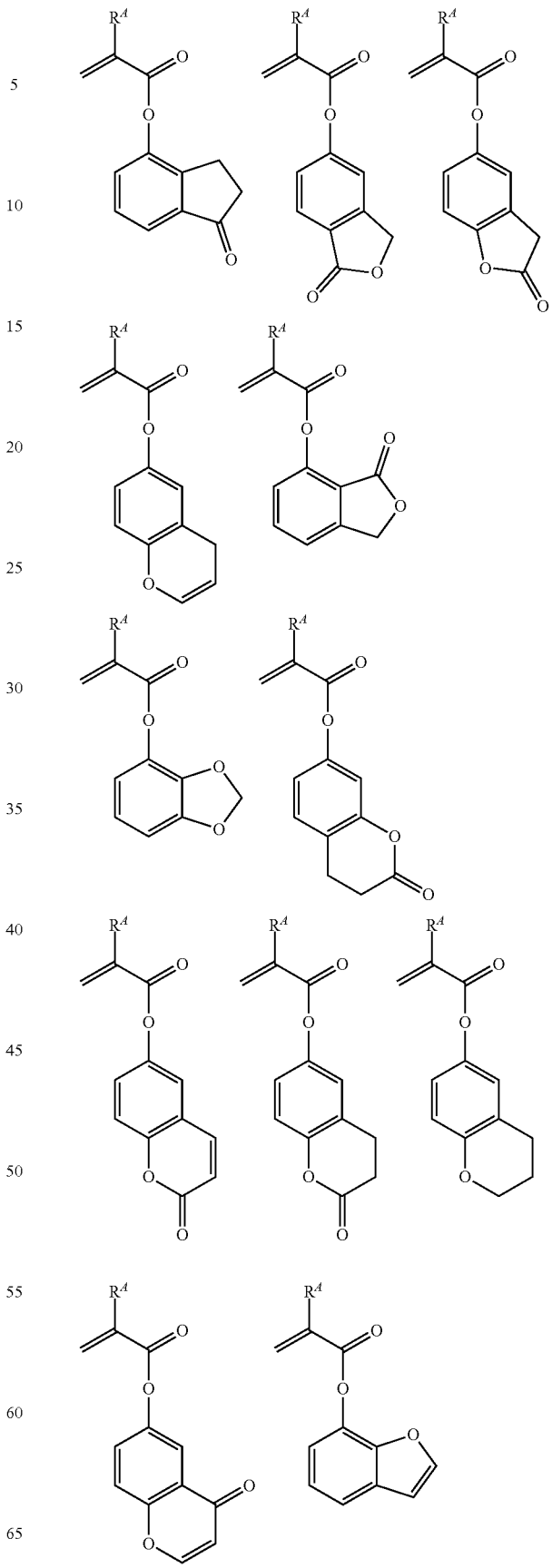

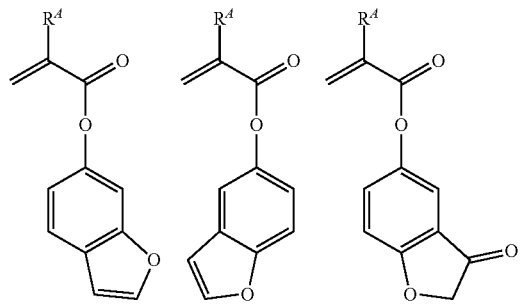
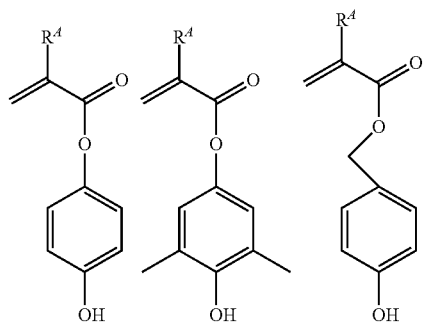
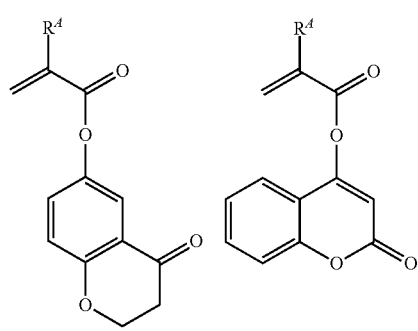
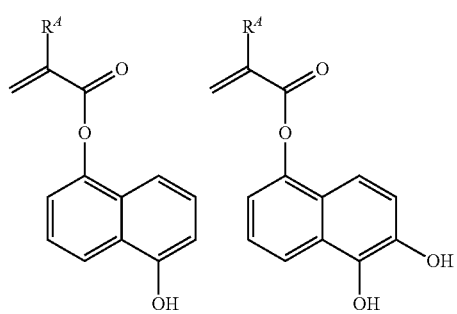
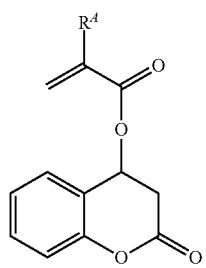
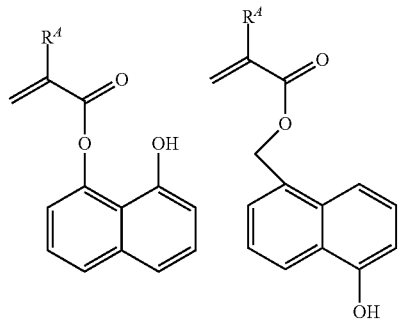
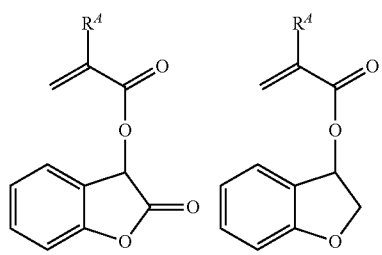
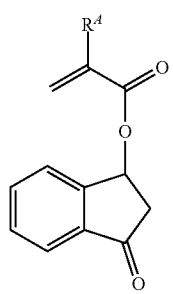
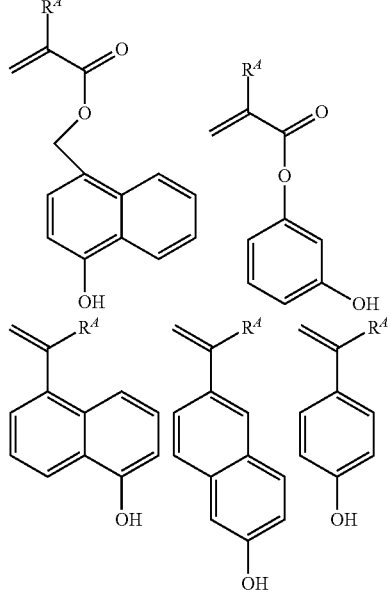

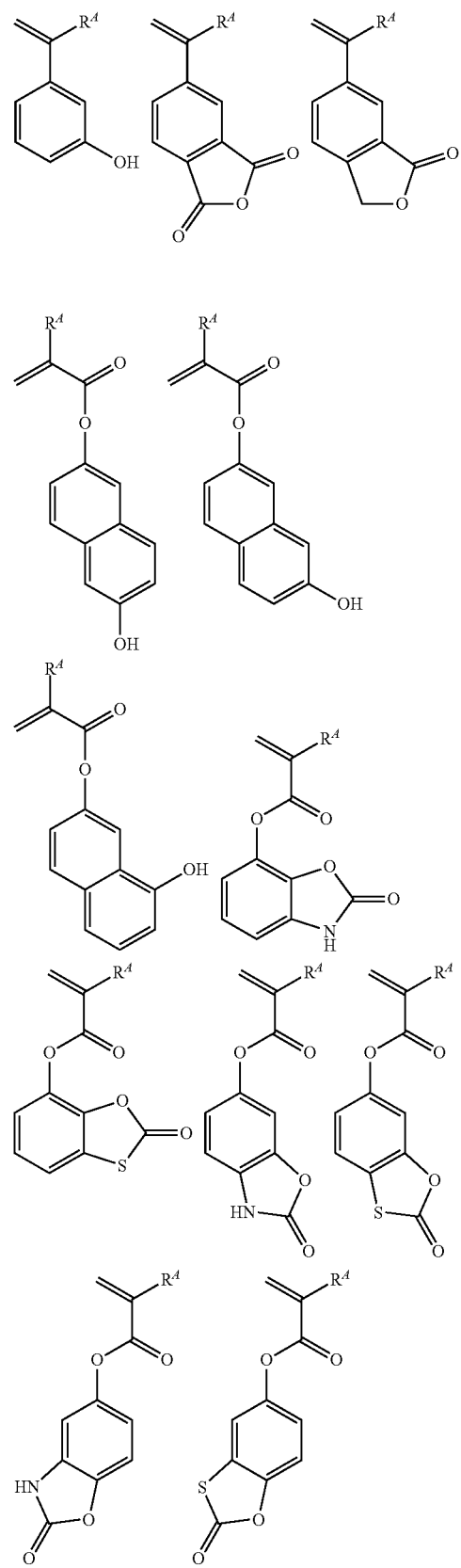
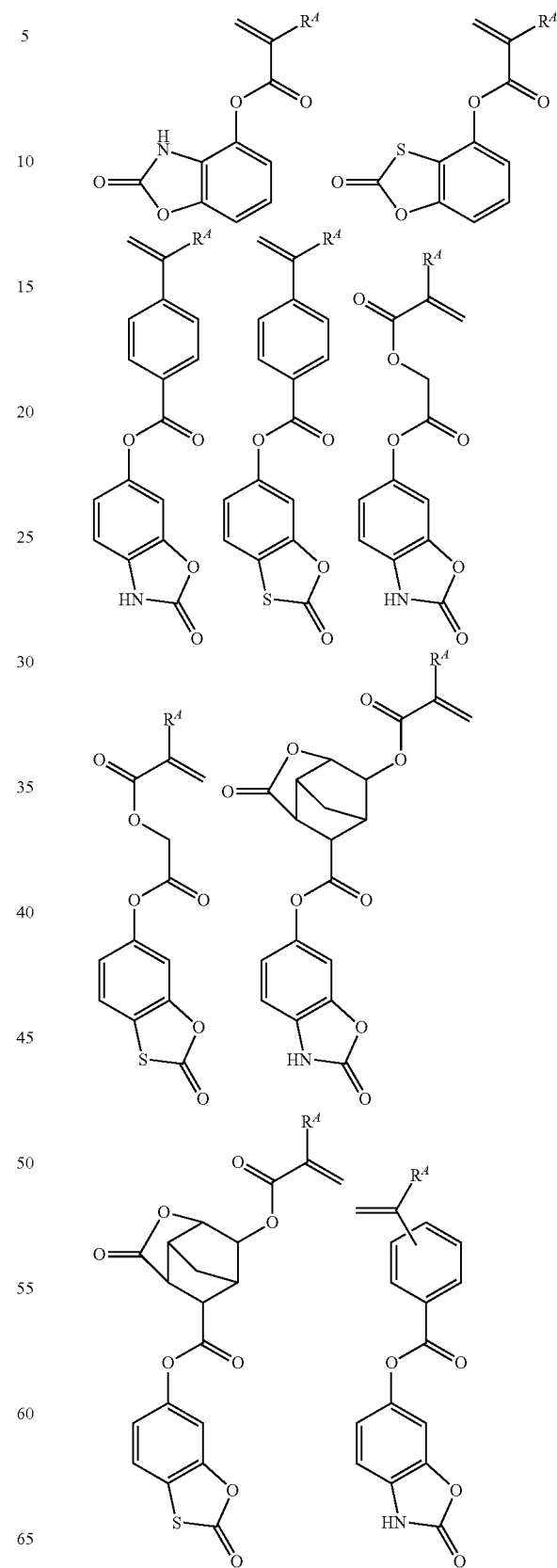

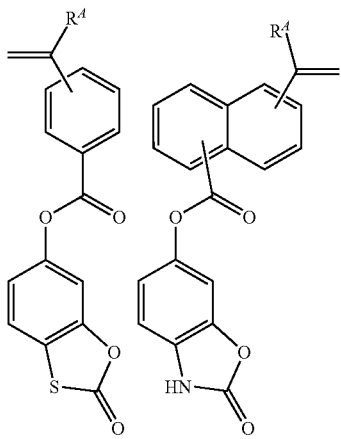

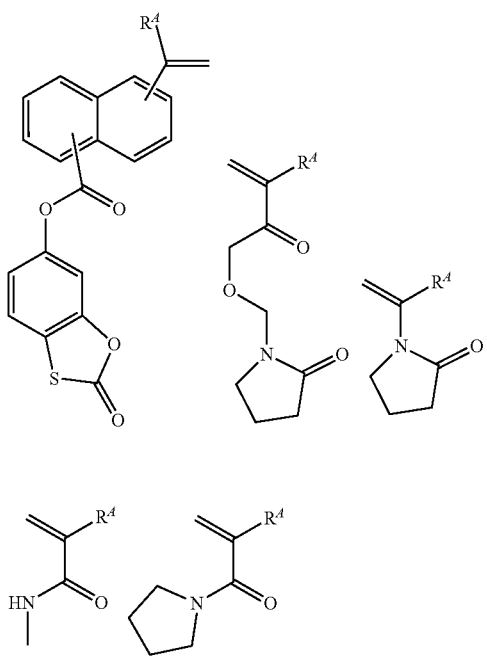

The base polymer may further comprise recurring units (d) derived from an onium salt having a polymerizable unsaturated bond. Suitable units (d) are recurring units having the following formulae (d1), (d2) and (d3). These units are simply referred to as recurring units (d1), (d2) and (d3), which may be used alone or in combination of two or more types.

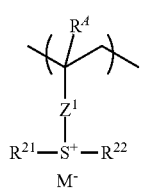
(d1)

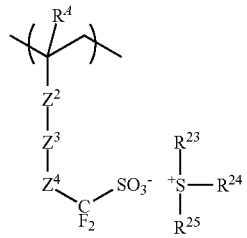
(d2)

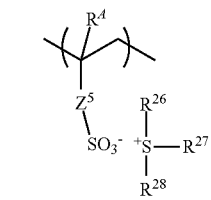
(d3)

In the formulae (d1) to (d3), $R^A$ is each independently hydrogen or a methyl group. $Z^1$ is a single bond, a $C_1$-$C_6$ aliphatic hydrocarbylene group, a phenylene group, a naphthylene group, a $C_7$-$C_{18}$ group obtained from combination thereof, —O—$Z^{11}$—, —C(=O)—O—$Z^{11}$—, or —C(=O)—NH—$Z^{11}$—. $Z^{11}$ is a $C_1$-$C_6$ aliphatic hydrocarbylene group, a phenylene group, a naphthylene group, or a $C_7$-$C_{18}$ combination thereof, which may contain a carbonyl group, an ester bond, an ether bond, or a hydroxyl group. $Z^2$ is a single bond or an ester bond. $Z^3$ is a single bond, —$Z^{31}$—C(=O)—O—, —$Z^{31}$—O—, or —$Z^{31}$—O—C(=O)—. $Z^{31}$ is a $C_1$-$C_{12}$ hydrocarbylene group, a phenylene group, or a $C_7$-$C_{18}$ group obtained from combination thereof, which may contain a carbonyl group, an ester bond, an ether bond, bromine, or iodine. $Z^4$ is a methylene group, a 2,2,2-trifluoro-1,1-ethanediyl group, or a carbonyl group. $Z^5$ is a single bond, a methylene group, an ethylene group, a phenylene group, a fluorinated phenylene group, a trifluoromethyl-substituted phenylene group, —O—$Z^{51}$—, —C(=O)—O—$Z^{51}$—, or —C(=O)—NH—$Z^{51}$—. $Z^{51}$ is a $C_1$-$C_{16}$ aliphatic hydrocarbylene group, a phenylene group, a fluorinated phenylene group, or a trifluoromethyl-substituted phenylene group, which may contain a carbonyl group, an ester bond, an ether bond, a halogen, or a hydroxyl group.

In the formulae (d1) to (d3), $R^{21}$ to $R^{28}$ are each independently a $C_1$-$C_{20}$ hydrocarbyl group which may contain a heteroatom. The hydrocarbyl group may be saturated or unsaturated, and may be straight, branched, or cyclic. Illustrative examples areas exemplified below for $R^{101}$ to $R^{10}$ in the formulae (1-1) and (1-2).

A pair of $R^{23}$ and $R^{24}$, or $R^2$ and $R^{27}$ may bond together to form a ring with the sulfur atom to which they are attached. Examples of the ring are as will be exemplified for the ring that $R^{101}$ and $R^{102}$ in the formula (1-1), taken together, form with the sulfur atom to which they are attached.

In the formula (d1), M⁻ is a non-nucleophilic counter ion. Examples of the non-nucleophilic counter ion include halide ions such as chloride and bromide; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate: imide ions such as bis(trifluoromethylsulfonyl)imide, bis(perfluoroethylsulfonyl)imide, and bis(perfluorobutylsulfonyl)imide; and methide ions such as tris(trifluoromethylsulfonyl)methide and tris (pefluoroethylsulfonyl)methide.

Also included are sulfonate ions having fluorine substituted at α-position as represented by the formula (d1-1) and sulfonate ions having fluorine substituted at α-position and trifluoromethyl at β-position as represented by the formula (d1-2).

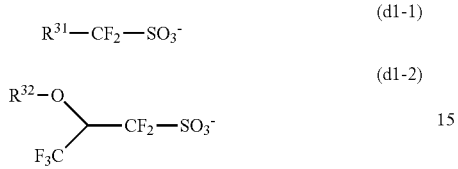

In the formula (d1-1), $R^{31}$ is hydrogen or a $C_1$-$C_{20}$ hydrocarbyl group which may contain an ether bond, an ester bond, a carbonyl group, a lactone ring, or a fluorine atom. The hydrocarbyl group may be straight, branched, or cyclic, Examples thereof are as will be exemplified for the hydrocarbyl group represented by $R^{107}$ in the formula (1A').

In the formula (d1-2) $R^{32}$ is hydrogen, a $C_1$-$C_{30}$ hydrocarbyl group, or a $C_2$-$C_{30}$ hydrocarbylcarbonyl group, which may contain an ether bond, an ester bond, a carbonyl group, or a lactone ring. The hydrocarbyl group and the hydrocarbyl moiety of the hydrocarbylcarbonyl group may be saturated or unsaturated, and straight, branched, or cyclic. Examples of the hydrocarbyl group are as will be exemplified later for the hydrocarbyl group $R^{107}$ in the formula (1A').

Examples of the cation in the monomer from which the recurring unit (d1) is derived are shown below, but not limited thereto. Herein $R^A$ is as defined above.

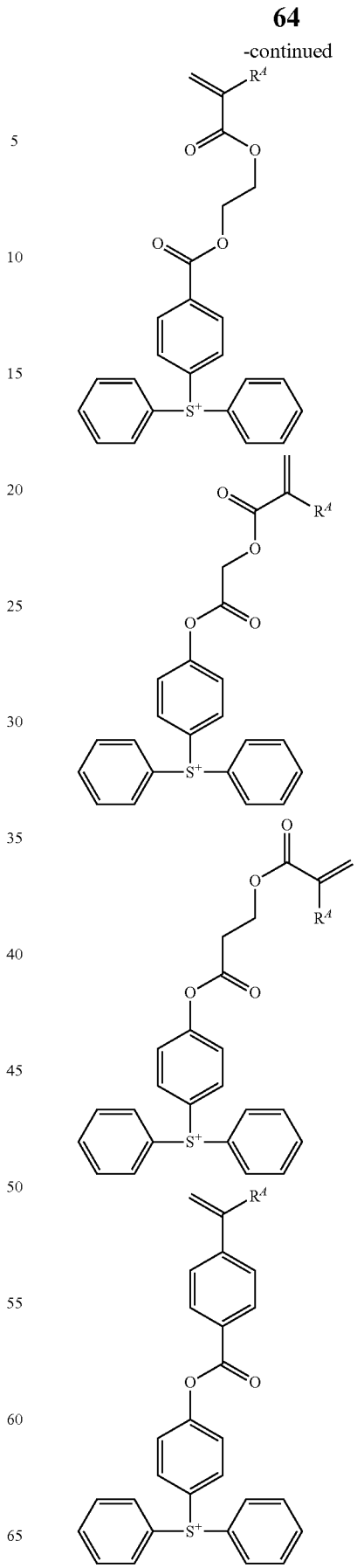

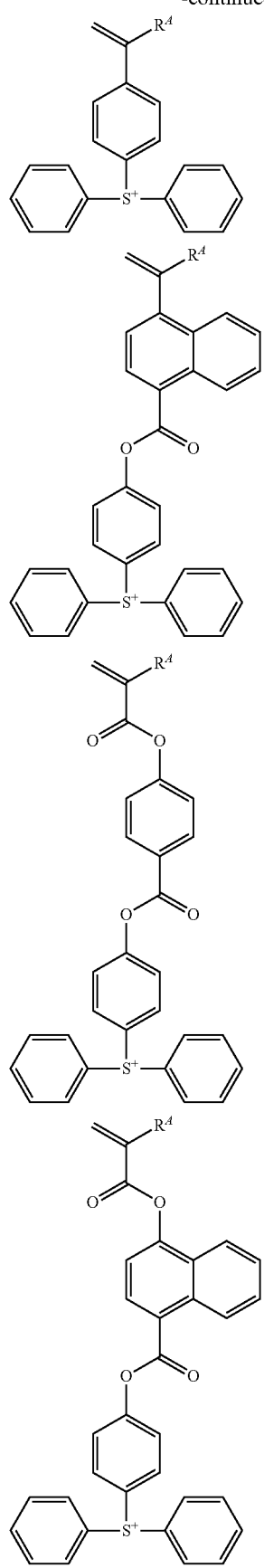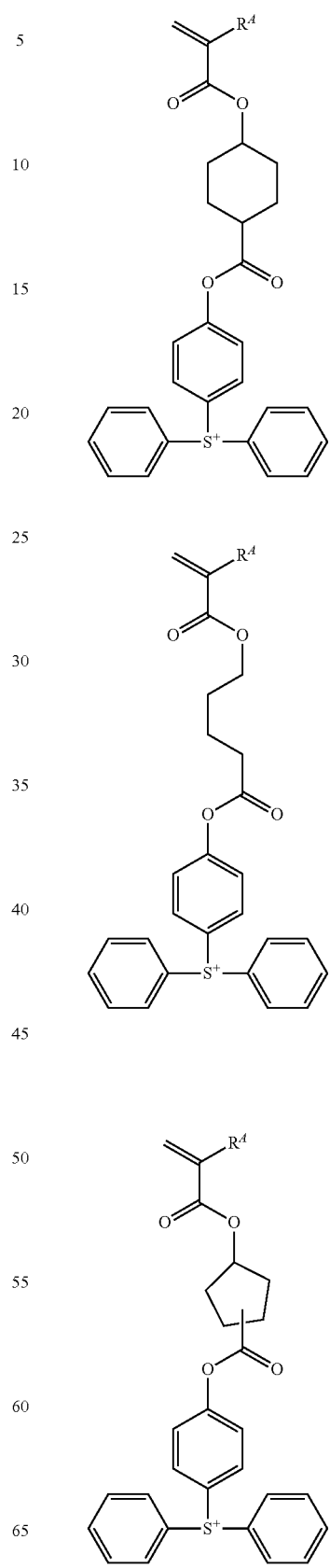

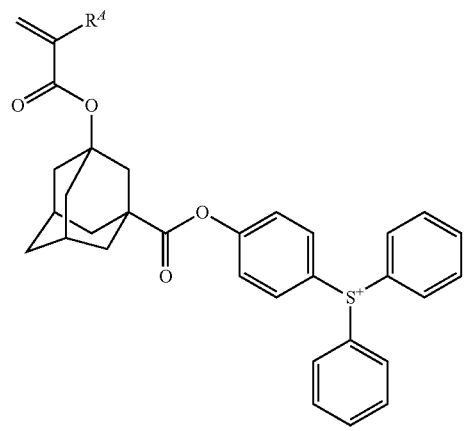
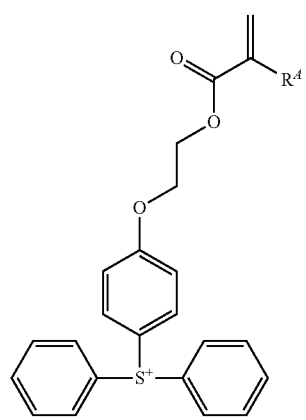
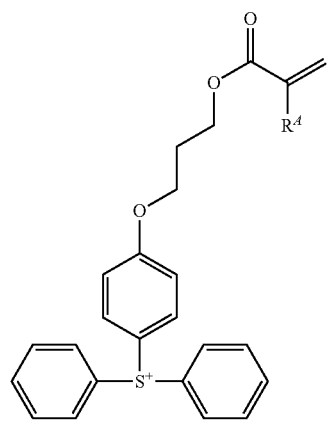
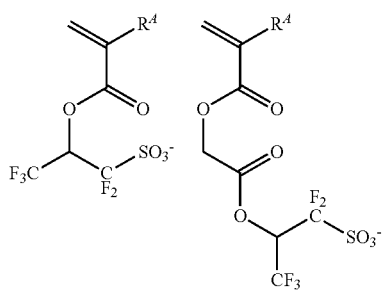
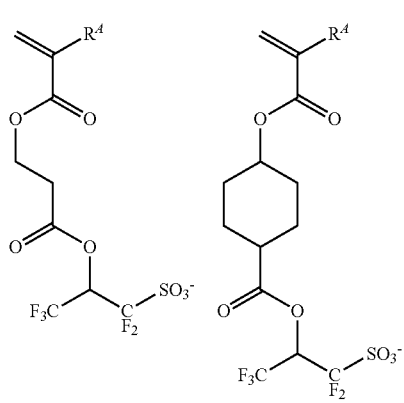
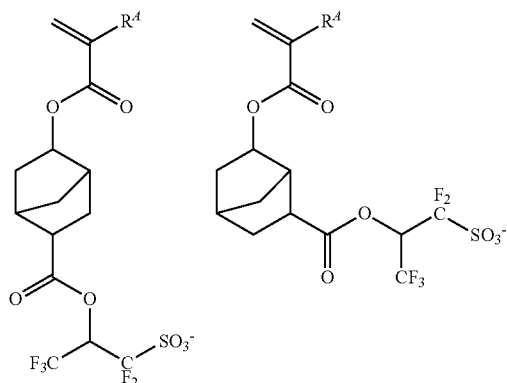
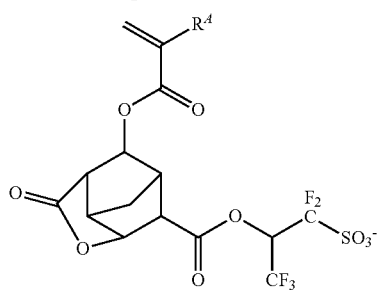
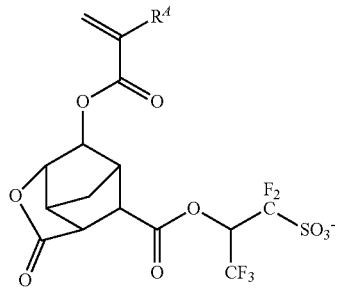
Examples of the cation in the monomer from which the recurring unit (d2) or (d3) is derived are as will be exemplified later for the cation in a sulfonium salt having the formula (1-1).
Examples of the anion in the monomer from which the recurring unit (d2) is derived are shown below, but not limited thereto. Herein $R^A$ is as defined above.

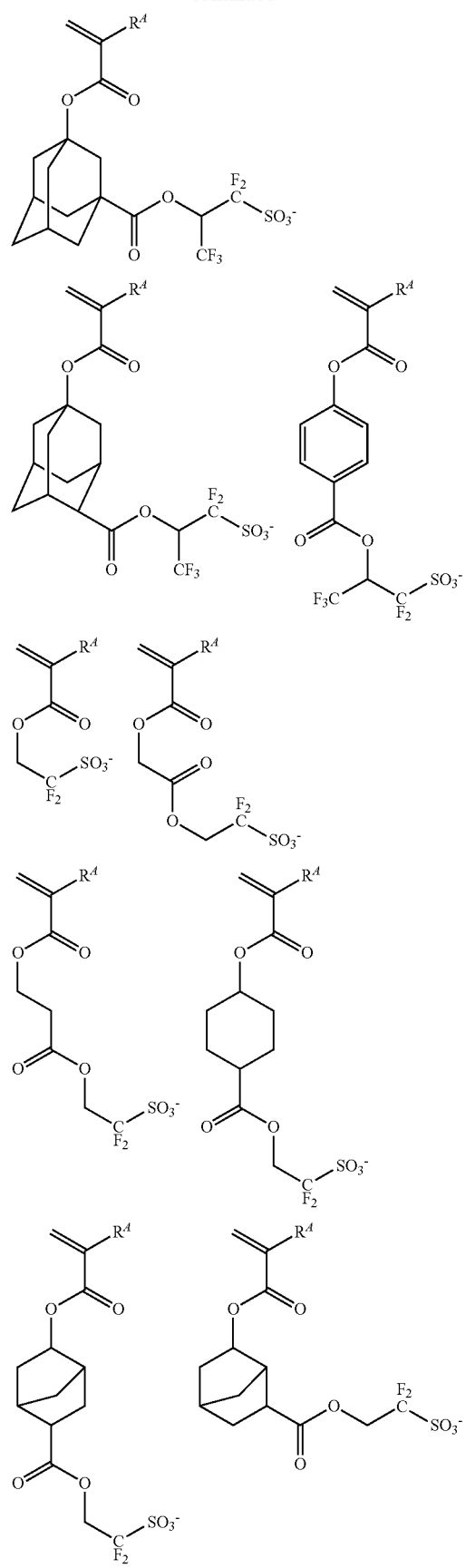
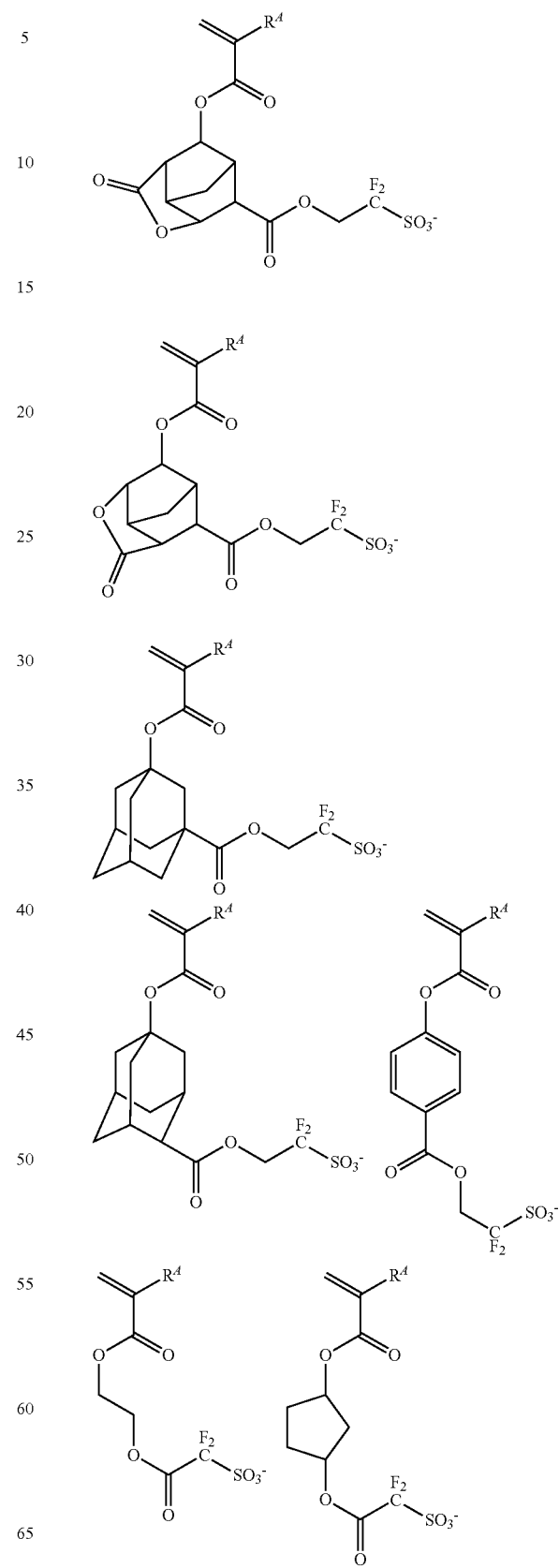

71
-continued
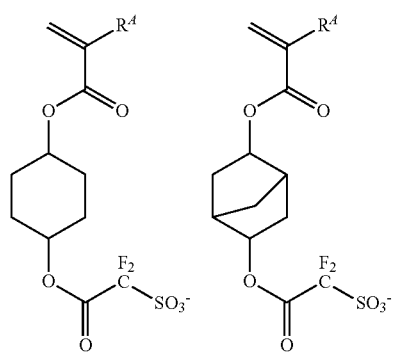
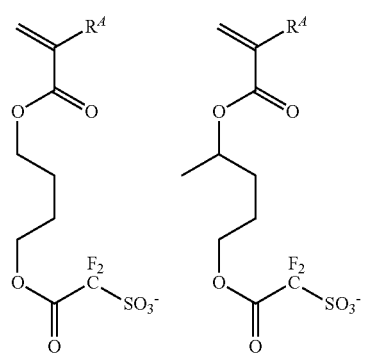
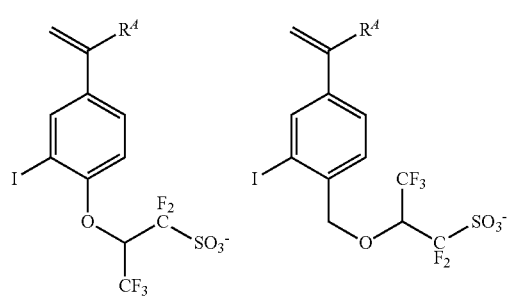
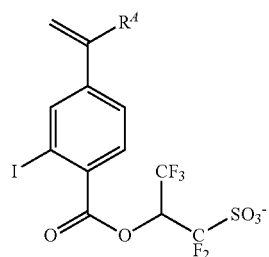
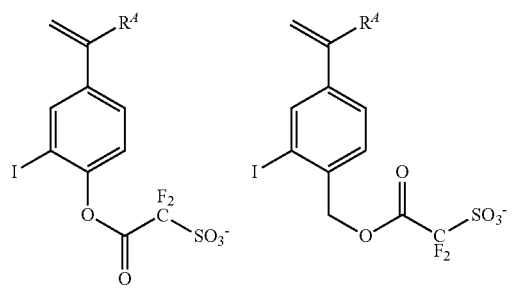
72
-continued
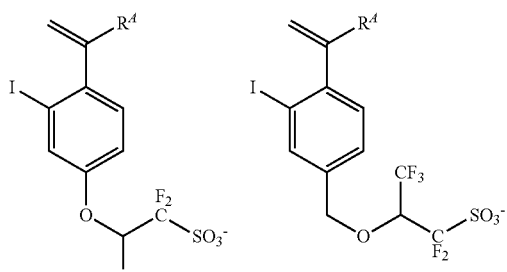
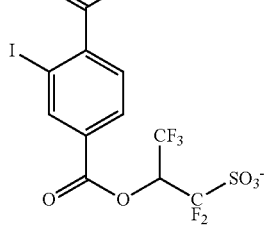
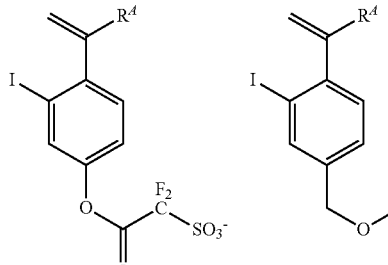
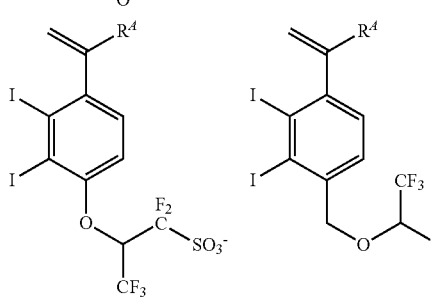
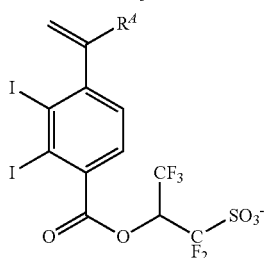
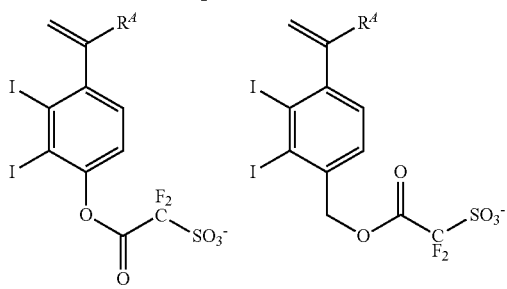

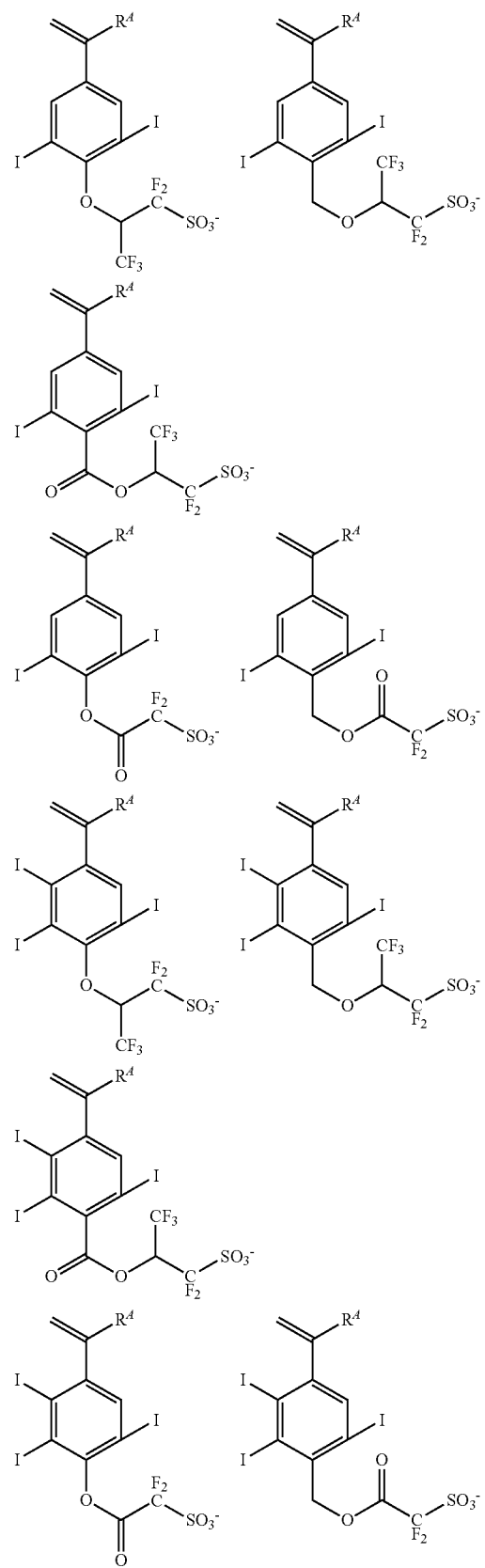
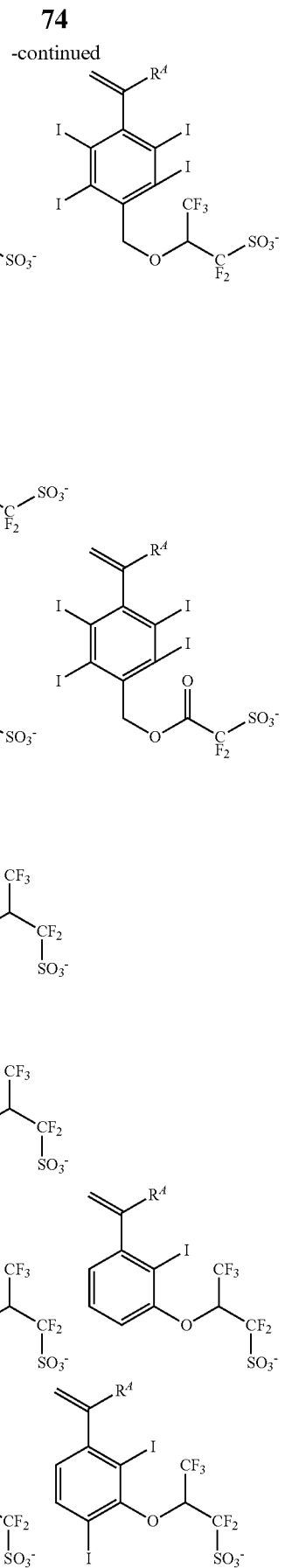

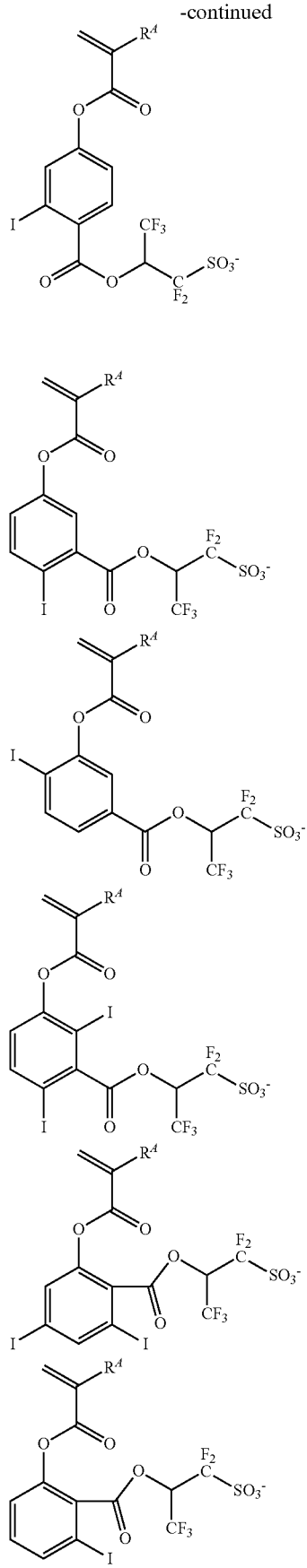
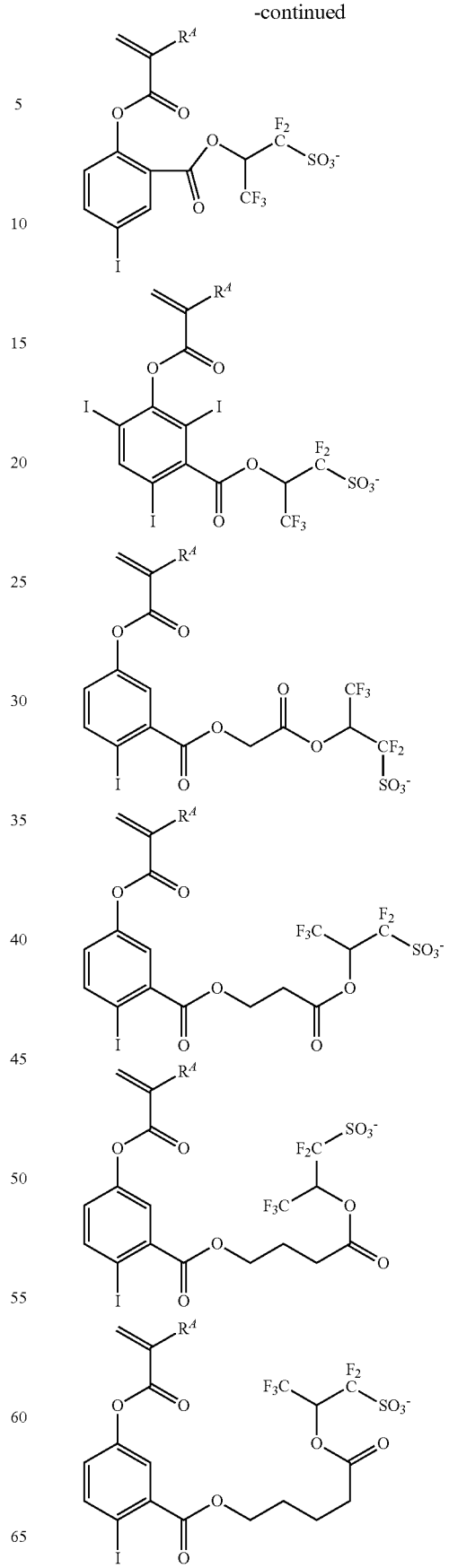

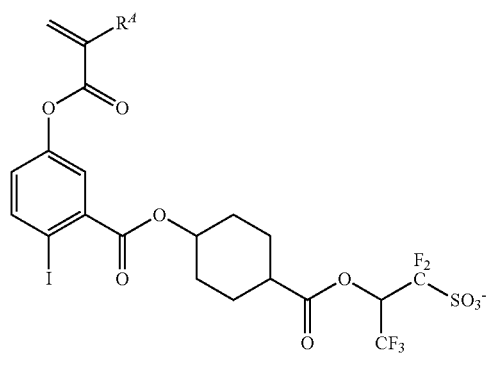
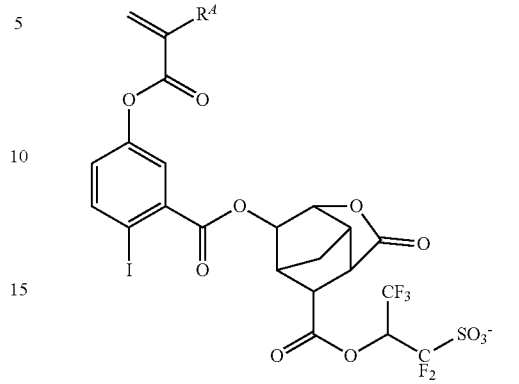
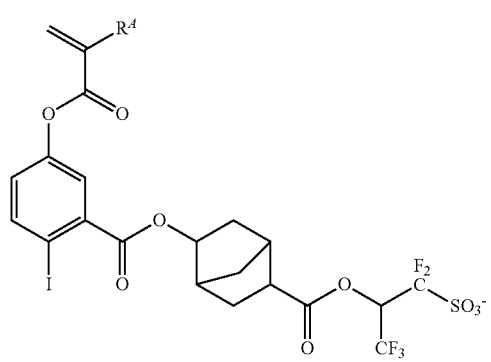
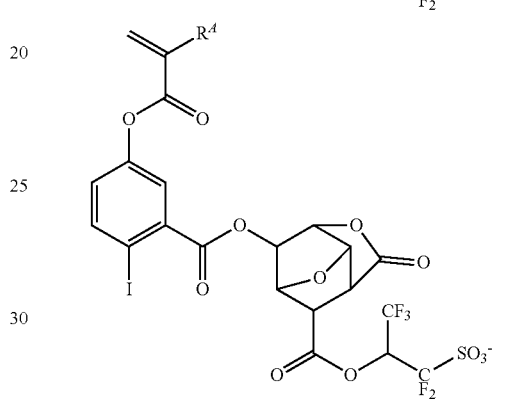
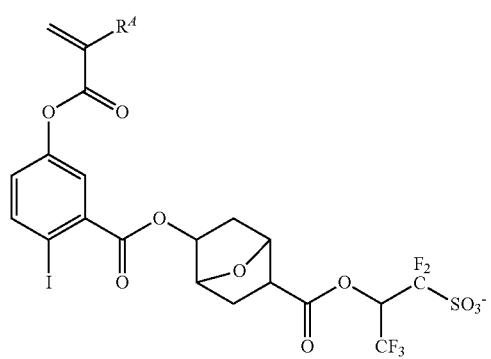
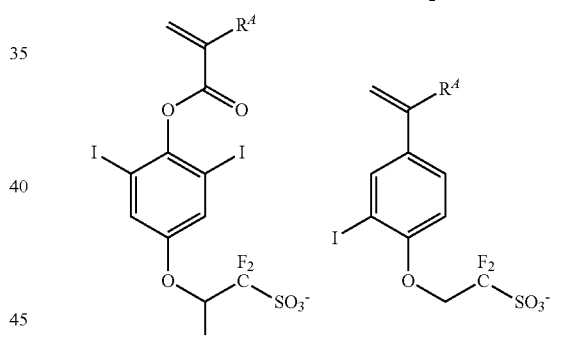
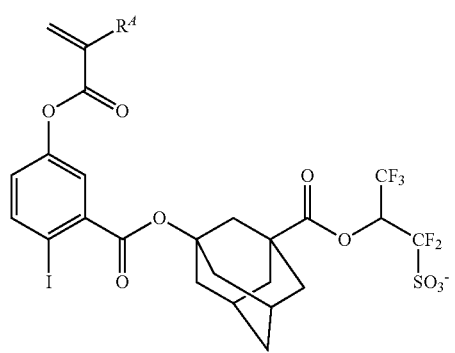
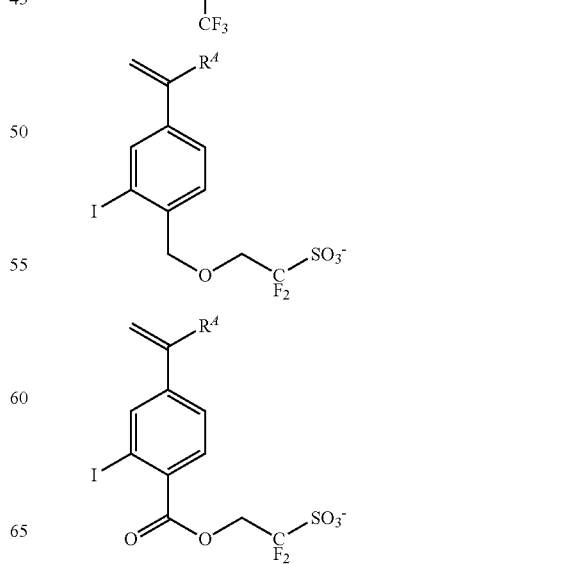

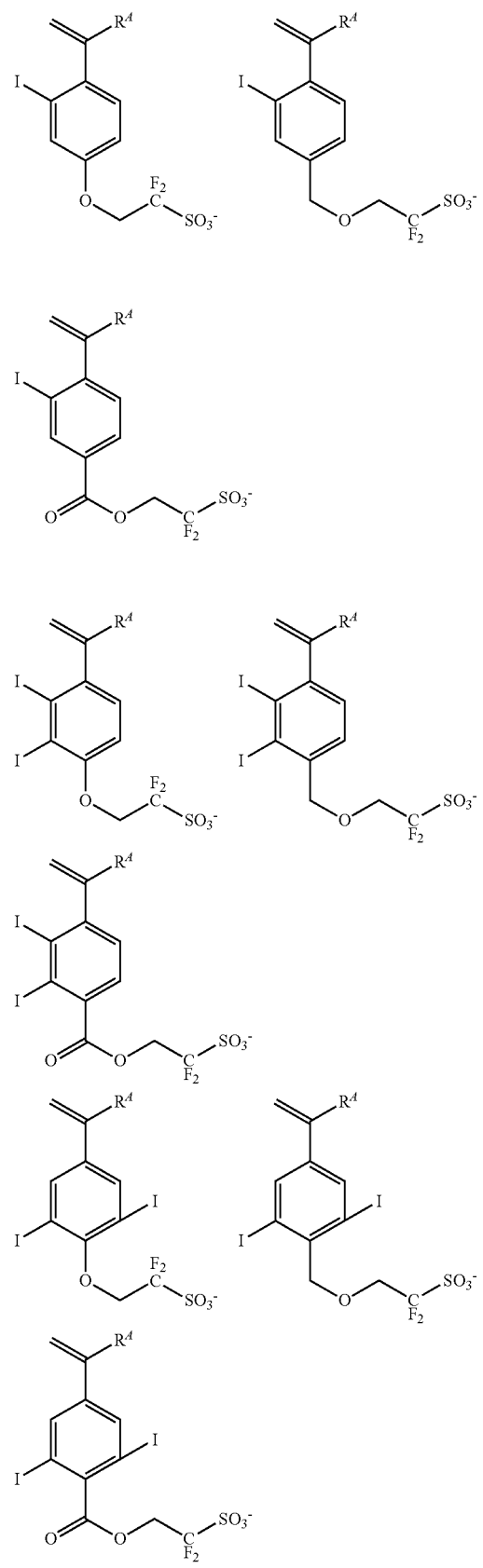
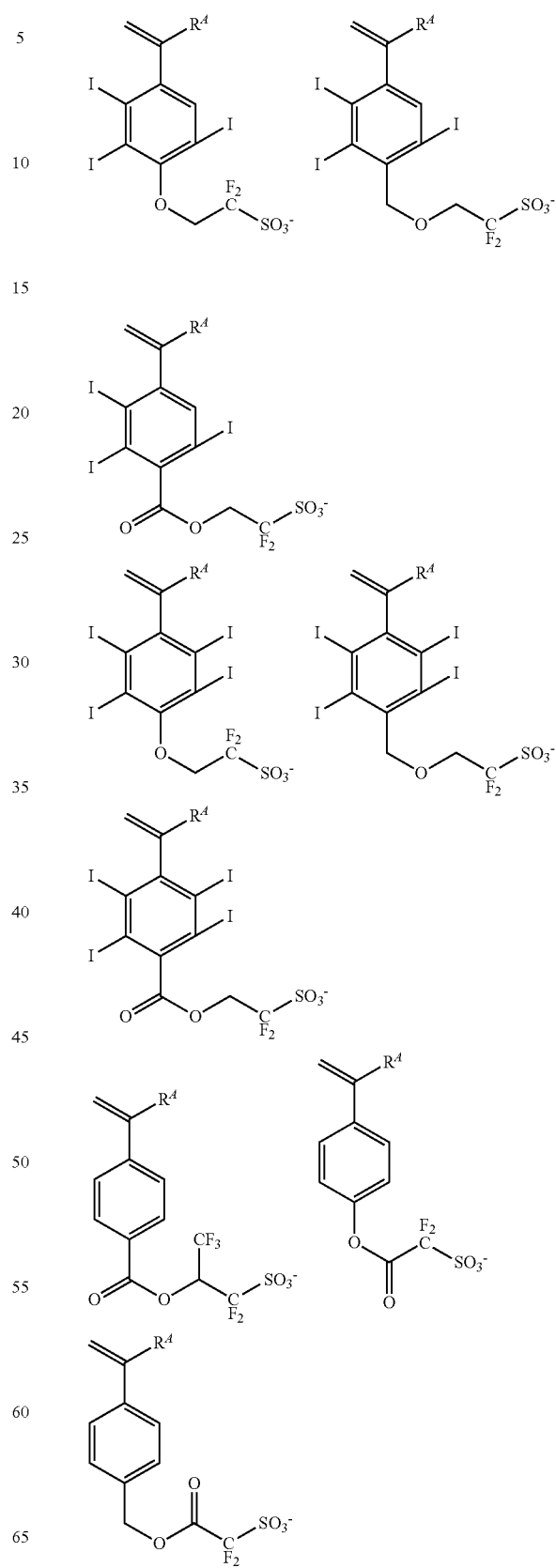

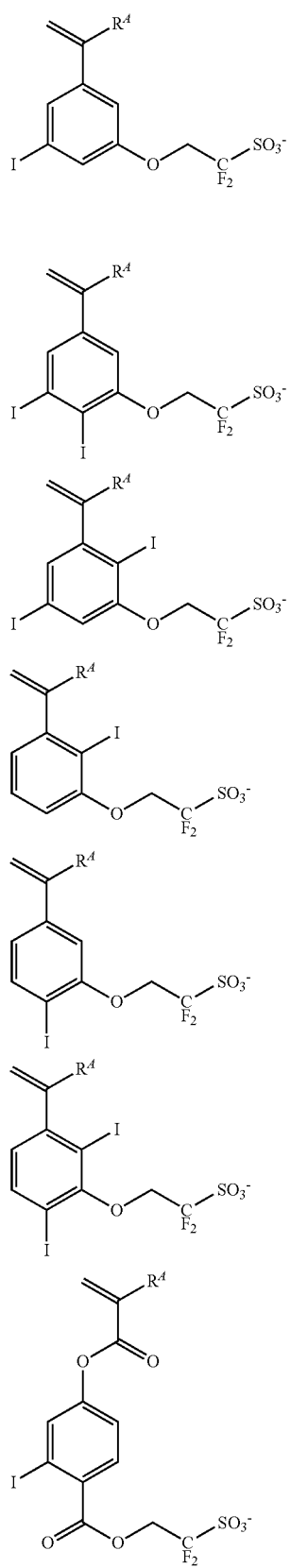
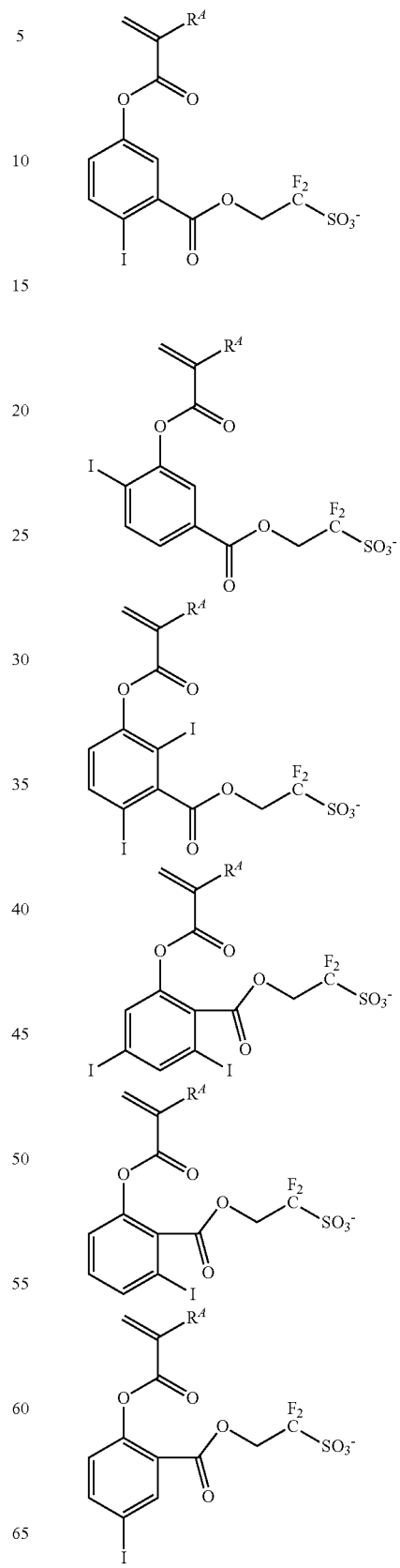

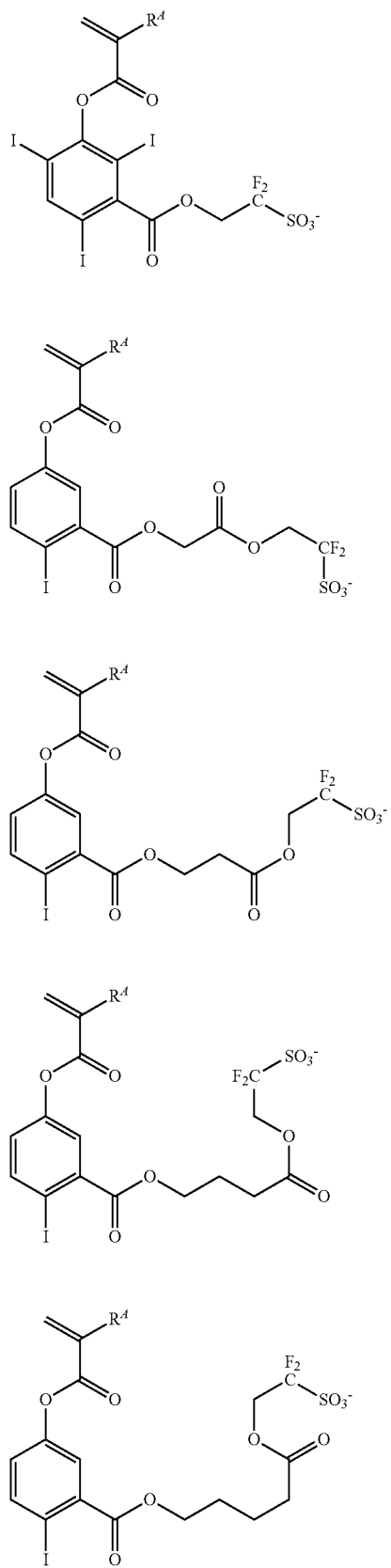
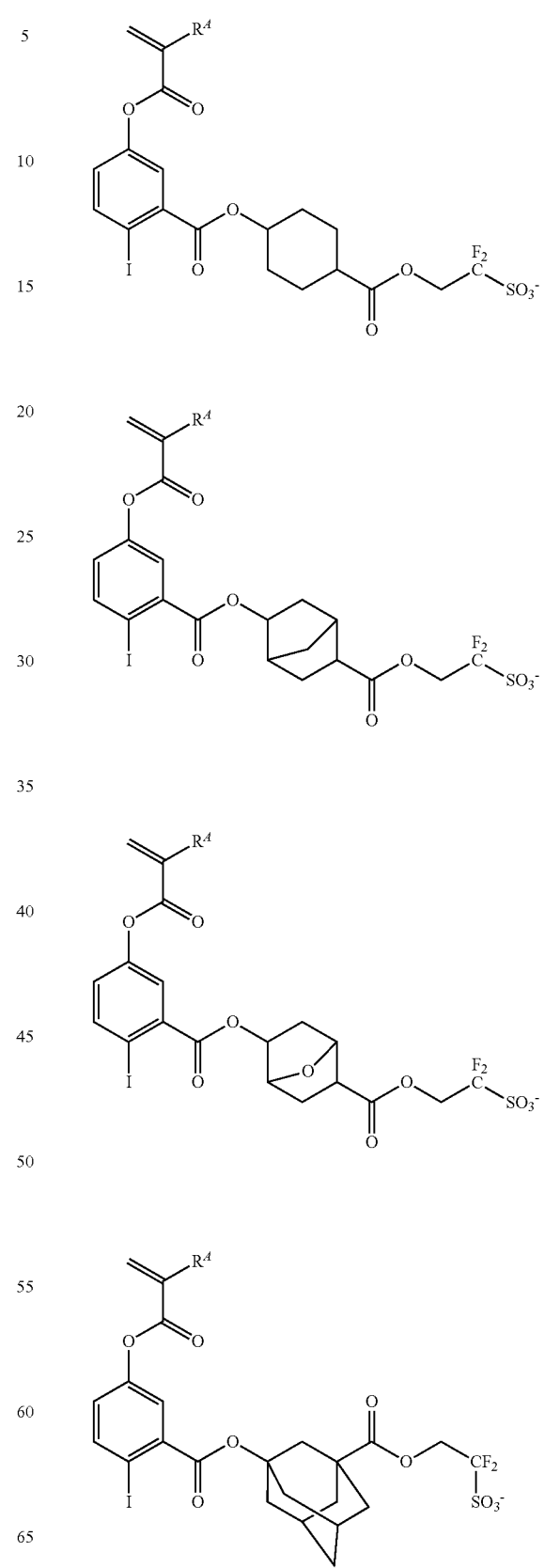

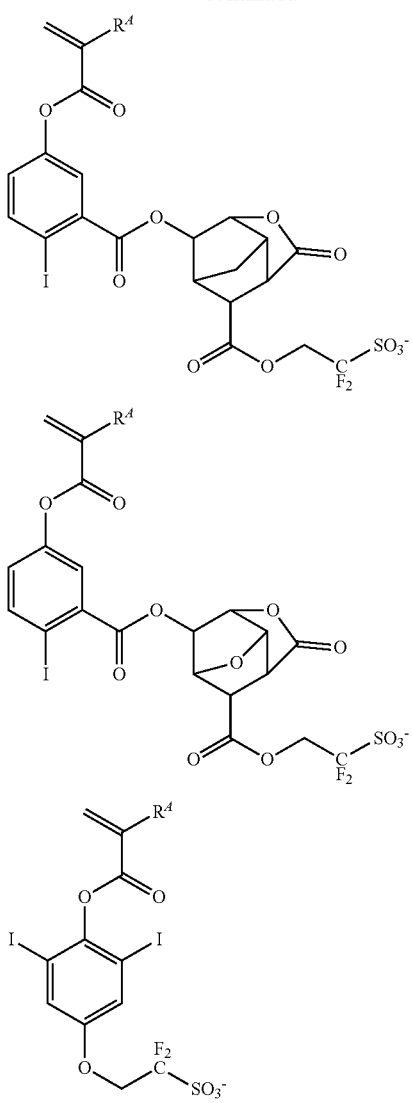
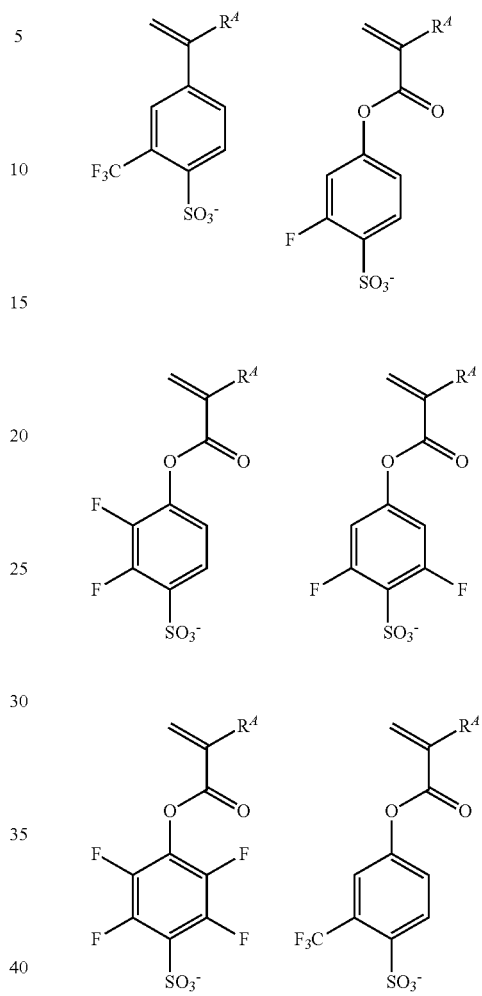
Examples of the anion in the monomer from which the recurring unit (d3) is derived are shown below, but not limited thereto. Herein $R^A$ is as defined above.
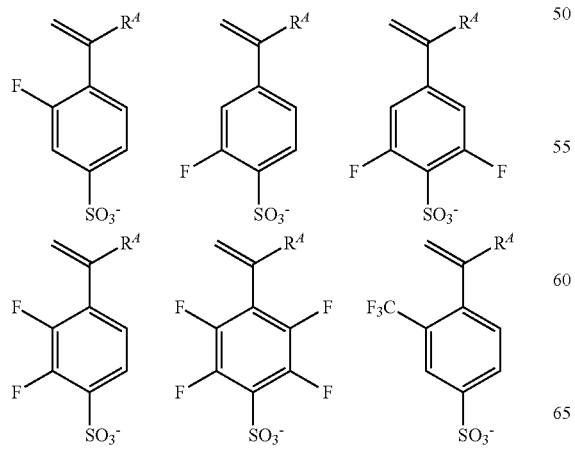
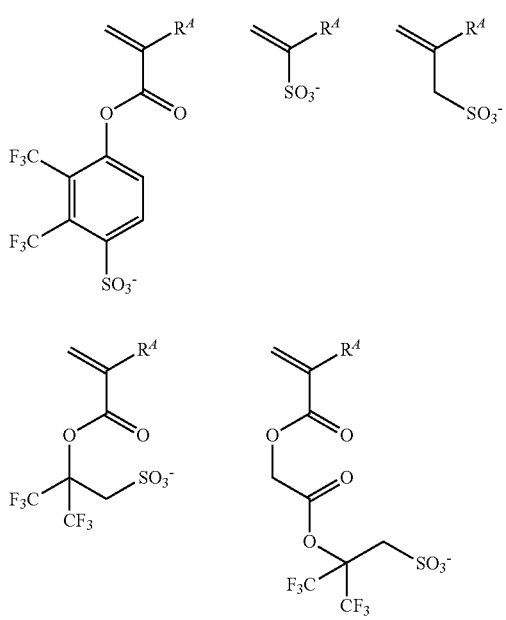

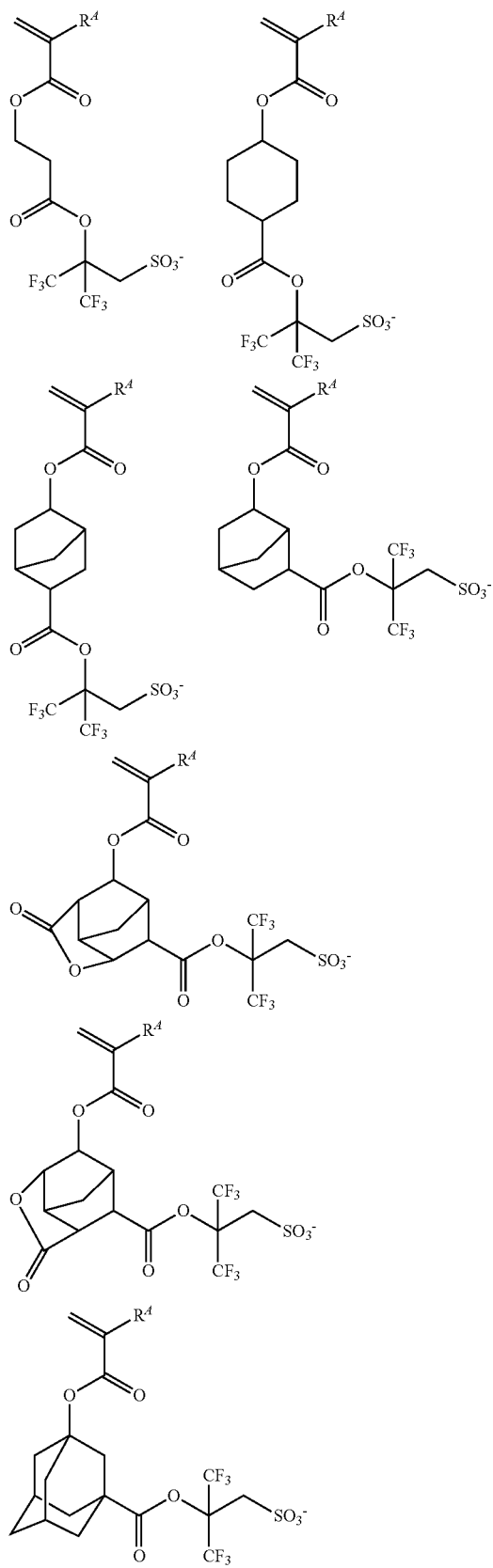
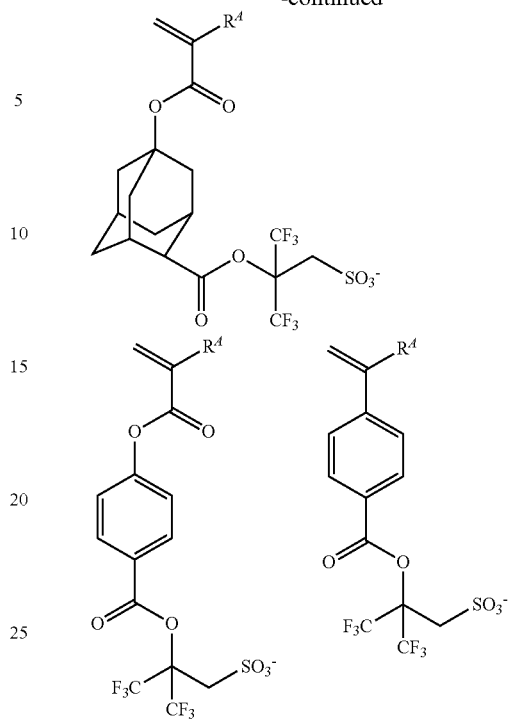

The recurring units (d1) to (d3) have the function of acid generator. The attachment of an acid generator to the polymer main chain is effective in restraining acid diffusion, thereby preventing a reduction of resolution due to blur by acid diffusion. Also edge roughness and size variation are improved since the acid generator is uniformly distributed. When a base polymer comprising the recurring units (d) is used, an acid generator of addition type (to be described later) may be omitted.

Besides the recurring units described above, the base polymer may further comprise recurring units (e), which are derived from a monomer such as styrene, acenaphthylene, indene, coumarin, or coumarone.

In the base polymer comprising recurring units (a), (b1), (b2) (c), (d1), (d2), (d3), and (e), a fraction of these units is: preferably $0<a<1.0$, $0≤b1≤0.9$, $0≤b2≤0.9$, $0≤b1+b2≤0.9$, $0≤c≤0.9$, $0≤d1≤0.5$, $0≤d2≤0.5$, $0≤d3≤0.5$, $0≤d1+d2+d3≤0.5$, and $0≤e≤0.5$; more preferably $0.01≤a≤0.8$, $0≤b1≤0.8$, $0≤b≤0.8$, $0≤b1+b2≤0.8$, $0≤c≤0.8$, $0≤d1≤0.4$, $0≤d2≤0.4$, $0≤d3≤0.4$, $0≤d1+d2+d3≤0.4$, and $0≤e≤0.4$; and still more preferably $0.02≤a≤0.7$, $0≤b1≤0.7$, $0≤b2≤0.7$, $0≤b1+b2≤0.7$, $0≤c≤0.7$, $0≤d1≤0.3$, $0≤d2≤0.3$, $0≤d3≤0.3$, $0≤d1+d2+d3≤0.3$, and $0≤e≤0.3$. Notably, $a+b1+b2+c+d1+d2+d3+e=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization.

Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl-2,2-azobis(2-methylpropionate), benzoyl peroxide, and lauroyl peroxide. The polymerization temperature is preferably 50 to 80° C. The reaction time is preferably 2 to 100 hours, and more preferably 5 to 20 hours.

When a monomer having a hydroxyl group is copolymerized, the hydroxyl group may be replaced by an acetal group susceptible to deprotection with acid, typically ethoxyethoxy, prior to polymerization, and the polymerization may be followed by deprotection with weak acid and water. Alternatively, the hydroxyl group may be replaced by an acetyl, formyl, pivaloyl or similar group prior to polymerization, and the polymerization may be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene.

For alkaline hydrolysis, a base such as aqueous ammonia or triethylamine may be used. The reaction temperature is preferably −20° C. to 100° C., and more preferably 0° C. to 60° C. The reaction time is preferably 0.2 to 100 hours, and more preferably 0.5 to 20 hours.

The base polymer should preferably have a weight average molecular weight (Mw) in the range of 1,000 to 500.000, and more preferably 2,000 to 30,000, as measured by gel permeation chromatography (GPC) versus polystyrene standards using THF solvent. With too low a Mw, the resist composition may become less heat resistant. A polymer with too high a Mw may lose alkaline solubility and give rise to a footing phenomenon after pattern formation.

If the base polymer has a wide molecular weight distribution or dispersity (Mw/Mn), which indicates the presence of lower and higher molecular weight polymer fractions, there is a possibility that foreign matter is left on the pattern or the pattern profile is degraded after exposure. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

In the base polymer, it is understood that a blend of two or more polymers which differ in compositional ratio. Mw or Mw/Mn is acceptable. It may also be a blend of a polymer containing the recurring units (a) and a polymer not containing the recurring units (a) and containing the recurring units (b1) and/or (b2).

Acid Generator

The positive resist composition may further contain an acid generator capable of generating a strong acid, also referred to as acid generator of addition type. As used herein, the "strong acid" is a compound having a sufficient acidity to induce deprotection reaction of acid labile groups on the base polymer. The acid generator is typically a compound capable of generating an acid upon exposure to actinic ray or radiation (photoacid generator (PAG)). Although the photoacid generator used herein is not particularly limited as long as it is capable of generating an acid upon exposure to high-energy radiation, photoacid generators capable of generating a sulfonic acid, an imide acid, or a methide acid are preferred. Suitable examples of the photoacid generator include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142].

As the PAG used herein, sulfonium salts having the formula (1-1) and iodonium salts having the formula (1-2) are also preferred.

(1-1)

(1-2)

In the formulae (1-1) and (1-2), $R^{101}$ to $R^{105}$ are each independently fluorine, chlorine, bromine, iodine, or a $C_1$-$C_{20}$ hydrocarbyl group which may contain a heteroatom.

The hydrocarbyl groups represented by $R^{101}$ to $R^{105}$ may be saturated or unsaturated, and straight, branched, or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl, and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl, and hexenyl; $C_2$-$C_{20}$ cyclic unsaturated aliphatic hydrocarbyl groups such as cyclohexenyl and norbornenyl; $C_2$-$C_{20}$ alkynyl groups such as ethynyl, propynyl, and butynyl: $C_6$-$C_{20}$ aryl groups such as phenyl, methylphenyl, ethylphenyl, n-propylphenyl, isopropylpheny, n-butylphenyL isobutylphenyl, se-butylphenyl, tert-butylphenyl, naphthyl, uethylnaphthyl, ethylnaphthyl, n-propynaphthyl, isopropylnaphthyl, n-butylnaphthyl, isobutylnaphthyl, sec-butylnaphthyl, and tert-butylnaphthyl; and $C_7$-$C_{20}$ aralkyl groups such as benzyl and phenethyl. In these groups, some hydrogen atoms may be substituted by a group containing a heteroatom such as oxygen, sulfur, nitrogen, or halogen, or some carbon may be replaced by a group containing a heteroatom such as oxygen, sulfur, or nitrogen, so that the group may contain a hydroxyl group, a cyano group, a carbonyl group, an ether bond, an ester bond, a sulfonic acid ester bond, a carbonate group, a lactone ring, a sultone ring, a carboxylic anhydride, or a haloalkyl group.

$R^{101}$ and $R^{102}$ may bond together to form a ring with the sulfur atom to which they are attached. Rings of the following structure are preferred.

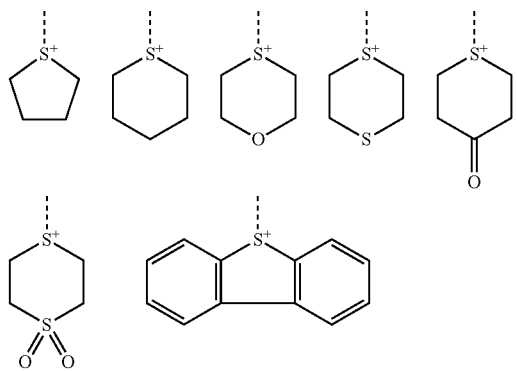

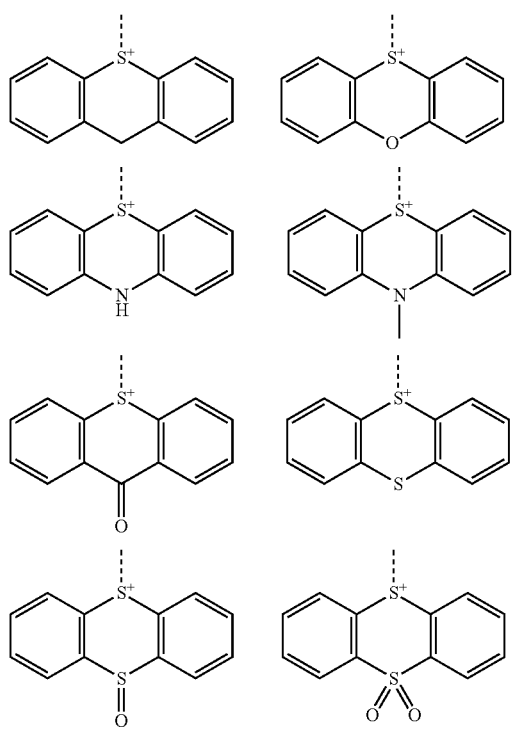
Herein the broken line designates a valence bond to $R^{103}$.
Examples of the cation in the sulfonium salt having the formula (1-1) are shown below, but not limited thereto.
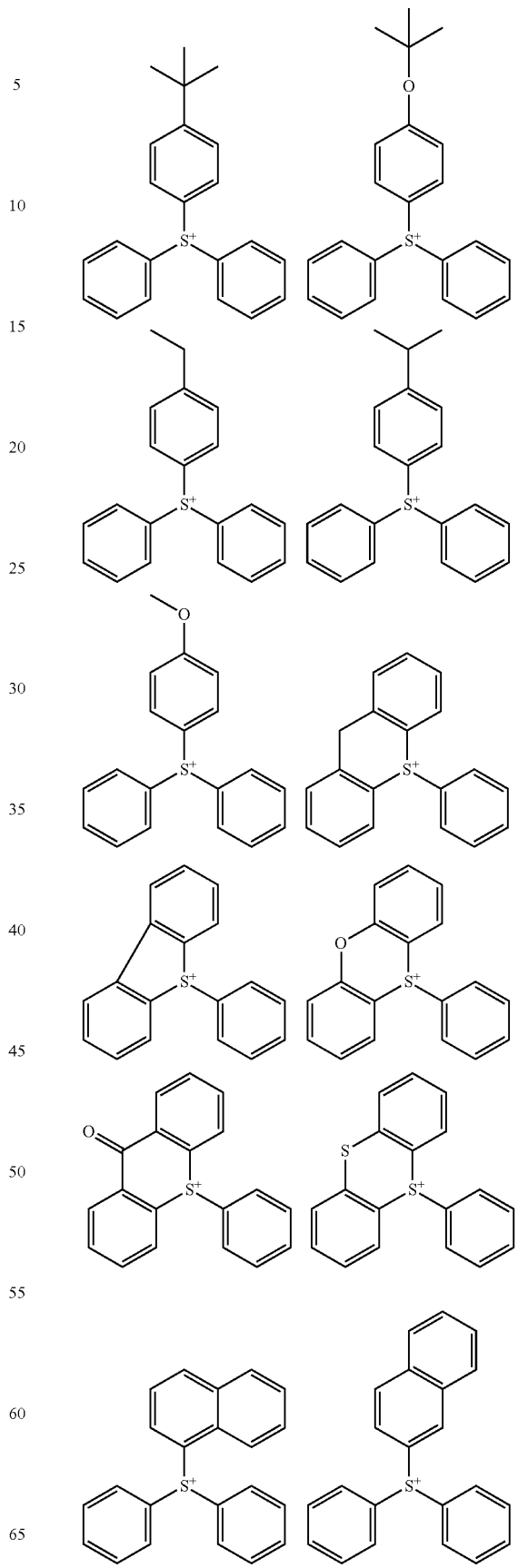

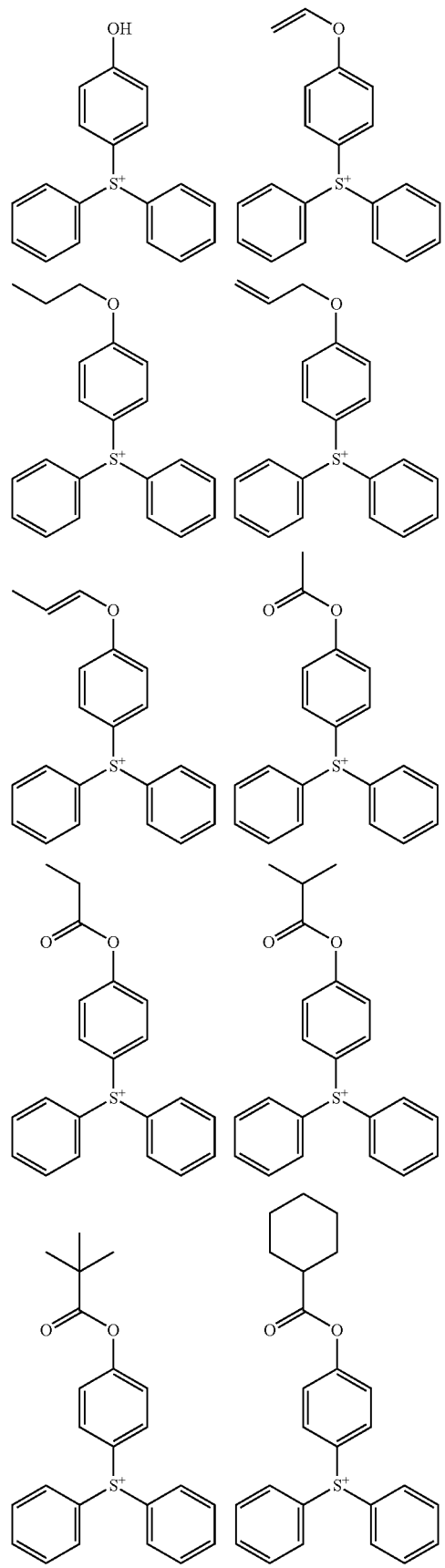
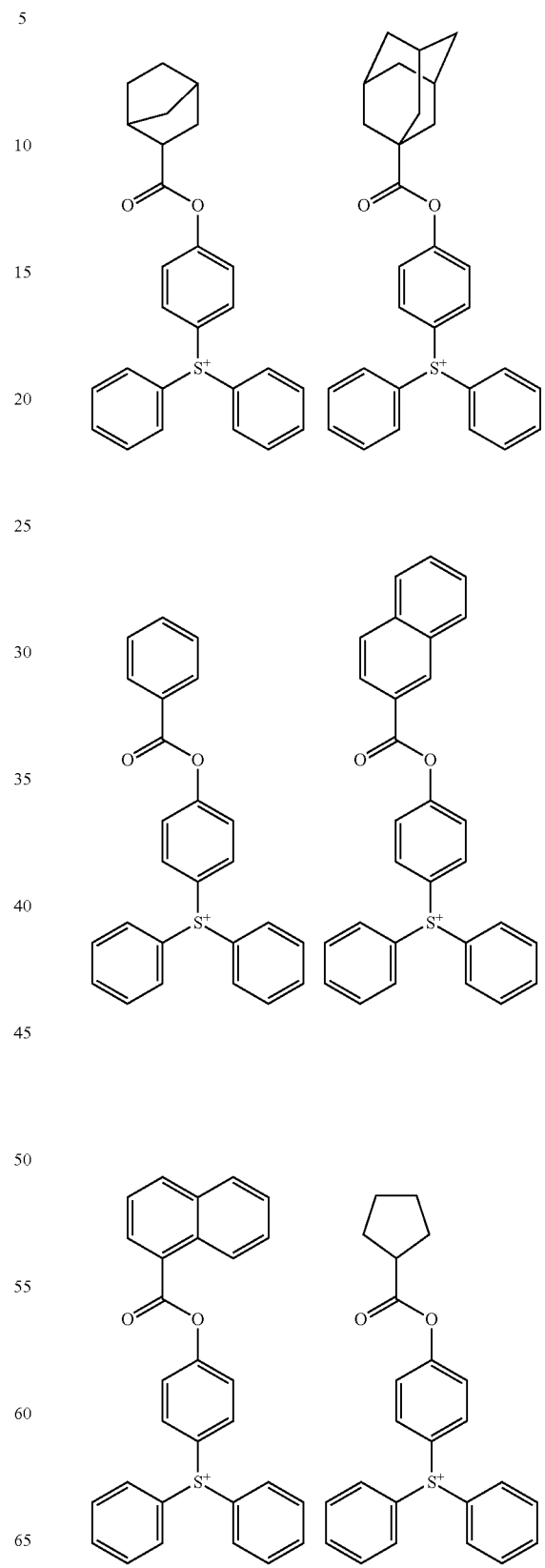

95
-continued
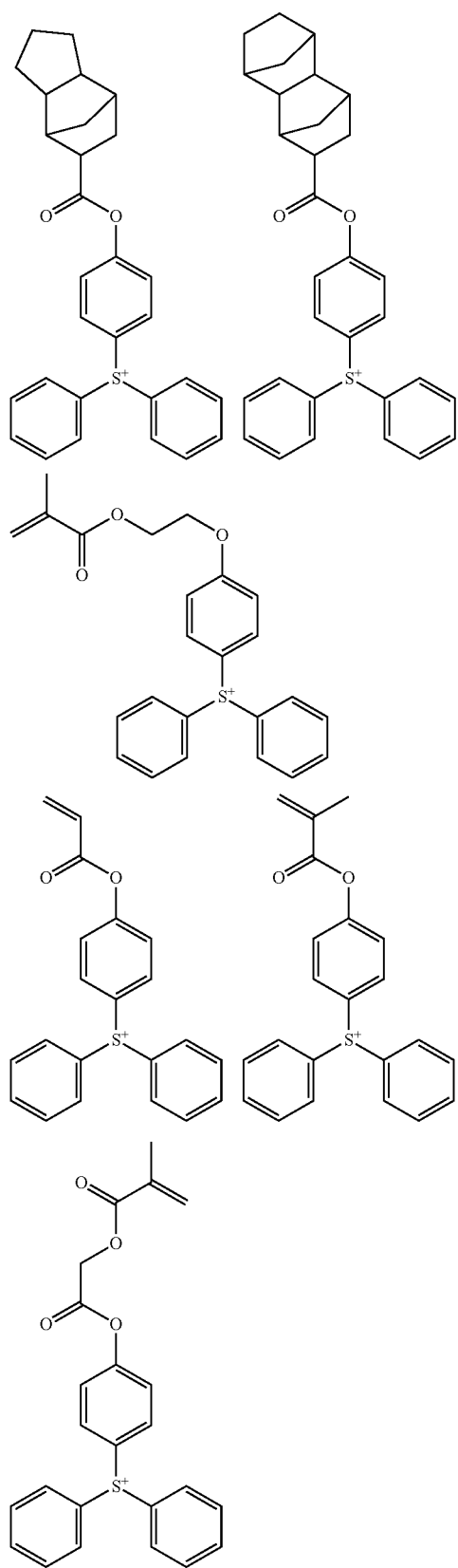
96
-continued
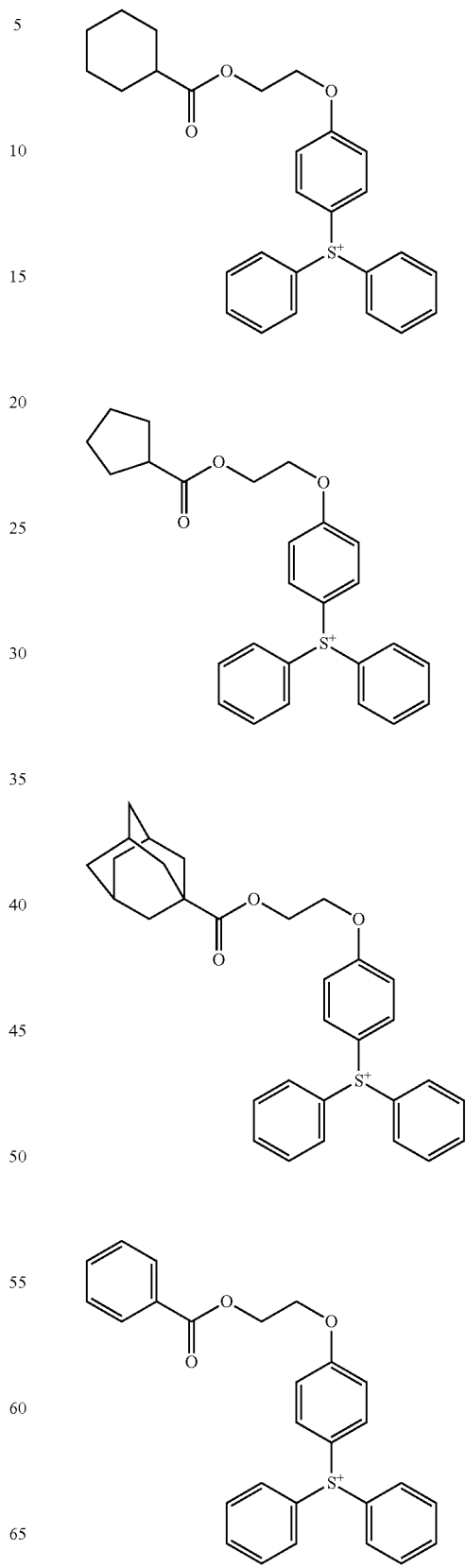

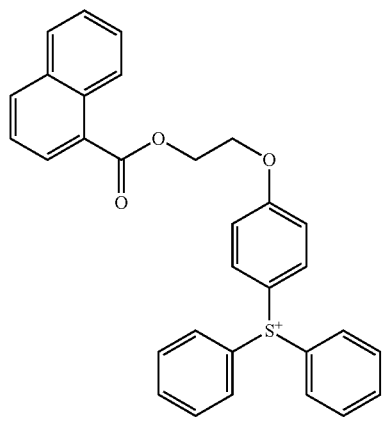
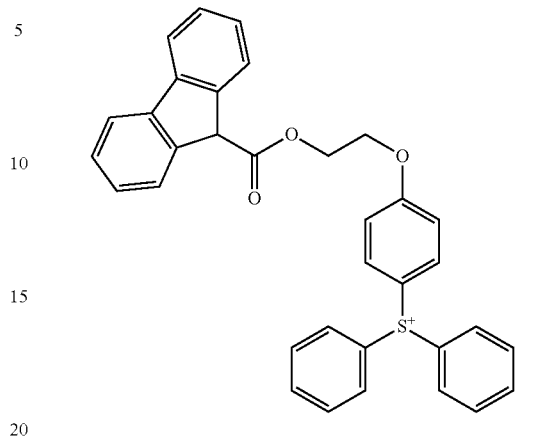
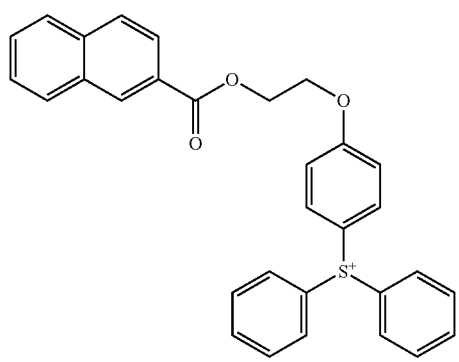
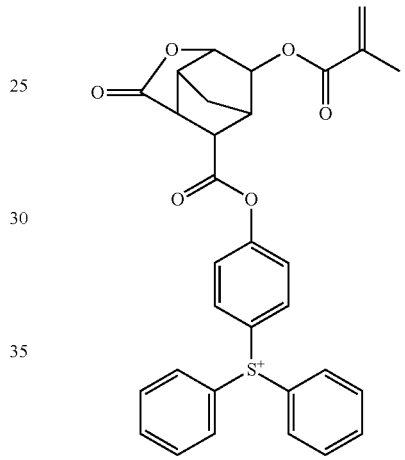
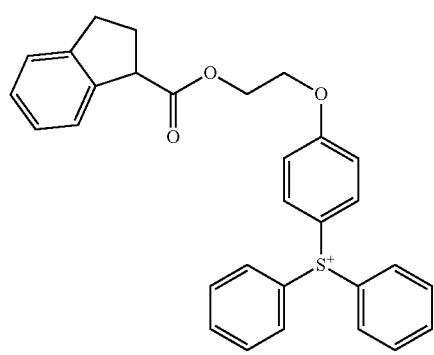
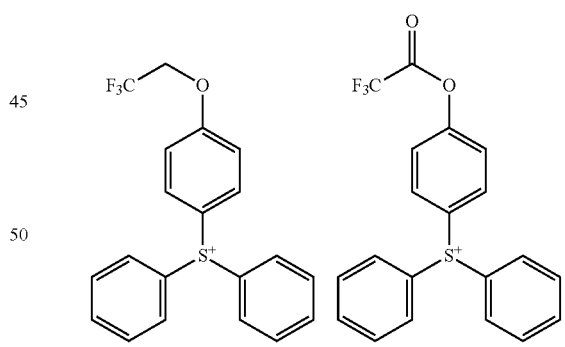
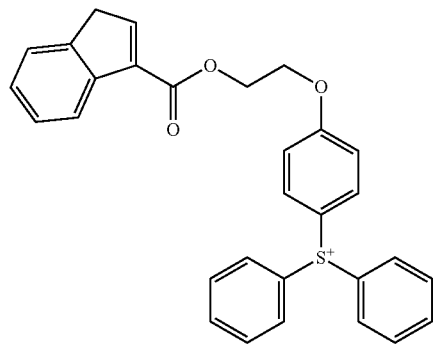
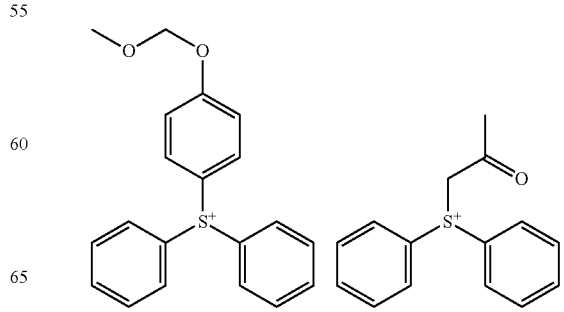

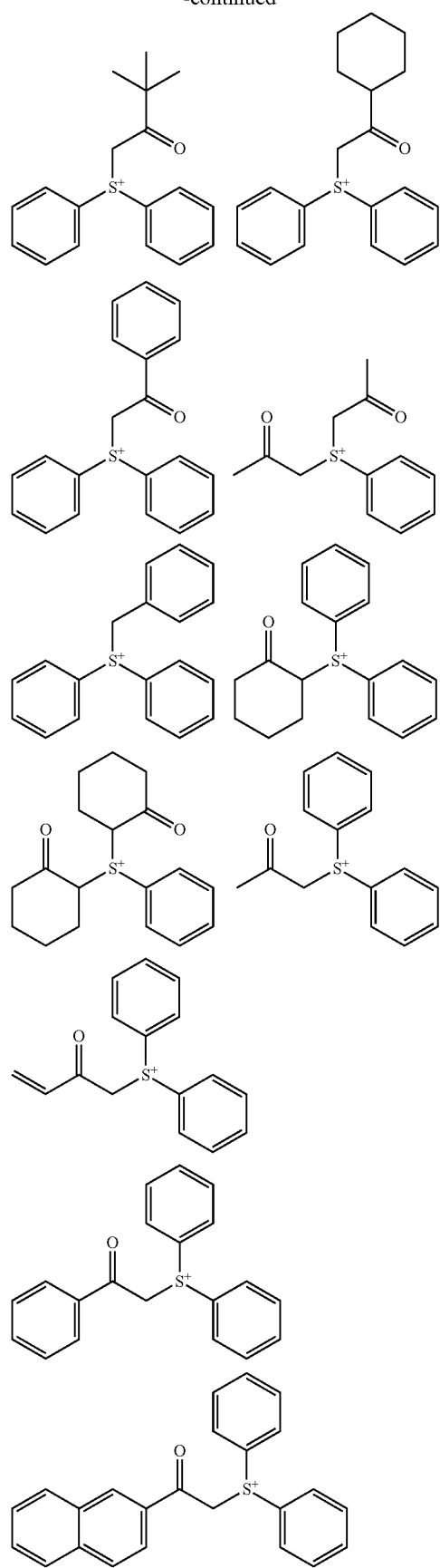
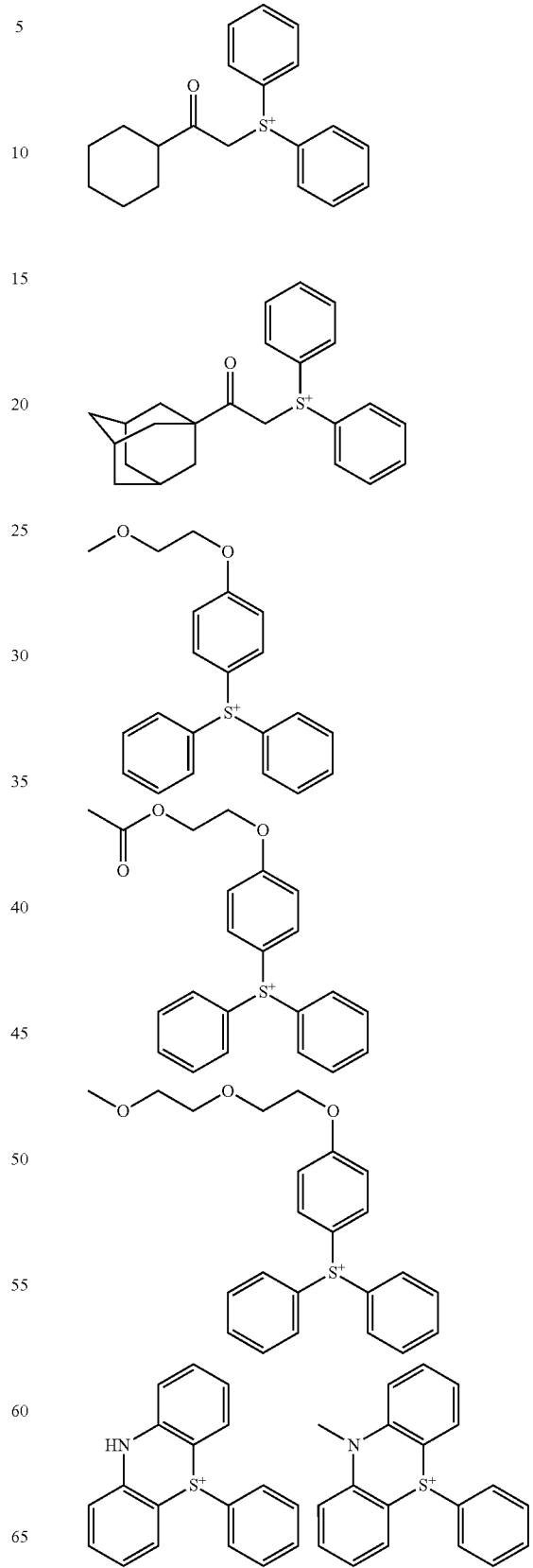

101
-continued
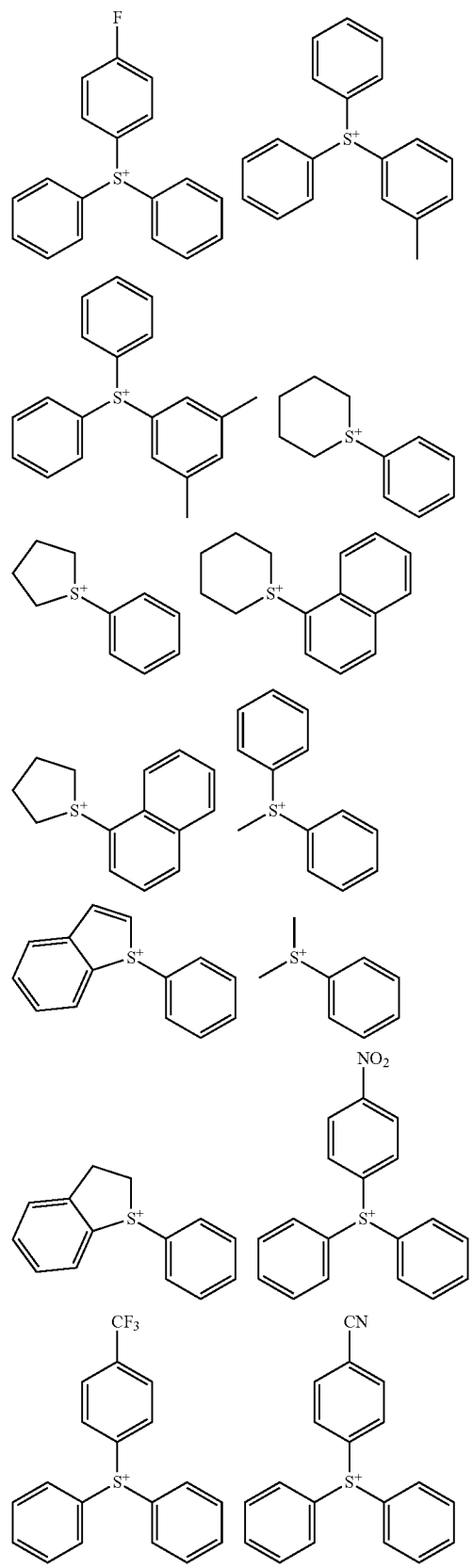
102
-continued
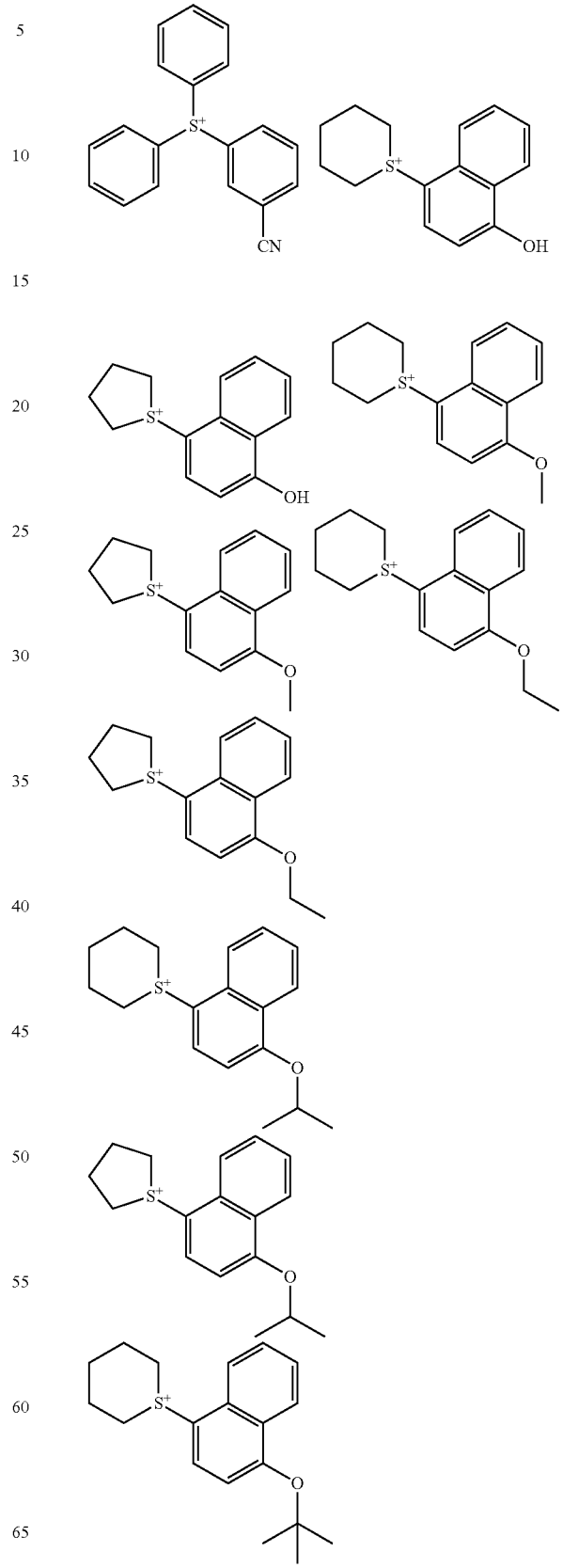

103
-continued
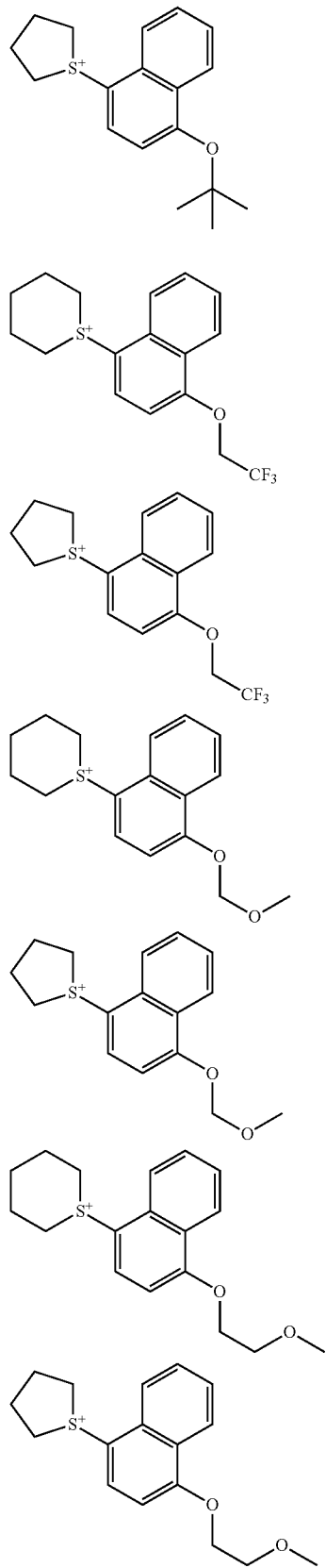
104
-continued
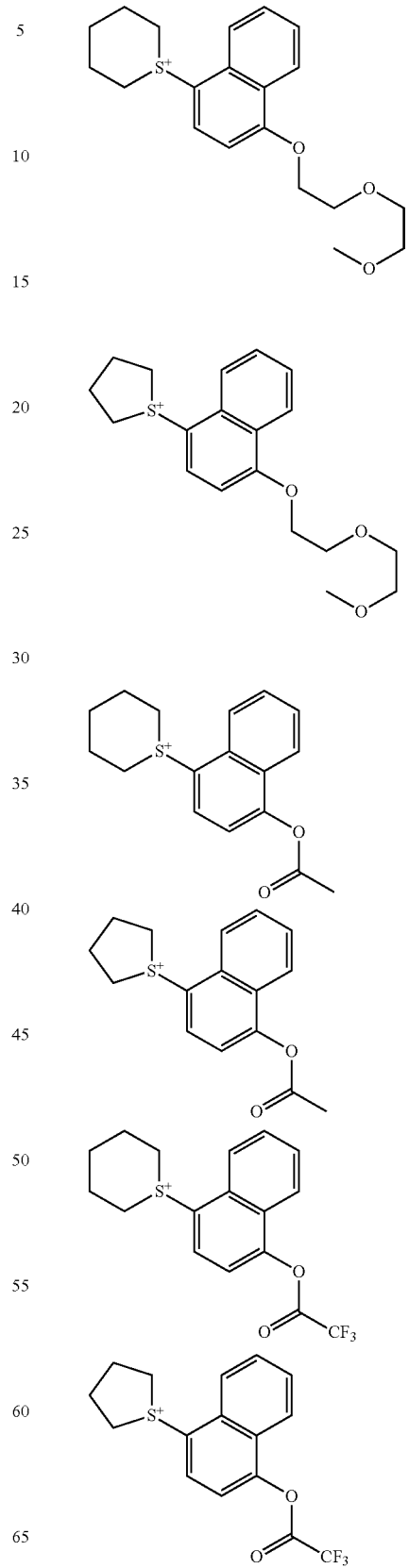

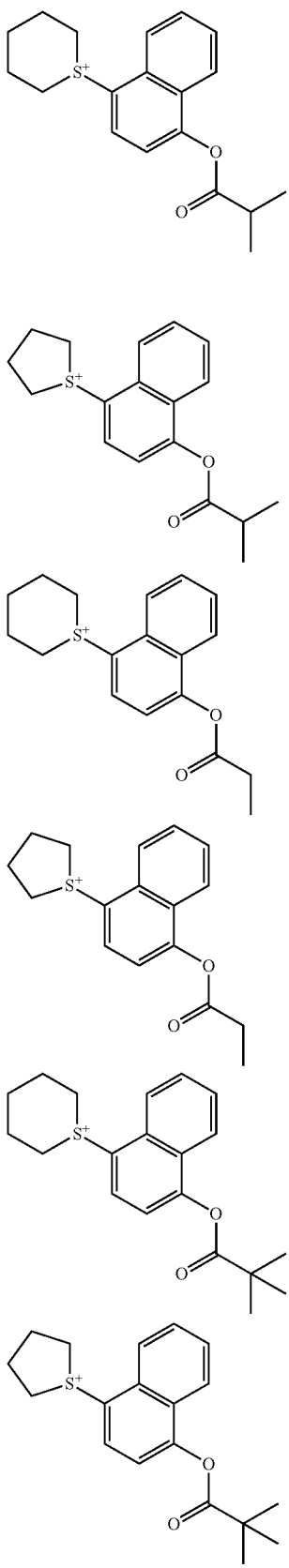
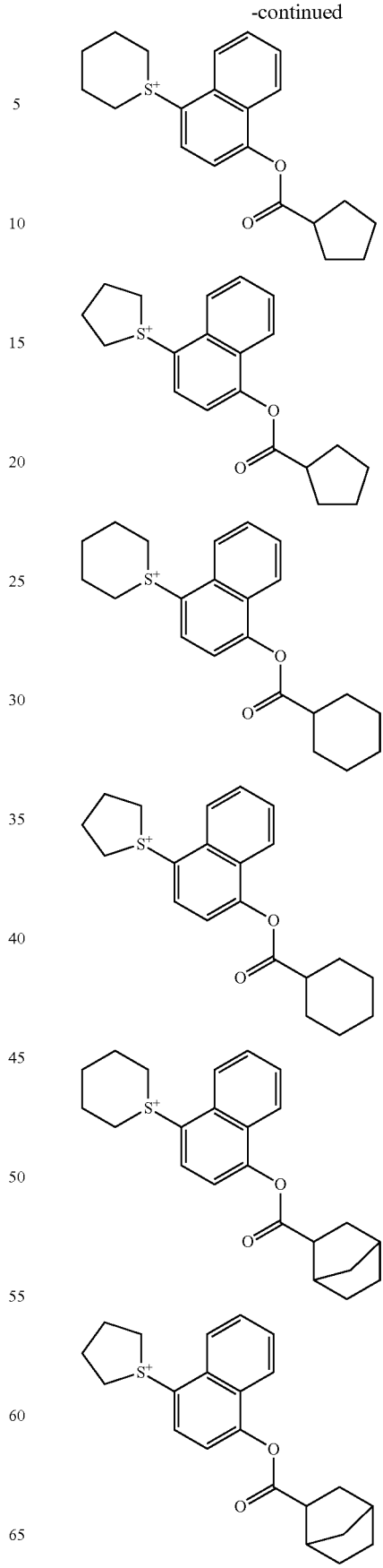

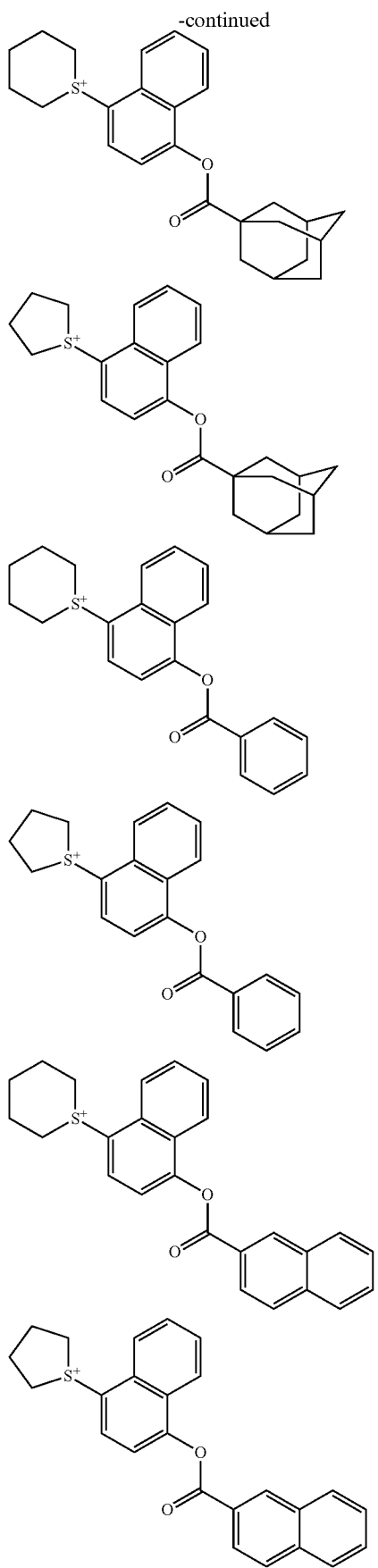
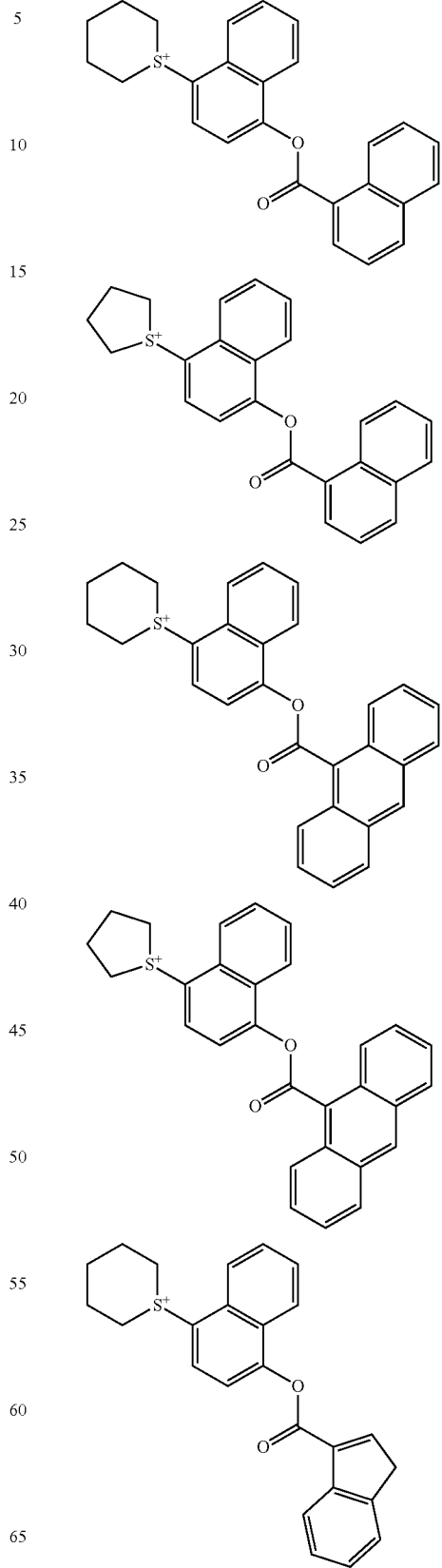

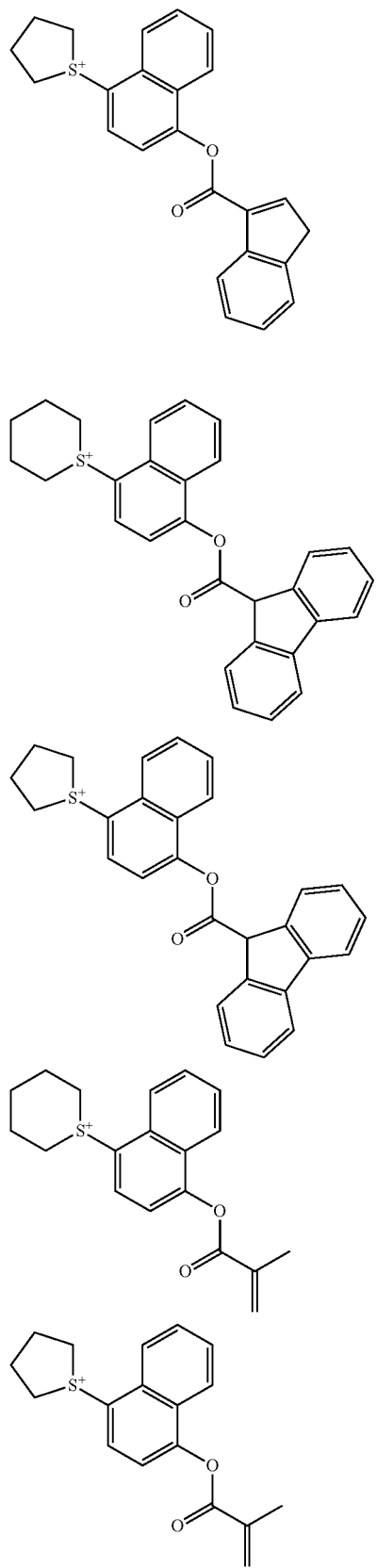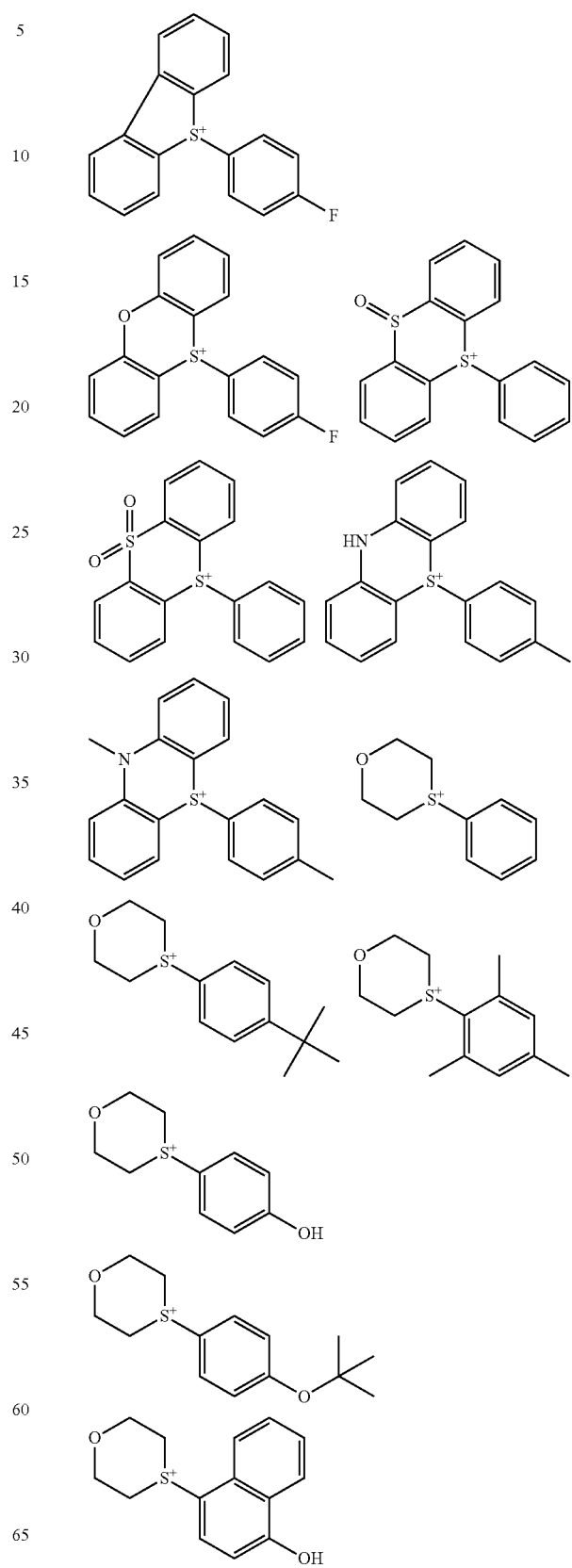

111
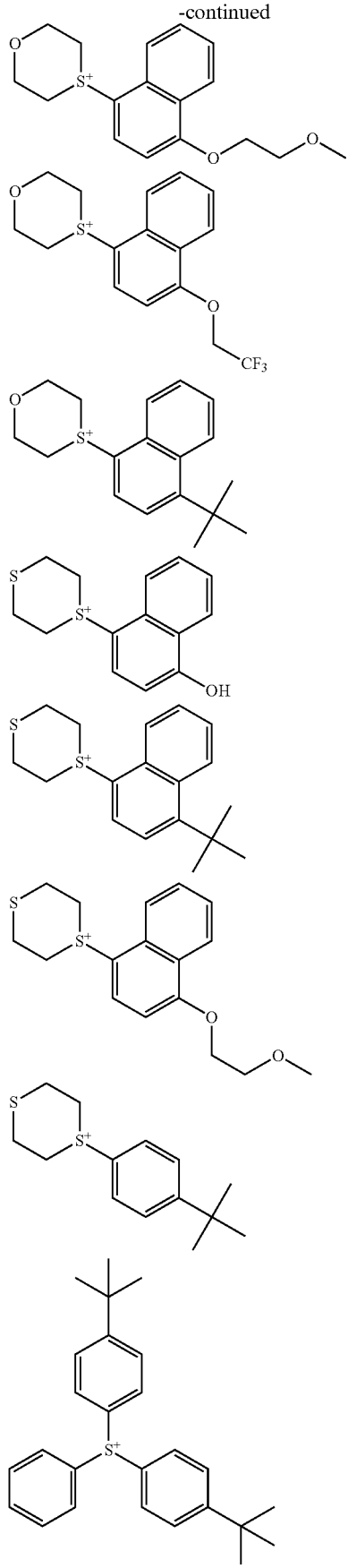
112
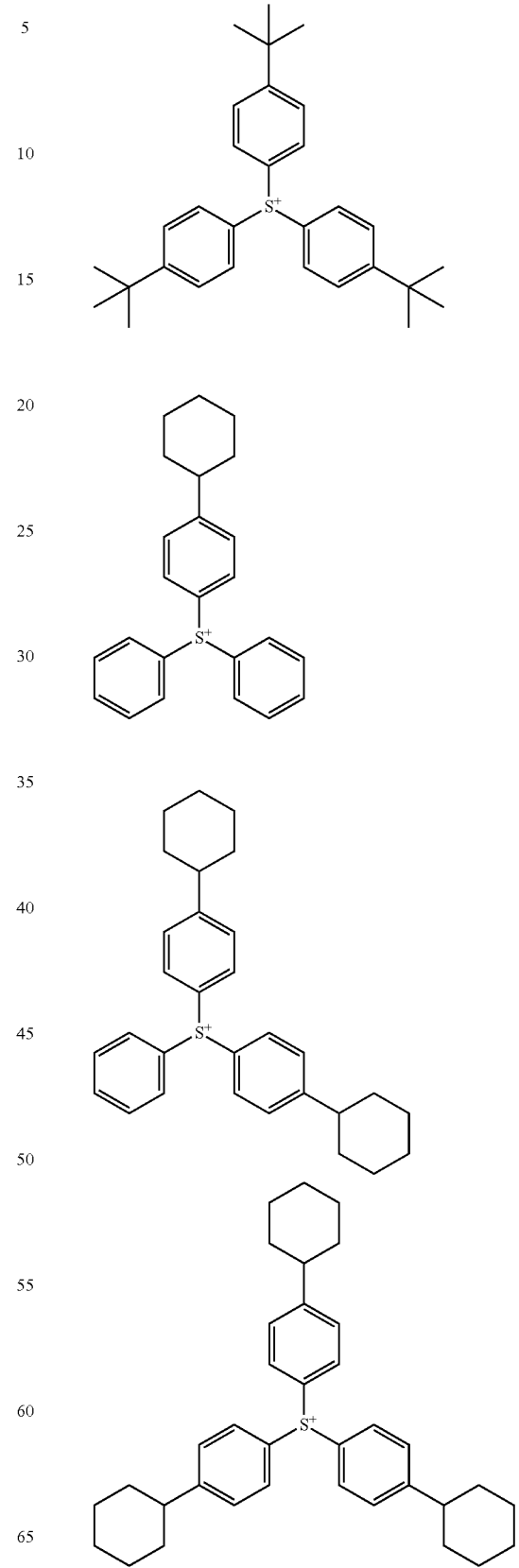

113
-continued
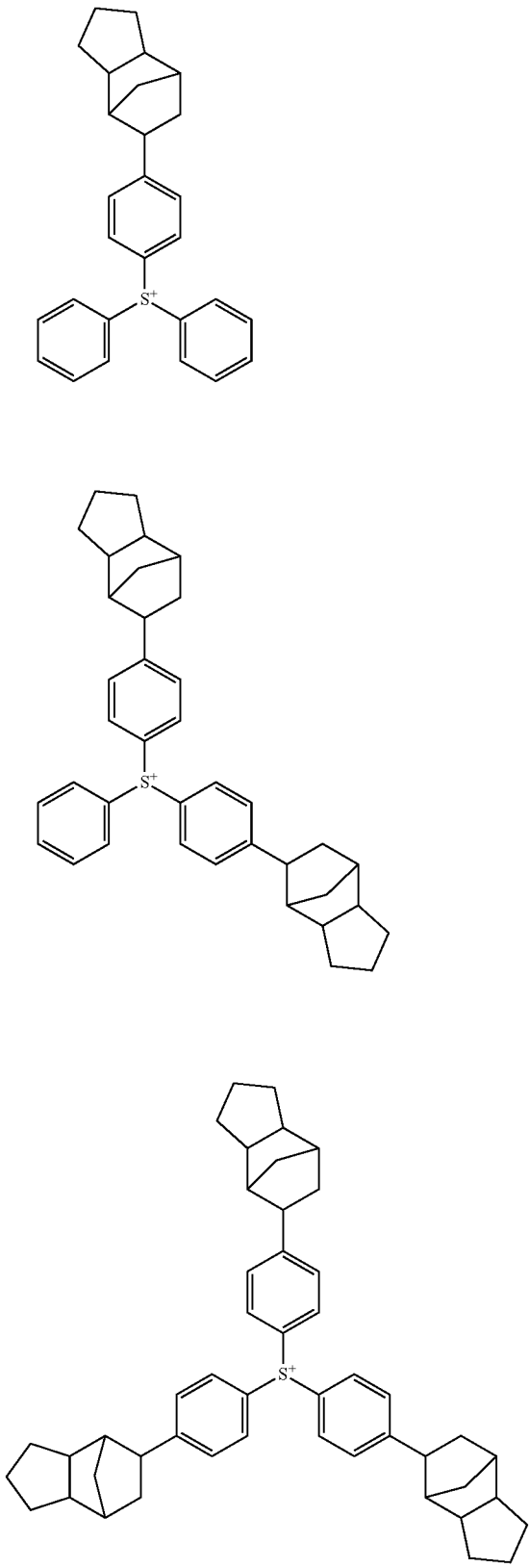
114
-continued
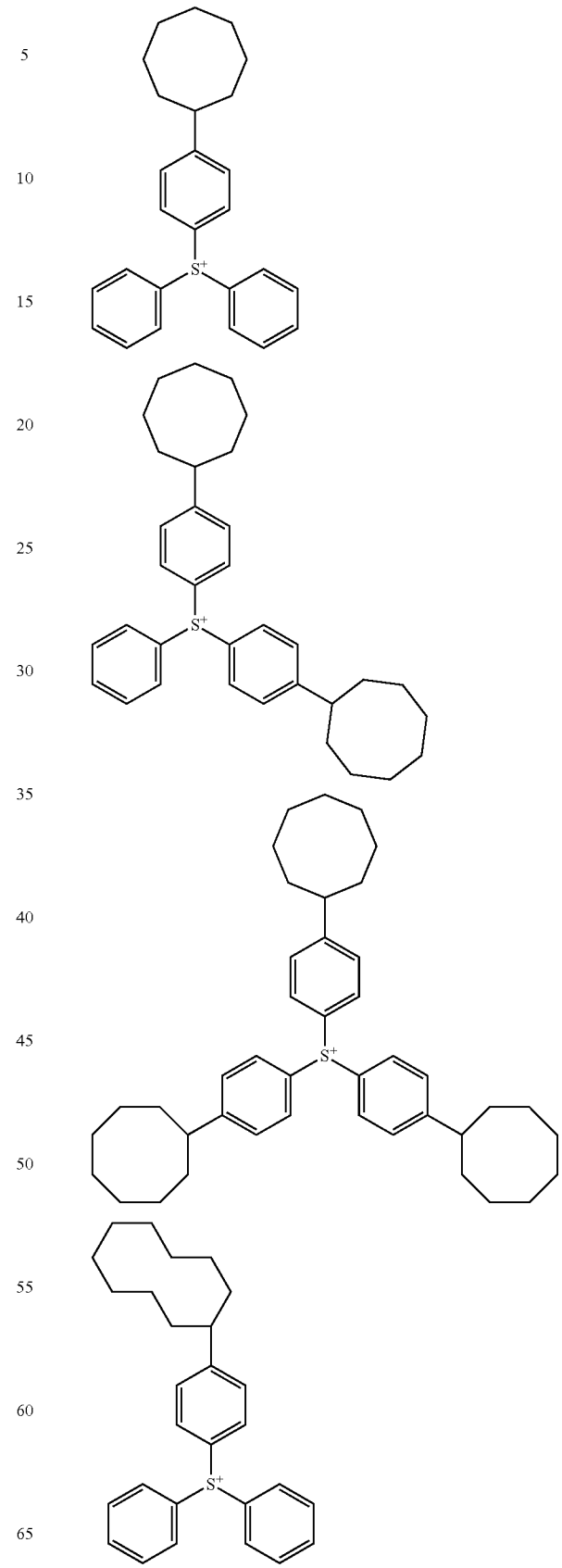

115
-continued
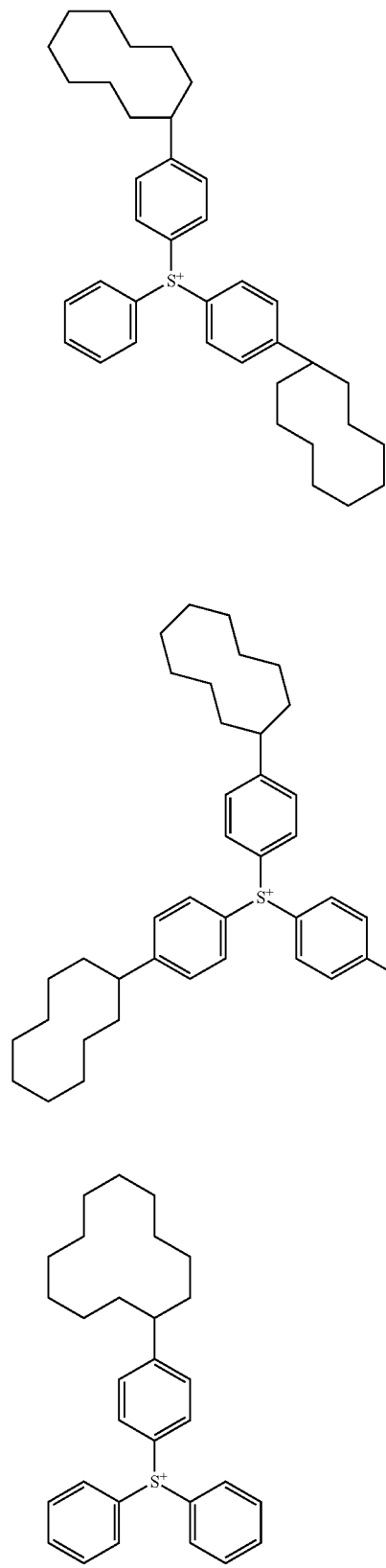
116
-continued
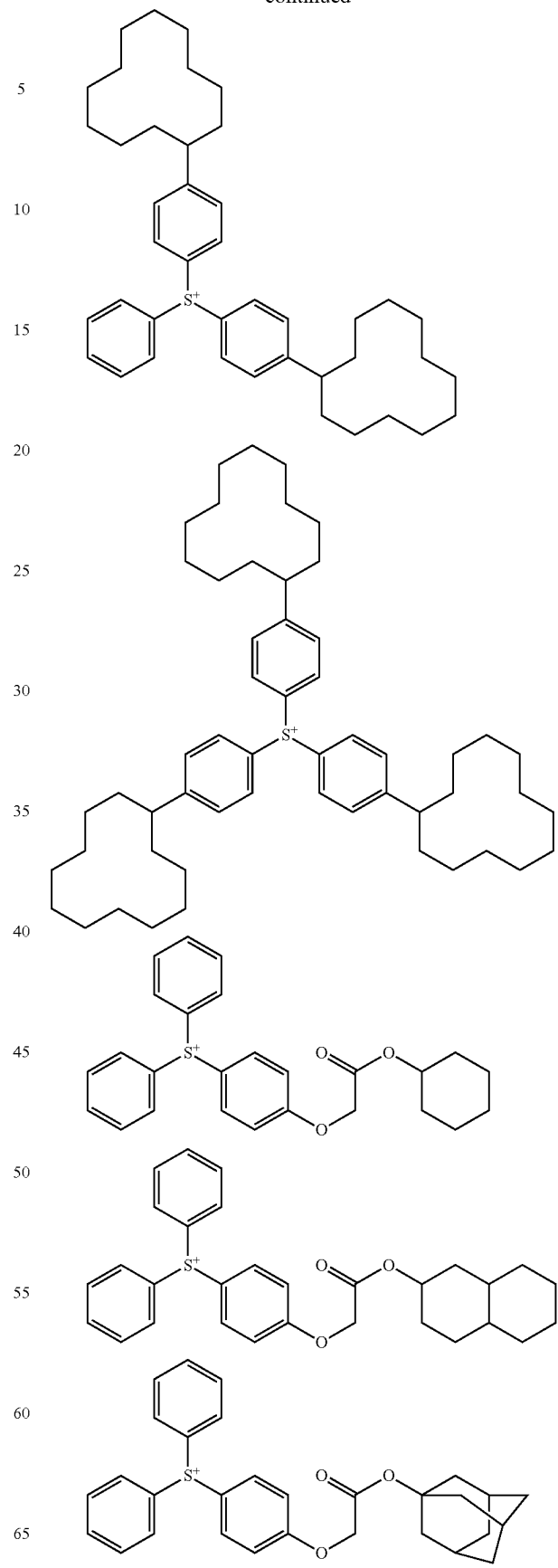

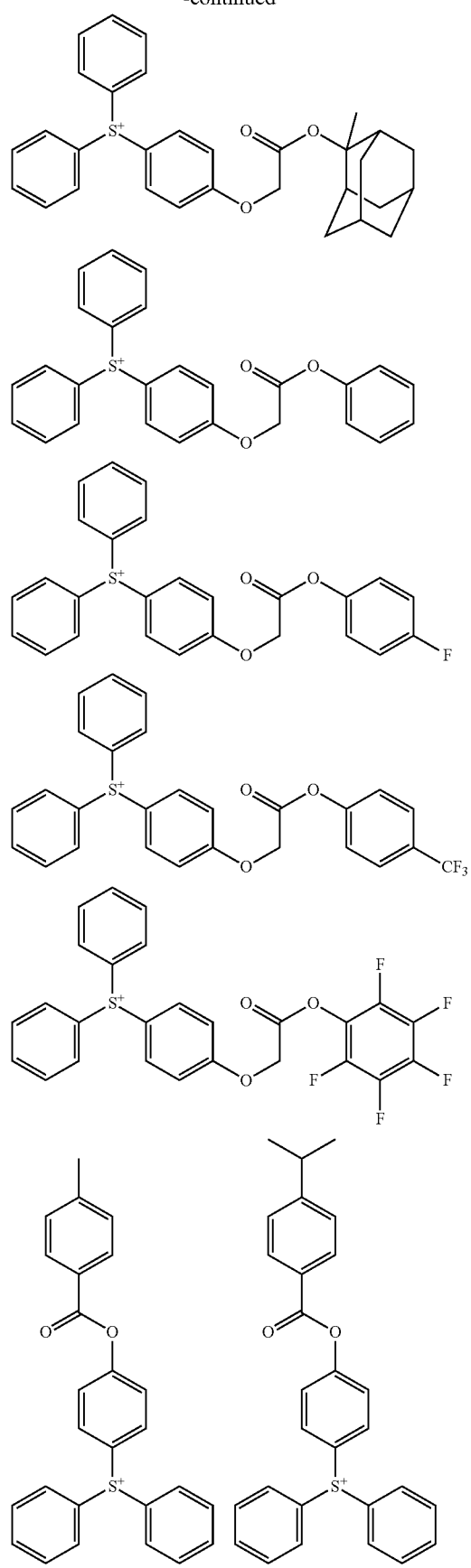
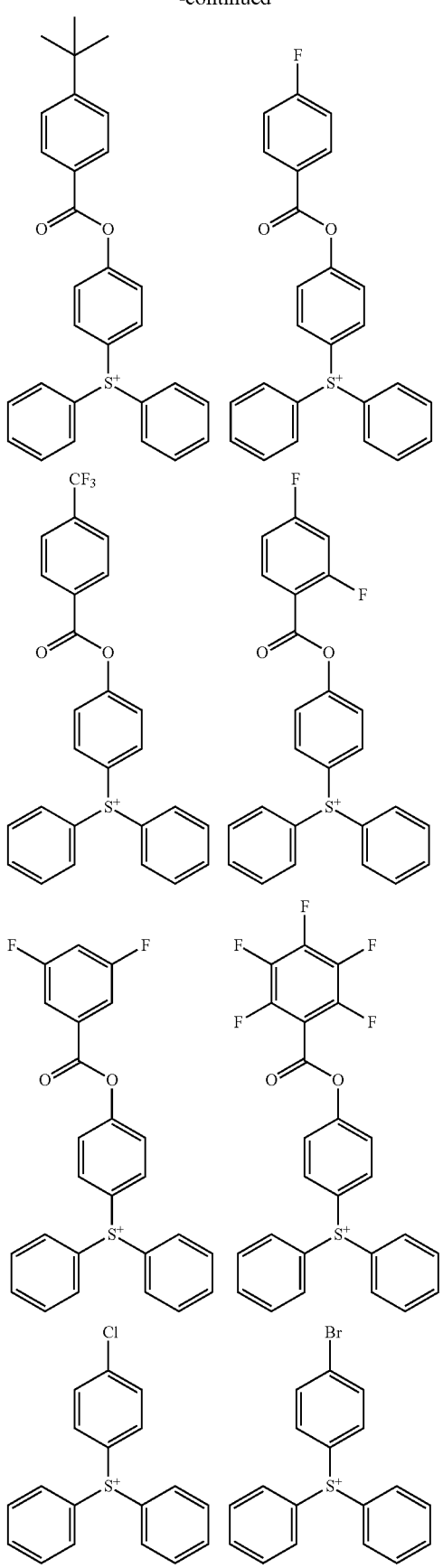

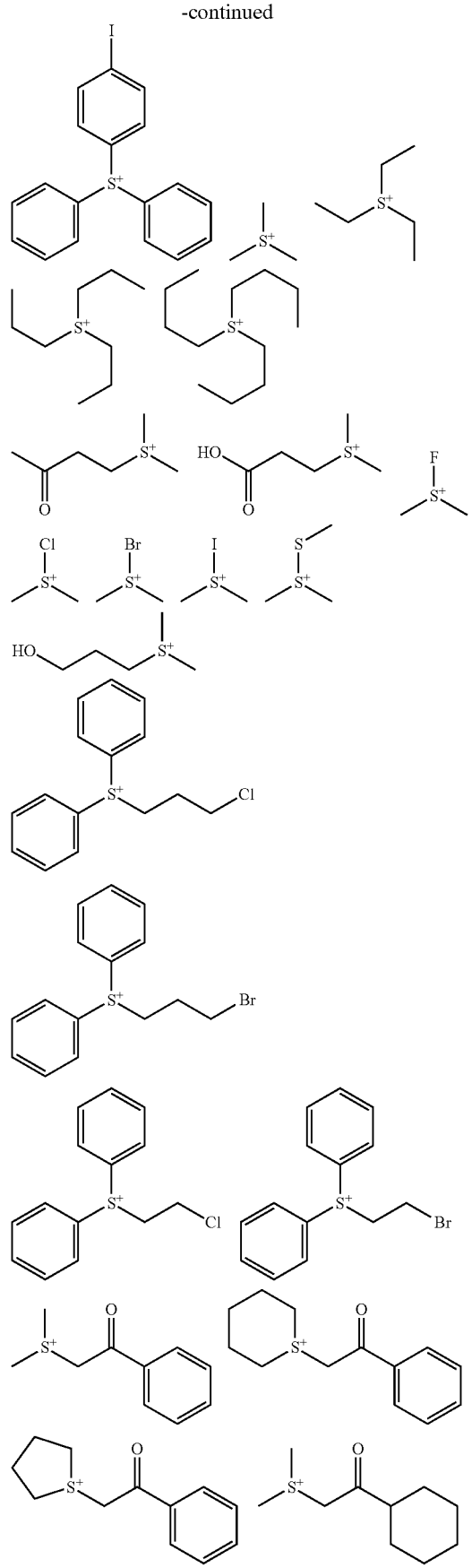
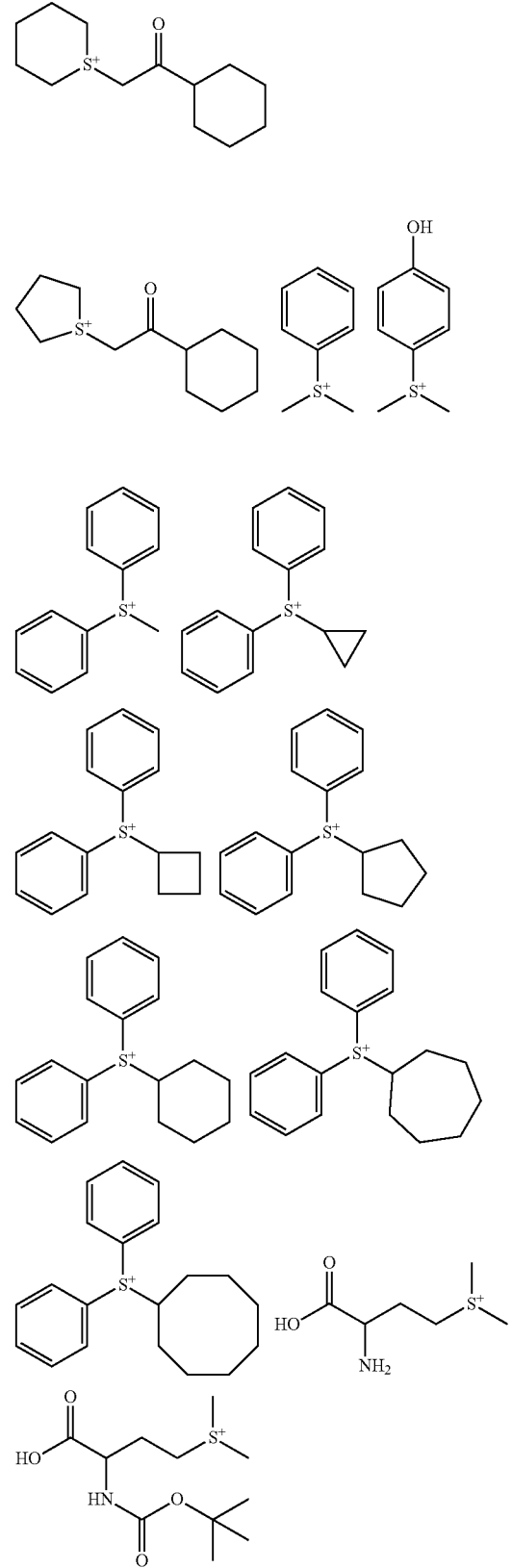

Examples of the cation in the iodonium salt having the formula (1-2) are shown below, but not limited thereto.
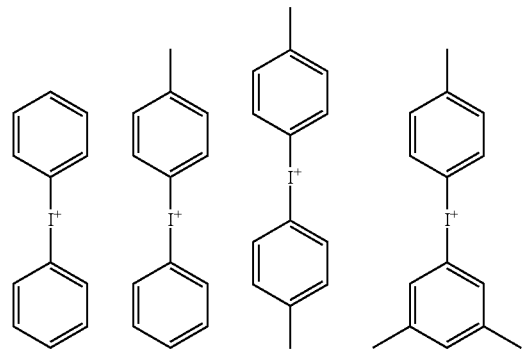
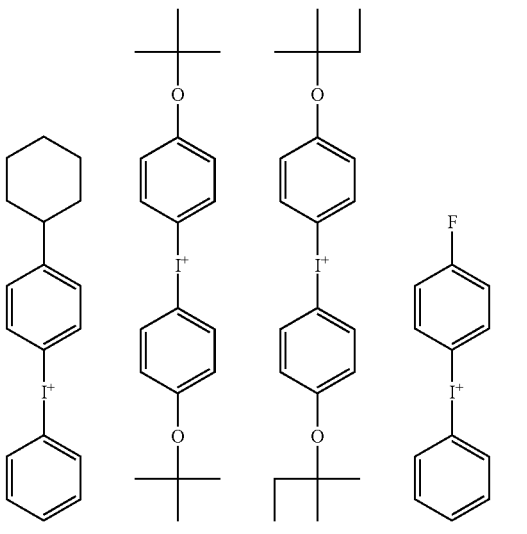
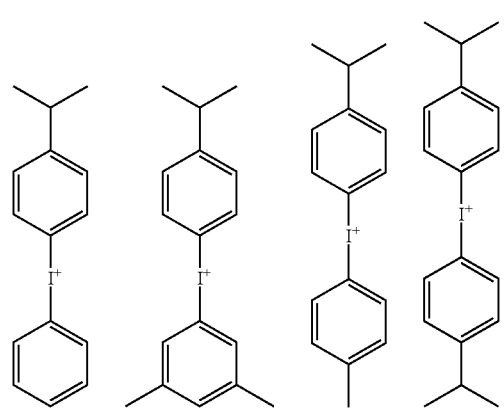
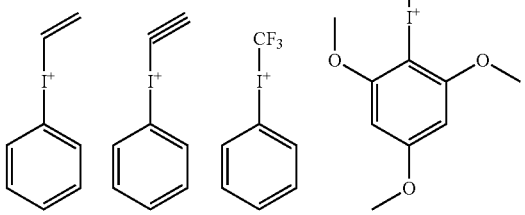
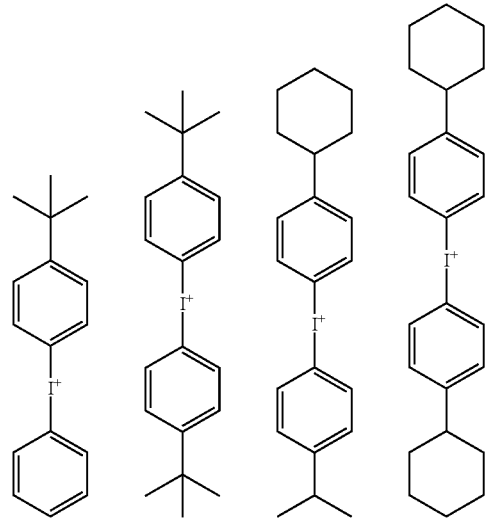
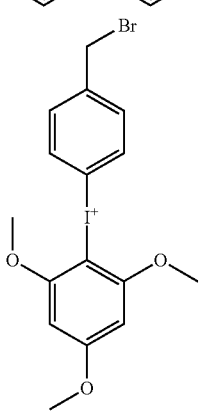

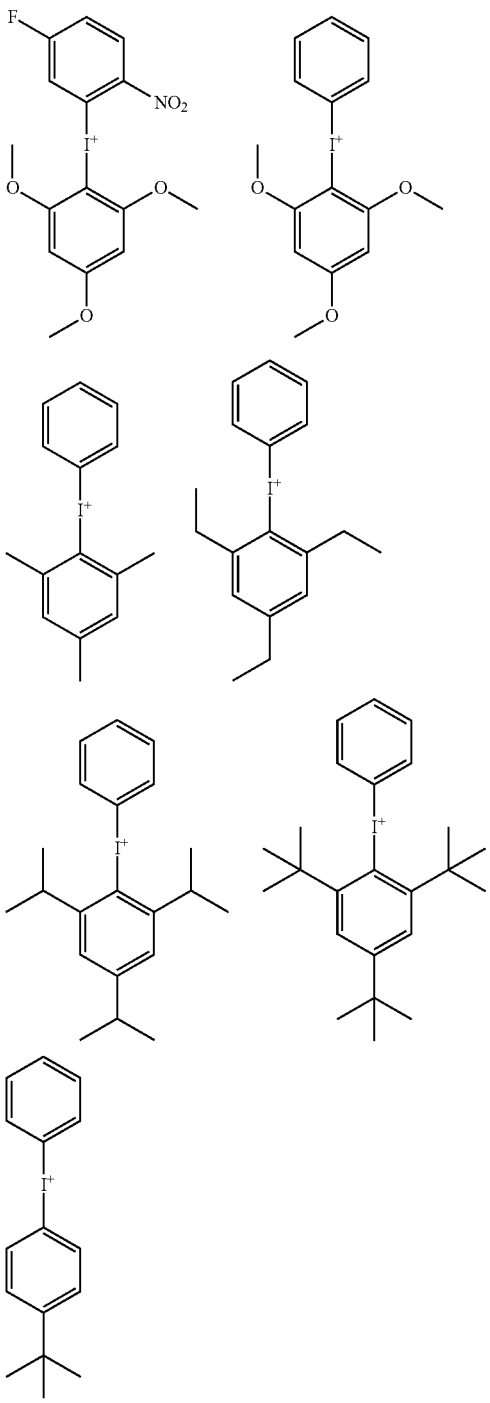

In the formulae (1-1) and (1-2), X⁻ is an anion of the following formula (1A), (1B), (1C) or (1D).

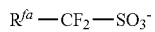

(1A)

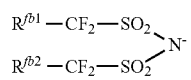

(1B)

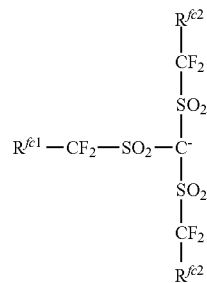

(1C)

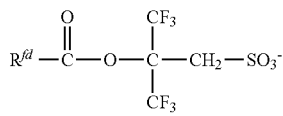

(1D)

In the formula (1A), $R^{fa}$ is fluorine or a $C_1$-$C_{40}$ hydrocarbyl group which may contain a heteroatom. The hydrocarbyl group may be saturated or unsaturated, and may be straight, branched, or cyclic. Examples thereof are as will be exemplified for the hydrocarbyl group represented by $R^{107}$ in the formula (1A').

Of the anions having the formula (1A), an anion having the formula (1A') is preferred.

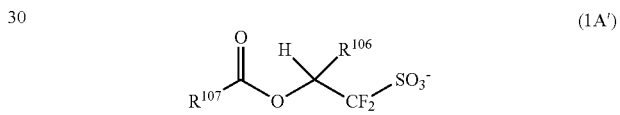

(1A')

In the formula (1A), $R^{106}$ is hydrogen or trifluoromethyl, preferably trifluoromethyl. $R^{107}$ is a $C_1$-$C_{38}$ hydrocarbyl group which may contain a heteroatom. As the heteroatom, oxygen, nitrogen, sulfur, and halogen atoms are preferred, with oxygen being most preferred. Of the hydrocarbyl groups represented by $R^{107}$, those groups of 6 to 30 carbon atoms are preferred from the aspect of achieving a high resolution in micropatterning.

The hydrocarbyl group represented by $R^{107}$ may be saturated or unsaturated, and straight, branched, or cyclic. Examples thereof include alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, and icosanyl; cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; unsaturated hydrocarbyl groups such as allyl and 3-cyclohexenyl; aryl groups such as phenyl, l-naphthyl, and 2-naphthyl; and aralkyl groups such as benzyl and diphenylmethyl.

In these groups, some or all of the hydrogen atoms may be substituted by a group containing a heteroatom such as oxygen, sulfur, nitrogen, or halogen, or some carbon may be replaced by a group containing a heteroatom such as oxygen, sulfur, or nitrogen, so that the group may contain a hydroxyl group, a cyano group, a carbonyl group, an ether bond, an ester bond, a sulfonic acid ester bond, a carbonate group, a lactone ring, a sultone ring, a carboxylic anhydride, or a haloalkyl group. Examples of the heteroatom-containing hydrocarbyl group include groups such as tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of the formula (1A'), reference may be made to JP-A 2007-145797, JP-A 2008-106045, JP-A 2009-7327, and JP-A 2009-258695. Also useful are the sulfonium salts described in JP-A 2010-215608. JP-A 2012-41320, JP-A 2012-106986, and JP-A 2012-153644.

Examples of the anion having the formula (1A) are as exemplified for the anion having the formula (1A) in JP-A 2018-197853.

In the formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated, and may be straight, branched, or cyclic. Examples thereof are as exemplified above for $R^{107}$ in the formula (1A'). Preferably $R^{fb1}$ and $R^{fb2}$ are each fluorine or a $C_1$-$C_4$ straight fluorinated alkyl group. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In the formula (1C), $R^{fc1}$, $R^{fc2}$, and $R^{fc3}$ are each independently fluorine or a $C_1$-$C_{40}$ hydrocarbyl group which may contain a heteroatom. The hydrocarbyl group may be saturated or unsaturated, and may be straight, branched, or cyclic. Examples thereof are as exemplified above for $R^{107}$ in the formula (1A'). Preferably $R^{fc1}$, $R^{fc2}$, and $R^{fc3}$ are each fluorine or a $C_1$-$C_4$ straight fluorinated alkyl group. Also, $R^{fc1}$ and $R^{fc2}$ may bond together to form a ring with the linkage: —$CF_2$—$SO_2$—$C^-$—$SO_2$—$CF_2$— to which they are attached. It is preferred that a combination of $R^{fc1}$ and $R^{fc2}$ be a fluorinated ethylene or fluorinated propylene group.

In the formula (1D), $R^{fd}$ is a $C_1$-$C_{40}$ hydrocarbyl group which may contain a heteroatom. The hydrocarbyl group may be saturated or unsaturated, and may be straight, branched, or cyclic. Examples thereof are as exemplified above for $R^{17}$ in the formula (1A').

With respect to the synthesis of the sulfonium salt having an anion of the formula (1D), reference may be made to JP-A 2010-215608 and JP-A 2014-133723.

Examples of the anion having the formula (1D) are as exemplified for the anion having the formula (1D) in JP-A 2018-197853.

Notably, the photoacid generator having the anion of the formula (1D) does not have fluorine at the α-position relative to the sulfo group, but two trifluoromethyl groups at the β-position. For this reason, it has a sufficient acidity to sever the acid labile groups in the base polymer. Thus the compound is an effective PAG.

Another preferred PAG is a compound having the formula (2).

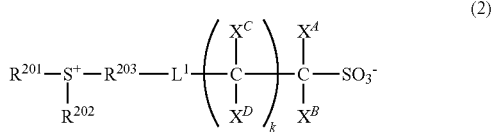

(2)

In the formula (2), $R^{201}$ and $R^{202}$ are each independently a $C_1$-$C_{30}$ hydrocarbyl group which may contain a heteroatom. $R^{203}$ is a $C_1$-$C_{30}$ hydrocarbylene group which may contain a heteroatom. $R^{201}$ and $R^{202}$, or $R^{201}$ and $R^{203}$ may bond together to form a ring with the sulfur atom to which they are attached. Exemplary rings are the same as described above for the ring that $R^{101}$ and $R^{102}$ in the formula (1-1), taken together, form with the sulfur atom to which they are attached.

The hydrocarbyl groups represented by $R^{201}$ and $R^{202}$ may be saturated or to unsaturated, and straight, branched, or cyclic. Examples thereof include alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$] decanyl, and adamantyl; and aryl groups such as phenyl, methylphenyl, ethylphenyl, n-propylphenyl, isopropylphenyl n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl. In these groups, some or all of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, sulfonic acid ester bond, carbonate, lactone ring, sultone ring, carboxylic anhydride, or haloalkyl group.

The hydrocarbylene group represented by $R^{203}$ may be saturated or unsaturated, and straight, branched, or cyclic. Examples thereof include alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl decane-1,10-diyl, undecane-1,11-diyl, dodecane-1,12-diyl, tridecane-1,13-diyl, tetradecane-1,14-diyl, pentadecane-1,15-diyl, hexadecne-1,16-diyl, and heptadecane-1,17-diyl; cyclic saturated hydrocarbylene groups such as cyclopentanediyl, cyclohexanediyl, norbornanediyl, and aamantanediyl; and arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene, and tert-butylnaphthylene. In these groups, some or all of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, sulfonic acid ester bond, carbonate, lactone ring, sultone ring, carboxylic anhydride, or haloalkyl group. Of the heteroatoms, oxygen is preferred.

In the formula (2), $L^1$ is a single bond, an ether bond, or a $C_1$-$C_{20}$ hydrocarbylene group which may contain a heteroatom. The hydrocarbylene group may be saturated or unsaturated, and straight, branched, or cyclic. Examples thereof are as exemplified above for $R^{203}$.

In the formula (2), $X^A$, $X^B$, $X^C$, and $X^D$ are each independently hydrogen, fluorine, or trifluoromethyl, with the proviso that at least one of $X^A$, $X^B$, $X^C$, or $X^D$ is fluorine or trifluoromethyl.

In the formula (2), k is an integer of 0 to 3.

Of the PAGs having the formula (2), those having the formula (2') are preferred.

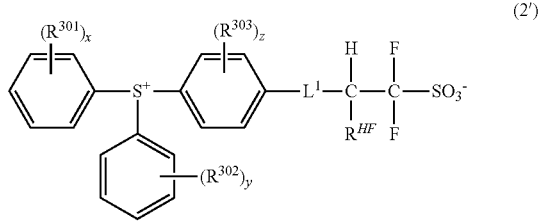

(2')

In the formula (2'), $L^1$ is as defined above. $R^{HF}$ is hydrogen or trifluoromethyl, preferably trifluoromethyl. $R^{301}$, $R^{302}$, and $R^{303}$ are each independently hydrogen or a $C_1$-$C_{20}$ hydrocarbyl group which may contain a heteroatom. The hydrocarbyl group may be saturated or unsaturated, and may be straight, branched, or cyclic. Examples thereof are as exemplified above for $R^{107}$ in the formula (1A'). The subscripts x and y are each independently an integer of 0 to 5, and z is an integer of 0 to 4.

Examples of the PAG having the formula (2) are as exemplified for the PAG having the formula (2) in JP-A 2017-026980.

Of the foregoing PAGs, those having an anion of the formula (1A') or (1D) are especially preferred because of reduced acid diffusion and high solubility in the solvent. Also those having an anion of the formula (2') are especially preferred because of extremely reduced acid diffusion.

Also a sulfonium or iodonium salt having an iodized or brominated aromatic ring-containing anion may be used as the PAG. Suitable are sulfonium and iodonium salts having the formulae (3-1) and (3-2).

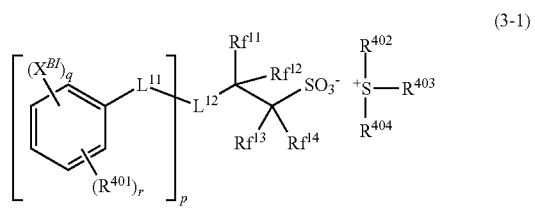

(3-1)

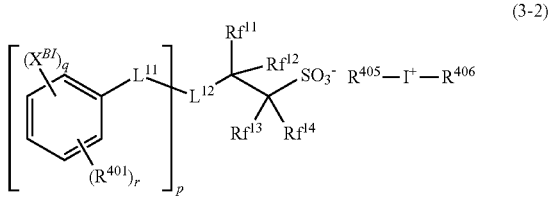

(3-2)

In the formulae (3-1) and (3-2), p is an integer of 1 to 3, q is an integer of 1 to 5, r is an integer of 0 to 3, and 1≤q+r≤5. Preferably, q is an integer of 1 to 3, more preferably 2 or 3, and r is an integer of 0 to 2.

In the formulae (3-1) and (3-2), $X^{B1}$ is iodine or bromine. Groups $X^{B1}$ may be the same or different when p and/or q is 2 or more.

In the formulae (3-1) and (3-2), $L^{11}$ is a single bond, an ether bond, an ester bond, or a $C_1$-$C_6$ saturated hydrocarbylene group which may contain an ether bond or ester bond. The saturated hydrocarbylene group may be straight, branched, or cyclic.

In the formulae (3-1) and (3-2), $L^{12}$ is a single bond or a $C_1$-$C_{20}$ divalent linking group when r=1, or a $C_1$-$C_{20}$ trivalent or tetravalent linking group when r=2 or 3, the linking group optionally containing an oxygen, sulfur, or nitrogen atom.

In the fornmlae (3-1) and (3-2), $R^{401}$ is a hydroxyl group, a carboxyl group, fluorine, chlorine, bromine, an amino group, or a $C_1$-$C_{20}$ hydrocarbyl, $C_1$-$C_{20}$ hydrocarbyloxy, $C_2$-$C_{10}$ hydrocarbyloxycarbonyl, $C_2$-$C_{20}$ hydrocarbylcarbonyloxy, or $C_1$-$C_{20}$ hydrocarbylsulfonyloxy group, which may contain fluorine, chlorine, bromine, hydroxyl, amino, or ether bond, or —N($R^{401A}$)—C(=O)—$R^{104B}$ or —N($R^{401A}$)—C(=O)—O—$R^{401B}$. $R^{401A}$ is hydrogen or a $C_1$-$C_6$ saturated hydrocarbyl group which may contain a halogen, a hydroxyl group, a $C_1$-$C_6$ alkoxy, $C_2$-$C_6$ saturated hydrocarbylcarbonyl, or $C_2$-$C_6$ saturated hydrocarbylcarbonyloxy group. $R^{401B}$ is a $C_1$-$C_{16}$ aliphatic hydrocarbyl or $C_6$-$C_{12}$ aryl group, which may contain a halogen, a hydroxyl group, a $C_1$-$C_6$ saturated hydrocarbyloxy, $C_2$-$C_6$ saturated hydrocarbylcarbonyl, or $C_2$-$C_6$ saturated hydrocarbylcarbonyloxy group. The aliphatic hydrocarbyl group may be saturated or unsaturated, and straight, branched, or cyclic. The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched, or cyclic. Groups $R^0$ may be the same or different when p and/or r is 2 or more.

Of these, $R^{401}$ is preferably hydroxyl, —N($R^{401A}$)—C(=O)—$R^{401B}$, —N($R^{401A}$)—C(=O)—O—$R^{401B}$, fluorine, chlorine, bromine, methyl, or methoxy.

In the formulae (3-1) and (3-2), $Rf^{11}$ to $Rf^{14}$ are each independently hydrogen, fluorine, or trifluoromethyl. At least one of $Rf^{11}$ to $Rf^{14}$ is fluorine or trifluoromethyl, or $Rf^{11}$ and $Rf^{12}$ taken together, may forma carbonyl group. Preferably, both $Rf^{13}$ and $Rf^{14}$ are fluorine.

In the formulae (3-1) and (3-2), $R^{402}$, $R^{403}$, $R^{404}$, $R^{405}$, and $R^{406}$ are each independently fluorine, chlorine, bromine, iodine, or a $C_1$-$C_{20}$ hydrocarbyl group which may contain a heteroatom. The hydrocarbyl group may be saturated or unsaturated, and may be straight, branched, or cyclic. Examples thereof are as exemplified above for the hydrocarbyl groups represented by $R^{101}$ to $R^{103}$ in the formulae (1-1) and (1-2). In these groups, some or all of the hydrogen atoms may be substituted by hydroxyl, carboxy, halogen, cyano, nitro, mercapto, sultone, sulfone, or a sulfonium salt-containing group, and some carbon may be replaced by an ether bond, ester bond, carbonyl group, amide bond, carbonate group, or sulfonic acid ester bond. $R^{402}$ and $R^{403}$ may bond together to form a ring with the sulfur atom to which they are attached. Exemplary rings are the same as described above for the ring that $R^{101}$ and $R^{102}$ in the formula (1-1), taken together, form with the sulfur atom to which they are attached.

Examples of the cation in the sulfonium salt having the formula (3-1) include those exemplified above as the cation in the sulfonium salt having the formula (1-1). Examples of the cation in the iodonium salt having the formula (3-2) include those exemplified above as the cation in the iodonium salt having the formula (1-2).

Examples of the anion in the onium salts having the formulae (3-1) and (3-2) are shown below, but not limited thereto. Herein $X^{BI}$ is as defined above.

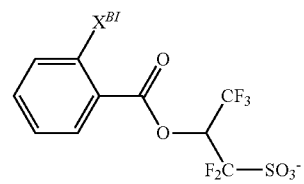

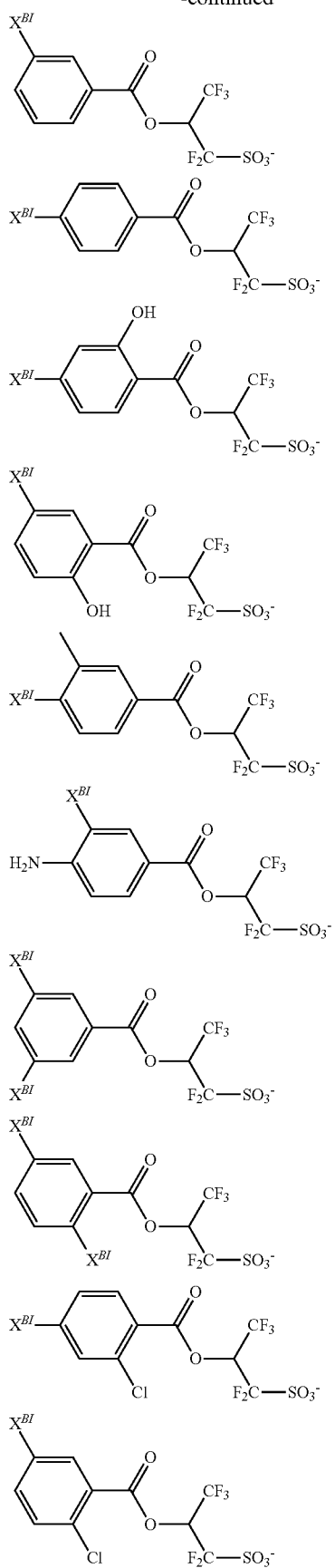
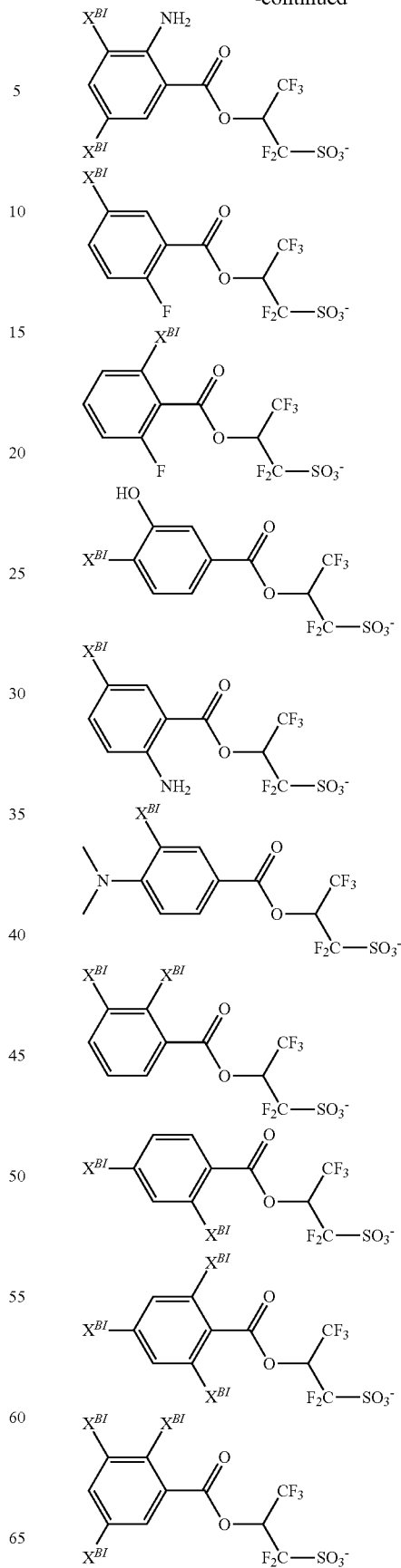

131
-continued
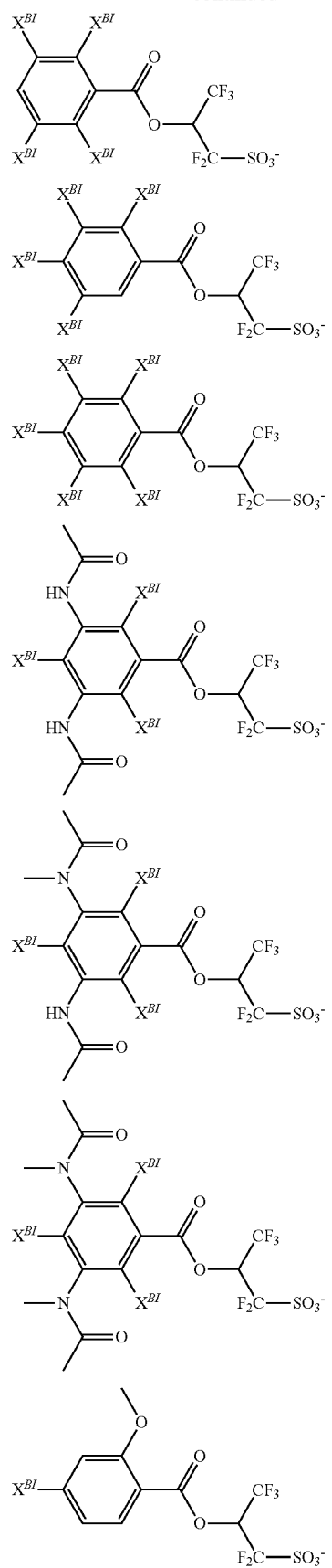
132
-continued
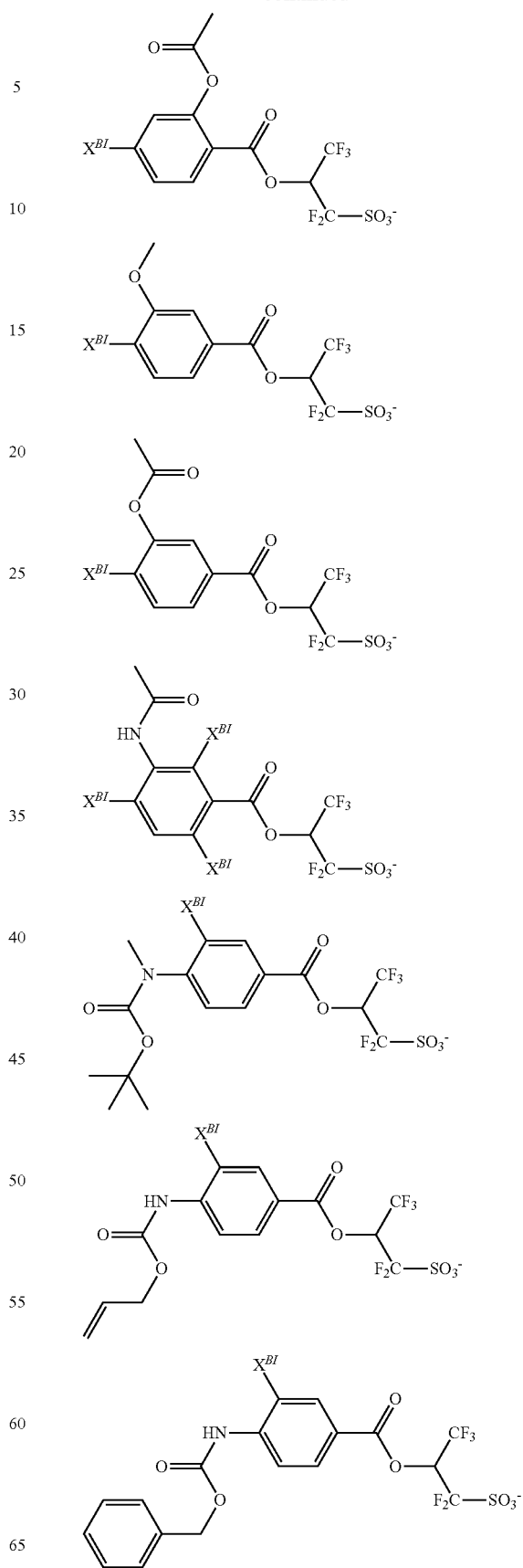

133
-continued
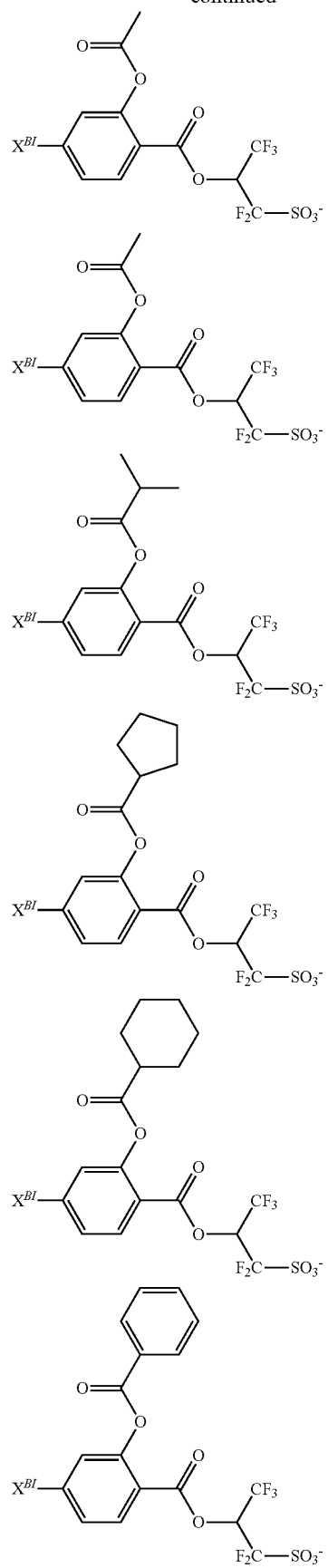
134
-continued
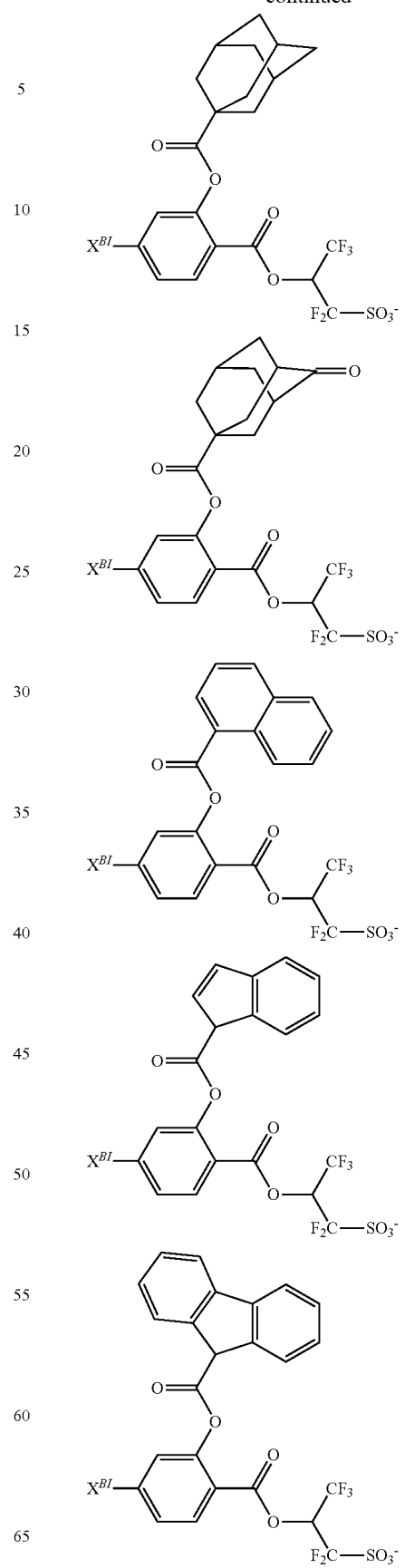

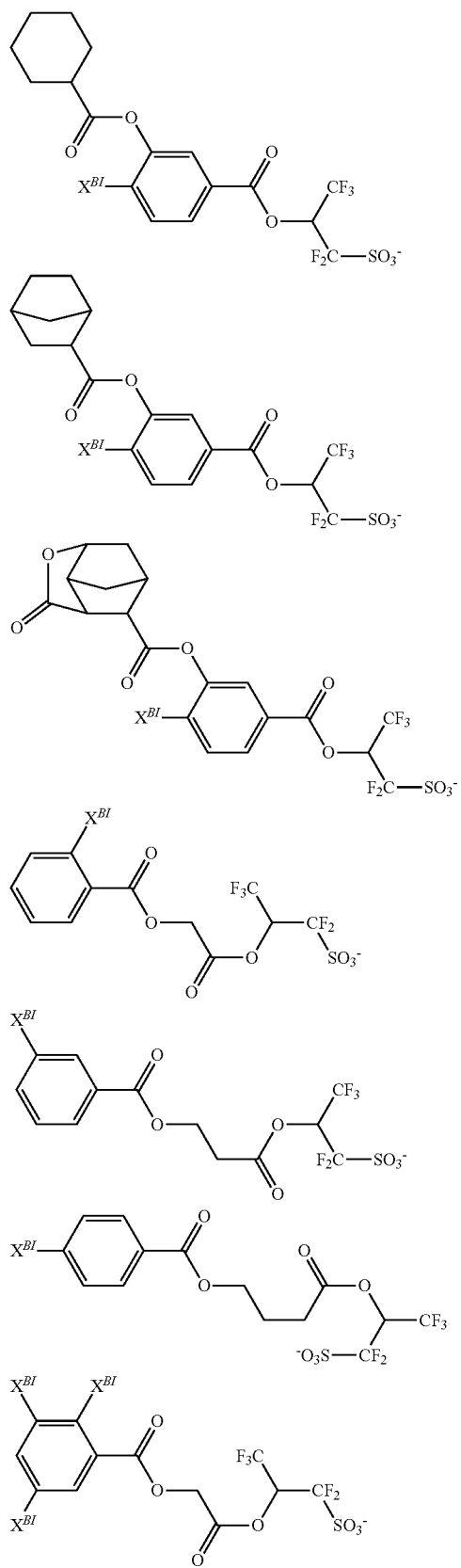
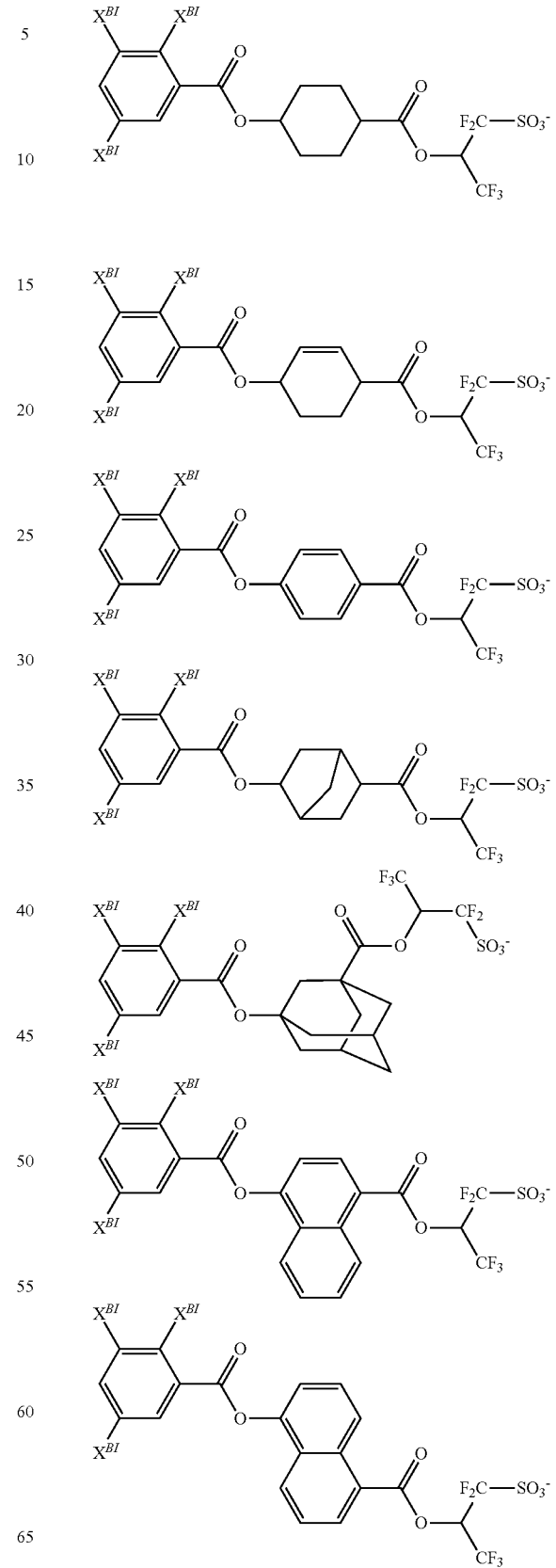

-continued
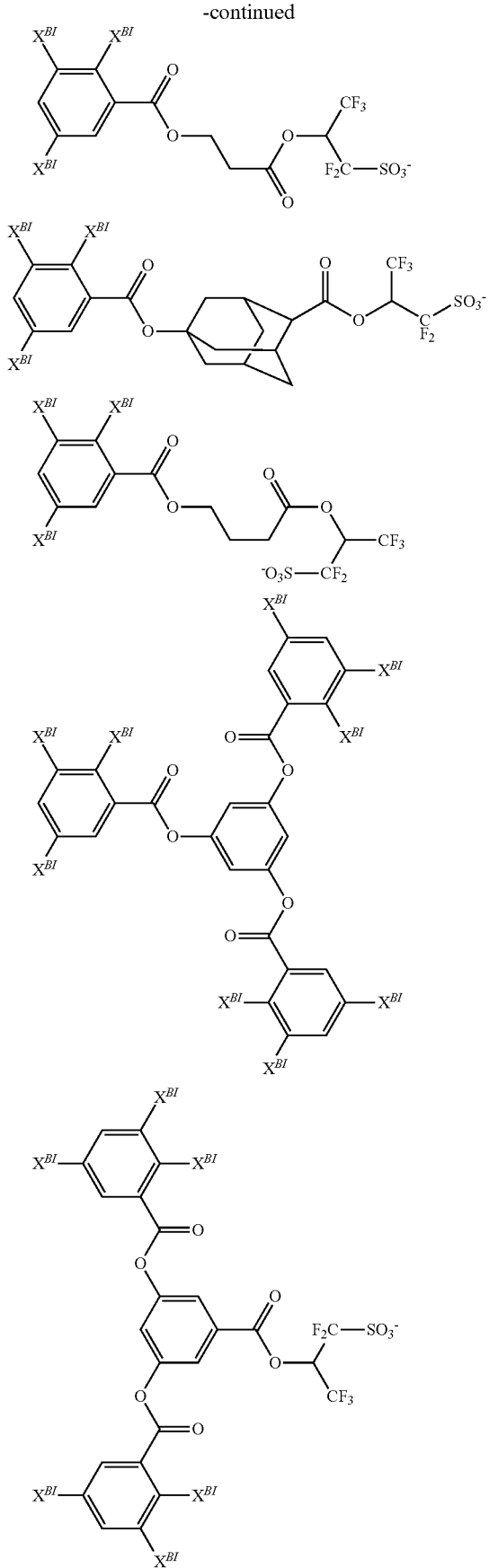
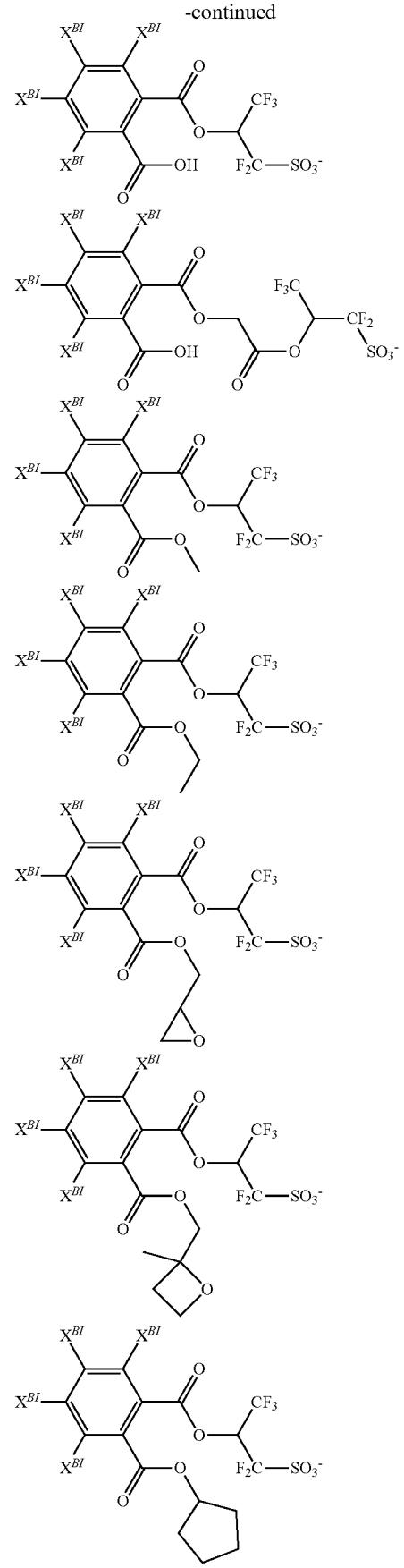

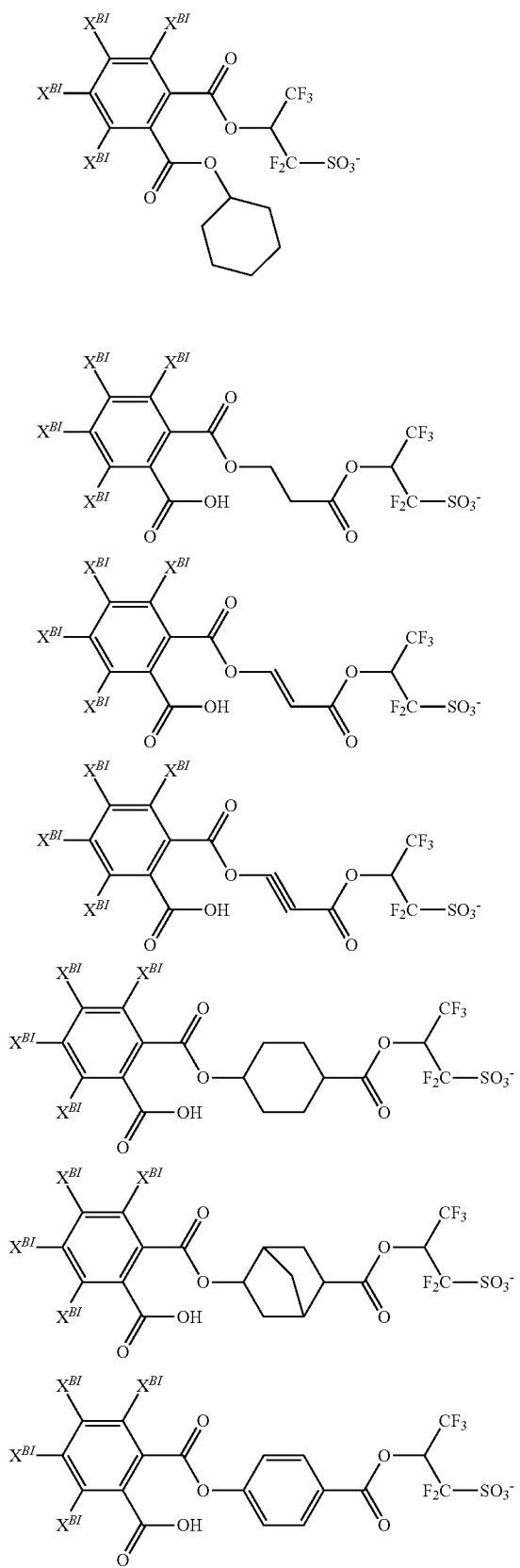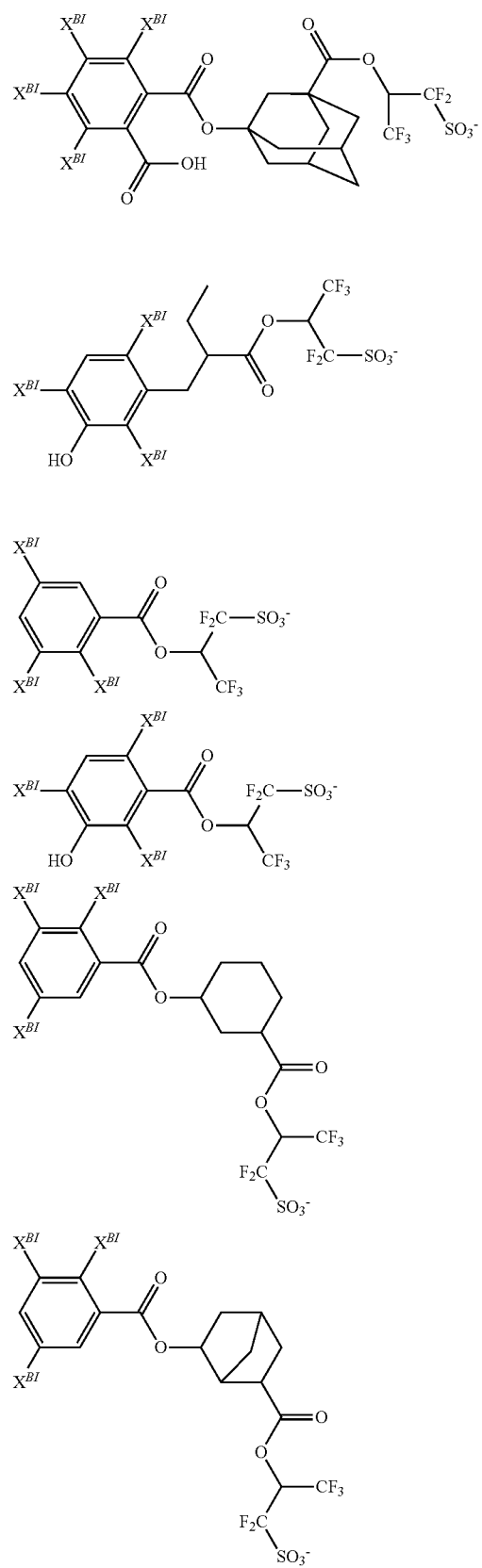

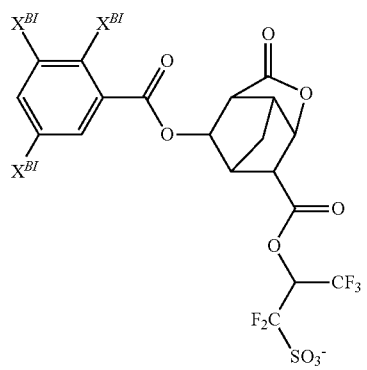
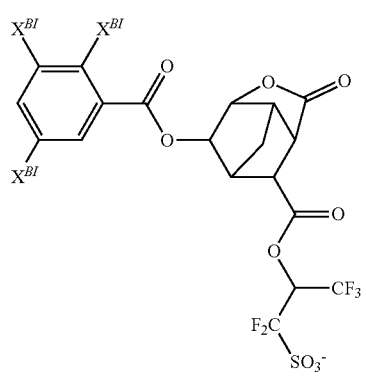
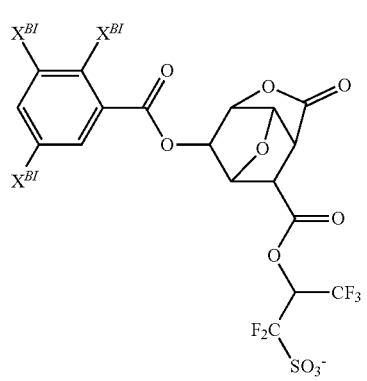
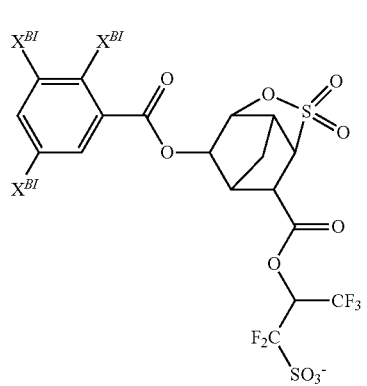
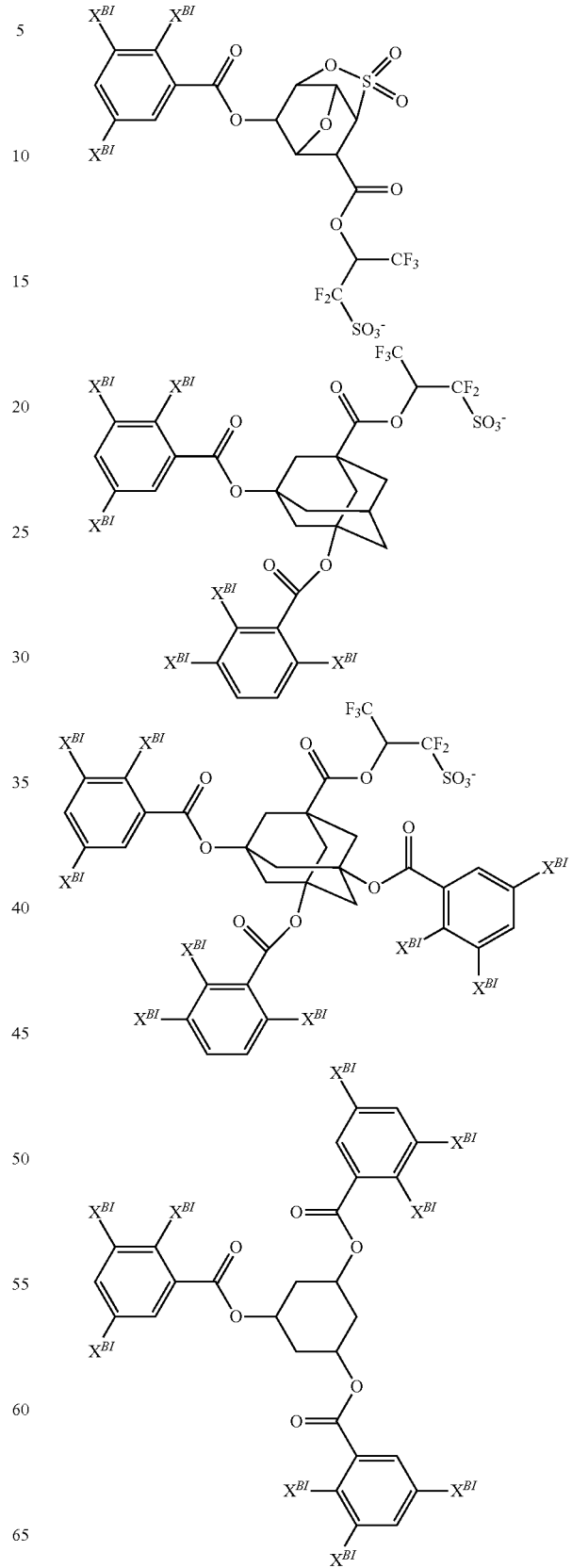

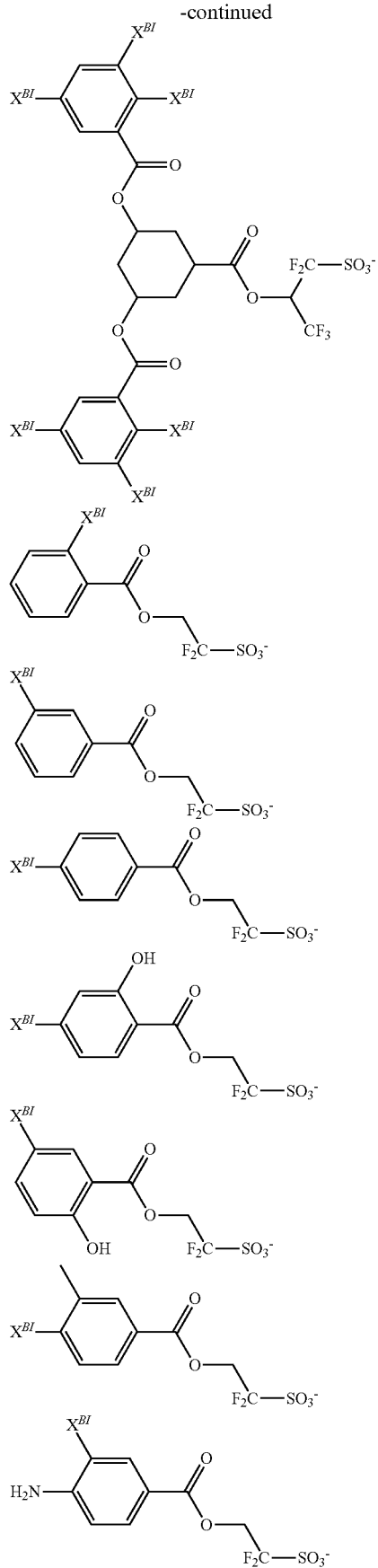
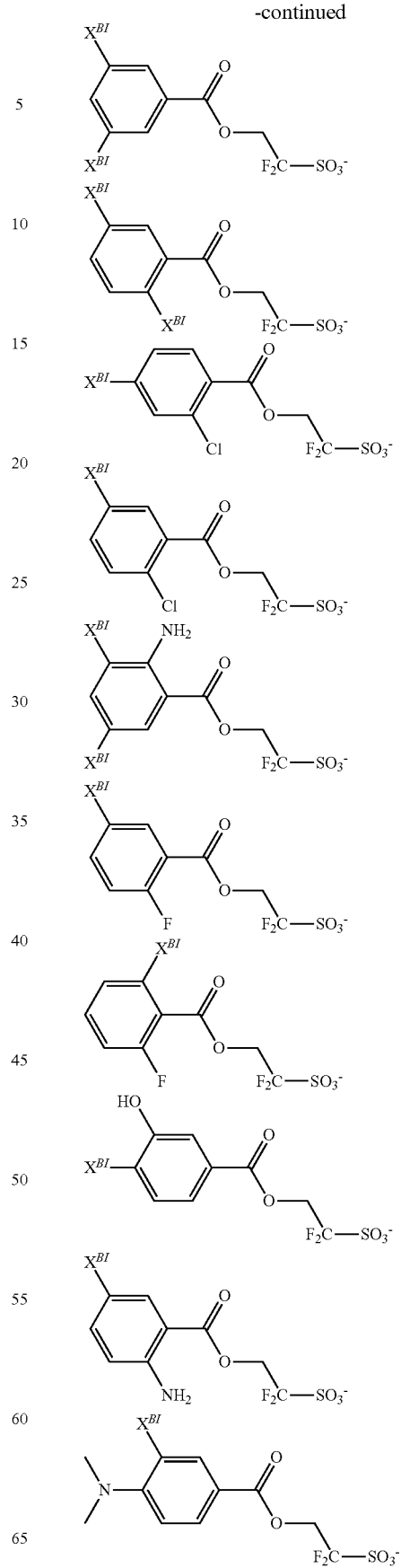

-continued
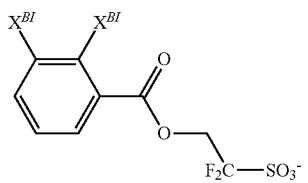
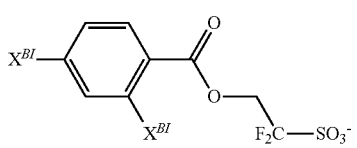
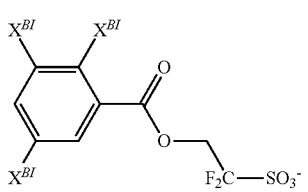
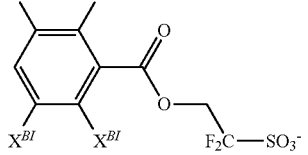
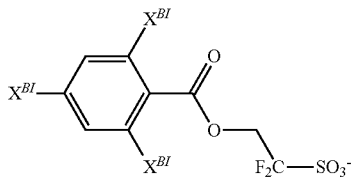
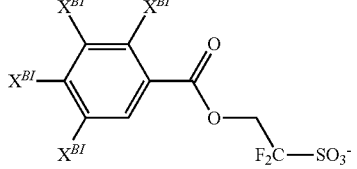
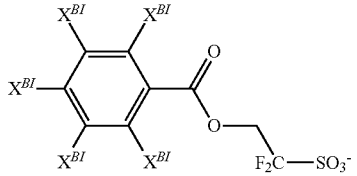
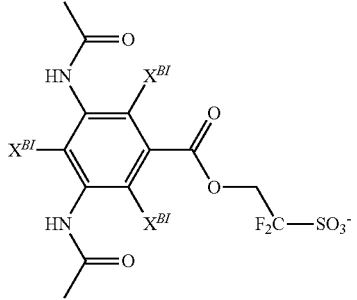
-continued
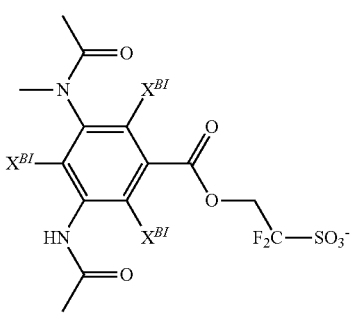
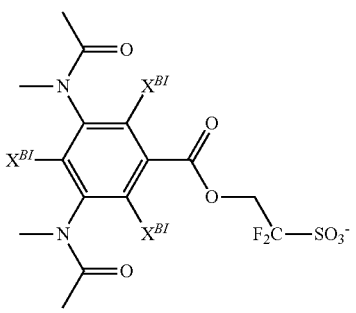
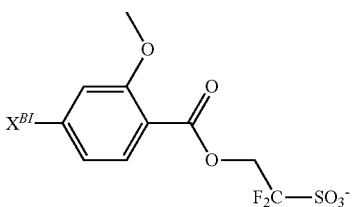
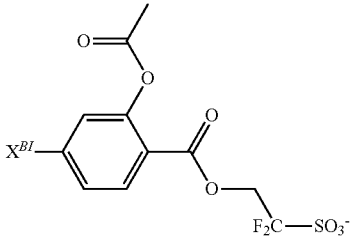
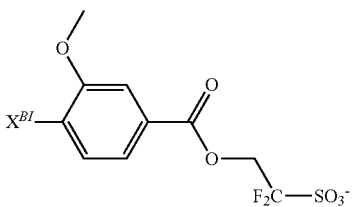
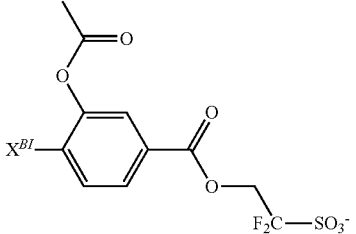

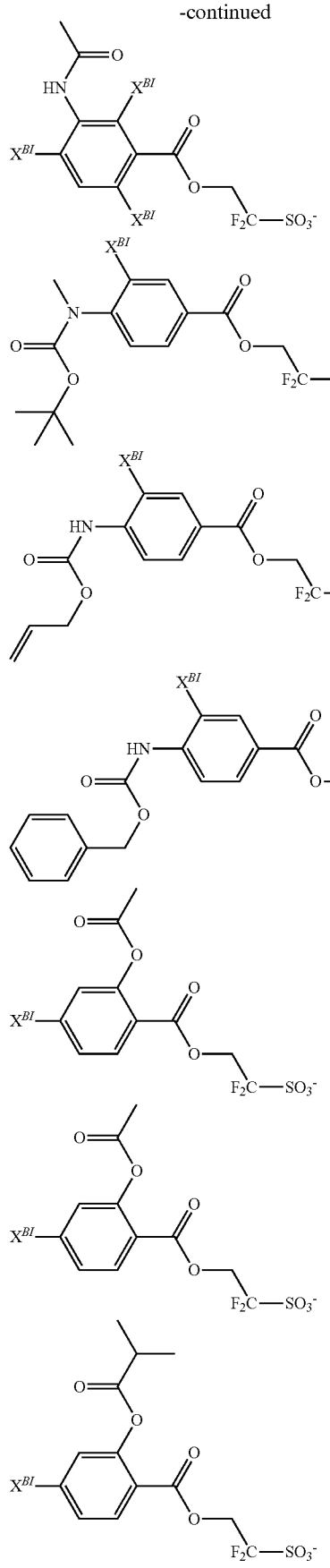
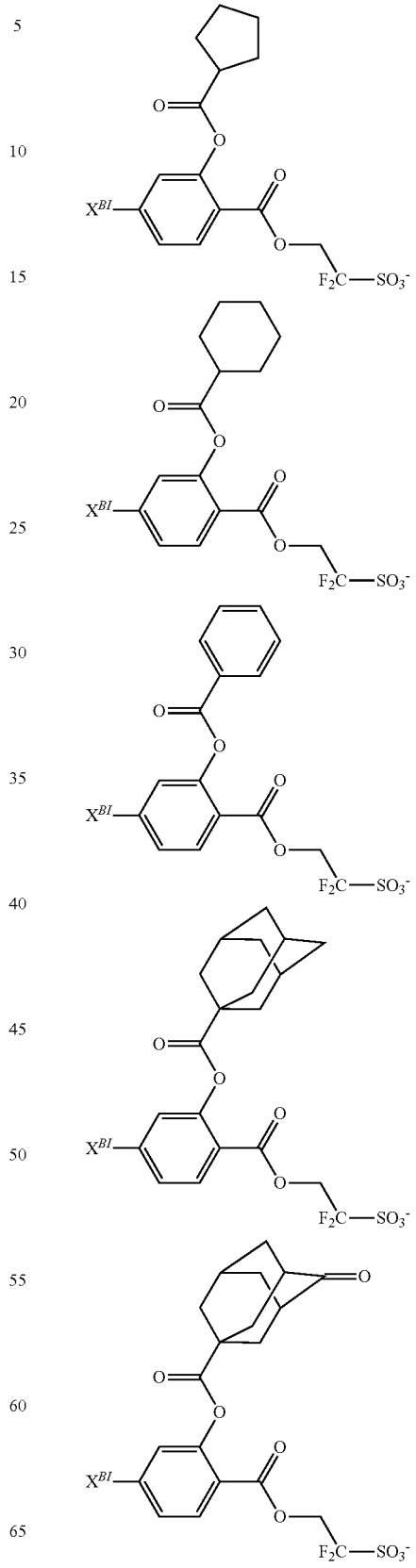

149
-continued
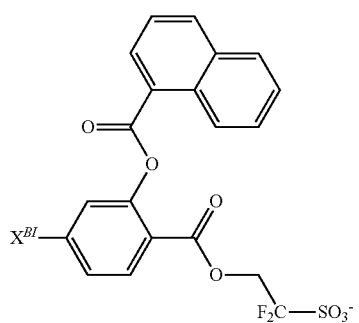
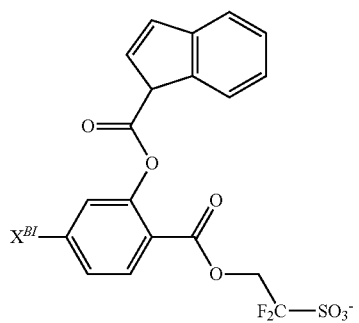
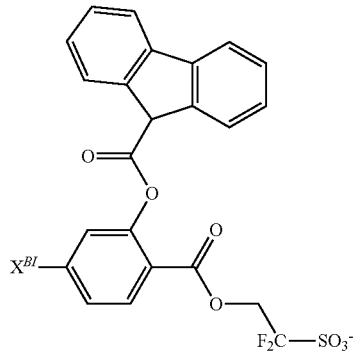
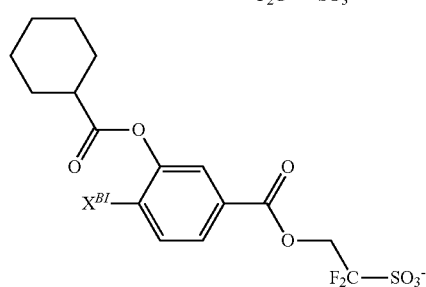
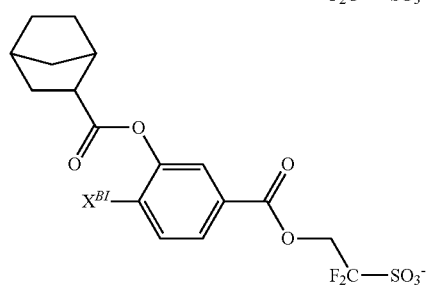
150
-continued
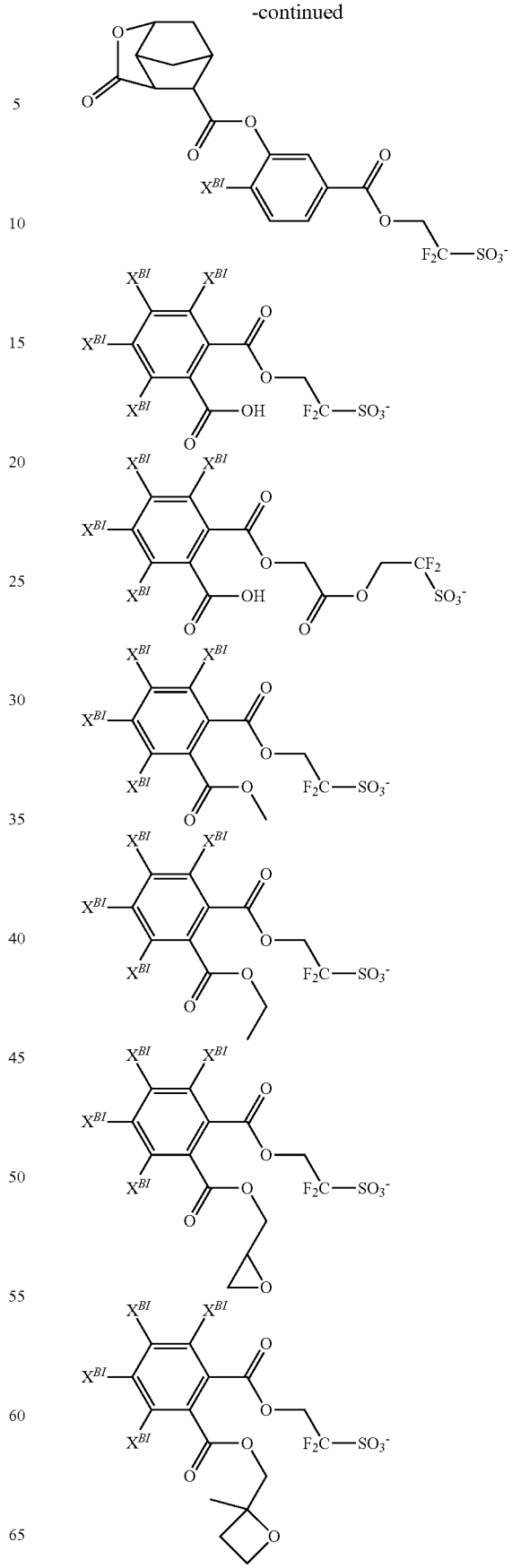

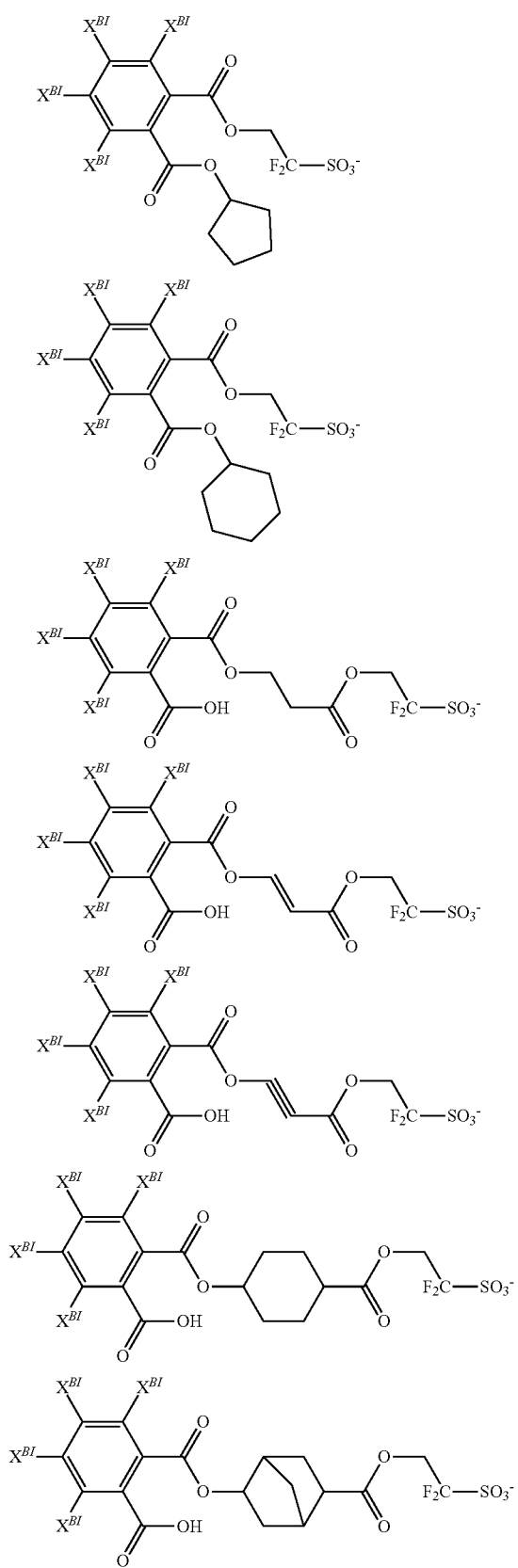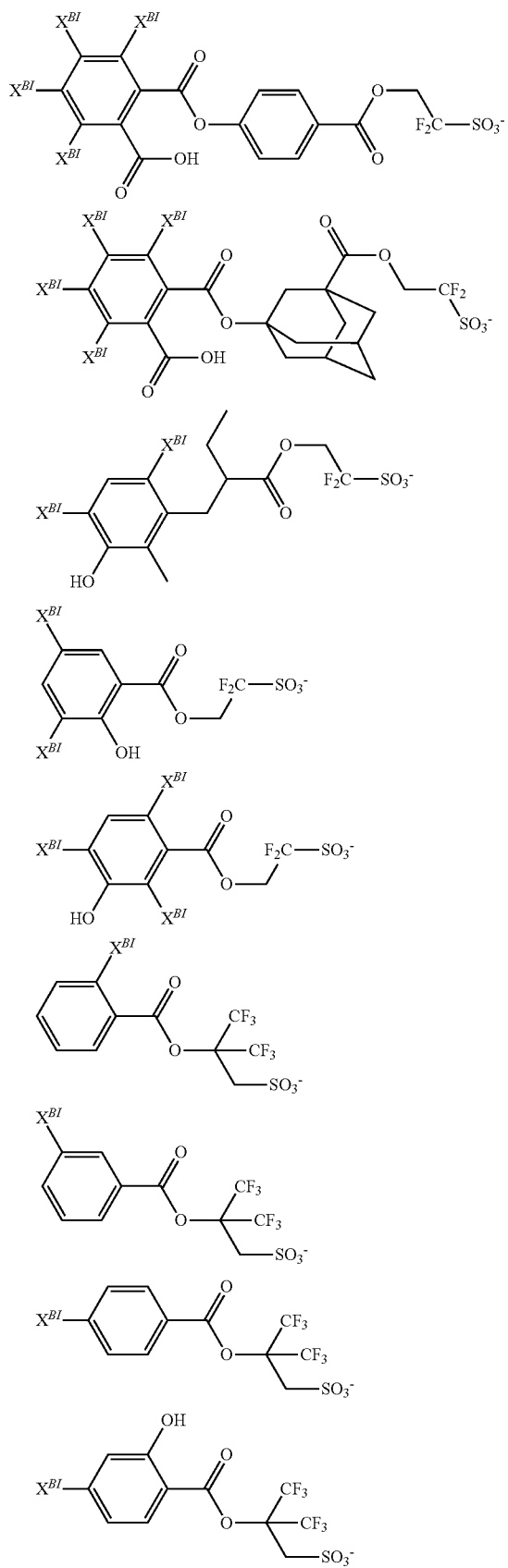

153
-continued
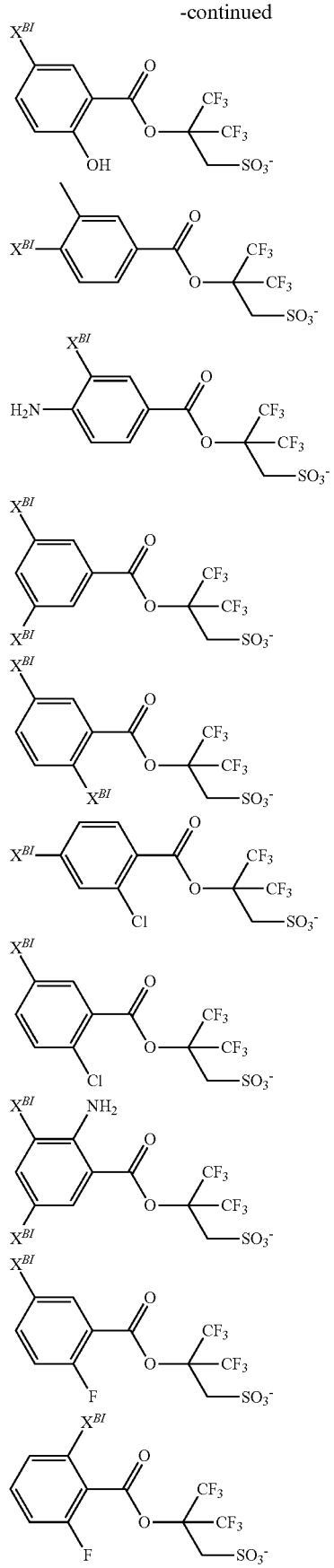
154
-continued
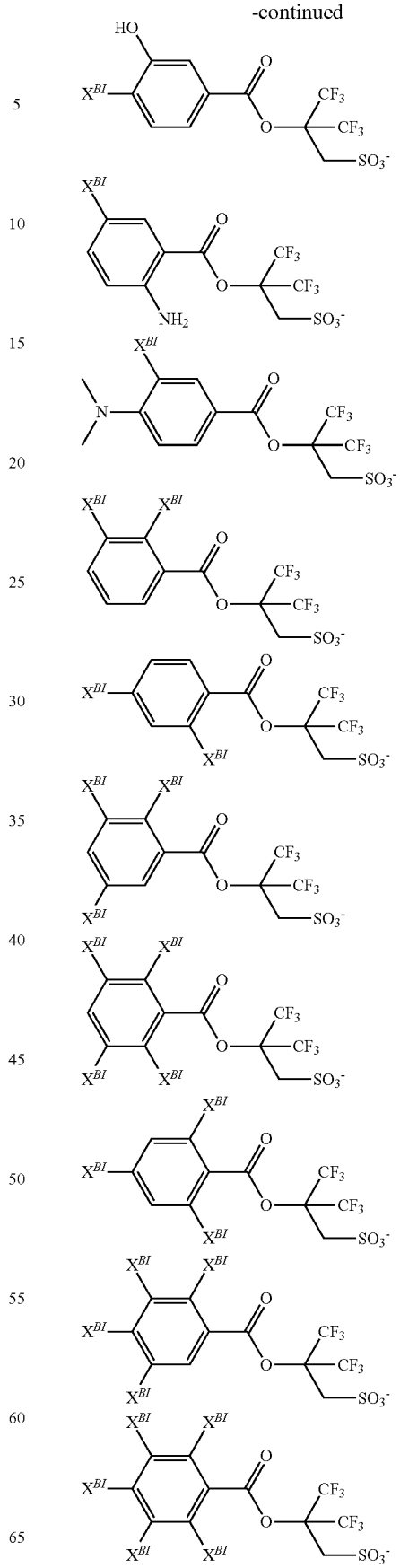

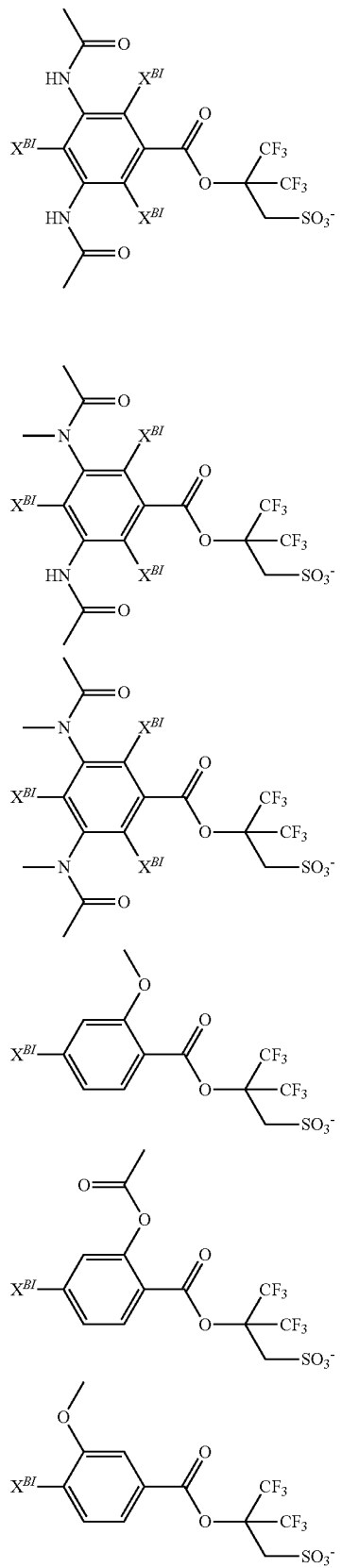
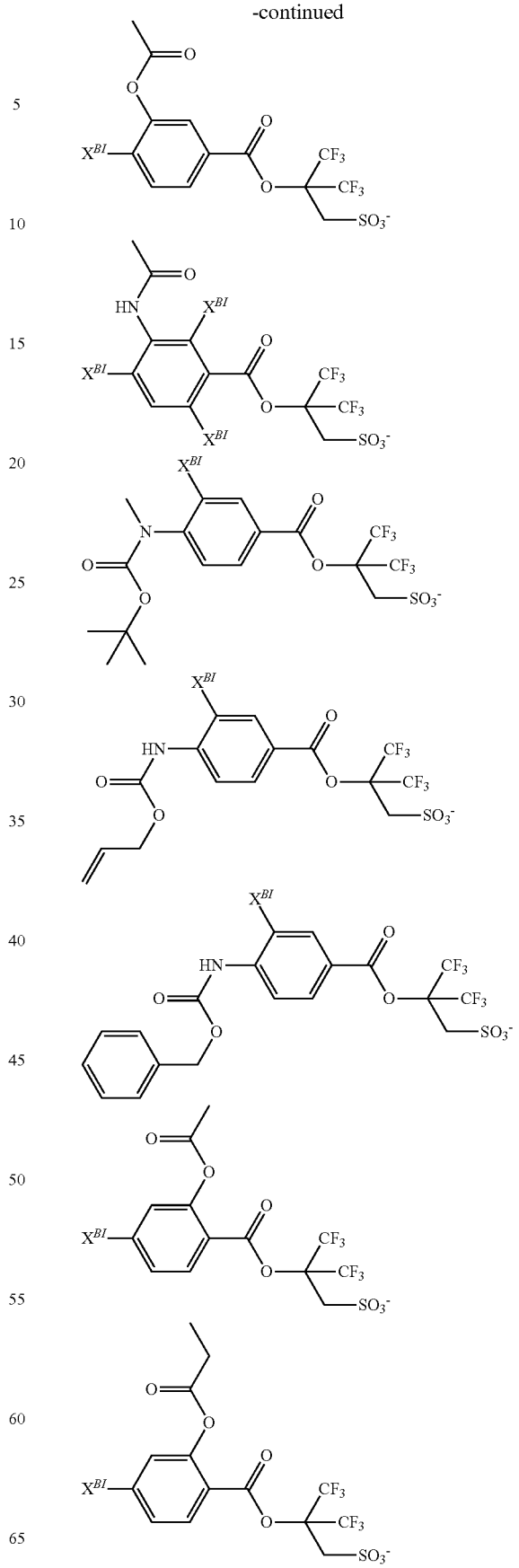

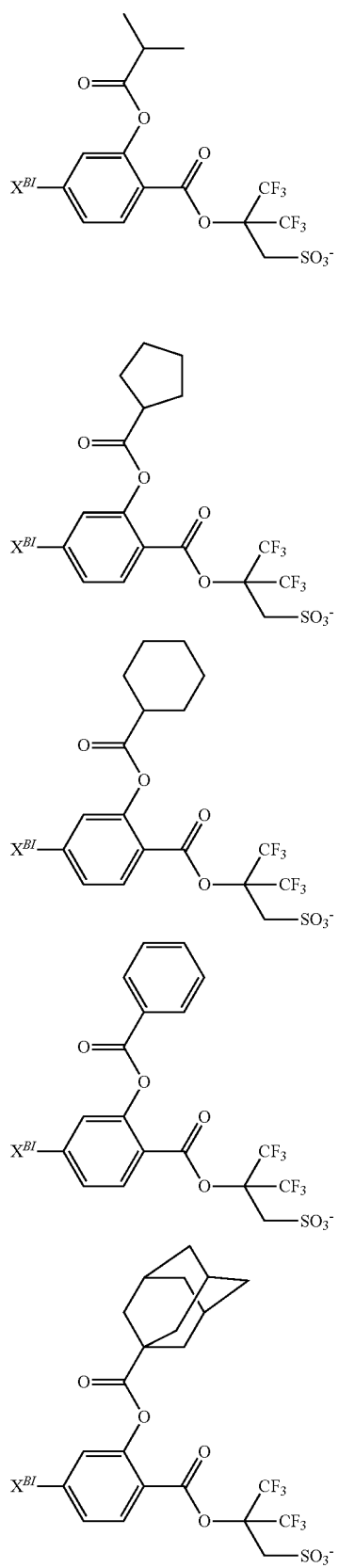
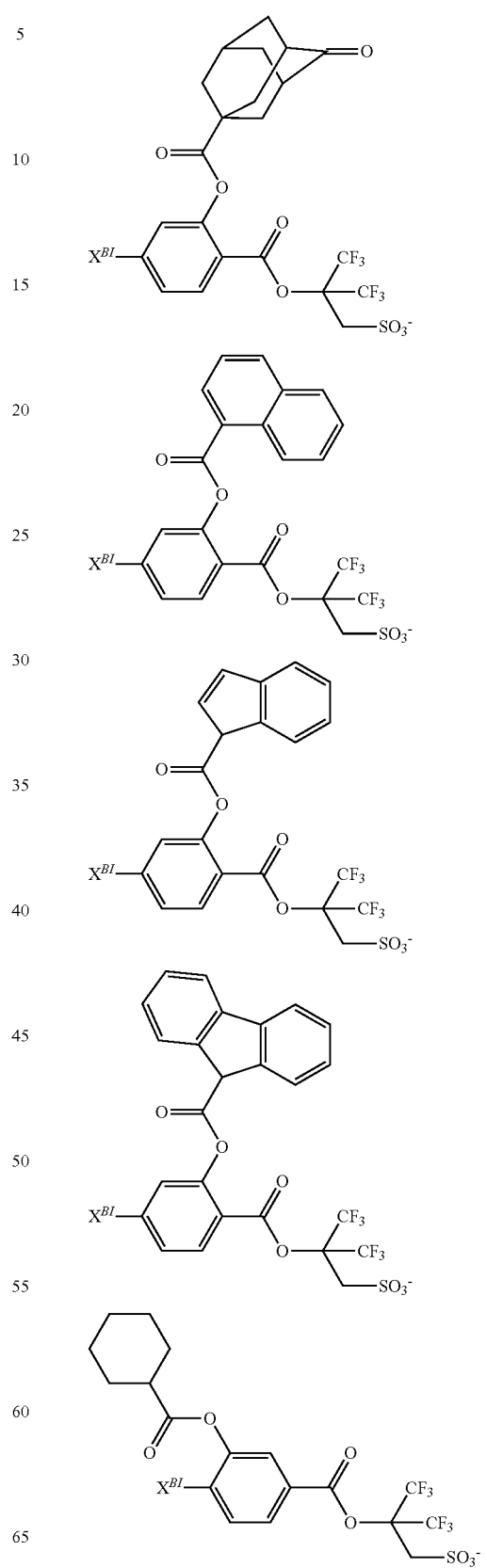

159
-continued
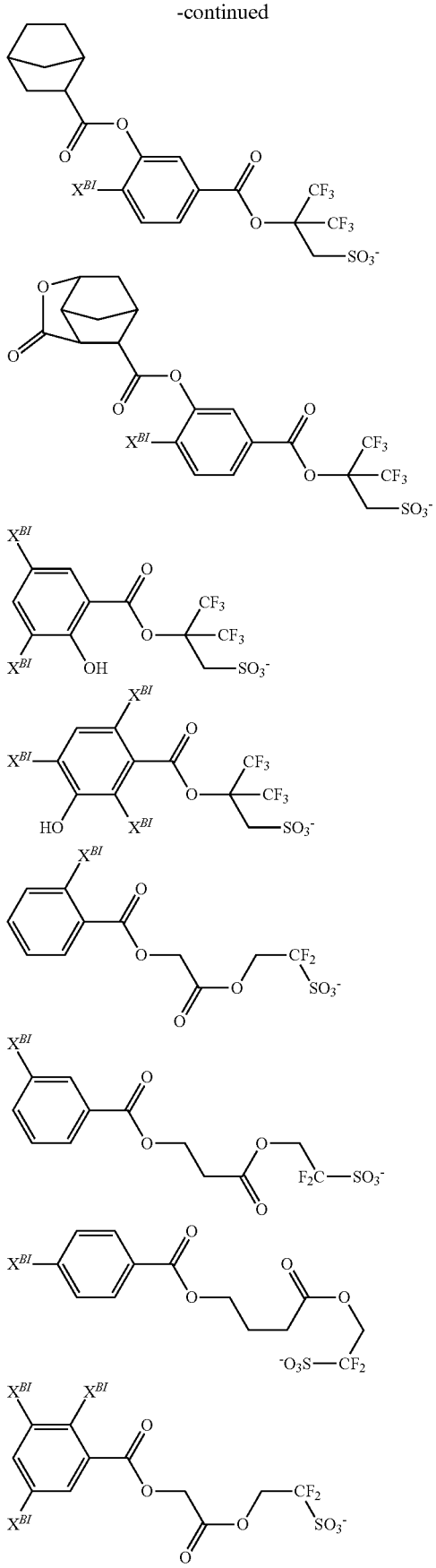
160
-continued
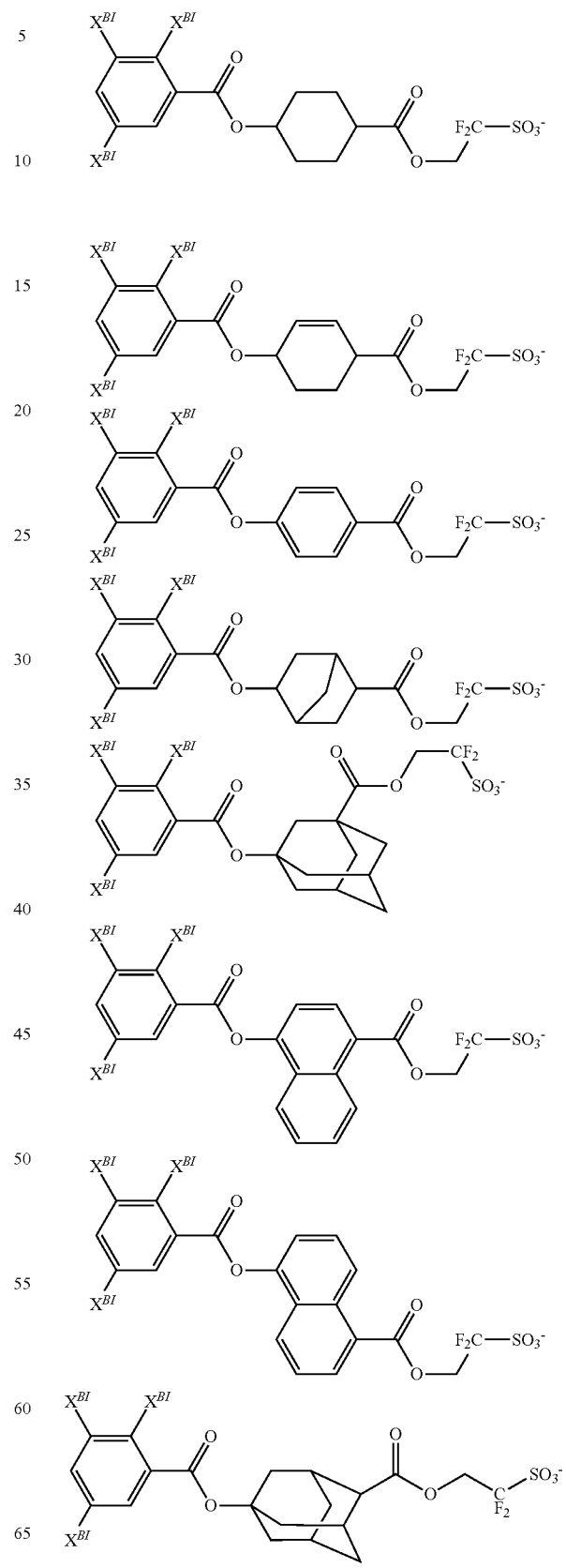

161
-continued
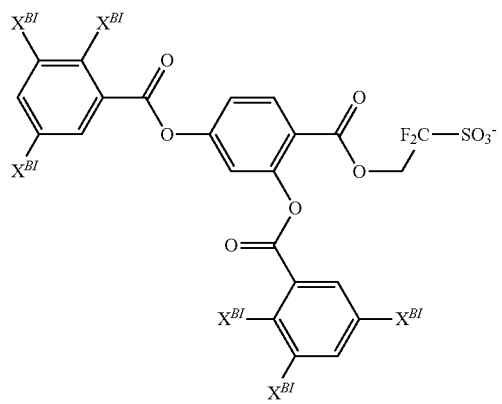
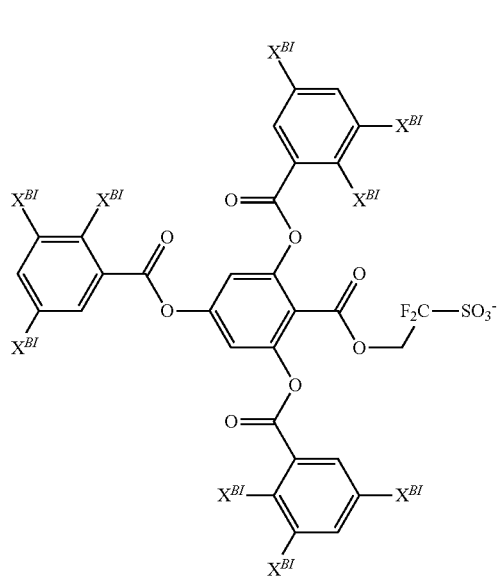
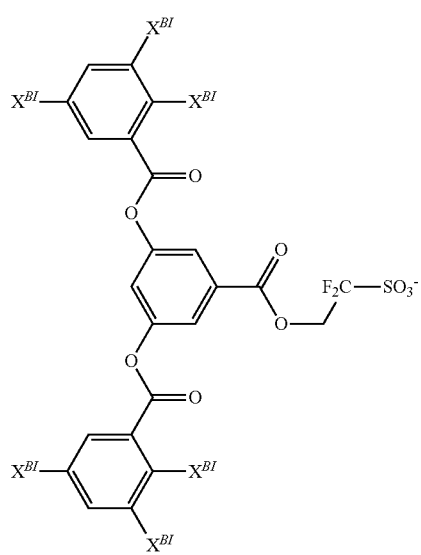
162
-continued
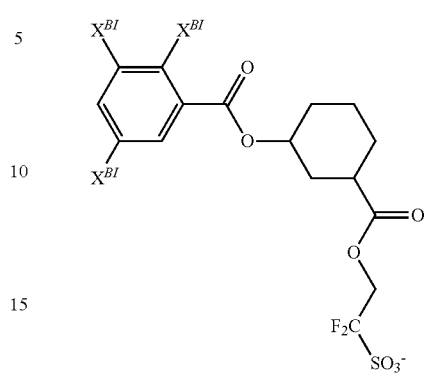
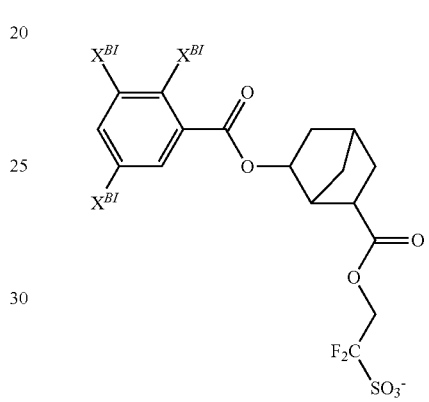
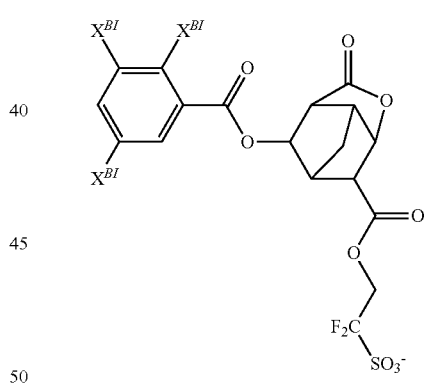
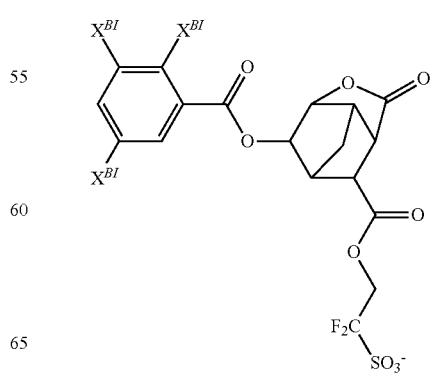

163
-continued
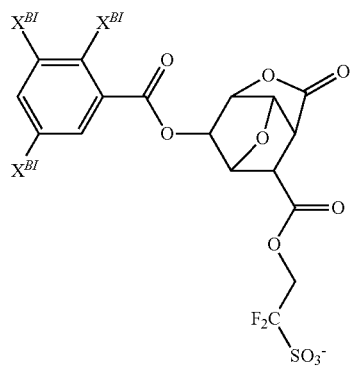
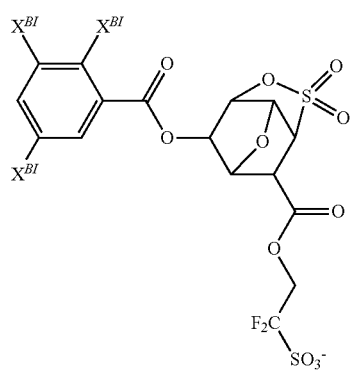
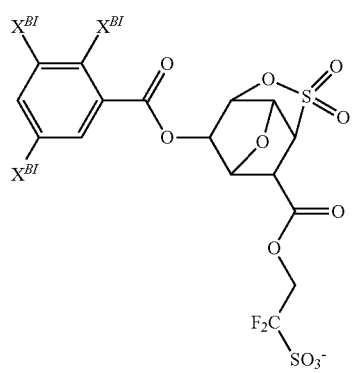
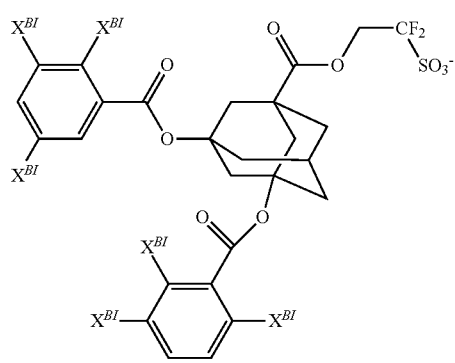
164
-continued
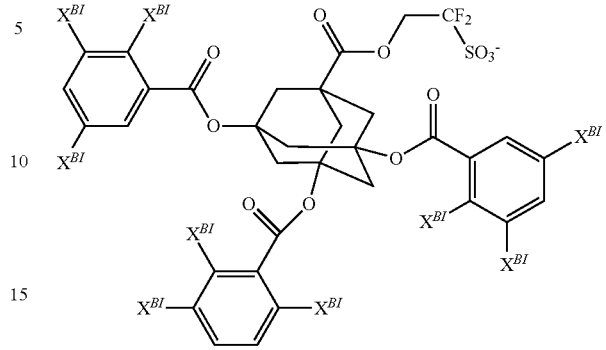
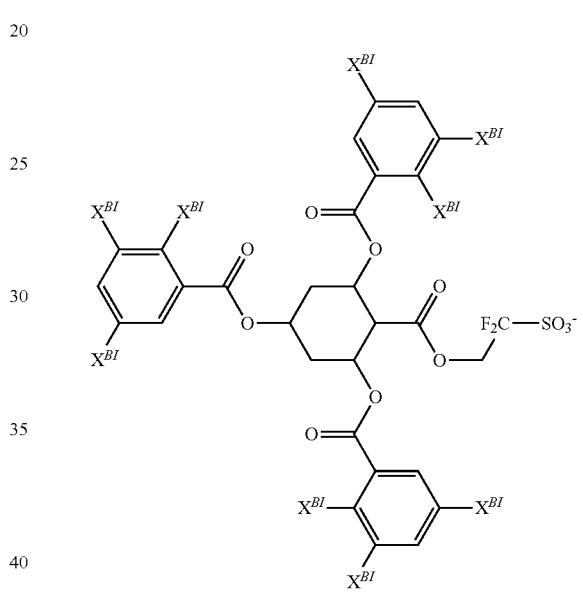

-continued
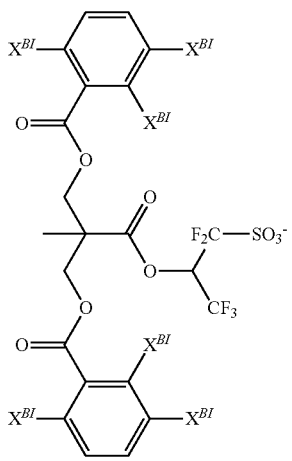
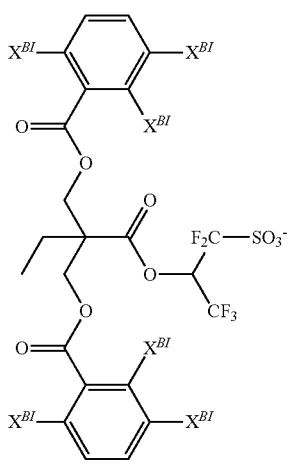
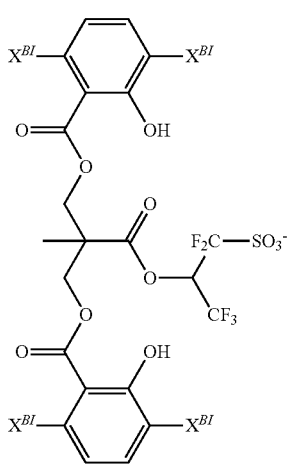
-continued
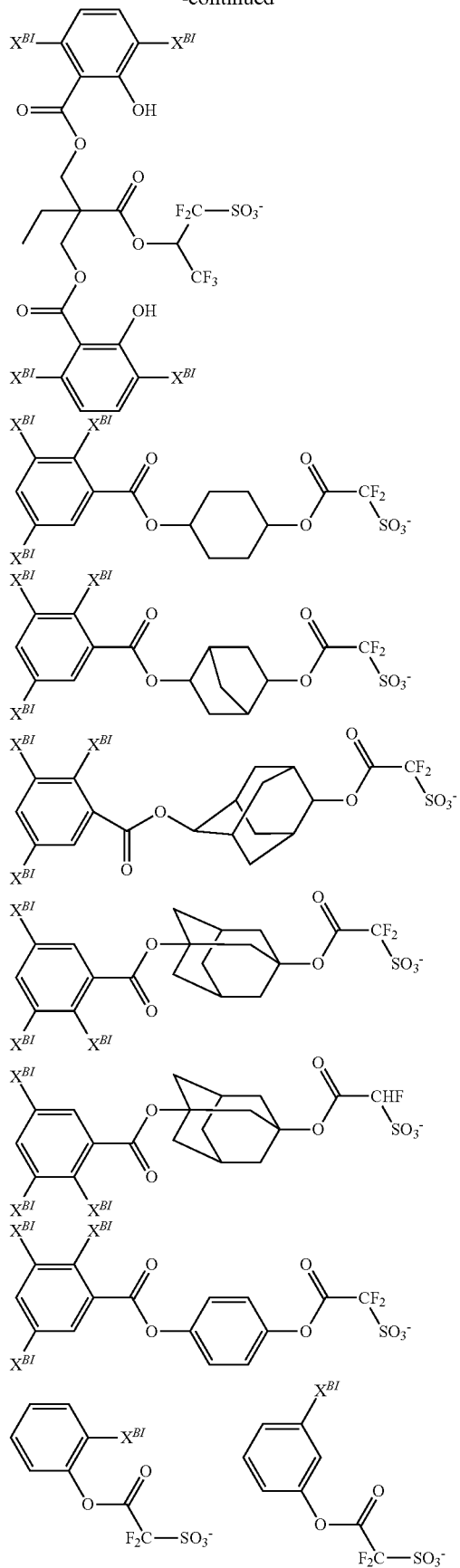

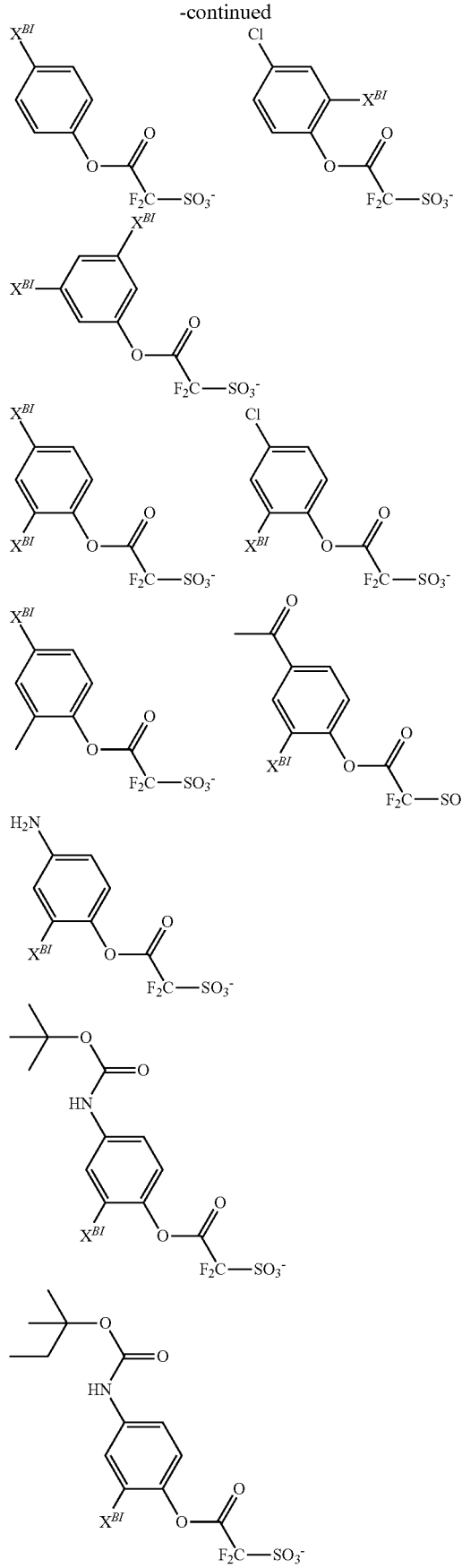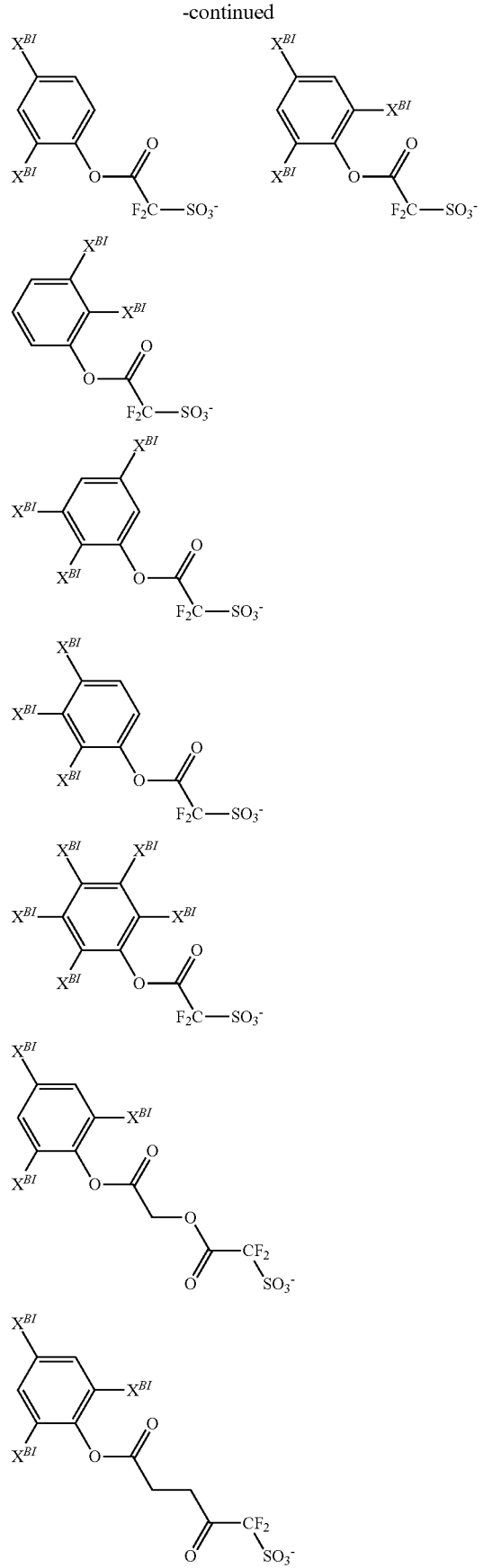

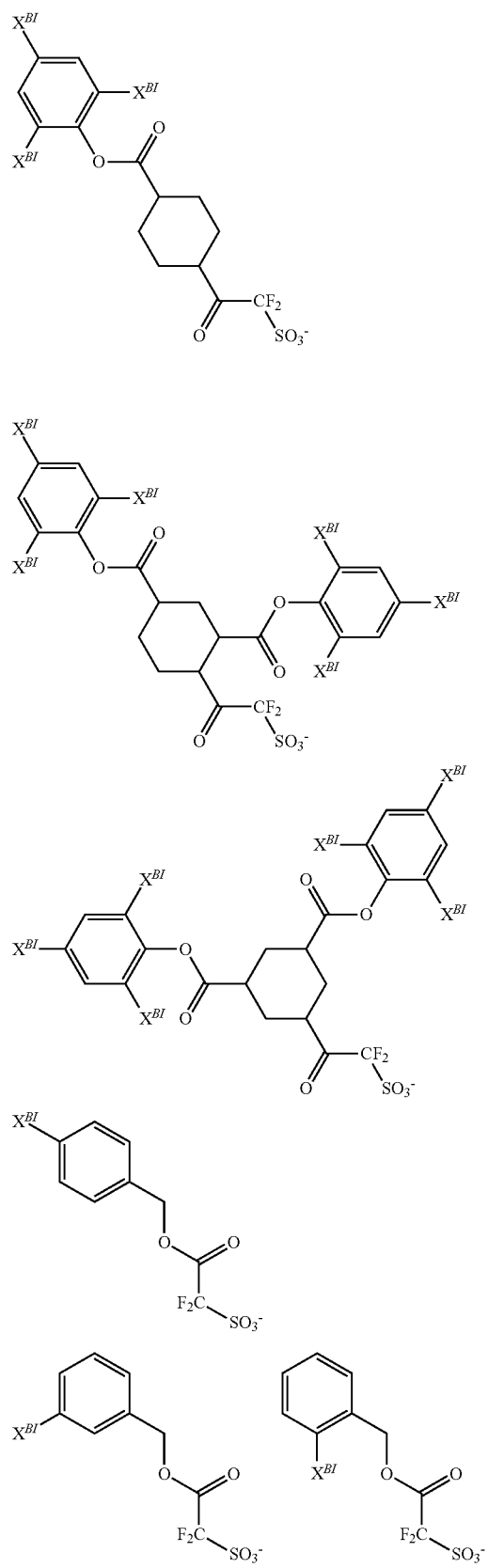
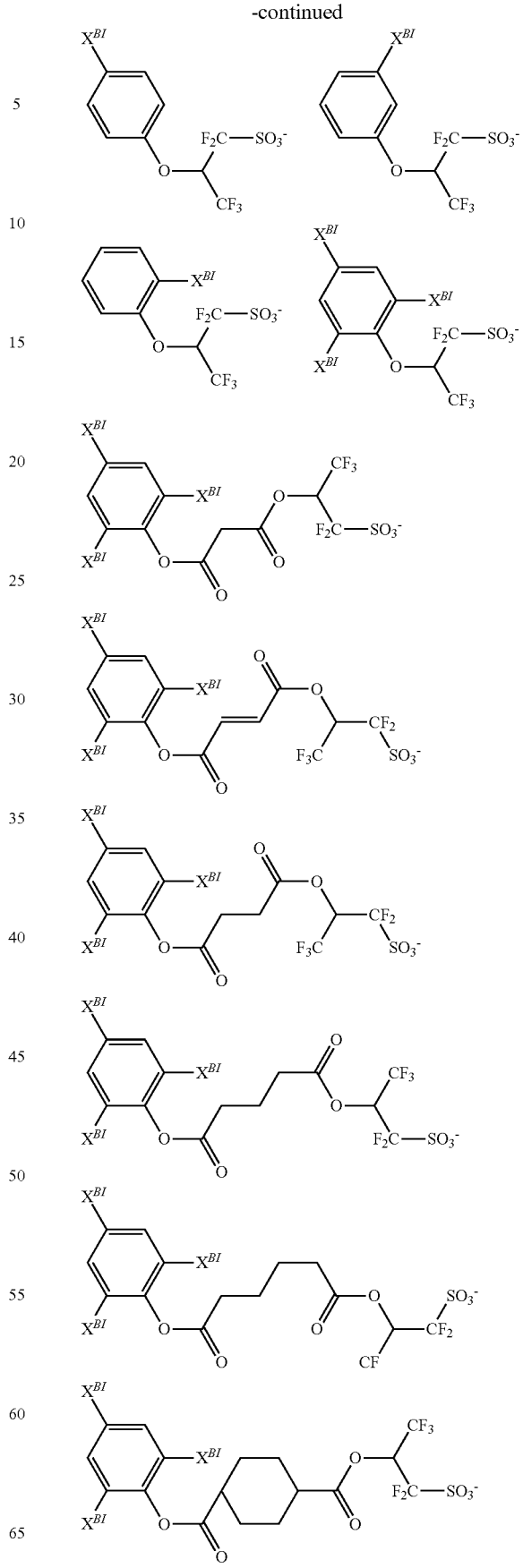

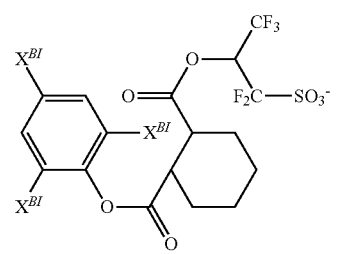
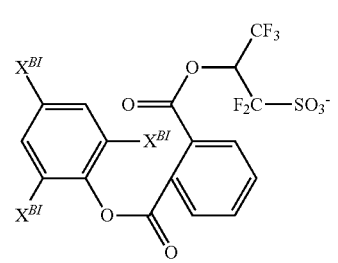
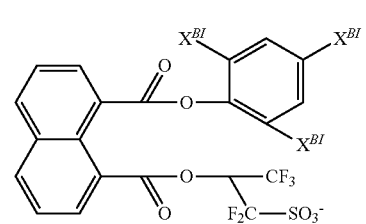
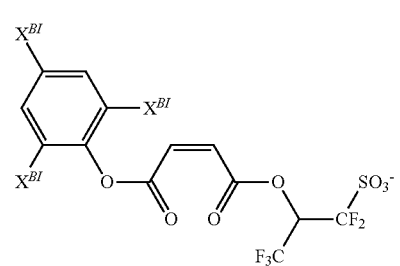
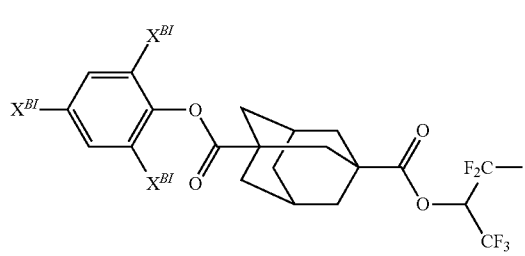
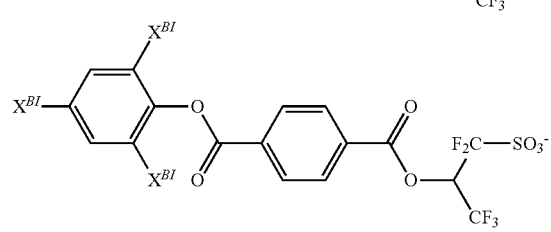
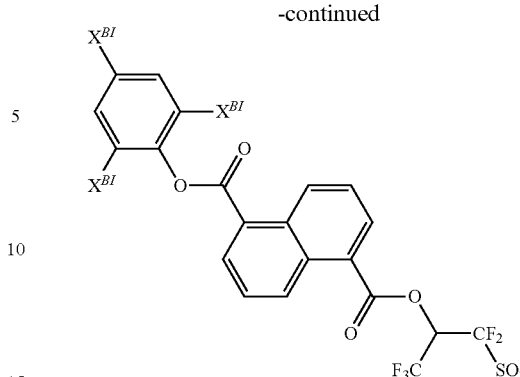
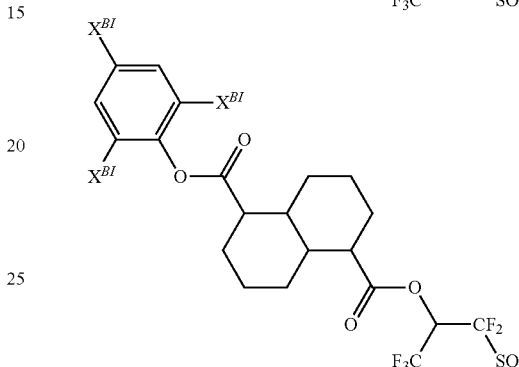
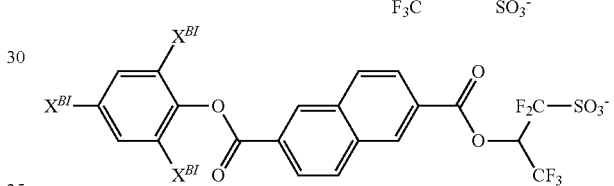
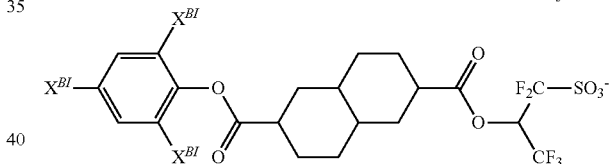
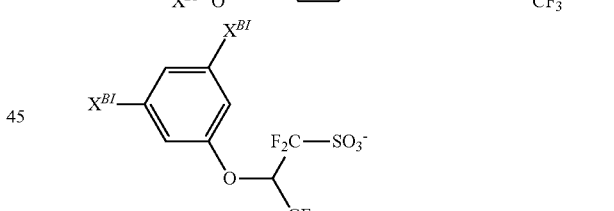
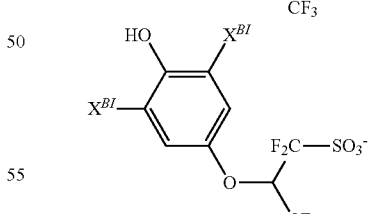
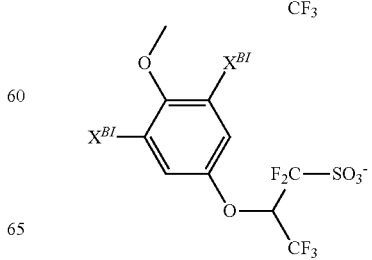

-continued
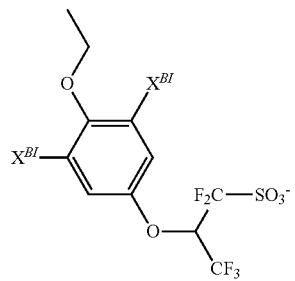
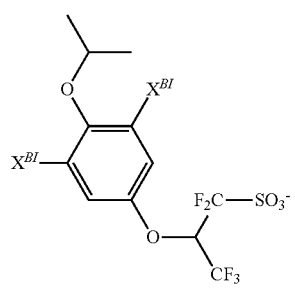
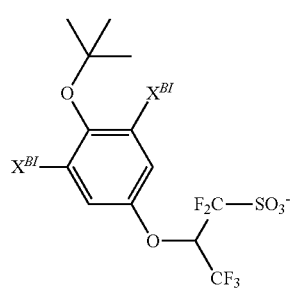
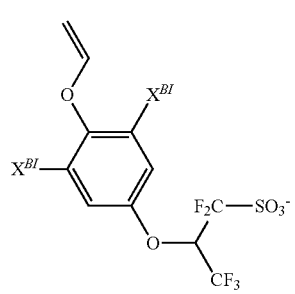
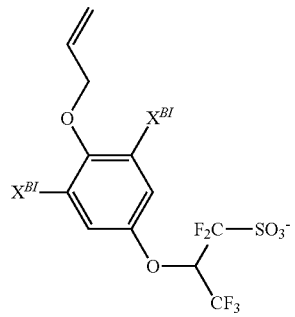
-continued
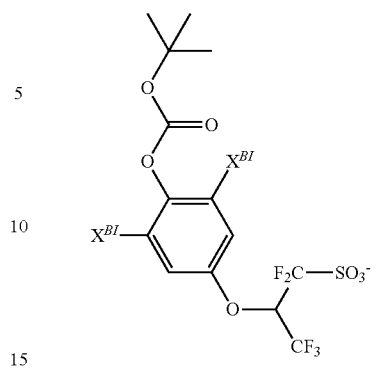
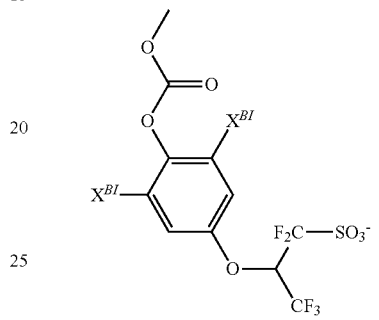
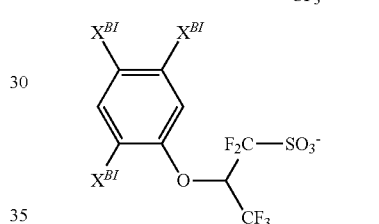
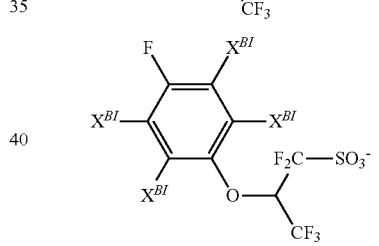
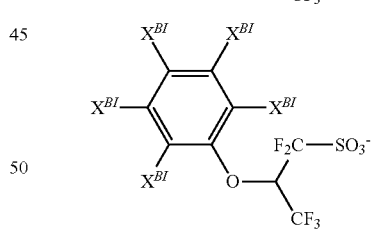
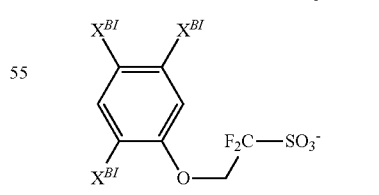
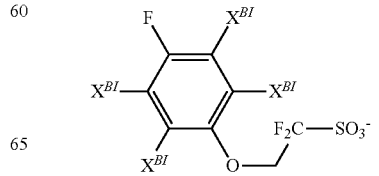

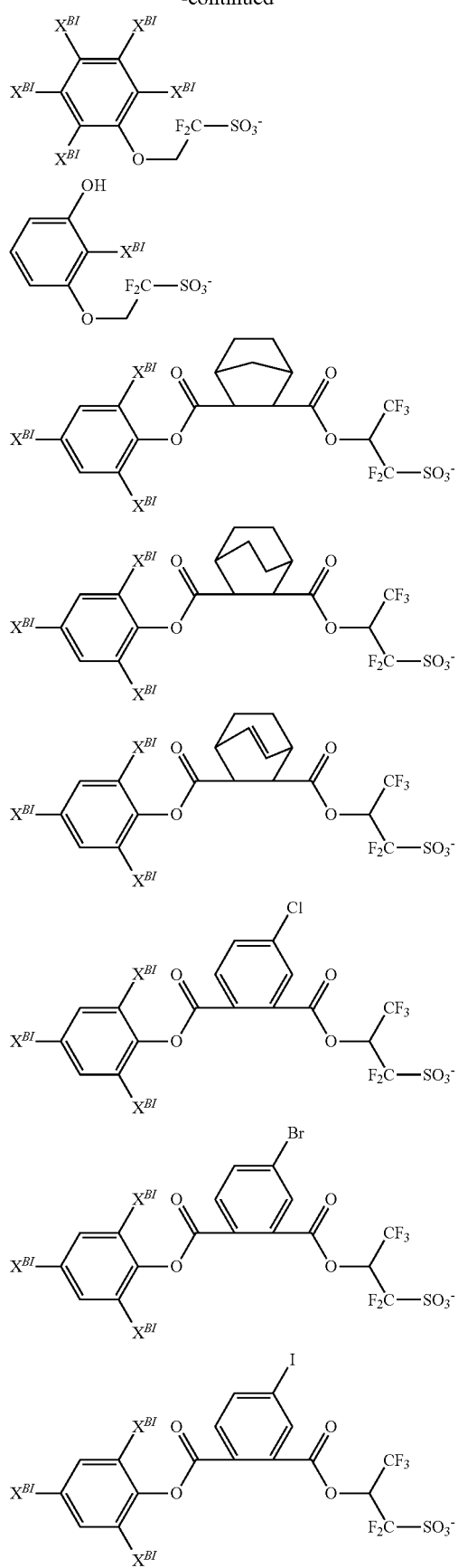
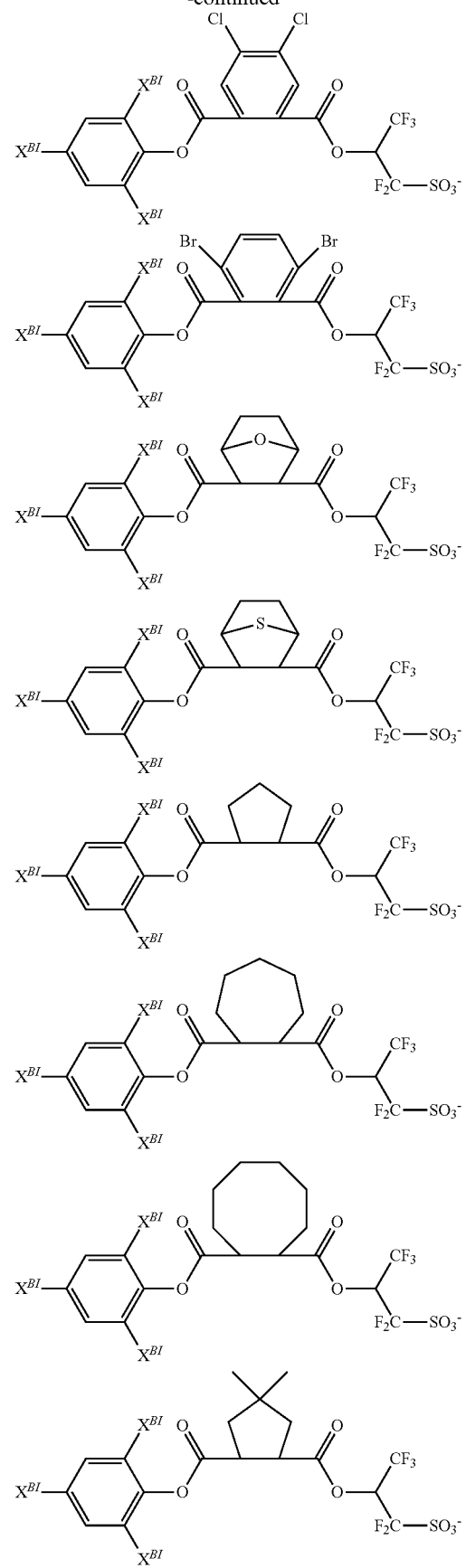

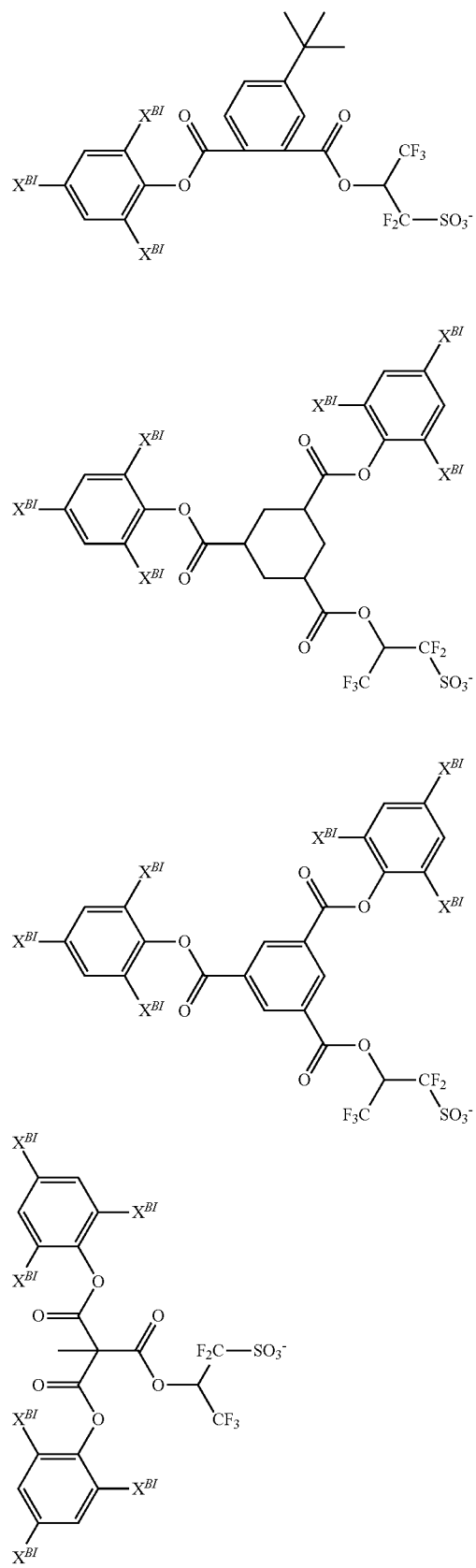
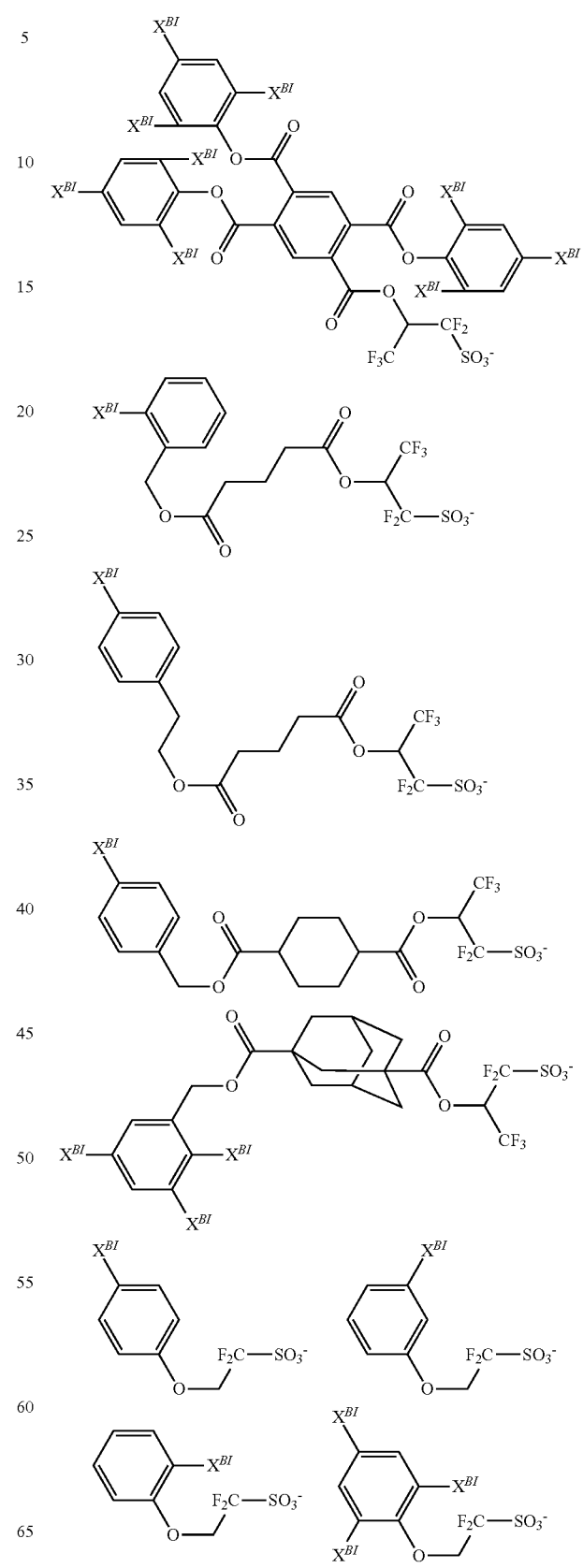

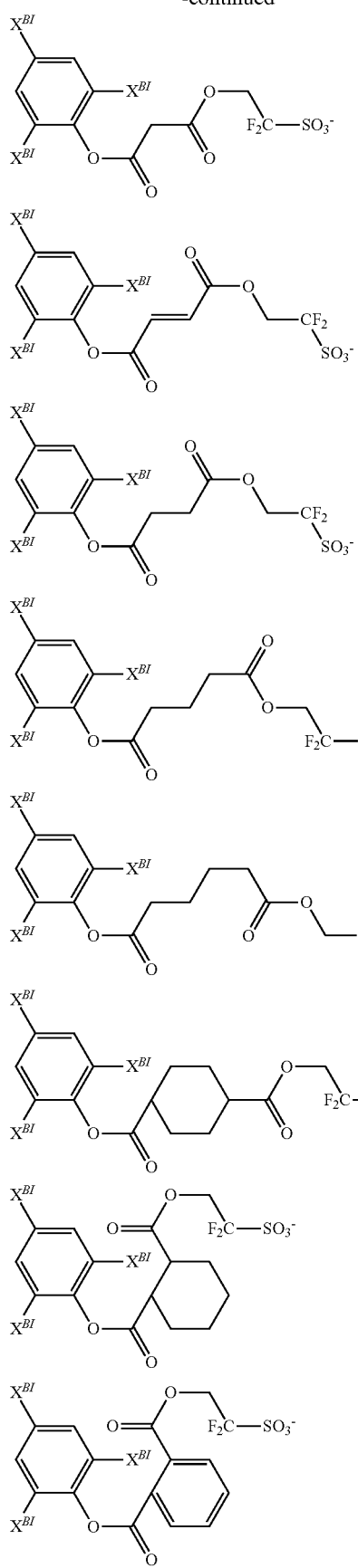
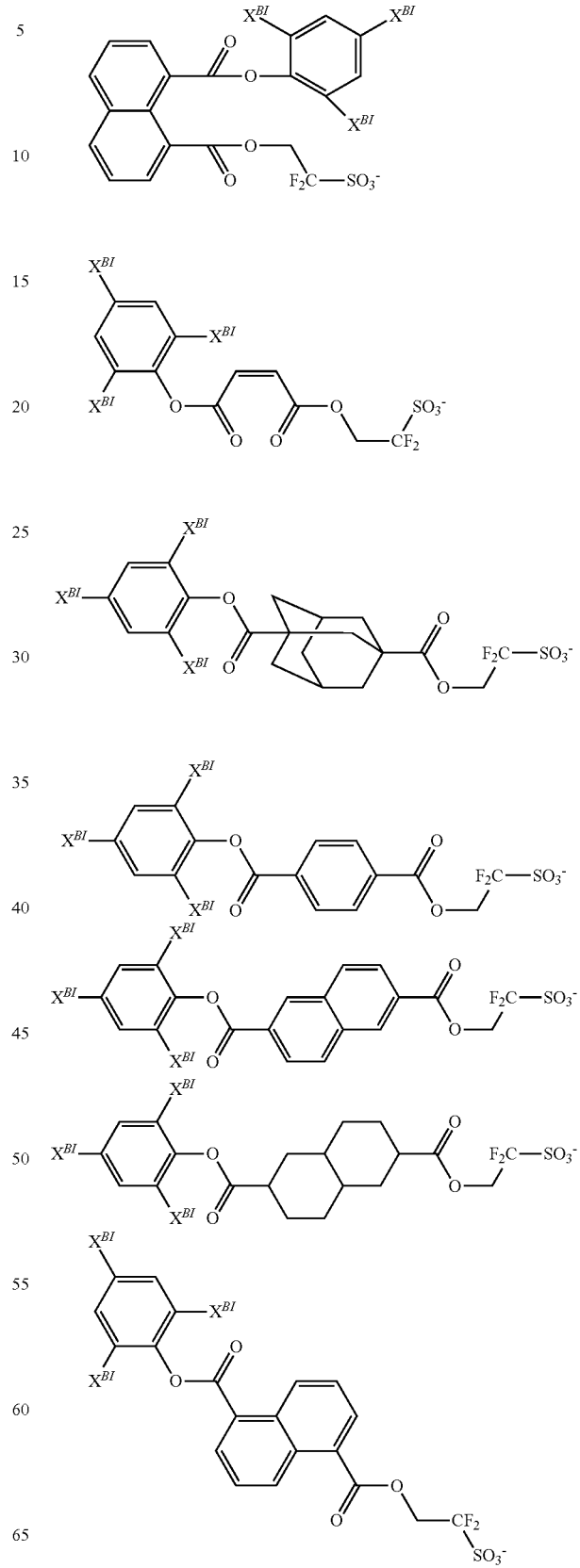

181
-continued
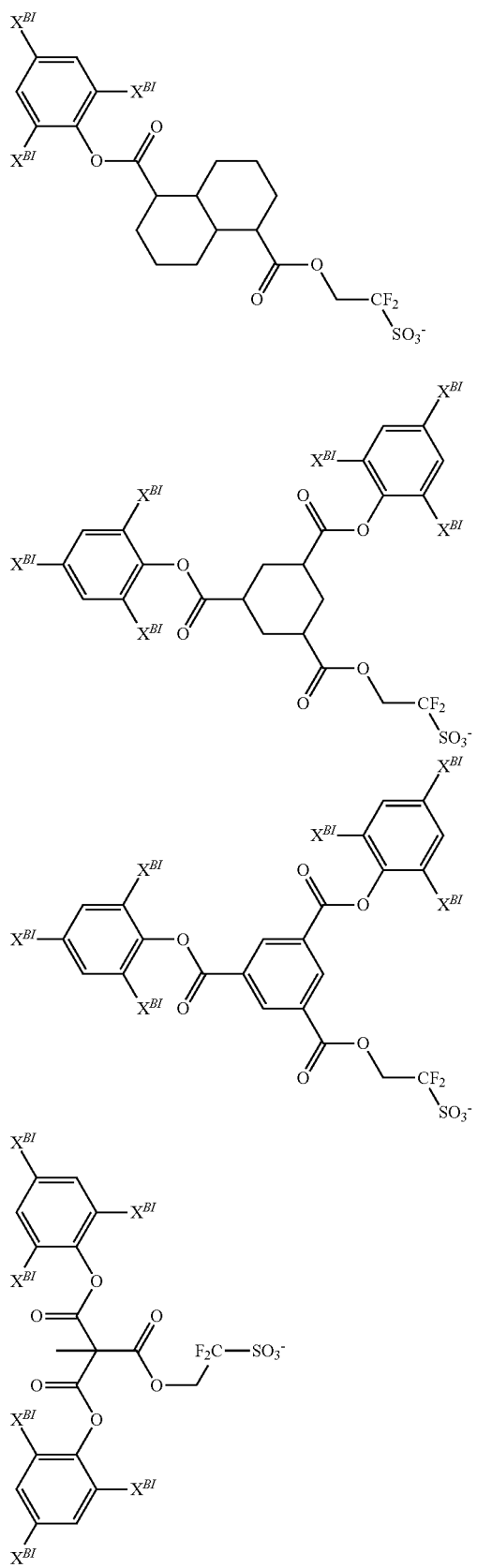
182
-continued
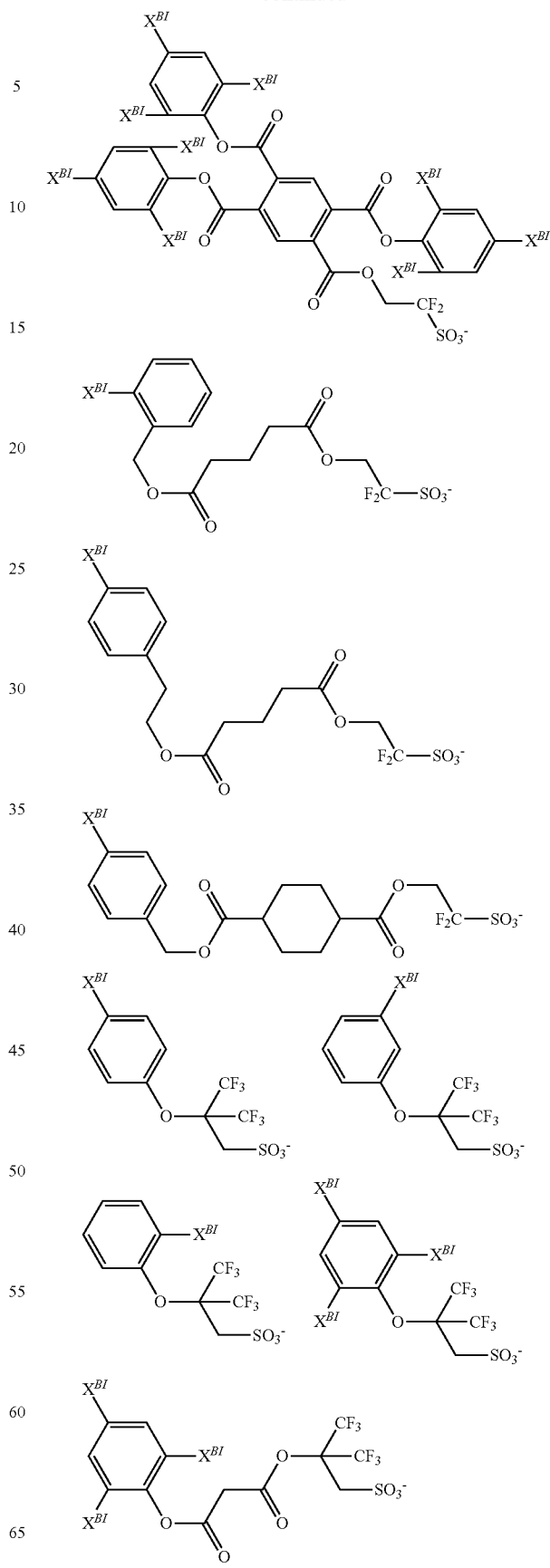

-continued
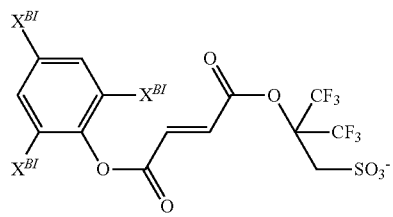
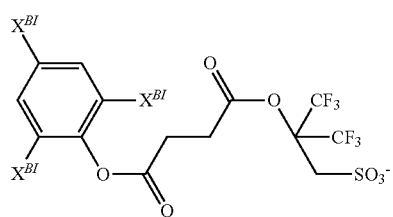
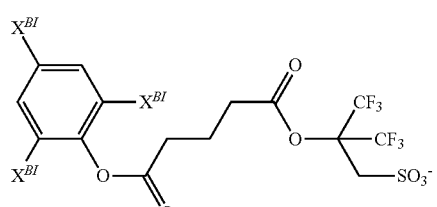
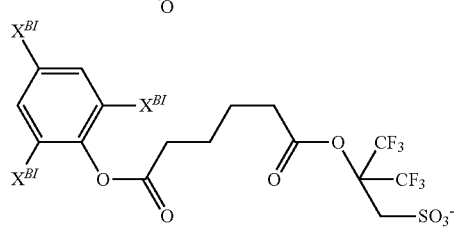
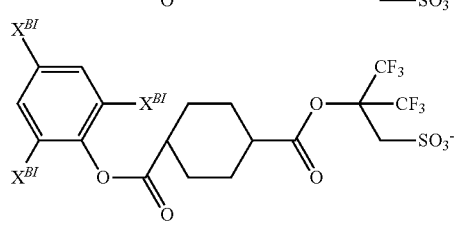
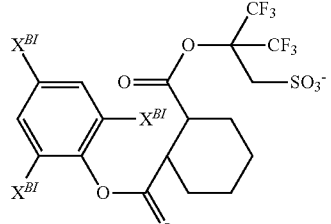
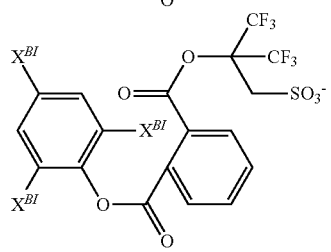
-continued
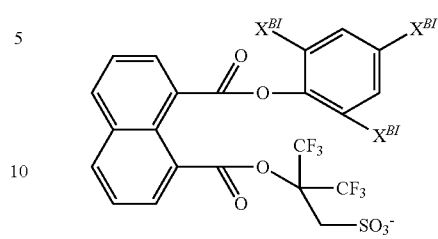
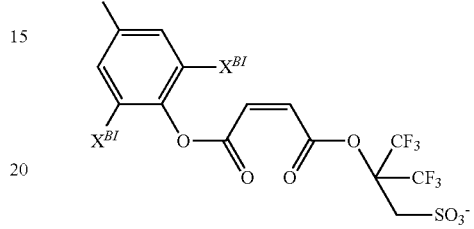
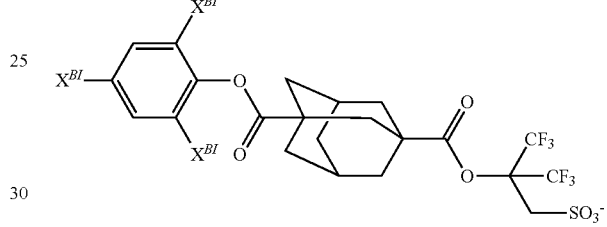
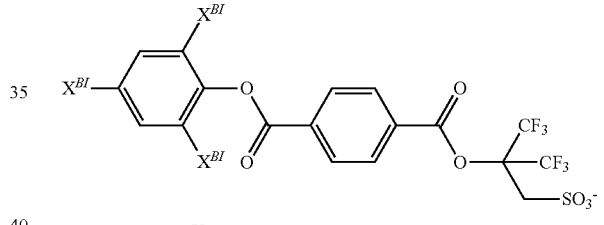
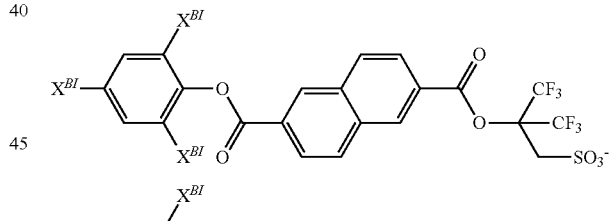
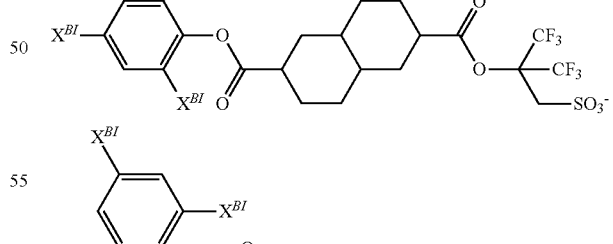
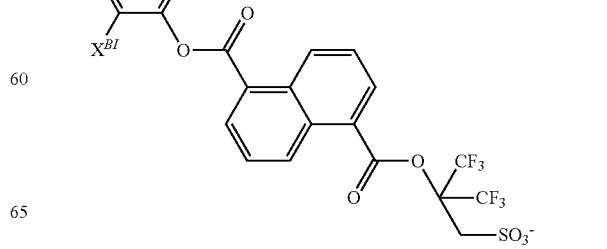

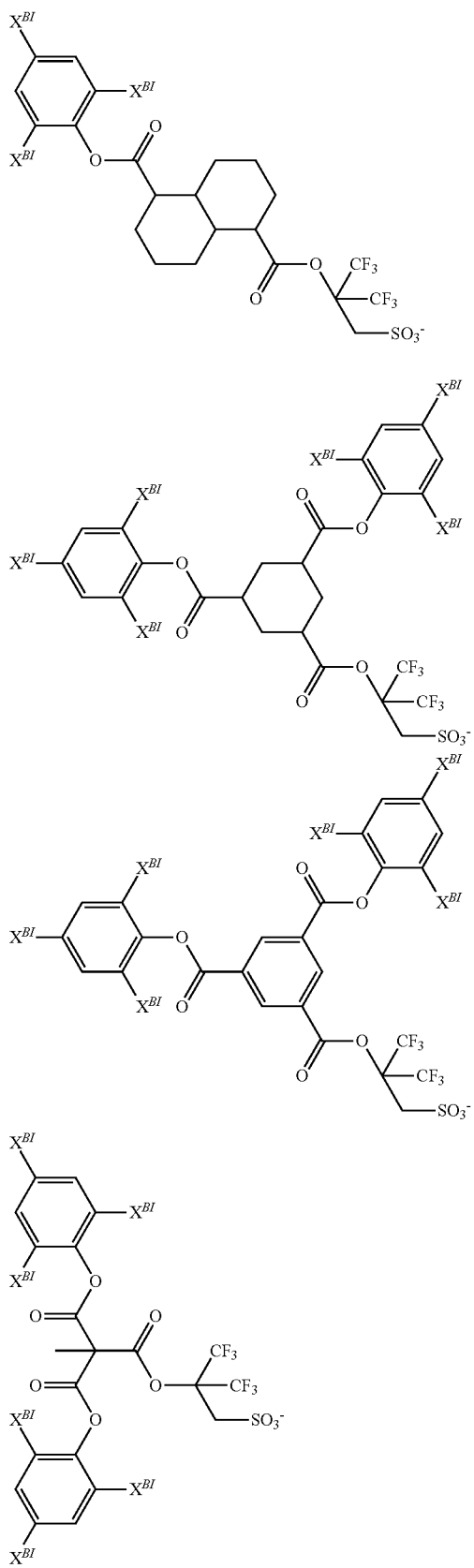
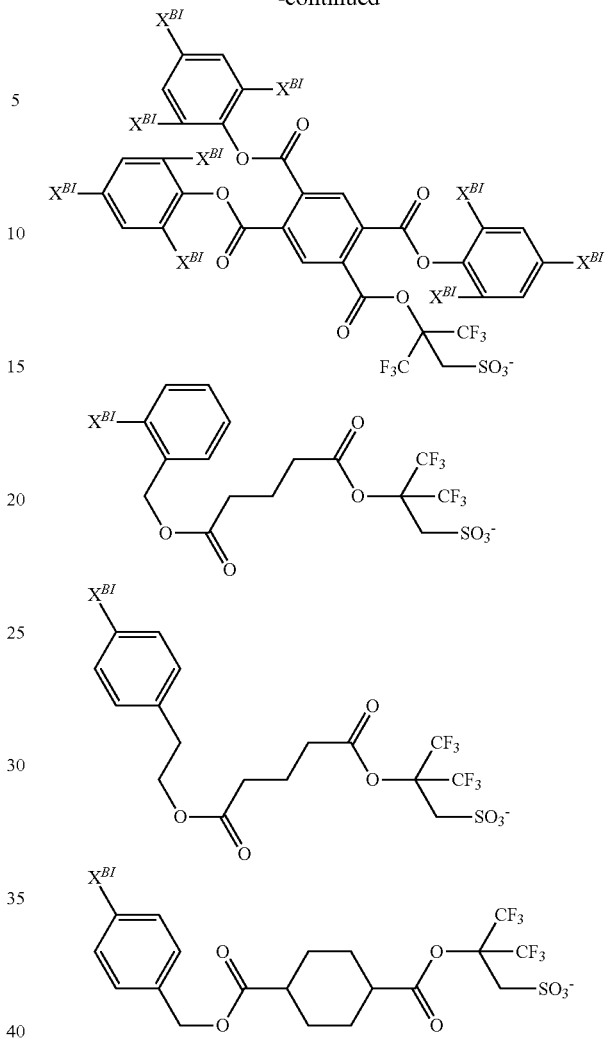

To the positive resist composition, the acid generator of addition type is preferably added in an amount of 0.1 to 50 parts, and more preferably 1 to 40 parts by weight per 100 parts by weight of the base polymer. When the base polymer contains the recurring units (d1) to (d3) and/or the acid generator of addition type is added, the positive resist composition functions as a chemically amplified positive resist composition.

Organic Solvent

The positive resist composition may contain an organic solvent. The organic solvent is not particularly limited as long as each component described above and each component described below can be dissolved in the organic solvent. Examples of the organic solvent are described in JP-A 2008-111103, paragraphs [0144]-[0145], and include ketones such as cyclohexanone, cyclopentanone, methyl-2-n-pentyl ketone, and 2-heptanone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

To the positive resist composition, the organic solvent is preferably added in an amount of 100 to 10,000 parts, and more preferably 200 to 8,000 parts by weight per 100 parts by weight of the base polymer.

Quencher

In the positive resist composition, a quencher may be blended. The quencher is typically selected from conventional basic compounds. Examples of conventional basic compounds include primary, secondary, and tertiary aliphatic amines, mixed amines, aromatic amines, heterocyclic amines, nitrogen-containing compounds with a carboxyl group, nitrogen containing compounds with a sulfonyl group, nitrogen-containing compounds with a hydroxyl group, nitrogen-containing compounds with a hydroxyphenyl group, alcoholic nitrogen-containing compounds, amide derivatives, imide derivatives, and carbamate derivatives. Particularly preferable compounds among the conventional basic compounds are primary, secondary, and tertiary amine compounds, specifically amine compounds having a hydroxyl group, an ether bond, an ester bond, a lactone ring, a cyano group, or a sulfonic acid ester bond as described in JP-A 2008-111103, paragraphs [0146] to [0164], and compounds having a carbamate group as described in JP 3790649. Addition of such a basic compound may be effective for further suppressing the diffusion rate of acid in the resist film, correcting the pattern profile, or the like.

Onium salts such as sulfonium salts, iodonium salts, and ammonium salts of sulfonic acids which are not fluorinated at α-position as described in JP-A 2008-158339 and similar onium salts of carboxylic acids may also be used as the quencher. While an α-fluorinated sulfonic acid, imide acid, and methide acid are necessary to deprotect the acid labile group of a carboxylic acid ester, an α-non-fluorinated sulfonic acid or carboxylic acid is released by salt exchange with an α-non-fluorinated onium salt. An α-non-fluorinated sulfonic acid and a carboxylic acid function as a quencher because they do not induce deprotection reaction.

Examples of the quencher include a compound (onium salt of α-non-fluorinated sulfonic acid) having the formula (4) and a compound (onium salt of carboxylic acid) having the formula (5).

$$R^{501}\text{—}SO_3^-Mq^+ \quad (4)$$

$$R^{502}\text{—}CO_2^-Mq^+ \quad (5)$$

In the formula (4), $R^{501}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or a fluoroalkyl group.

The hydrocarbyl group may be saturated or unsaturated, and may be straight, branched, or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; alkenyl groups such as vinyl, allyl, propenyl, butenyl, and hexenyl; cyclic unsaturated aliphatic hydrocarbyl groups such as cyclohexenyl; aryl groups such as phenyl, naphthyl, alkylphenyl groups (e.g., 2-methylphenyl, 3-methylphenyl, 4-methylphenyl, 4-ethylphenyl, 4-tert-butylphenyl, and 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); heteroaryl groups such as thienyl; and aralkyl groups such as benzyl, 1-phenylethyl, and 2-phenylethyl.

In these groups, some hydrogen may be substituted by a group containing a heteroatom such as oxygen, sulfur, nitrogen, or a halogen, and some carbon may be replaced by a group containing a heteroatom such as oxygen, sulfur, or nitrogen, so that the group may contain a hydroxyl group, cyano group, carbonyl group, ether bond, ester bond, sulfonic acid ester bond, carbonate bond, lactone ring, sultone ring, carboxylic anhydride, or haloalkyl group. Suitable heteroatom-containing hydrocarbyl groups include alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl; alkoxynaphthyl groups such as methoxynaphthyl, ethoxynaphthyl, n-propoxynaphthyl, and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(1-naphthyl)-2-oxoethyl, and 2-(2-naphthyl)-2-oxoethyl.

In the formula (5), $R^{502}$ is a $C_1$-$C_{40}$ hydrocarbyl group which may contain a heteroatom. Examples of the hydrocarbyl group represented by $R^{502}$ are as exemplified above for the hydrocarbyl group represented by $R^{501}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

In the formulae (4) and (5), $Mq^+$ is an onium cation. The onium cation is preferably a sulfonium cation, an iodonium cation, or an ammonium cation, and more preferably a sulfonium cation or an iodonium cation. Examples of the sulfonium cation are the same as exemplified above as the cation in the sulfonium salt having the formula (1-1). Examples of the iodonium cation are the same as exemplified above as the cation in the iodonium salt having the formula (1-2).

A sulfonium salt of iodized benzene ring-containing carboxylic acid having the formula (6) is also useful as the quencher.

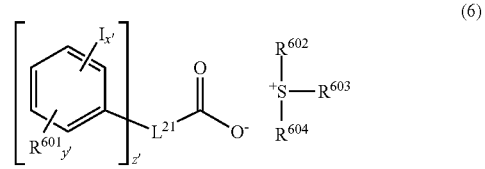

(6)

In the formula (6), $R^{601}$ is hydroxyl, fluorine, chlorine, bromine, amino, nitro, cyano, or a $C_1$-$C_6$ saturated hydrocarbyl, $C_1$-$C_6$ saturated hydrocarbyloxy $C_2$-$C_6$ saturated hydrocarbylcarbonyloxy, or $C_1$-$C_4$ saturated hydrocarbylsulfonyloxy group, in which some or all hydrogen may be substituted by a halogen, or —N($R^{601A}$)—C(=O)—$R^{601B}$, or —N($R^{601A}$)—C(=O)—O—$R^{601B}$. $R^{601A}$ is hydrogen or a $C_1$-$C_6$ saturated hydrocarbyl group. $R^{601B}$ is a $C_1$-$C_6$ saturated hydrocarbyl or $C_2$-$C_8$ unsaturated aliphatic hydrocarbyl group.

In the formula (6), x' is an integer of 1 to 5, y' is an integer of 0 to 3, and z' is an integer of 1 to 3. $L^{21}$ is a single bond, or a $C_1$-$C_{20}$ (z'+1)-valent linking group which may contain at least one group selected from an ether bond, a carbonyl group, an ester bond, an amide bond, a sultone ring, a lactam ring, a carbonate group, a halogen, a hydroxyl group, and a carboxyl group. The saturated hydrocarbyl, saturated hydrocarbyloxy, saturated hydrocarbylcarbonyloxy, and saturated hydrocarbylsulfonyloxy groups may be straight, branched, or cyclic. Groups $R^{601}$ may be the same or different when y' and/or z' is 2 or more.

In the formula (6), $R^{602}$, $R^{603}$, and $R^{604}$ are each independently fluorine, chlorine, bromine, iodine, or a $C_1$-$C_{20}$ hydrocarbyl group which may contain a heteroatom. The hydrocarbyl group may be saturated or unsaturated, and may be straight, branched, or cyclic. Examples thereof include $C_1$-$C_{20}$ alkyl-, $C_2$-$C_{20}$ alkenyl, $C_6$-$C_{20}$ aryl, and $C_7$-$C_{20}$ aralkyl groups. In these groups, some or all hydrogen may be substituted by hydroxyl, carboxyl, halogen, oxo, cyano, nitro, sultone, sulfone, or a sulfonium salt-containing group, or some carbon may be replaced by an ether bond, ester bond, carbonyl group, amide bond, carbonate group, or sulfonic acid ester bond. Also $R^{602}$ and $R^{603}$ may bond together to form a ring with the sulfur atom to which they are attached.

Examples of the compound having the formula (6) include those described in JP-A 2017-219836. Since iodine is highly absorptive to EUV of wavelength 13.5 nm, it generates secondary electrons during exposure, with the energy of secondary electrons being transferred to the acid generator. This promotes the decomposition of the quencher, contributing to a higher sensitivity.

Also useful are quenchers of polymer type as described in JP-A 2008-239918. This quencher segregates at the resist film surface and thus enhances the rectangularity of resist pattern. When a protective film is applied as is often the case in the immersion lithography, the polymeric quencher is also effective for preventing a film thickness loss of resist pattern or rounding of pattern top.

To the positive resist composition, the quencher is preferably added in an amount of 0 to 5 parts, more preferably 0 to 4 parts by weight per 100 parts by weight of the base polymer. The quencher may be used alone or in admixture.

Other Components

In addition to the foregoing components, other components such as surfactant and dissolution inhibitor may be blended in any desired combination to formulate a positive resist composition. This positive resist composition has a very high sensitivity in that the dissolution rate in developer of the base polymer in exposed areas is accelerated by catalytic reaction. In this case, the resist film has a high dissolution contrast, a high resolution, exposure latitude, and excellent process adaptability, and provides a good pattern profile after exposure, and minimal proximity bias because of restrained acid diffusion. By virtue of these advantages, the resist composition is fully useful in commercial application and suited as a pattern-forming material for the fabrication of VLSIs.

Examples of the surfactant include the surfactants described in JP-A 2008-111103, paragraphs [0165] to [0166]. Addition of a surfactant may improve or control the coating characteristics of the resist composition. To the positive resist composition, the surfactant is preferably added in an amount of 0.0001 to 10 parts by weight per 100 parts by weight of the base polymer. The surfactant may be used alone or in admixture.

The inclusion of a dissolution inhibitor may lead to an increased difference in dissolution rate between exposed and unexposed areas and a further improvement in resolution. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds preferably having a molecular weight of 100 to 1,000, and more preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in JP-A 2008-122932, paragraphs [0155] to [0178].

The dissolution inhibitor is preferably added in an amount of 0 to 50 parts, more preferably 5 to 40 parts by weight per 100 parts by weight of the base polymer. The dissolution inhibitor may be used alone or in admixture.

To the positive resist composition, a water repellency improver may also be added for improving the water repellency on the surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver should be soluble in alkaline developers and organic solvent developers. The water repellency improver of specific structure with a 1,1,1,3,3,3-hexafluoro-2-propanol residue is well soluble in the developer. A polymer having an amino group or amine salt copolymerized as recuing units may serve as the water repellency improver and is effective for preventing evaporation of acid during PEB, thus preventing any hole pattern opening failure after development. In the positive resist composition, an appropriate amount of the water repellency improver is 0 to 20 pats, preferably 0.5 to 10 parts by weight per 100 parts by weight of the base polymer. The water repellency improver may be used alone or in combination of two or more.

Also, an acetylene alcohol may be blended in the positive resist composition. Examples of the acetylene alcohol include the acetylene alcohols described in JP-A 2008-122932, paragraphs [0179] to [0182]. In the positive resist composition, an appropriate amount of the acetylene alcohol blended is 0 to 5 parts by weight per 100 parts by weight of the base polymer.

Pattern Forming Process

The positive resist composition is used in the fabrication of various integrated circuits. Pattern formation using the resist composition may be performed by well-known lithography processes. The pattern forming process generally involves the steps of applying the resist composition onto a substrate to form a resist film thereon, exposing the resist film to high-energy radiation, and developing the exposed resist film in a developer.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying, or doctor coating. The resulting resist film is generally 0.01 to 2 μm thick. The coating is prebaked on a hotplate preferably at a temperature of 60 to 150° C. for 10 seconds to 30 minutes, more preferably at 80 to 120° C. for 30 seconds to 20 minutes. The resulting resist film is generally 0.01 to 2 μm thick.

Then the resist film is exposed to high-energy radiation. Examples of the high-energy radiation include ultraviolet (UV), deep-UV, EB, EUV, x-rays, soft x-rays, excimer laser radiation, γ-rays, and synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 $mJ/cm^2$. On use of EB as the high-energy radiation, a pattern may be written directly or through a mask having a desired pattern, preferably in a dose of about 0.1 to 100 $\mu C/cm^2$, more preferably about 0.5 to 50 $\mu C/cm^2$. The positive resist composition is suited for micropatterning using high-energy radiation such as i-line of wavelength 365 nm, KrF excimer laser radiation, ArF excimer laser radiation. EB, EUV, x-rays, soft x-rays, γ-rays, or synchrotron radiation, especially EB or EUV.

After the exposure, the resist film may be baked (PEB) on a hotplate or in an oven preferably at 50 to 150° C. for 10 seconds to 30 minutes, more preferably at 60 to 120° C. for 30 seconds to 20 minutes.

After the exposure or PEB, the resist film is developed in a developer in the form of an aqueous base solution for 3 seconds to 3 minutes, preferably 5 seconds to 2 minutes by a conventional technique such as a dip, puddle, or spray technique. A typical developer is a 0.1 to 10 wt %, preferably 2 to 5 wt % of an alkaline aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate.

In an alternative embodiment using the positive resist composition, a negative pattern may be formed via organic solvent development. Examples of the developer used at this time include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. The organic solvents may be used alone or in admixture.

At the end of development, the resist film is rinsed. As the rinsing liquid, a solvent which is miscible with the developer and does not dissolve the resist film is preferred. Suitable examples of the solvent include alcohols of 3 to 10 carbon atoms, ether compounds of 8 to 12 carbon atoms, alkanes, alkenes, and alkynes of 6 to 12 carbon atoms, and aromatic solvents.

Specific examples of the alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol.

Examples of the ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether.

Examples of the alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Examples of the alkenes of 6 to 12 carbon atoms include hexene, heptene, octene, cyclohexene, methylcyclohexene, dimethylcyclohexene, cycloheptene, and cyclooctene. Examples of the alkynes of 6 to 12 carbon atoms include hexyne, heptyne, and octyne.

Examples of the aromatic solvents include toluene, xylene, ethylbenzene, isopropylbenzene, tert-butylbenzene, and mesitylene.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, the shrink agent may undergo crosslinking at the resist surface as a result of the acid catalyst diffusing from the resist film during bake, and the shrink agent may attach to the sidewall of the hole pattern. The bake is preferably at a temperature of 70 to 180° C., more preferably 80 to 170° C., preferably for a time of 10 to 300 seconds. The extra shrink agent is stripped and the hole pattern is shrunk.

EXAMPLES

Hereinafter, the invention is specifically described with reference to Synthesis Examples, Examples, and Comparative Examples, but the invention is not limited to the following Examples. The devices used are as follows.

IR: NICOLET 6700 manufactured by Thermo Fisher Scientific Inc.

$^1$H-NMR: ECA-500 manufactured by JEOL Ltd.

[1] Synthesis of Monomers

Synthesis Example 1-1

Synthesis of Monomer 1

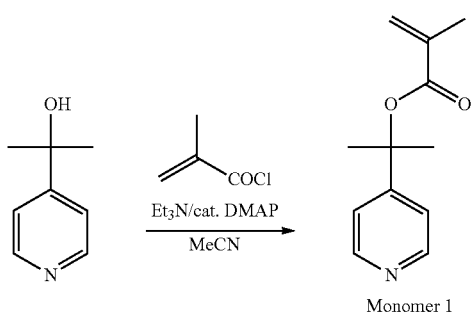

Monomer 1

In a reactor, 68.6 g of 2-(4-pyridyl)-2-propanol, 86.0 g of triethylamine, and 6.1 g of 4-dimethylaminopyridine were dissolved in 250 mL of acetonitrile, and 73.2 g of methacrylic acid chloride was added dropwise while the temperature in the reactor (internal temperature) was kept to 40 to 60° C. The reaction solution was stirred at an internal temperature of 60° C. for 19 hours and then cooled, and 170 mL of saturated aqueous sodium hydrogen carbonate was added to stop the reaction. The target product was extracted with a mixed solvent of 250 mL of toluene, 150 mL of hexane, and 150 mL of ethyl acetate, subjected to normal aqueous work-up to distill off the solvent, and then subjected to vacuum distillation to obtain Monomer 1 as 80.2 g of a colorless and transparent oil (yield: 78%, boiling point: 68° C./5 Pa).

The IR spectrum data of Monomer 1 and the results of nuclear magnetic resonance spectrum ($^1$H-NMR) are shown below.

IR (D-ATR): ν=3415, 2983, 2929, 1718, 1637, 1599, 1558, 1495, 1453, 1410, 1384, 1367, 1328, 1303, 1275, 1223, 1175, 1143, 1112, 1091, 1071, 1009, 995, 943, 852, 820, 728, 654, 614, 569 cm$^{-1}$ $^1$H-NMR (600 MHz in DMSO-d6):

δ=8.52 (2H, d), 7.31 (2H, d), 6.07 (1H, s), 5.68 (1H, s), 1.86 (3H, s), 1.71 (6H, s) ppm

Synthesis Example 1-2

Synthesis of Monomer 2

Monomer 2 having the following formula was obtained in the same manner as in Synthesis Example 1-1 except that the methacrylic acid chloride was changed to 4-styrene carboxylic acid chloride.

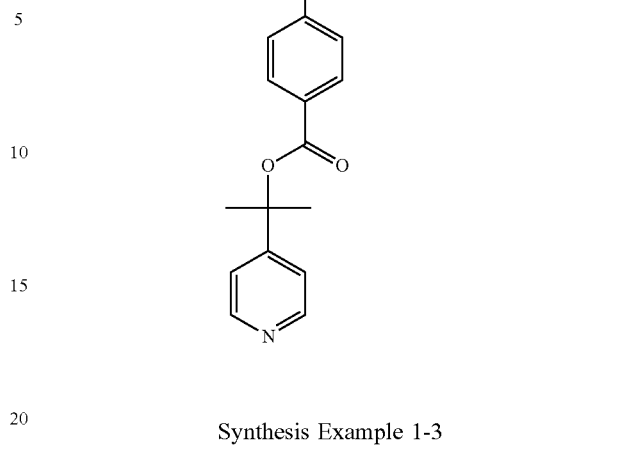

Monomer 2

Synthesis Example 1-3

Synthesis of Monomer 3

Monomer 3 having the following formula was obtained in the same manner as in Synthesis Example 1-1 except that the methacrylic acid chloride was changed to 3-styrene carboxylic acid chloride.

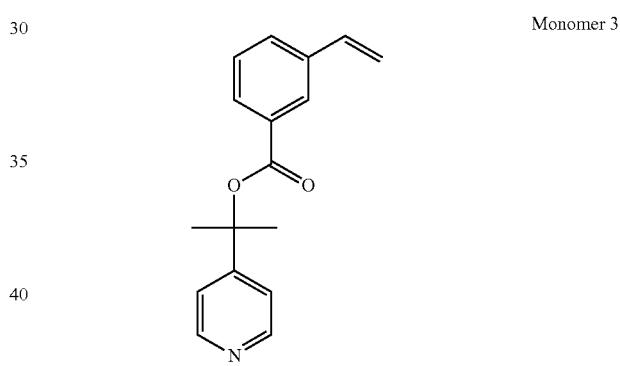

Monomer 3

Synthesis Example 1-4

Synthesis of Monomer 4

Monomer 4 having the following formula was obtained in the same manner as in Synthesis Example 1-1 except that 2-(4-pyridyl)-2-propanol was changed to 2-(3-pyridyl)-2-propanol.

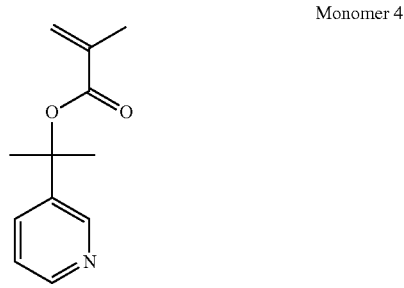

Monomer 4

Synthesis Example 1-5

Synthesis of Monomer 5

Monomer 5 having the following formula was obtained in the same manner as in Synthesis Example 1-1 except that 2-(4-pyridyl)-2-propanol in Synthesis Example 1-1 was changed to 1-hydroxy-1-(3-pyridyl)cyclopentane.

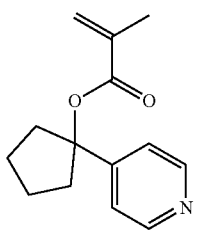

Monomer 5

[2] Synthesis of Polymers

PAG Monomers 1 to 8 and ALG Monomers 1 to 9 identified below were used in the synthesis of polymers. The Mw of the polymer is a value measured by GPC versus polystyrene standards using THF as a solvent.

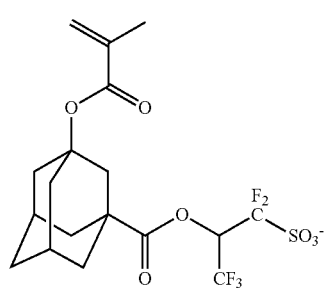

PAG Monomer 1

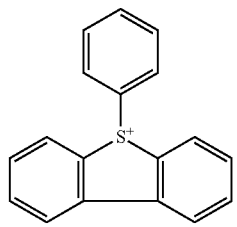

PAG Monomer 2

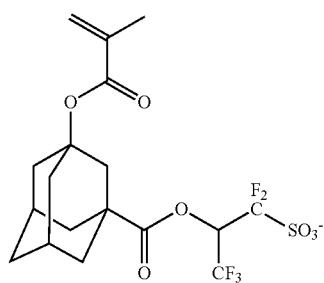

PAG Monomer 3

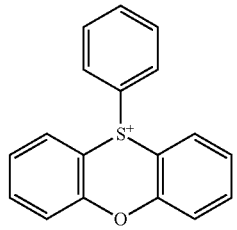

PAG Monomer 4

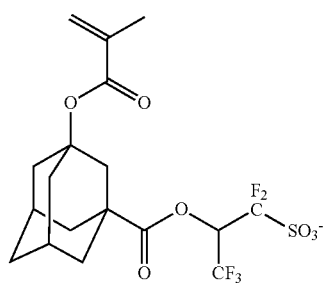

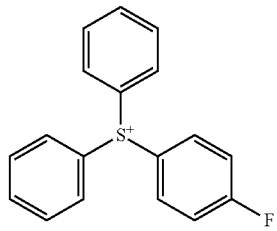

PAG Monomer 5

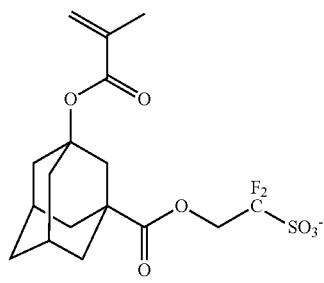

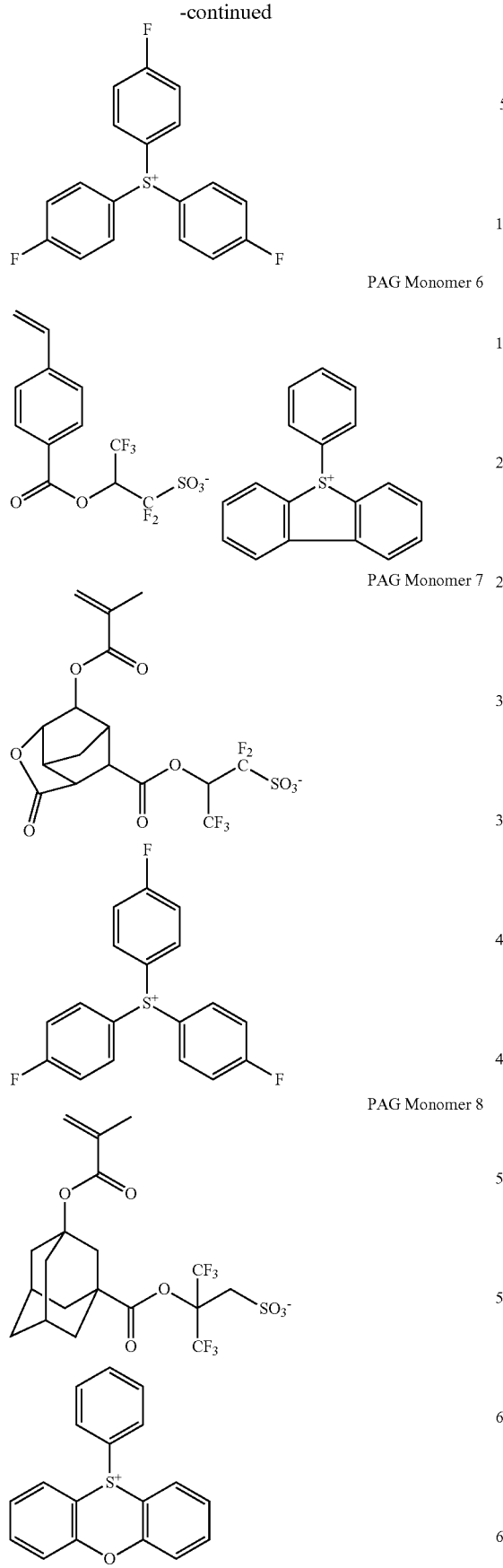
PAG Monomer 6
PAG Monomer 7
PAG Monomer 8
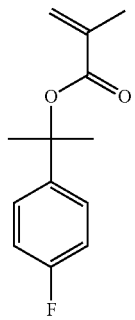 ALG Monomer 1
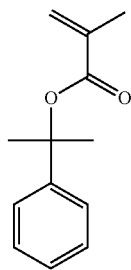 ALG Monomer 2
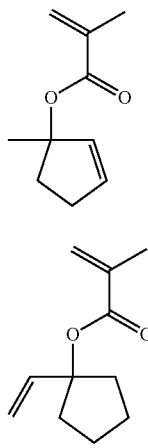 ALG Monomer 3
ALG Monomer 4
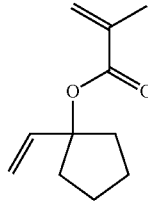 ALG Monomer 5
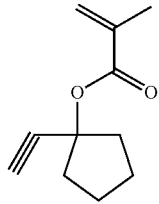 ALG Monomer 6
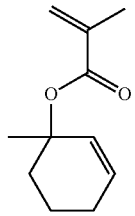

ALG Monomer 7

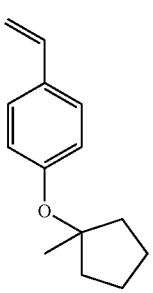

ALG Monomer 8

ALG Monomer 9

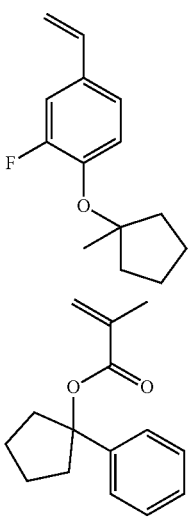

Synthesis Example 2-1

Synthesis of Polymer 1

A 2-L flask was charged with 4.1 g of Monomer 1, 6.7 g of 1-methyl-1-cyclopentyl methacrylate, 4.8 g of 4-hydroxystyrene, and 40 g of tetrahydrofuran (THF) as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 1. Polymer 1 was analyzed for composition by $^{13}$C- and $^{1}$H-NMR and for Mw and Mw/Mn by GPC.

Polymer 1

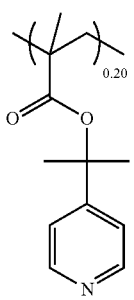

Mw = 7,700
Mw/Mn = 1.61

Synthesis Example 2-2

Synthesis of Polymer 2

A 2-L flask was charged with 4.1 g of Monomer 1, 5.5 g of 1-methyl-1-cyclohexyl methacrylate, 4.2 g of 4-hydroxystyrene, 11.9 g of PAG Monomer 1, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 2. Polymer 2 was analyzed for composition by $^{13}$C- and $^{1}$H-NMR and for Mw and Mw/Mn by GPC.

Polymer 2

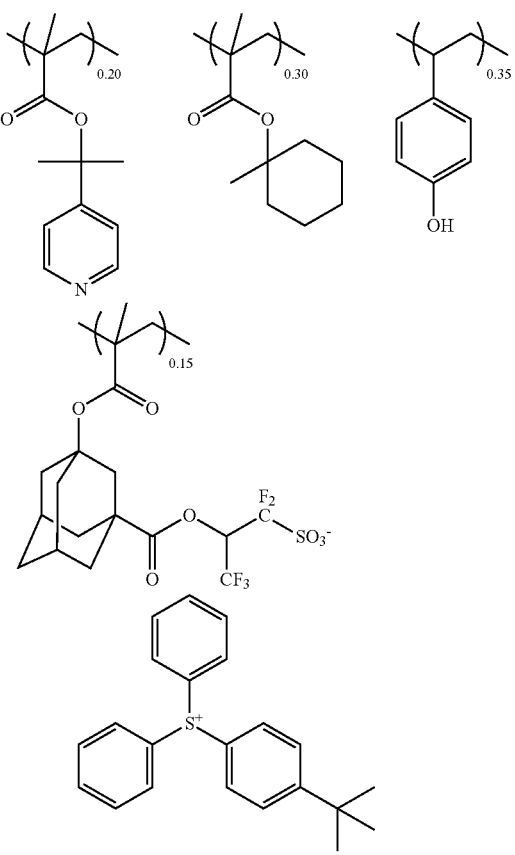

Mw = 9,300
Mw/Mn = 1.77

Synthesis Example 2-3

Synthesis of Polymer 3

A 2-L flask was charged with 2.1 g of Monomer 1, 5.2 g of 1-(cyclopropyl-1-yl)-1-methylethyl methacrylate, 3.5 g of 3-fluoro-4-(methylcyclohexyloxy)styrene, 4.8 g of 3-hydroxystyrene, 11.2 g of PAG Monomer 3, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 3. Polymer 3 was analyzed for composition by $^{13}$C- and $^1$H-NMR and for Mw and Mw/Mn by GPC.

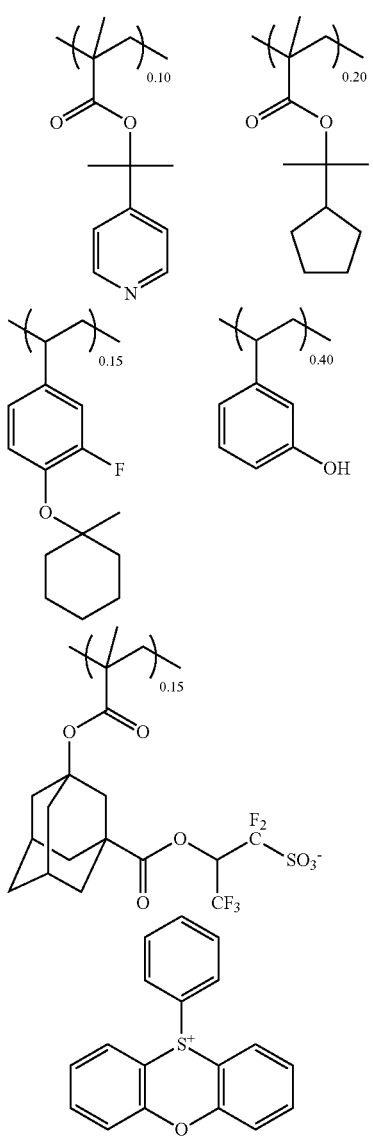

Polymer 3

Mw = 9,200
Mw/Mn = 1.83

Synthesis Example 2-4

Synthesis of Polymer 4

A 2-L flask was charged with 2.5 g of Monomer 1, 6.4 g of 1-methyl-1-cyclopentyl methacrylate, 4.2 g of 4-hydroxystyrene, 11.0 g of PAG Monomer 2, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 4. Polymer 4 was analyzed for composition by $^{13}$C- and $^1$H-NMR and for Mw and Mw/Mn by GPC.

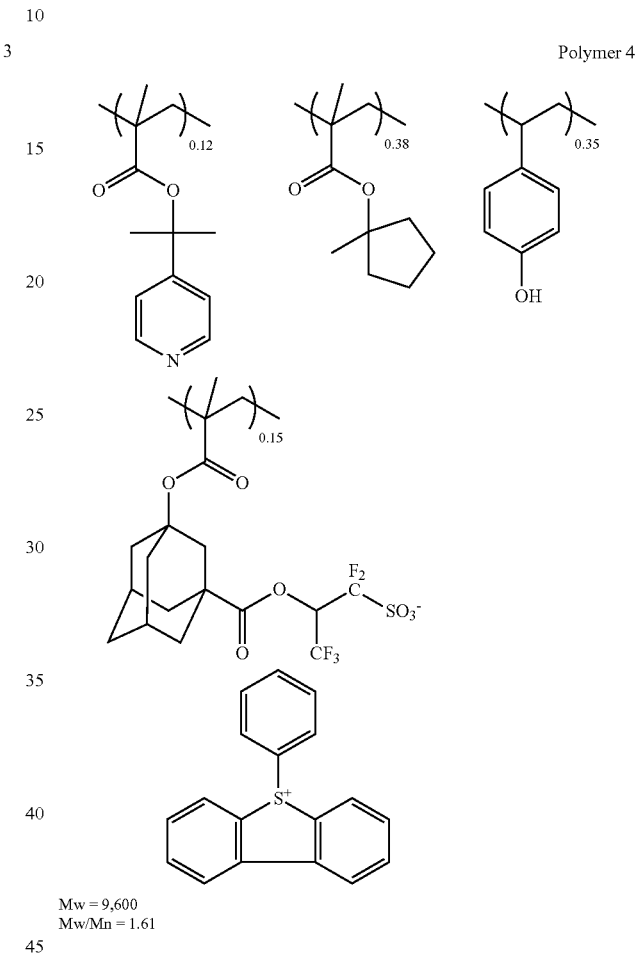

Polymer 4

Mw = 9,600
Mw/Mn = 1.61

Synthesis Example 2-5

Synthesis of Polymer 5

A 2-L flask was charged with 3.1 g of Monomer 1, 6.4 g of 1-ethyl-1-cyclopentyl methacrylate, 4.2 g of 4-hydroxystyrene, 11.0 g of PAG Monomer 2, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 5. Polymer 5 was analyzed for composition by $^{13}$C- and $^1$H-NMR and for Mw and Mw/Mn by GPC. P Polymer 5

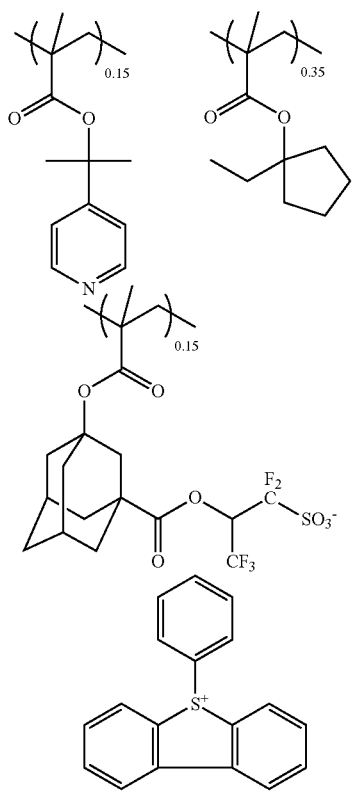

Mw = 9,500
Mw/Mn = 1.66

Synthesis Example 2-6

Synthesis of Polymer 6

A 2-L flask was charged with 3.1 g of Monomer 1, 7.8 g of ALG Monomer 1, 4.2 g of 3-hydroxystyrene, 11.0 g of PAG Monomer 2, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 6. Polymer 6 was analyzed for composition by $^{13}$C- and $^{1}$H-NMR and for Mw and Mw/Mn by GPC.

Polymer 6

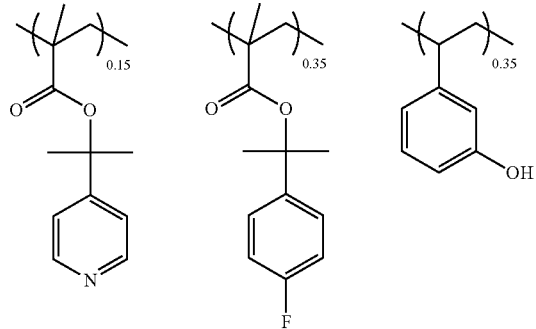

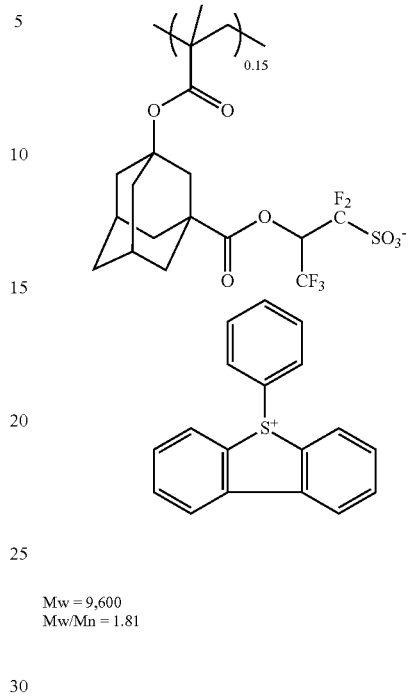

Mw = 9,600
Mw/Mn = 1.81

Synthesis Example 2-7

Synthesis of Polymer 7

A 2-L flask was charged with 2.5 g of Monomer 1, 6.4 g of 1-methyl-1-cyclopentyl methacrylate, 4.2 g of 4-hydroxystyrene, 11.3 g of PAG Monomer 4, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 7. Polymer 7 was analyzed for composition by $^{13}$C- and $^{1}$H-NMR and for Mw and Mw/Mn by GPC.

Polymer 7

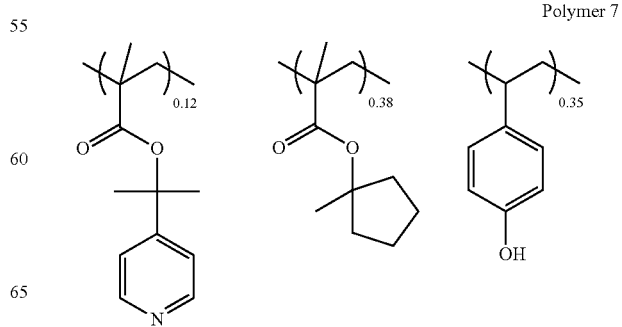

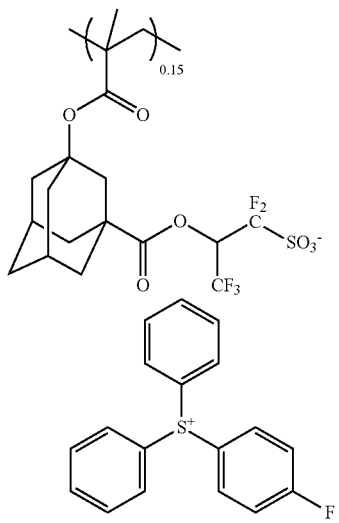

Mw = 9,800
Mw/Mn = 1.60

Mw = 9,900
Mw/Mn = 1.65

Synthesis Example 2-8

Synthesis of Polymer 8

A 2-L flask was charged with 2.5 g of Monomer 1, 6.4 g of 1-methyl-1-cyclopentyl methacrylate, 4.2 g of 4-hydroxystyrene, 10.9 g of PAG Monomer 5, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 8. Polymer 8 was analyzed for composition by $^{13}$C- and $^{1}$H-NMR and for Mw and Mw/Mn by GPC.

Synthesis Example 2-9

Synthesis of Polymer 9

A 2-L flask was charged with 2.5 g of Monomer 1, 5.4 g of tert-butyl methacrylate, 4.2 g of 4-hydroxystyrene, 9.3 g of PAG Monomer 6, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (PA) for precipitation. The precipitated white solid was collected by filtration and vacuum dried at 60° C., yielding Polymer 9. Polymer 9 was analyzed for composition by $^{13}$C- and $^{1}$H-NMR and for Mw and Mw/Mn by GPC.

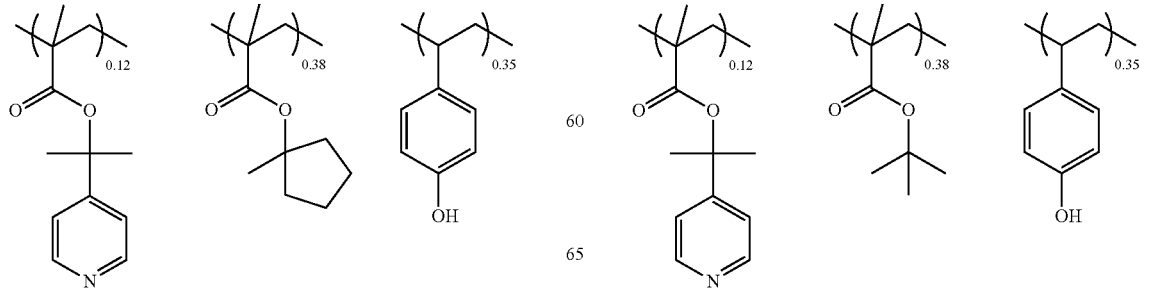

Polymer 8

Polymer 9

-continued

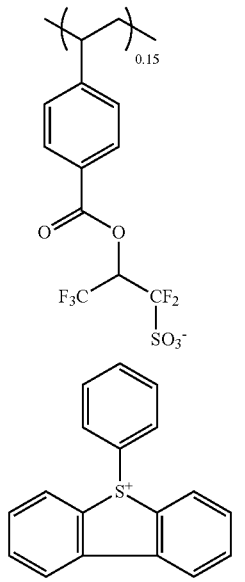

Mw = 9,700
Mw/Mn = 1.65

Synthesis Example 2-10

Synthesis of Polymer 10

A 2-L flask was charged with 2.5 g of Monomer 1, 5.9 g of tert-amyl methacrylate, 4.2 g of 4-hydroxystyrene, 11.9 g of PAG Monomer 7, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 10. Polymer 10 was analyzed for composition by $^{13}$C- and $^{1}$H-NMR and for Mw and Mw/Mn by GPC.

-continued

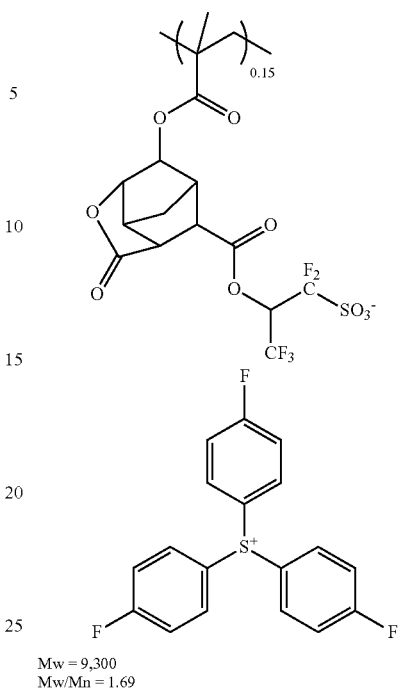

Mw = 9,300
Mw/Mn = 1.69

Synthesis Example 2-11

Synthesis of Polymer 11

A 2-L flask was charged with 4.1 g of Monomer 1, 8.2 g of ALG Monomer 2, 4.8 g of 3-hydroxystyrene, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 11. Polymer 11 was analyzed for composition by $^{13}$C- and $^{1}$H-NMR and for Mw and Mw/Mn by GPC.

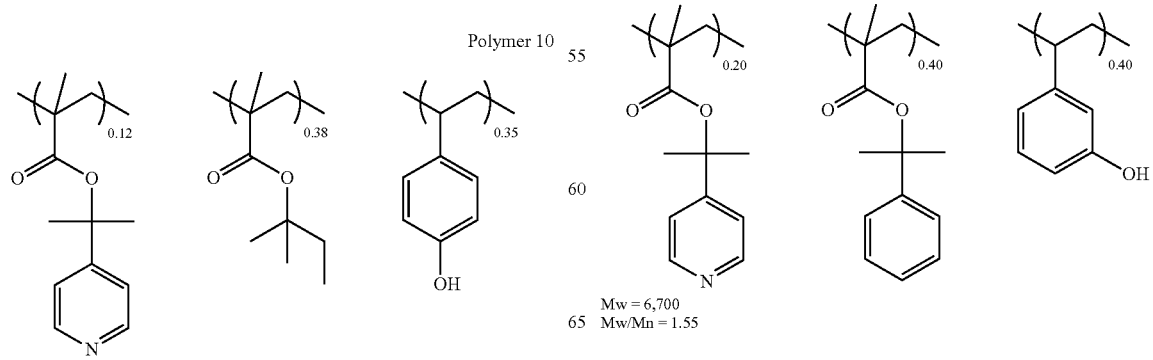

Mw = 6,700
Mw/Mn = 1.55

Synthesis Example 2-12

Synthesis of Polymer 12

A 2-L flask was charged with 4.1 g of Monomer 1, 6.6 g of ALG Monomer 3, 4.8 g of 3-hydroxystyrene, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C. whereupon reaction ran for 15 hours. The reaction solution was poured into 1 L of isopropyl alcohol (IPA) for precipitation. The precipitated white solid was collected by filtration and vacuum dried at 60° C., yielding Polymer 12. Polymer 12 was analyzed for composition by $^{13}C$- and $^{1}H$-NMR and for Mw and Mw/Mn by GPC.

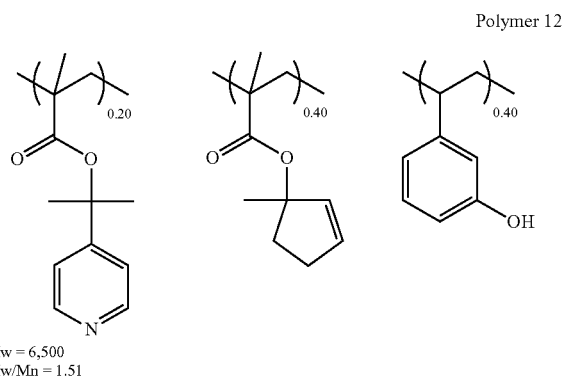

Polymer 12

Mw = 6,500
Mw/Mn = 1.51

Synthesis Example 2-13

Synthesis of Polymer 13

A 2-L flask was charged with 4.1 g of Monomer 1, 7.2 g of ALG Monomer 4, 4.8 g of 3-hydroxystyrene, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C. whereupon reaction ran for 15 hours. The reaction solution was poured into 1 L of isopropyl alcohol (IPA) for precipitation. The precipitated white solid was collected by filtration and vacuum dried at 60° C., yielding Polymer 13. Polymer 13 was analyzed for composition by $^{13}C$- and $^{1}H$-NMR and for Mw and Mw/Mn by GPC.

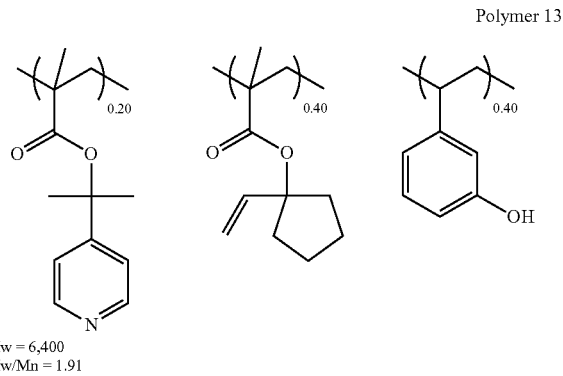

Polymer 13

Mw = 6,400
Mw/Mn = 1.91

Synthesis Example 2-14

Synthesis of Polymer 14

A 2-L flask was charged with 4.1 g of Monomer 1, 7.1 g of ALG Monomer 5, 4.8 g of 3-hydroxystyrene, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C. whereupon reaction ran for 15 hours. The reaction solution was poured into 1 L of isopropyl alcohol (IPA) for precipitation. The precipitated white solid was collected by filtration and vacuum dried at 60° C., yielding Polymer 14. Polymer 14 was analyzed for composition by $^{13}C$- and $^{1}H$-NMR and for Mw and Mw/Mn by GPC.

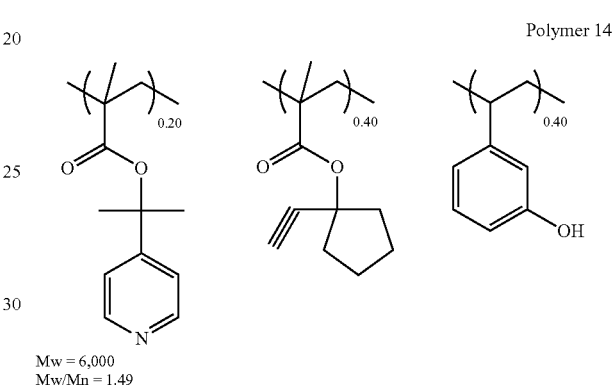

Polymer 14

Mw = 6,000
Mw/Mn = 1.49

Synthesis Example 2-15

Synthesis of Polymer 15

A 2-L flask was charged with 4.1 g of Monomer 1, 7.2 g of ALG Monomer 6, 4.8 g of 3-hydroxystyrene, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C. whereupon reaction ran for 15 hours. The reaction solution was poured into 1 L of isopropyl alcohol (IPA) for precipitation. The precipitated white solid was collected by filtration and vacuum dried at 60° C., yielding Polymer 15. Polymer 15 was analyzed for composition by $^{13}C$- and $^{1}H$-NMR and for Mw and Mw/Mn by GPC.

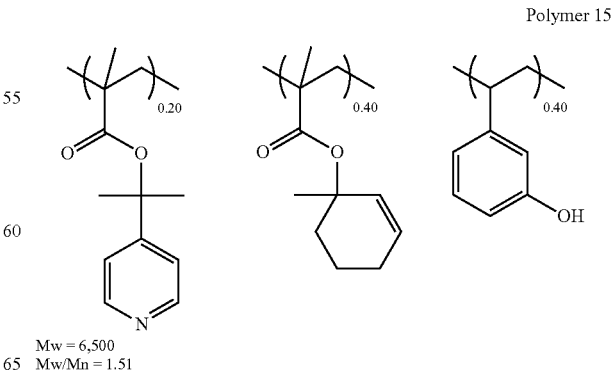

Polymer 15

Mw = 6,500
Mw/Mn = 1.51

Synthesis Example 2-16

Synthesis of Polymer 16

A 2-L flask was charged with 2.5 g of Monomer 1, 7.7 g of ALG Monomer 7, 4.2 g of 4-hydroxystyrene, 11.9 g of PAG Monomer 7, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (PA) for precipitation. The precipitated white solid was collected by filtration and vacuum dried at 60° C., yielding Polymer 16. Polymer 16 was analyzed for composition by $^{13}$C- and $^1$H-NMR and for Mw and Mw/Mn by GPC.

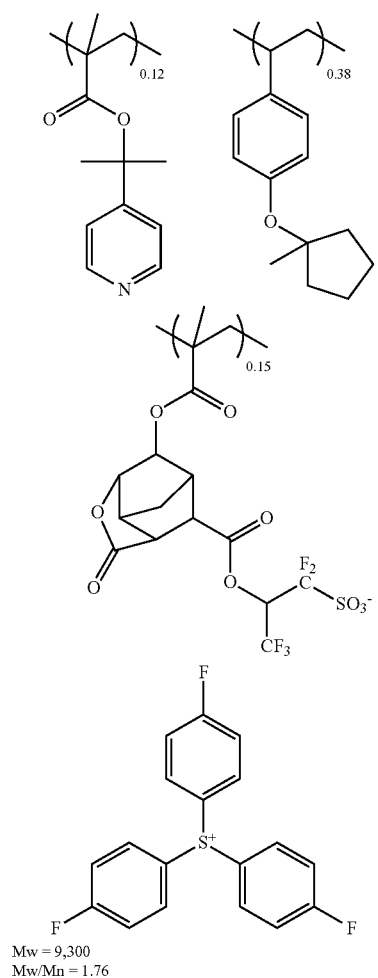

Polymer 16

Mw = 9,300
Mw/Mn = 1.76

Synthesis Example 2-17

Synthesis of Polymer 17

A 2-L flask was charged with 2.5 g of Monomer 1, 8.4 g of ALG Monomer 8, 4.2 g of 4-hydroxystyrene, 11.9 g of PAG Monomer 7, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 17. Polymer 17 was analyzed for composition by $^{13}$C- and $^1$H-NMR and for Mw and Mw/Mn by GPC.

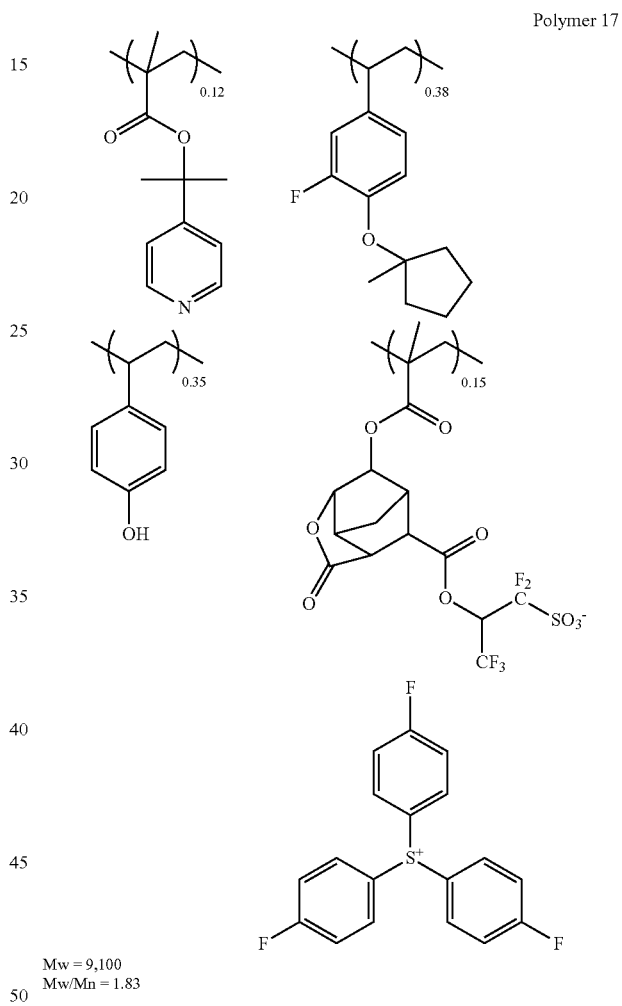

Polymer 17

Mw = 9,100
Mw/Mn = 1.83

Synthesis Example 2-18

Synthesis of Polymer 18

A 2-L flask was charged with 3.2 g of Monomer 2, 6.4 g of 1-methyl-1-cyclopentyl methacrylate, 4.2 g of 4-hydroxystyrene, 10.9 g of PAG Monomer 5, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 18.

Polymer 18 was analyzed for composition by $^{13}$C- and $^1$H-NMR and for Mw and Mw/Mn by GPC.

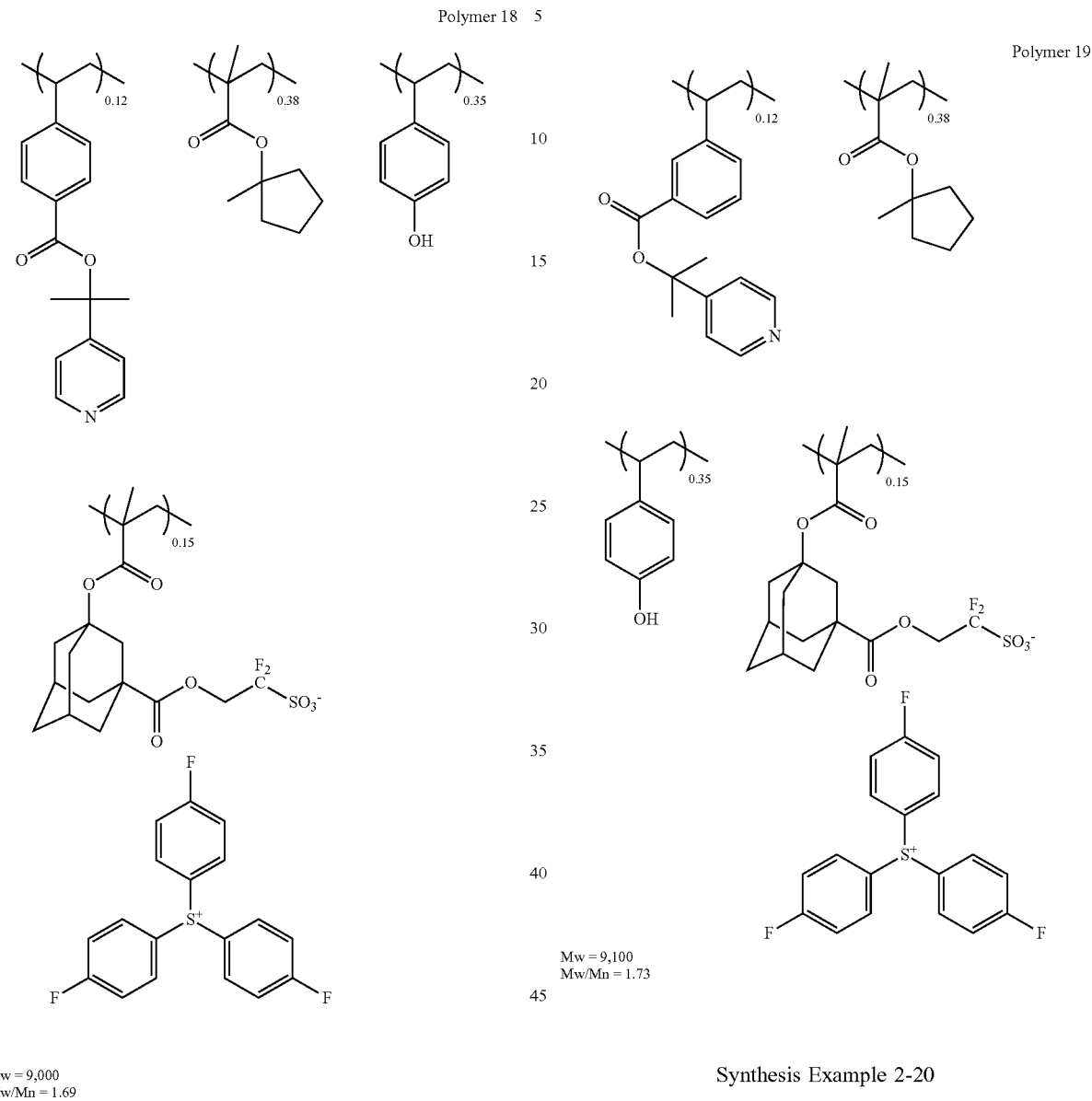

Mw = 9,000
Mw/Mn = 1.69

Mw = 9,100
Mw/Mn = 1.73

Synthesis Example 2-19

Synthesis of Polymer 19

A 2-L flask was charged with 3.2 g of Monomer 3, 6.4 g of 1-methyl-1-cyclopentyl methacrylate, 4.2 g of 4-hydroxystyrene, 10.9 g of PAG Monomer 5, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 19. Polymer 19 was analyzed for composition by $^{13}$C- and $^1$H-NMR and for Mw and Mw/Mn by GPC.

Synthesis Example 2-20

Synthesis of Polymer 20

A 2-L flask was charged with 2.5 g of Monomer 4, 6.4 g of 1-methyl-1-cyclopentyl methacrylate, 4.2 g of 4-hydroxystyrene, 11.0 g of PAG Monomer 2, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 20. Polymer 20 was analyzed for composition by $^{13}$C- and $^1$H-NMR and for Mw and Mw/Mn by GPC.

Polymer 20

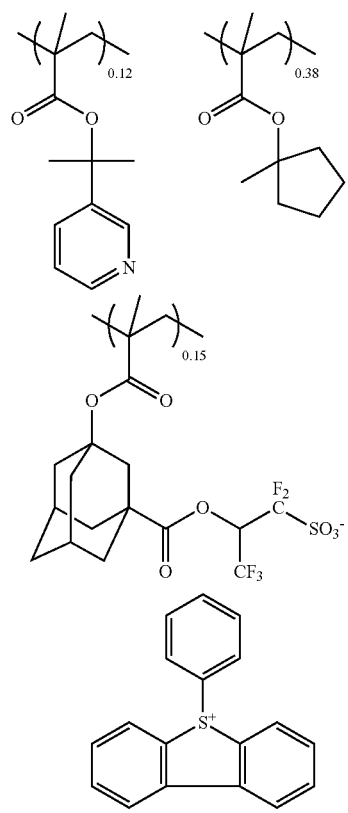

Mw = 9,500
Mw/Mn = 1.64

Synthesis Example 2-21

Synthesis of Polymer 21

A 2-L flask was charged with 2.5 g of Monomer 1, 6.4 g of 1-methyl-1-cyclopentyl methacrylate, 4.2 g of 4-hydroxystyrene, 11.8 g of PAG Monomer 8, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (IPA) for precipitation. The precipitated white solid was collected by filtration and vacuum dried at 60° C., yielding Polymer 21. Polymer 21 was analyzed for composition by $^{13}$C- and $^{1}$H-NMR and for Mw and Mw/Mn by GPC.

Polymer 21

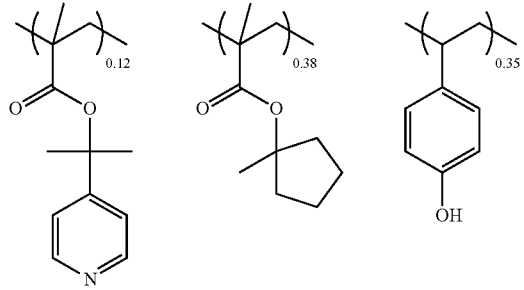

Polymer 20
-continued

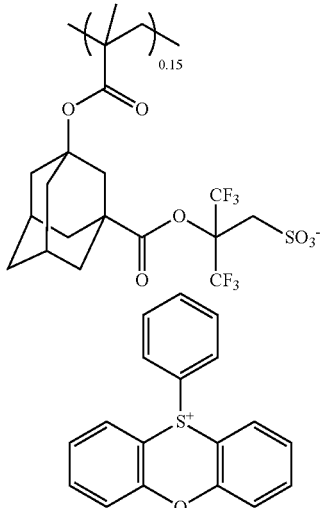

Mw = 9,300
Mw/Mn = 1.68

Synthesis Example 2-22

Synthesis of Polymer 22

A 2-L flask was charged with 2.7 g of Monomer 5, 8.7 g of ALG Monomer 9, 4.2 g of 4-hydroxystyrene, 11.0 g of PAG Monomer 2, and 40 g of THF as a solvent. The reactor was cooled to −70° C. in nitrogen atmosphere, after which vacuum pumping and nitrogen blow were repeated three times. The reactor was warmed up to room temperature, whereupon 1.2 g of AIBN as a polymerization initiator was added. The reactor was heated to 60° C., whereupon reaction ran for 15 hours. The reaction solution was poured into 1 L of isopropyl alcohol (PA) for precipitation. The precipitated white solid was collected by filtration and vacuum dried at 60° C., yielding Polymer 22. Polymer 22 was analyzed for composition by $^{13}$C- and $^{1}$H-NMR and for Mw and Mw/Mn by GPC.

Polymer 22

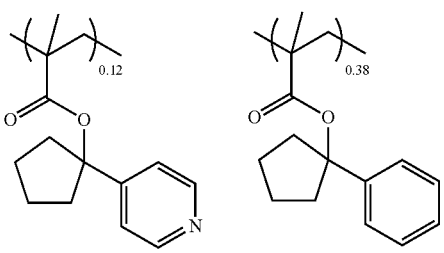

-continued

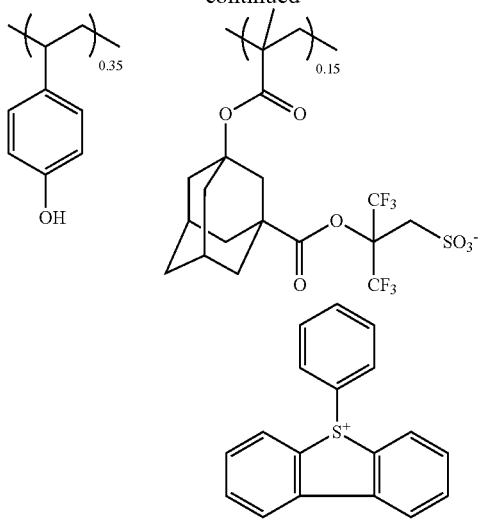

Mw = 9,700
Mw/Mn = 1.61

-continued

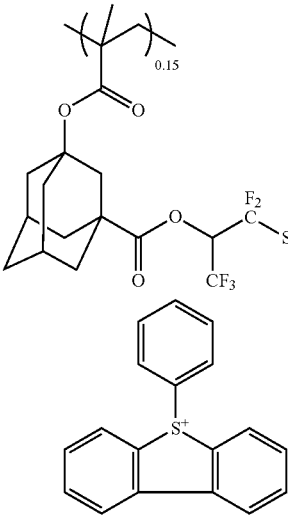

Mw = 9,800
Mw/Mn = 1.72

[3] Preparation and Evaluation of Positive Resist Composition

Examples 1 to 24 and Comparative Examples 1 and 2

(1) Preparation of Positive Resist Composition

Positive resist compositions in solution form were prepared by dissolving components in a solvent in accordance with the recipe shown in Table 1, and filtering through a filter having a pore size of 0.2 μm. The solvent contained 100 ppm of a surfactant, FC-4430 manufactured by 3M.

The components in Table 1 are as identified below.

Organic Solvent:
  PGMEA (propylene glycol monomethyl ether acetate)
  DAA (diacetone alcohol)
Acid Generator: PAG 1

Comparative Synthesis Example 1

Synthesis of Comparative Polymer 1

Comparative Polymer 1 was obtained by the same procedure as in Synthesis Example 2-1 except that Monomer 1 was omitted. Comparative Polymer 1 was analyzed for composition by $^{13}$C- and $^{1}$H-NMR and for Mw and Mw/Mn by GPC.

Comparative Polymer 1

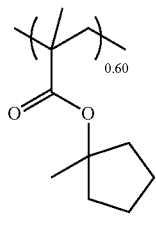 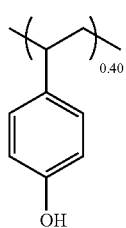

Mw = 9,900
Mw/Mn = 1.99

Comparative Synthesis Example 2

Synthesis of Comparative Polymer 2

Comparative Polymer 2 was obtained by the same procedure as in Synthesis Example 2-4 except that Monomer 1 was omitted. Comparative Polymer 2 was analyzed for composition by $^{13}$C- and $^{1}$H-NMR and for Mw and Mw/Mn by GPC.

Comparative Polymer 2

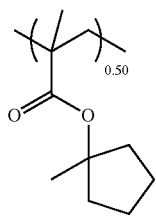 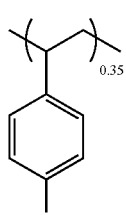

PAG 1

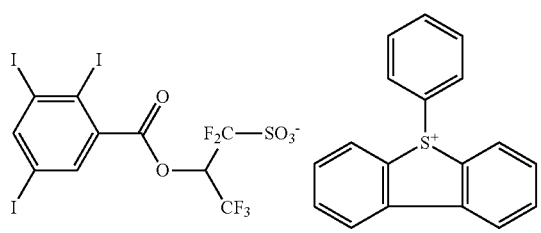

Quencher: Q-1 to Q-4

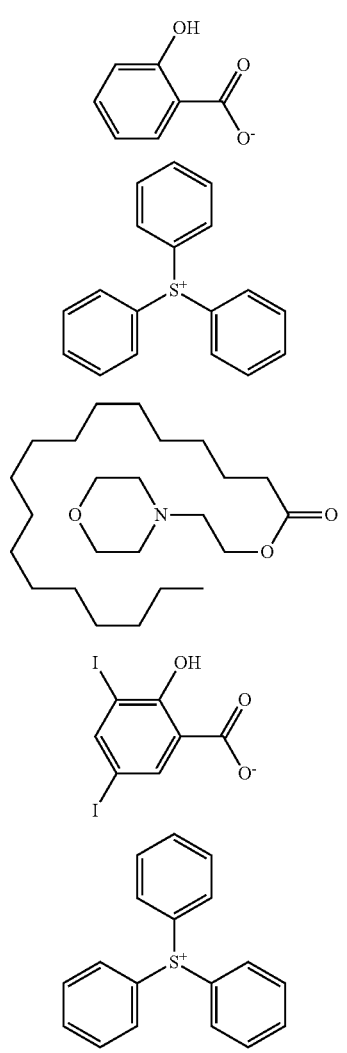

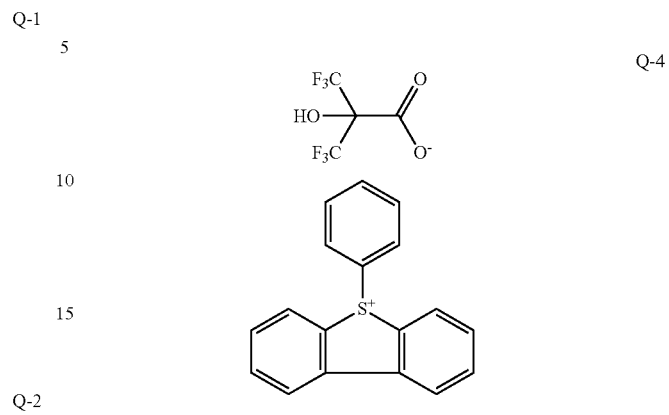

(2) EUV Lithography Test

Each of the resist compositions in Table 1 was spin coated on a silicon substrate having a 20-nm coating of silicon-containing spin-on hard mask SHB-A940 (manufactured by Shin-Etsu Chemical Co., Ltd., silicon content 43 wt %) and prebaked on a hotplate at 105° C. for 60 seconds to form a resist film of 60 nm thick. Using an EUV scanner NXE3300 (manufactured by ASML, NA: 0.33, σ: 0.9/0.6, quadrupole illumination), the resist film was exposed through a mask bearing a hole pattern at a pitch 46 nm (on-wafer size) and +20% bias. The resist film was baked (PEB) on a hotplate at the temperature shown in Table 1 for 60 seconds and developed in a 2.38 wt % TMAH aqueous solution for 30 seconds to form a hole pattern having a size of 23 nm.

The exposure dose that provided a hole pattern having a size of 23 nm was measured and reported as the sensitivity. Using a critical dimension-scanning electron microscope manufactured by Hitachi High-Technologies Corporation (CG-5000), the sizes of 50 holes were measured, the standard deviation (σ) of the sizes was calculated, and three times of the standard deviation (3σ) was reported as the size variation (CDU).

Table 1 shows the resists.

TABLE 1

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG 1 (25.0) | Q-3 (2.25) | PGMEA (2,000) DAA (500) | 90 | 34 | 3.0 |
|  | 2 | Polymer 2 (100) | — | Q-1 (2.00) | PGMEA (2,000) DAA (500) | 95 | 26 | 2.7 |
|  | 3 | Polymer 3 (100) | — | Q-1 (1.00) Q-2 (1.00) | PGMEA (2,000) DAA (500) | 95 | 27 | 2.8 |
|  | 4 | Polymer 4 (100) | — | Q-3 (2.25) | PGMEA (2,000) DAA (500) | 95 | 27 | 2.3 |
|  | 5 | Polymer 5 (100) | — | Q-3 (2.25) | PGMEA (2,000) DAA (500) | 95 | 29 | 2.6 |
|  | 6 | Polymer 5 (100) | — | Q-4 (2.25) | PGMEA (2,000) DAA (500) | 95 | 35 | 2.2 |
|  | 7 | Polymer 5 (100) | PAG 1 (10.0) | Q-1 (2.00) | PGMEA (2,000) DAA (500) | 95 | 23 | 2.3 |
|  | 8 | Polymer 6 (100) | — | Q-4 (2.25) | PGMEA (2,000) DAA (500) | 95 | 33 | 2.4 |
|  | 9 | Polymer 7 (100) | — | Q-4 (2.25) | PGMEA (2,000) DAA (500) | 95 | 32 | 2.3 |

TABLE 1-continued

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
|  | 10 | Polymer 8 (100) | — | Q-4 (2.25) | PGMEA (2,000) DAA (500) | 95 | 31 | 2.2 |
|  | 11 | Polymer 9 (100) | — | Q-4 (2.25) | PGMEA (2,000) DAA (500) | 95 | 33 | 2.4 |
|  | 12 | Polymer 10 (100) | — | Q-4 (2.25) | PGMEA (2,000) DAA (500) | 95 | 33 | 2.2 |
|  | 13 | Polymer 11 (100) | PAG 1 (25.0) | Q-3 (2.25) | PGMEA (2,000) DAA (500) | 80 | 35 | 3.2 |
|  | 14 | Polymer 12 (100) | PAG 1 (25.0) | Q-3 (2.25) | PGMEA (2,000) DAA (500) | 80 | 32 | 3.1 |
|  | 15 | Polymer 13 (100) | PAG 1 (25.0) | Q-3 (2.25) | PGMEA (2,000) DAA (500) | 80 | 35 | 2.8 |
|  | 16 | Polymer 14 (100) | PAG 1 (25.0) | Q-3 (2.25) | PGMEA (2,000) DAA (500) | 80 | 35 | 2.7 |
|  | 17 | Polymer 15 (100) | PAG 1 (25.0) | Q-3 (2.25) | PGMEA (2,000) DAA (500) | 80 | 35 | 2.9 |
|  | 18 | Polymer 16 (100) | — | Q-4 (2.25) | PGMEA (2,000) DAA (500) | 90 | 36 | 2.4 |
|  | 19 | Polymer 17 (100) | — | Q-4 (2.25) | PGMEA (2,000) DAA (500) | 90 | 34 | 2.4 |
|  | 20 | Polymer 18 (100) | — | Q-4 (2.25) | PGMEA (2,000) DAA (500) | 90 | 36 | 2.5 |
|  | 21 | Polymer 19 (100) | — | Q-4 (2.25) | PGMEA (2,000) DAA (500) | 90 | 37 | 2.6 |
|  | 22 | Polymer 20 (100) | — | Q-4 (2.25) | PGMEA (2,000) DAA (500) | 90 | 35 | 2.5 |
|  | 23 | Polymer 21 (100) | — | Q-4 (2.25) | PGMEA (2,000) DAA (500) | 105 | 38 | 2.3 |
|  | 24 | Polymer 22 (100) | — | Q-4 (2.25) | PGMEA (2,000) DAA (500) | 80 | 33 | 2.3 |
| Comparative Example | 1 | Comparative Polymer 1 (100) | PAG 1 (25.0) | Q-3 (3.25) | PGMEA (2,000) DAA (500) | 90 | 33 | 5.6 |
|  | 2 | Comparative Polymer 2 (100) | — | Q-1 (3.00) | PGMEA (2,000) DAA (500) | 95 | 35 | 3.9 |

It is demonstrated in Table 1 that the positive resist composition comprising a base polymer comprising recurring units having a carboxyl group whose hydrogen is substituted by a pyridine ring-containing tertiary hydrocarbyl group offers a high sensitivity and improved CDU.

Japanese Patent Application No. 2020-017215 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition comprising a base polymer comprising recurring units having a carboxyl group whose hydrogen is substituted by a pyridine ring-containing tertiary hydrocarbyl group.

2. The positive resist composition of claim 1, wherein the recurring units have the formula (a):

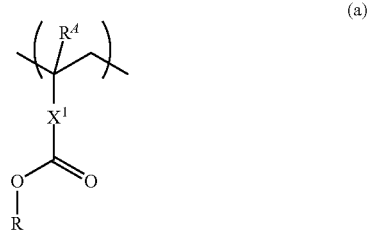

wherein $R^A$ is hydrogen or a methyl group,
$X^1$ is a single bond, a phenylene group, a naphthylene group, or a $C_1$-$C_{12}$ linking group containing at least one selected from an ester bond, an ether bond, and a lactone ring,
R is a group having the formula (a1):

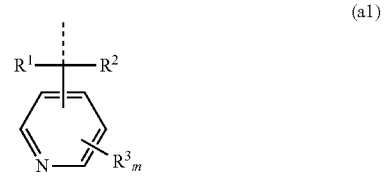

wherein $R^1$ and $R^2$ are each independently a $C_1$-$C_6$ aliphatic hydrocarbyl group which may contain a heteroatom, $R^1$ and $R^2$ may bond together to form a ring with a carbon atom to which $R^1$ and $R^2$ are attached,
$R^3$ is hydrogen or a $C_1$-$C_6$ alkyl group,
m is an integer of 1 to 4, and
a broken line designates a valence bond.

3. The positive resist composition of claim 1, further comprising recurring units of at least one type selected from recurring units having a carboxyl group whose hydrogen is substituted by an acid labile group other than a pyridine ring-containing tertiary hydrocarbyl group, or recurring units having a phenolic hydroxyl group whose hydrogen is substituted by an acid labile group.

4. The positive resist composition of claim 3, wherein the recurring units having a carboxyl group whose hydrogen is substituted by an acid labile group other than a pyridine ring-containing tertiary hydrocarbyl group, and the recurring units having a phenolic hydroxyl group whose hydrogen is substituted by an acid labile group are recurring units having the formula (b1) and recurring units having the formula (b2), respectively:

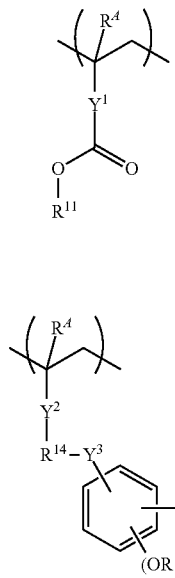

(b1)

(b2)

wherein $R^A$ is each independently hydrogen or a methyl group, $Y^1$ is a single bond, a phenylene group, a naphthylene group, or a $C_1$-$C_{12}$ linking group containing at least one selected from an ester bond, an ether bond, and a lactone ring, $Y^2$ is a single bond, an ester bond, or an amide bond, $Y^3$ is a single bond, an ether bond, or an ester bond, $R^{11}$ is an acid labile group other than a pyridine ring-containing tertiary hydrocarbyl group, $R^{12}$ is an acid labile group, $R^{13}$ is fluorine, a trifluoromethyl group, a cyano group, or a $C_1$-$C_6$ saturated hydrocarbyl group, $R^{14}$ is a single bond or a $C_1$-$C_6$ alkanediyl group in which some carbon may be replaced by an ether bond or an ester bond, a is 1 or 2, b is an integer of 0 to 4, and 1≤a+b≤5.

5. The positive resist composition of claim 1, wherein the base polymer further comprises recurring units having an adhesive group selected from the group consisting of a hydroxyl group, a carboxyl group, a lactone ring, a carbonate group, a thiocarbonate group, a carbonyl group, a cyclic acetal group, an ether bond, an ester bond, a sulfonic acid ester bond, a cyano group, an amide bond, —O—C(=O)—S—, and —O—C(=O)—NH—.

6. The positive resist composition of claim 1, wherein the base polymer further comprises recurring units having any one of the formulae (d1) to (d3):

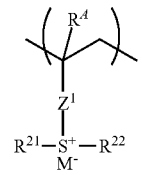

(d1)

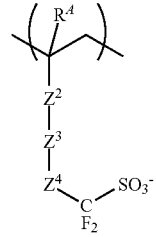

(d2)

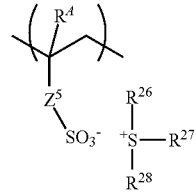

(d3)

wherein $R^A$ is each independently hydrogen or a methyl group, $Z^1$ is a single bond, a $C_1$-$C_6$ aliphatic hydrocarbylene group, a phenylene group, a naphthylene group, a $C_7$-$C_{18}$ group obtained from combination thereof, —O—$Z^{11}$—, —C(=O)—O—$Z^{11}$—, or —C(=O)—NH—$Z^{11}$—, $Z^{11}$ is a $C_1$-$C_6$ aliphatic hydrocarbylene group, a phenylene group, a naphthylene group, or a $C_7$-$C_{18}$ group obtained from combination thereof, which may contain a carbonyl group, an ester bond, an ether bond, or a hydroxyl group, $Z^2$ is a single bond or an ester bond, $Z^3$ is a single bond, —$Z^{31}$—C(=O)—O—, —$Z^{31}$—O—, or —$Z^{31}$—O—C(=O)—, $Z^{31}$ is a $C_1$-$C_{12}$ hydrocarbylene group, a phenylene group, or a $C_7$-$C_{18}$ group obtained from combination thereof, which may contain a carbonyl group, an ester bond, an ether bond, bromine, or iodine, $Z^4$ is a methylene group, a 2,2,2-trifluoro-1,1-ethanediyl group, or a carbonyl group, $Z^5$ is a single bond, a methylene group, an ethylene group, a phenylene group, a fluorinated phenylene group, a trifluoromethyl-substituted phenylene group, —O—$Z^{51}$—, —C(=O)—O—$Z^{51}$—, or —C(=O)—NH—$Z^{51}$—, $Z^{51}$ is a $C_1$-$C_{16}$ aliphatic hydrocarbylene group, a phenylene group, a fluorinated phenylene group, or a trifluoromethyl-substituted phenylene group, which may contain a carbonyl group, an ester bond, an ether bond, a halogen, or a hydroxyl group, $R^{21}$ to $R^{28}$ are each independently fluorine, chlorine, bromine, iodine, or a $C_1$-$C_{20}$ hydrocarbyl group which may contain a heteroatom, $R^{23}$ and $R^{24}$, or $R^{26}$ and $R^{27}$ may bond together to form a ring with a sulfur atom to which $R^{23}$ and $R^{24}$, or $R^{26}$ and $R^{27}$ are attached, and $M^-$ is a non-nucleophilic counter ion.

7. The positive resist composition of claim 1, further comprising an acid generator.

8. The positive resist composition of claim 1, further comprising an organic solvent.

9. The positive resist composition of claim 1, further comprising a quencher.

10. The positive resist composition of claim 1, further comprising a surfactant.

11. A pattern forming process comprising the steps of applying the positive resist composition of claim 1 onto a substrate to form a resist film thereon, exposing the resist film to high-energy radiation, and developing the exposed resist film in a developer.

12. The pattern forming process of claim 11 wherein the high-energy radiation is i-line, KrF excimer laser, ArF excimer laser, electron beam, or extreme ultraviolet of wavelength 3 to 15 nm.

\* \* \* \* \*